United States Patent
Lee et al.

(10) Patent No.: US 12,110,299 B2
(45) Date of Patent: Oct. 8, 2024

(54) THIAZOLE DERIVATIVES AND PHARMACEUTICALLY ACCEPTABLE SALTS THEREOF

(71) Applicant: YUNGJIN PHARM. CO., LTD., Songpa-gu (KR)

(72) Inventors: Kwang Ok Lee, Gyeonggi-Do (KR); Jakyung Yoo, Gyeonggi-Do (KR); Jun Hee Lee, Gwangjin-gu (KR); Mijung Lee, Hwaseong-Si (KR); Kangwoo Lee, Osan-Si (KR); Jieun Min, Suwon-Si (KR)

(73) Assignee: YUNGJIN PHARM. CO., LTD., Seoul (KR)

( * ) Notice: Subject to any disclaimer, the term of this patent is extended or adjusted under 35 U.S.C. 154(b) by 670 days.

(21) Appl. No.: 17/277,033

(22) PCT Filed: Sep. 11, 2019

(86) PCT No.: PCT/KR2019/011887
§ 371 (c)(1),
(2) Date: Mar. 17, 2021

(87) PCT Pub. No.: WO2020/060112
PCT Pub. Date: Mar. 26, 2020

(65) Prior Publication Data
US 2021/0284658 A1  Sep. 16, 2021

(30) Foreign Application Priority Data
Sep. 17, 2018 (KR) .................... 10-2018-0111001

(51) Int. Cl.
C07D 498/18  (2006.01)
C07D 277/46  (2006.01)
C07D 417/12  (2006.01)
C07D 417/14  (2006.01)
C07D 471/04  (2006.01)
C07D 487/18  (2006.01)

(52) U.S. Cl.
CPC ......... *C07D 498/18* (2013.01); *C07D 277/46* (2013.01); *C07D 417/12* (2013.01); *C07D 417/14* (2013.01); *C07D 471/04* (2013.01); *C07D 487/18* (2013.01)

(58) Field of Classification Search
None
See application file for complete search history.

(56) References Cited

U.S. PATENT DOCUMENTS

| | | |
|---|---|---|
| 4,259,341 A | 3/1981 | Baldwin et al. |
| 6,875,751 B2 | 4/2005 | Imbach et al. |
| 7,585,851 B2 | 9/2009 | Bryant et al. |
| 7,964,580 B2 | 6/2011 | Sofia et al. |
| 2007/0100141 A1 | 5/2007 | Bonaventure et al. |
| 2007/0105919 A1 | 5/2007 | Nakajima et al. |
| 2010/0029718 A1 | 2/2010 | Dales et al. |
| 2010/0249402 A1 | 9/2010 | Ryu et al. |
| 2010/0311703 A1 | 12/2010 | Gonzalez Lio et al. |
| 2012/0172362 A1 | 7/2012 | Kase et al. |
| 2013/0045982 A1 | 2/2013 | Wang et al. |
| 2017/0066759 A1 | 3/2017 | Yukimasa et al. |

FOREIGN PATENT DOCUMENTS

| | | | |
|---|---|---|---|
| JP | 2008-509950 A | 4/2008 | |
| JP | 2010-75194 A | 4/2010 | |
| JP | 2018-516917 A | 6/2018 | |
| KR | 10-2016-0118417 A | 10/2016 | |
| KR | 10-1802514 B1 | 11/2017 | |
| WO | 99/65884 A1 | 12/1999 | |
| WO | 2001/044217 A1 | 12/2001 | |
| WO | WO-2003/008365 A2 | 1/2003 | |
| WO | WO-2006/018188 A2 | 2/2006 | |
| WO | 2006/051270 A1 | 5/2006 | |
| WO | 2006/081172 A2 | 8/2006 | |
| WO | WO-2008/138755 A2 | 11/2008 | |
| WO | WO-2011/079036 A1 | 6/2011 | |
| WO | WO 2011/084985 A1 * | 7/2011 | ......... A61K 31/4545 |
| WO | WO-2012/123471 A1 | 9/2012 | |
| WO | 2012/161879 A1 | 11/2012 | |
| WO | WO-2014/063068 A1 | 4/2014 | |
| WO | WO-2014/113620 A2 | 7/2014 | |
| WO | WO-2015/058140 A1 | 4/2015 | |
| WO | WO-2015/082357 A1 | 6/2015 | |
| WO | WO-2016/051193 A1 | 4/2016 | |

(Continued)

OTHER PUBLICATIONS

International Search Report and Written Opinion for International Application No. PCT/KR2019/011887 dated Dec. 30, 2019.

(Continued)

*Primary Examiner* — Joseph K McKane
*Assistant Examiner* — David M Shim
(74) *Attorney, Agent, or Firm* — Hamilton, Brook, Smith & Reynolds, P.C.

(57) ABSTRACT

The present invention provides a novel thiazole derivative or a pharmaceutically acceptable salt thereof, and a method for preparing the same. The thiazole derivative or pharmaceutically acceptable salt thereof according to the present invention has selective inhibitory activity against cyclin-dependent kinase (CDK) and thus can be used as a preventive or therapeutic agent for various diseases associated with CDK.

17 Claims, 1 Drawing Sheet

(56) References Cited

FOREIGN PATENT DOCUMENTS

| WO | 2016/193931 A1 | 12/2016 |
| WO | WO-2016/193939 A1 | 12/2016 |
| WO | 2018/134464 A1 | 7/2018 |
| WO | WO-2020/060112 A1 | 3/2020 |

OTHER PUBLICATIONS

Wang et al., "CDK7-Dependent Transcriptional Addiction in Triple-Negative Breast Cancer," Cell, 163: 174-186 (36 pages)(2015).
Bundgaard, Hans. "Design of prodrugs." 2 pages (1985).
Cross, L. C., et al., "International Union of Pure and Applied Chemistry, Organic Chemistry Division Commission on Nomenclature of Organic Chemistry, Rules for the Nomenclature of Organic Chemistry Section E: Stereochemistry," Pure & Appl. Chtm., vol. 45, pp. 11-30 (1976).

* cited by examiner

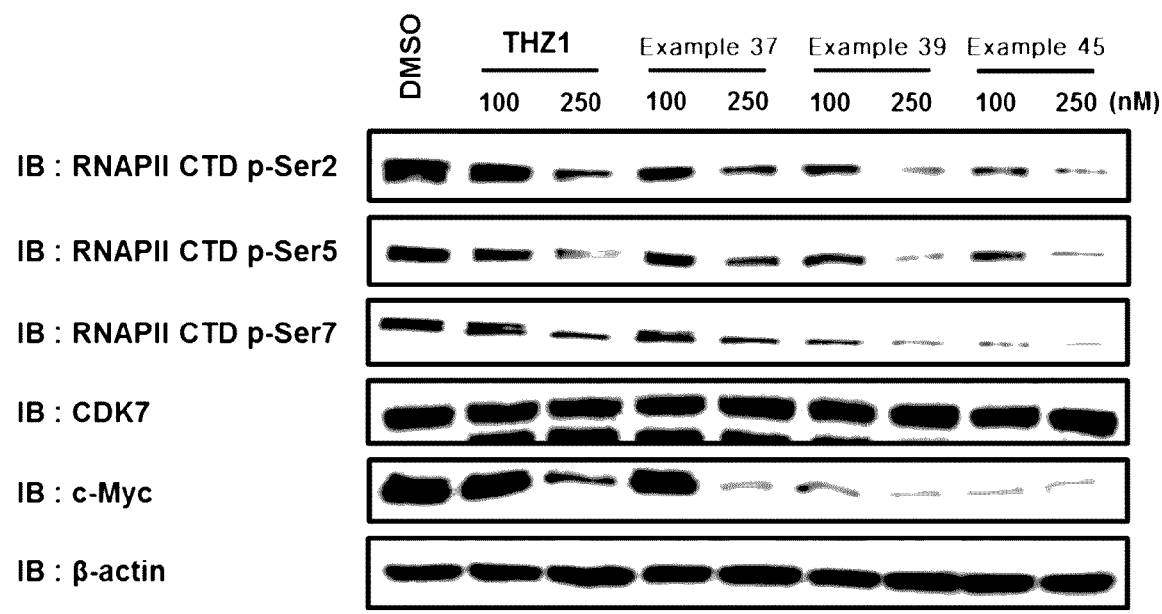

THIAZOLE DERIVATIVES AND PHARMACEUTICALLY ACCEPTABLE SALTS THEREOF

RELATED APPLICATIONS

This application is the National Stage of International Patent Application No. PCT/KR2019/011887, filed Sep. 11, 2019, which claims the benefit of priority to Korean Patent Application No. 10-2018-0111001, filed Sep. 17, 2018, the contents of each of which are hereby incorporated by reference herein in their entirety.

TECHNICAL FIELD

This application claims the benefit of priority to Korean Patent Application No. 10-2018-0111001, filed Sep. 17, 2018, the specification of which is hereby incorporated by reference herein in its entirety.

The present invention relates to novel thiazole derivatives, and pharmaceutically acceptable salts thereof, methods for preventing, ameliorating, or treating cancer comprising administering compounds of the invention, methods for preparing compounds of the invention, and pharmaceutical compositions comprising such compounds.

BACKGROUND ART

Cancer represents a pathological manifestation of uncontrolled cell division. In particular, cyclin-dependent kinases (CDKs) that promote transition through the cell cycle are expected to be key therapeutic targets. CDKs are family of serine/threonine protein kinases that plays an important role in cell proliferation. For example, proliferation is induced by CDK4 or CDK6 complexes acting on the G1 phase in many cancer-onset processes, Furthermore, S-phase and G2/M control mediated by CDK2 and CDK1 also play a key role in cancer. CDK1, 2, 4, and 6 are associated to cell cycle, whereas CDK8-13 is involved in the transcription of genes.

Among mammals, CDK7 is the only component of CDK-activating kinase (CAK) and general transcription factor TFIIH, and plays an essential role in both cell cycle and transcription. CDK7 phosphorylates the C-terminal domain (CTD) of RNA polymerase (RNAP) II to thereby regulate the expression of oncogenic transcription factors that induce cancer cell growth and survival.

Although cancer cells have features of increased genetic heterogeneity compared to normal cells, some cancer cells can inhibit the growth of cancer cells or induce apoptosis by targeted treatment of major oncogenic driver mutations. However, in the case of "transcriptionally addicted cancer cells" without specific driver mutations, they can be inhibited by transcriptional regulatory kinases such as CDK7. (Yubao Wang et al., Cell 163, 174-186, Sep. 24, 2015). Thus, there is a need for compounds that treat diseases and disorders associated with selective transcriptional CDKs, particularly CDK7.

DISCLOSURE OF INVENTION

Technical Problem

In accordance with an aspect of the present invention, there is provided a compound represented by the following Formula (I), or a pharmaceutically acceptable salt thereof:

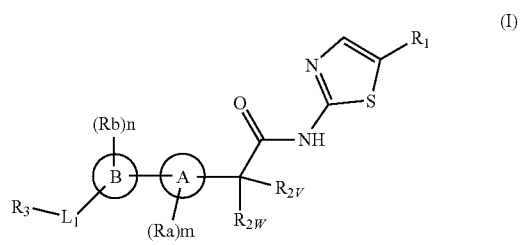

wherein,
ring A is cycloalkyl, aryl, heteroaryl, or heterocycloalkyl;
ring B is cycloalkyl, aryl, heteroaryl, or heterocycloalkyl;
$R_1$ is H, halo, alkyl, cycloalkyl, heterocycloalkyl, aryl, heteroaryl, haloalkyl, cyano, —$SR_c$, —$C(O)R_c$, —$C(O)OR_c$, —$C(O)N(R_c)(R_d)$, —$N(R_c)(R_d)$, —$(C(R_g)_2)_q$—$N(R_c)(R_d)$, —$OR_c$, or $(R_g)_2)_q$—$OR_c$;
$R_c$ and $R_{d'}$ are each independently H, alkyl, cycloalkyl, aryl, heterocycloalkyl, or heteroaryl; or
$R_c$ and $R_{d'}$ taken together with the atom to which they are attached, form a substituted or unsubstituted heterocycloalkyl;
each q is independently an integer from 1-3;
$R_g$ is H or alkyl;
$R_{2V}$ and $R_{2W}$ are each independently H, halo, hydroxy, alkyl, cycloalkyl, heterocycloalkyl, alkoxy, alkoxyalkyl, or amino; or
$R_{2V}$ and $R_{2W}$, taken together with the atom to which they are attached, form a cycloalkyl or heterocycloalkyl;
$L_1$ is absent, —$N(R_e)$—, —$CH_2N(R_e)$—, —$CH_2CH_2N(R_e)$—, or alkylene, provided that if $L_1$ is —$CH_2N(R_e)$— or —$CH_2CH_2N(R_e)$—, then ring B is attached to carbon terminus of the substituent and $R_{f3}$ is attached to the nitrogen terminus of the substituent;
where $R_e$ is H or alkyl; or $R_e$ is covalently bound to a position on ring B, thereby forming a heteroaryl or heterocycloalkyl ring structure, which is unsubstituted or substituted;
$R_{f3}$ is

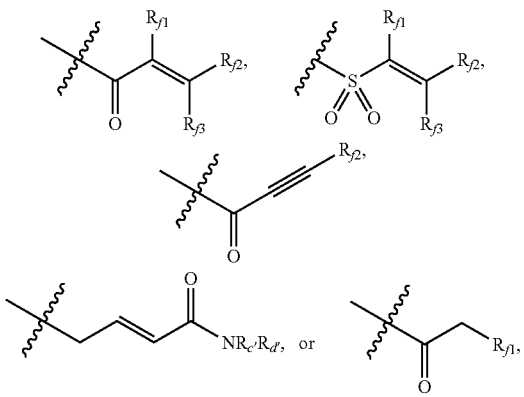

wherein $R_{f1}$ is H, halo, alkyl or cyano;
$R_{f2}$ and $R_{f3}$ are each independently H, halo, alkyl, cycloalkyl, heterocycloalkyl, heteroaryl, aryl, alkoxy, alkoxyalkyl, —$N(R_{c'})(R_{d'})$, or —$(C(R_g)_2)_q$—$N(R_{c'})(R_{d'})$
each $R_g$, is independently H or alkyl;
$R_{c'}$ and $R_{d'}$ are each independently H, alkyl, heterocycloalkyl, alkoxy or alkoxyalkyl; or R$_c$, and R$_d$, taken together with the atom to which they are attached, form a substituted or unsubstituted heterocycloalkyl, each R$_a$ is independently H, halo, hydroxyl, nitro, or cyano; or is alkyl, alkoxy, alkoxyalkyl, amino, haloalkyl, aryl, heteroaryl, heterocycloalkyl or cycloalkyl, which is unsubstituted or substituted;

each R$_b$ is independently H, halo, hydroxyl, nitro, or cyano, or is alkyl, alkoxy, alkoxyalkyl, amino, haloalkyl, aryl, heteroaryl, heterocycloalkyl, cycloalkyl or —NR$_h$R$_j$, which is unsubstituted or substituted;

R$_h$ and R$_j$ are each independently H, alkyl, —N(R$_{h'}$)(R$_{j'}$), —(C(R$_g$)$_2$)$_q$—N(R$_{h'}$)(R$_{j'}$), or heterocycloalkyl, R$_{h'}$ and R$_{j'}$ are each independently H or alkyl; or R$_{h'}$ and R$_{j'}$ taken together with the atom to which they are attached, form an unsubstituted or substituted heterocycloalkyl; and m and n are integers each independently selected from 1 to 4.

Compounds disclosed herein include compounds having highly selective inhibitory activity against a cyclin-dependent kinase (CDK), especially, CDK7.

Compounds and pharmaceutical compositions disclosed herein are useful for preventing or treating CDK-related disease, especially, CDK7-related disease, e.g., by administering the compound or composition to a subject.

BRIEF DESCRIPTION OF DRAWINGS

FIG. 1 shows the results of confirming the phosphorylation of RNA polymerase (RNAP) II C-terminal domain and the inhibition of expression of the oncogene c-Myc protein through western blotting, when TNBC (MDA-MB-468) cells were treated with a control substance (THZ1) and the compounds of Example 37, Example 39 and Example 45 for each concentration.

MODE FOR THE INVENTION

Hereinafter, the present invention will be described in more detail.

Definitions

Unless otherwise defined, all technical terms used herein have the same meaning as commonly understood by one of ordinary skill in the art to which this invention belongs. Furthermore, the numerical values set forth herein are considered to include the meaning of "about" unless explicitly stated.

The definition of moieties and substituents used herein are provided below. Unless otherwise indicated, each moiety has the following definition and is used in the sense as commonly understood by one of ordinary skill in the art.

According to the convention used in the art, "

" in the formulae herein is used to indicate that a moiety or substituent "R" is attached to a backbone structure.

"Alkyl" is a hydrocarbon having primary, secondary, tertiary, and/or quaternary carbon atoms, and encompasses saturated aliphatic groups that may be straight, branched, or cyclic, or a combination thereof. For example, an alkyl group may have 1 to 20 carbon atoms (i.e., C$_1$-C$_{20}$ alkyl), 1 to 10 carbon atoms (i.e., C$_1$-C$_{10}$ alkyl), or 1 to 6 carbon atoms (i.e., C$_1$-C$_6$ alkyl). Unless otherwise defined, in preferred embodiments, alkyl refers to C$_1$-C$_6$ alkyl. Examples of a suitable alkyl group include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, ipropyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH 3)$_2$CH$_2$CH$_3$), 3-methyl-2-butyl (—CH(CH$_3$)CH(CH$_3$)$_2$), 3-methyl-1-butyl (—CH$_2$CH$_2$ CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$ CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$ CH$_3$), 4-methyl-2-pentyl (—CH(CH$_3$)CH$_2$CH(CH$_3$)$_2$), 3-methyl-3-pentyl (—C(CH$_3$)(CH$_2$ CH$_3$)$_2$), 2-methyl-3-pentyl (—CH(CH$_2$CH$_3$)CH(CH$_3$)$_2$), 2,3-dimethyl-2-butyl (—C(CH$_3$)$_2$ CH(CH$_3$)$_2$), 3,3-dimethyl-2-butyl (—CH(CH$_3$) C(CH$_3$)$_3$), and octyl (—(CH$_2$)$_7$CH$_3$), but it is not limited thereto.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "C$_{x-y}$" or "C$_x$-C$_y$", when used in conjunction with a chemical moiety, such as, acyl, acyloxy, alkyl, alkenyl, alkynyl, or alkoxy is meant to include groups that contain from x to y carbons in the chain. C$_0$alkyl indicates a hydrogen where the group is in a terminal position, a bond if internal. A (C$_1$-C$_6$)alkyl group, for example, contains from one to six carbon atoms in the chain.

"Acyl" refers to —C(=O)-alkyl, —C(=O)-carbocycle (which is substituted or unsubstituted), and —C(=O)-heterocycle (which is substituted or unsubstituted), wherein the alkyl, carbocycle, or heterocycle moiety is as defined herein. Non-limiting examples of "acyl" include —C(=O)CH$_3$, —C(=O)CH$_2$CH$_3$, —C(=O)CH(CH$_3$)$_2$, —C(=O)C (CH$_3$)$_3$, —C(=O)-phenyl (which is substituted or unsubstituted), —C(=O)-cyclopropyl (which is substituted or unsubstituted), —C(=O)-cyclobutyl (which is substituted or unsubstituted), —C(=O)-cyclopentyl (which is substituted or unsubstituted), —C(=O)-cyclohexyl (which is substituted or unsubstituted), and —C(=O)-pyridyl (which is substituted or unsubstituted).

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

"Alkoxy" refers to a group having the formula —O-alkyl, wherein the alkyl group as defined above is attached to the parent compound via an oxygen atom. The alkyl moiety of the alkoxy group may have, for example, 1 to 20 carbon atoms (i.e., C$_1$-C$_{20}$ alkoxy), 1 to 12 carbon atoms (i.e., C$_1$-C$_{12}$ alkoxy), 1 to 10 carbon atoms (i.e., C$_1$-C$_{10}$ alkoxy), or 1 to 6 carbon atoms (i.e., C$_1$-C$_6$ alkoxy). Examples of a suitable alkoxy group include methoxy (—O—CH₃ or —OMe), ethoxy (—OCH₂CH₃ or -OEt), and t-butoxy (—OC(CH₃)₃ or —O-tBu), but it is not limited thereto.

The term "alkoxyalkyl" refers to an alkyl group substituted with an alkoxy group and may be represented by the general formula -alkyl-O-alkyl.

The term "alkylamino", as used herein, refers to an amino group substituted with at least one alkyl group.

The term "alkylthio", as used herein, refers to a thiol group substituted with an alkyl group and may be represented by the general formula alkylS-.

"Alkenyl" is a hydrocarbon having primary, secondary, tertiary, and/or quaternary carbon atoms, and encompasses straight, branched, and cyclic groups, or a combination thereof, and having at least one unsaturated region, i.e., a carbon-carbon sp² double bond. For example, an alkenyl group may have 2 to 20 carbon atoms (i.e., $C_2$—$C_{20}$ alkenyl), 2 to 12 carbon atoms (i.e., $C_2$-$C_{12}$ alkenyl), 2 to 10 carbon atoms (i.e., $C_2$—$C_{10}$ alkenyl), or 2 to 6 carbon atoms (i.e., $C_2$-$C_6$ alkenyl). Examples of a suitable alkenyl group include vinyl (—CH═CH₂), allyl (—CH₂CH═CH₂), cyclopentenyl (—C₅H7), and 5-hexenyl (—CH₂CH₂CH₂CH₂CH═CH₂), but it is not limited thereto.

"Alkynyl" is a hydrocarbon having primary, secondary, tertiary, and/or quaternary carbon atoms, and encompasses straight, branched, and cyclic groups, or a combination thereof, and having at least one carbon-carbon sp triple bond. For example, an alkynyl group may have 2 to 20 carbon atoms (i.e., $C_2$-$C_{20}$ alkynyl), 2 to 12 carbon atoms (i.e., $C_2$-$C_{12}$ alkynyl), 2 to 10 carbon atoms (i.e., $C_2$-$C_{10}$ alkynyl), or 2 to 6 carbon atoms (i.e., $C_2$-$C_6$ alkynyl). Examples of a suitable alkynyl group include acetylenic (—C≡CH) and propargyl (—CH₂C≡CH), but it is not limited thereto.

"Alkylene" refers to a saturated hydrocarbon group that may be branched, straight, or cyclic (or may have a combination of branched, straight, or cyclic moieties) and has two valencies derived by a removal of two hydrogen atoms from the same carbon atom or two different carbon atoms of a parent alkane. For example, an alkylene group may have 1 to 20 carbon atoms, 1 to 10 carbon atoms, or 1 to 6 carbon atoms. Examples of a typical alkylene group include 1,2-ethylene (—CH₂—CH₂—), but it is not limited thereto.

"Alkenylene" refers to an unsaturated hydrocarbon group that may be branched, straight, or cyclic (or may have a combination of branched, straight, or cyclic moieties) and has two valencies derived by a removal of two hydrogen atoms from the same carbon atom or two different carbon atoms of a parent alkene. For example, an alkenylene group may have 1 to 20 carbon atoms, 1 to 10 carbon atoms, or 1 to 6 carbon atoms. Examples of a typical alkenylene group include 1,2-ethenylene (—CH═CH—), but it is not limited thereto.

"Alkynylene" refers to an unsaturated hydrocarbon group that may be branched, straight, or cyclic (or may have a combination of branched, straight, or cyclic moieties) and has two valencies derived by a removal of two hydrogen atoms from the same carbon atom or two different carbon atoms of a parent alkyne. For example, an alkynylene group may have 1 to 20 carbon atoms, 1 to 10 carbon atoms, or 1 to 6 carbon atoms. Examples of a typical alkynylene radical include acetylenylene (—C≡C—), propargylene (—CH₂C≡C—), and 4-pentynylene (—CH₂CH₂CH₂C≡C—), but it is not limited thereto.

The term "amide", as used herein, refers to a group

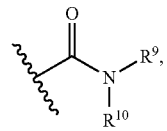

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

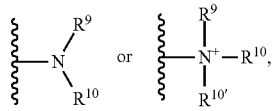

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure. In certain embodiments, amino is —NH₂.

The term "aminoalkyl", as used herein, refers to an alkyl group substituted with an amino group.

The term "aryl" as used herein include substituted or unsubstituted monovalent or divalent aromatic hydrocarbon groups that are monocyclic, bicyclic, or polycyclic, in which each atom of the ring is carbon. Preferably the aryl ring is a 6- to 20-membered ring, a 6- to 14-membered ring, a 6- to 10-membered ring, or more preferably a 6-membered ring. The aryl group may be a polycyclic ring system having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocycloalkyls. Aryl groups include benzene, naphthalene, phenanthrene, anthracene, indene, indane, phenol, aniline, and the like.

The term "aralkyl", or the term "arylalkyl" as used herein, refers to an alkyl group substituted with an aryl group. Examples of a typical arylalkyl group include benzyl, 2-phenylethan-1-yl, naphthylmethyl, 2-naphthylethan-1-yl, naphthobenzyl, 2-naphthophenylethan-1-yl, and the like (each of which may be substituted or unsubstituted), but it is not limited thereto. An arylalkyl group may have 7 to 20 carbon atoms. For example, the alkyl moiety thereof may have 1 to 6 carbon atoms, and the aryl moiety thereof may have 6 to 14 carbon atoms.

"Arylalkenyl" refers to an acyclic alkenyl group in which one of the hydrogen atoms bonded to a carbon atom, typically a terminal or other sp³ carbon atom, although an sp² carbon atom may also be used, is replaced by an aryl group. The aryl moiety of the arylalkenyl may be, for example, any aryl group described herein, and the alkenyl moiety of the arylalkenyl may comprise, for example, any of the alkenyl groups described herein. An arylalkenyl group may have 8 to 20 carbon atoms. For example, the alkenyl moiety thereof may have 2 to 6 carbon atoms, and the aryl moiety thereof may have 6 to 14 carbon atoms.

"Arylalkynyl" refers to an acyclic alkynyl group in which one of the hydrogen atoms bonded to a carbon atom, typically a terminal or other sp³ carbon atom, although an sp carbon atom may also be used, is replaced by an aryl group. The aryl moiety of the arylalkynyl may be, for example, any aryl group described herein, and the alkynyl moiety of the arylalkynyl may comprise, for example, any of the alkynyl groups described herein. An arylalkynyl group may have 8 to 20 carbon atoms. For example, the alkynyl moiety thereof may have 2 to 6 carbon atoms, and the aryl moiety thereof may have 6 to 14 carbon atoms.

"Arylheteroalkyl" refers to a heteroalkyl as defined herein, wherein a hydrogen atom (which may be attached to either a carbon atom or a heteroatom) is replaced by an aryl group as defined herein. If the resulting group is chemically stable, the aryl group may be attached to a carbon atom of the heteroalkyl group or the heteroatom of the heteroalkyl group. For example, an arylheteroalkyl group may have a formula of -alkylene-O-aryl, -alkylene-O-alkylene-aryl, -alkylene-NH-aryl, -alkylene-NH-alkylene-aryl, -alkylene-S-aryl, -alkylene-S-alkylene-aryl, or the like. In addition, any alkylene moiety in the above formulae may be further substituted with any of the substituents defined or exemplified herein.

The term "carbamate" is art-recognized and refers to a group

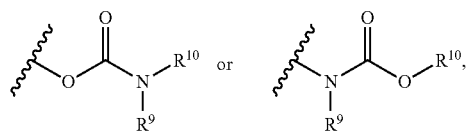

wherein $R^9$ and $R^{10}$ independently represent hydrogen or a hydrocarbyl group.

The term "carbocyclylalkyl", or "cycloalkylalkyl", or "(cycloalkyl)alkyl", as used herein, refers to an alkyl group substituted with a carbocycle group or a cycloalkyl group.

The terms "carbocycle", "carbocyclyl", "carbocyclic", or "cycloalkyl" as used herein, refers to a non-aromatic saturated or unsaturated, monovalent or divalent ring that may be monocyclic, bicyclic, or polycyclic and in which each atom of the ring is carbon. A cycloalkyl group may have 3 to 7 carbon atoms as a monocycle, 7 to 12 carbon atoms as a bicycle, and up to about 20 carbon atoms as a polycycle. A monocyclic cycloalkyl has 3 to 7 ring atoms, more typically 5 or 6 ring atoms. A bicyclic cycloalkyl may have 7 to 12 ring atoms and may be a fused ring system, a spirocyclic ring system, or a bridged ring system. In exemplary cycloalkyl groups, the atoms may be arranged in a bicyclo[4,5], [5,5], [5,6], or [6,6] system. In certain embodiments, cycloalkyl contains from 3 to 20 atoms, or 3 to 10 atoms, or more preferably from 3 to 7 atoms. Examples of cycloalkyl include cyclopropyl, cyclobutyl, cyclopentyl, cyclohexyl, cycloheptyl, cyclooctyl, and the like. Unless otherwise indicated, cycloalkyl may be substituted by one or more substituents described herein.

The term "carbonate" is art-recognized and refers to a group —OCO₂—.

The term "carboxy", as used herein, refers to a group represented by the formula —CO₂H.

The term "ester", as used herein, refers to a group —C(O)OR⁹ wherein R⁹ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

"Haloalkyl" is an alkyl group in which at least one of the hydrogen atoms of the alkyl group as defined above is replaced by a halogen atom. The alkyl moiety of the haloalkyl group may have 1 to 20 carbon atoms (i.e., $C_1$-$C_{20}$ haloalkyl), 1 to 12 carbon atoms (i.e., $C_1$-$C_{12}$ haloalkyl), 1 to 10 carbon atoms (i.e., $C_1$-$C_{10}$ haloalkyl), or 1 to 6 carbon atoms (i.e., $C_1$-$C_6$ haloalkyl). Exemplary haloalkyl groups include —CF₃, —CHF₂, —CFH₂, and —CH₂CF₃, but are not limited thereto.

"Heteroalkyl" refers to an alkyl group in which at least one carbon atom is replaced by a heteroatom such as O, N, or S. For example, if a carbon atom of the alkyl group attached to a parent molecule is replaced by a heteroatom (e.g., O, N, or S), the resulting heteroalkyl group may be an alkoxy group (e.g., —OCH₃), an amine group (e.g., —NHCH₃, —N(CH₃)₂, or the like), or a thioalkyl group (e.g., —SCH3), respectively. If a non-terminal carbon atom of the alkyl group that is not attached to a parent molecule is replaced by a heteroatom (e.g., O, N, or S), the resulting heteroalkyl group may be an alkyl ether (e.g., —CH₂CH₂—O—CH₃ or the like), an alkylamine (e.g., —CH₂ NHCH₃, —CH₂N(CH₃)₂, or the like), or a thioalkyl ether (e.g., —CH₂—S—CH₃), respectively. If the terminal carbon atom of the alkyl group is replaced by a heteroatom (for example, O, N, or S), the resulting heteroalkyl group may be a hydroxyalkyl group (e.g., —CH₂CH₂—OH), an aminoalkyl group (e.g., —CH₂NH₂), or an alkyl-SH group (e.g., —CH₂CH₂—SH), respectively. For example, a heteroalkyl group may have 1 to 20 carbon atoms, 1 to 10 carbon atoms, or 1 to 6 carbon atoms. Preferably, a heteroalkyl group has from 2 to 20, 2 to 10, or 2 to 6 total atoms in the chain (i.e., carbon atoms plus heteroatoms combined). A C1-C6 heteroalkyl group refers to a heteroalkyl group having 1 to 6 carbon atoms.

"Heteroaryl" refers to substituted or unsubstituted monovalent or divalent aromatic groups that are monocyclic, bicyclic, or polycyclic, containing at least one heteroatom in the ring. Non-limiting examples of a suitable heteroatom that may be contained in the aromatic ring include oxygen, sulfur, and nitrogen. In polycyclic heteroaryl ring systems, the ring system has two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, benzofuran, benzothiophene, pyrrole, furan, thiophene, imidazole, indole, isoindole, isoxazole, isothiazole, oxazole, thiazole, quinoline, isoquinoline, pyrazole, pyridine, pyrazine, pyridazine, and pyrimidine, and the like (each of which may be substituted or unsubstituted).

"Heteroarylalkyl" refers to an alkyl group as defined herein, wherein a hydrogen atom is replaced by a heteroaryl group as defined herein. Non-limiting examples of heteroarylalkyl include —CH₂-pyridinyl, —CH₂-pyrrolyl, —CH₂-oxazolyl, —CH₂-indolyl, —CH₂-isoindolyl, —CH₂-furanyl, —CH₂-thienyl, —CH₂-benzofuranyl, —CH₂— benzothiophenyl, —CH₂-carbazolyl, —CH₂-imidazolyl, —CH₂-thiazolyl, —CH₂-isoxazolyl, —CH₂-pyrazolyl, —CH₂-isothiazolyl, —CH₂-quinolyl, —CH₂-isoquinolyl, —CH₂-pyridazyl, —CH₂-pyrimidyl, —CH₂-pyrazyl, —CH(CH₃)-pyridinyl, —CH(CH₃)-pyrrolyl, —CH(CH₃)-oxazolyl, —CH(CH₃)-indolyl, —CH(CH₃)-isoindolyl, —CH(CH₃)-furanyl, —CH(CH₃)-thienyl, —CH(CH₃)-benzofuranyl, —CH(CH₃)-benzothiophenyl, —CH(CH₃)-carbazolyl, —CH(CH₃)-imidazolyl, —CH(CH₃)-thiazolyl, —CH(CH₃)-isoxazolyl, —CH(CH₃)-pyrazolyl, —CH(CH₃)-isothiazolyl, —CH(CH₃)-quinolyl, —CH(CH₃)-isoquinolyl, —CH(CH₃)-pyridazyl, —CH(CH₃)-pyrimidyl, —CH(CH₃)-pyrazyl, and the like.

The term "heterocyclylalkyl" and "heterocycloalkyl", as used herein, refers to an alkyl group substituted with a heterocycloalkyl group.

The terms "heterocyclyl", "heterocycle", "heterocyclic", and "heterocycloalkyl" refer to substituted or unsubstituted, monovalent or divalent, saturated or partially saturated non-aromatic ring structures, preferably 3- to 10-membered rings, more preferably 3 to 7-membered rings, whose ring structures include at least one heteroatom, preferably one to four heteroatoms, more preferably one or two heteroatoms. The terms "heterocyclyl," "heterocycle," "heterocyclic," and "heterocycloalkyl" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Bicyclic and polycyclic heterocyclic ring systems may be fused, bridged, or spiro ring systems. Substituted heterocycle, for example, includes a heterocyclic ring substituted with any of the substituents disclosed herein, inclusive of a carbonyl group. Heterocyclyl groups include, for example, piperidine, piperazine, pyrrolidine, morpholine, lactones, lactams, and the like. Further exemplary heterocycles include dihydropyridyl, dihydroindolyl, tetrahydropyridyl(piperidyl), tetrahydrothiophenyl, sulfur-oxidized tetrahydrothiophenyl, indolenyl, piperidinyl, 4-piperidinyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, 6H-1,2,5-thiadiazinyl, 2H,6H-1,5,2-dithiazinyl, pyranyl, chromenyl, xanthenyl, phenoxatinyl, 2H-pyrrolyl, 3H-indolyl, 4H-quinolizinyl, phthalazinyl, naphthyridinyl, quinoxalinyl, quinazolinyl, cinnolinyl, phtheridinyl, 4aH-carbazolyl, carbazolyl, Pcarbolinyl, phenanthridinyl, acridinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, quinuclidinyl, morpholinyl, and oxazolidinyl (each of which may be substituted or unsubstituted), but it is not limited thereto "Heterocyclylalkenyl" refers to an acyclic alkenyl radical in which one of the hydrogen atoms bonded to a carbon atom, typically a terminal or sp3 carbon atom although a sp2 carbon atom may also be used, is replaced by a heterocyclyl radical (i.e., a heterocyclyl-alkenylene moiety).

"Heterocyclylalkynyl" refers to an acyclic alkynyl radical in which one of the hydrogen atoms bonded to a carbon atom, typically a terminal or sp3 carbon atom although a sp carbon atom may also be used, is replaced by a heterocyclyl radical (i.e., a heterocyclyl-alkynylene moiety).

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO3H, or a pharmaceutically acceptable salt thereof.

The term "sulfonamide" is art-recognized and refers to the group represented by the general formulae

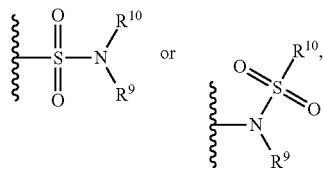

wherein R⁹ and R¹⁰ independently represents hydrogen or hydrocarbyl.

The term "sulfoxide" is art-recognized and refers to the group-S(O)—.

The term "sulfonate" is art-recognized and refers to the group SO₃H, or a pharmaceutically acceptable salt thereof.

The term "sulfone" is art-recognized and refers to the group —S(O)₂—.

"Silyloxy" refers to the group —O—SiR₃, wherein each R independently is alkyl, aryl (which is substituted or unsubstituted), or heteroaryl (which is substituted or unsubstituted). Non-limiting examples of silyloxy include —O—Si(CH₃)₃, —O—Si(CH₃)₂tBu, —O—Si(tBu)₂CH₃, —O—Si(tBu)₃, —O—Si(CH₃)₂Ph, —O—Si(Ph)₂CH₃, and —O—Si(Ph)₃.

The term "optionally substituted" refers to a particular moiety (e.g., an optionally substituted aryl group) of the compound of the invention that optionally has one, two, or more substituents.

The term "substituted" with respect to alkyl, alkylene, aryl, arylalkyl, heterocyclyl, and the like, for example, "substituted alkyl," "substituted alkylene," "substituted aryl," "substituted arylalkyl," "substituted heterocyclyl," and "substituted carbocyclyl (e.g., substituted cycloalkyl)," means that at least one hydrogen atom of the alkyl, alkylene, aryl, arylalkyl, heterocyclyl, or carbocyclyl (e.g., cycloalkyl) is each independently replaced by a non-hydrogen substituent. Substituents can include any substituents described herein, for example, halogen, hydroxyl, alkyl, hydroxyalkyl, haloalkyl, cyanoalkyl, alkoxyalkyl, carbonyl (such as carboxyl, alkoxycarbonyl, formyl, or acyl), thiocarbonyl (such as thioester, thioacetate, or thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

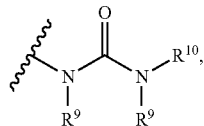

wherein R$^9$ and R$^{10}$ independently represent hydrogen or a hydrocarbyl.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of the invention for laboratory use, or for subsequent conversion to a pharmaceutically acceptable acid addition salt. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. Thus, in some examples, contemplated salts of the invention include alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The selection of the appropriate salt will be known to a person skilled in the art.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

The term "ester thereof" refers to any ester of a compound wherein any —COOH functional group of the molecule is modified to be a —COOR functional group or any —OH functional group of the molecule is modified to be a —OC(=O)R. Here, the R moiety of the ester may be any carbon-containing group that forms a stable ester moiety, which includes, but is not limited to, alkyl, alkenyl, alkynyl, cycloalkyl, cycloalkylalkyl, aryl, arylalkyl, heterocyclyl, heterocyclylalkyl, and substituted derivatives thereof.

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee.

Certain compounds useful in the methods and compositions of this disclosure may have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers).

Certain compounds of the invention have more than one stereogenic center. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configutations at the remaining stereogenic centers.

In certain embodiments, the enantiomeric excess of a given stereogeneric center in the compound is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound. The compound of formula (I) provides an example of a compound for which no stereochemistry is indicated.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present invention. Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of the invention. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

Thiazole Derivative Compounds

Representative embodiments of the compounds of the invention follow. Such compounds, like the compounds disclosed elsewhere herein, are suitable for formulation in any of the pharmaceutical compositions disclosed herein, or for use in any of the methods or treatments disclosed herein.

In accordance with a first representative embodiment, there is provided a compound represented by Formula (I), or a pharmaceutically acceptable salt thereof:

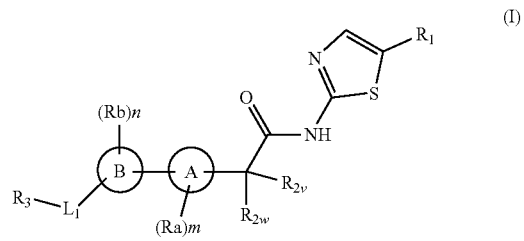

wherein,
ring A is cycloalkyl, aryl, heteroaryl, or heterocycloalkyl;
ring B is cycloalkyl, aryl, heteroaryl, or heterocycloalkyl;
$R_1$ is H, halo, alkyl, cycloalkyl, heterocycloalkyl, aryl, heteroaryl, haloalkyl, cyano, —$SR_c$, —$C(O)R_c$, —$C(O)OR_c$, —$C(O)N(R_c)(R_d)$, —$N(R_c)(R_d)$, —$(C(R_g)_2)_q$—$N(R_c)(R_d)$, —$OR_{c'}$ or —$(C(R_g)_2)_q$—$OR_c$;
$R_c$ and $R_{d'}$ are each independently H, alkyl, cycloalkyl, aryl, heterocycloalkyl, or heteroaryl; or
$R_c$ and $R_{d'}$ taken together with the atom to which they are attached, form a substituted or unsubstituted heterocycloalkyl;
each q is independently an integer from 1-3;
$R_g$ is H or alkyl;
$R_{2V}$ and $R_{2w}$ are each independently H, halo, hydroxy, alkyl, cycloalkyl, heterocycloalkyl, alkoxy, alkoxyalkyl, or amino; or
$R_{2V}$ and $R_{2w}$, taken together with the atom to which they are attached, form a cycloalkyl or heterocycloalkyl;
$L_1$ is absent, —$N(R_e)$—, —$CH_2N(R_e)$—, —$CH_2CH_2N(R_e)$—, or alkylene, provided that if $L_1$ is —$CH_2N(R_e)$— or —$CH_2CH_2N(R_e)$—, then ring B is attached to carbon terminus of the substituent and $R_3$ is attached to the nitrogen terminus of the substituent;
where $R_e$ is H or alkyl; or $R_e$ is covalently bound to a position on ring B, thereby forming a heteroaryl or heterocycloalkyl ring structure, which is unsubstituted or substituted;

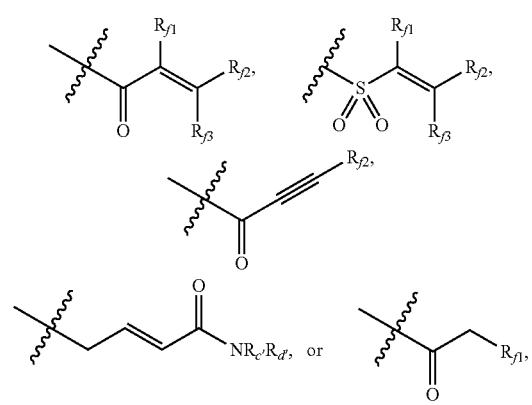

wherein $R_{f1}$ is H, halo, alkyl or cyano;
$R_{f2}$ and $R_{f3}$ are each independently H, halo, alkyl, cycloalkyl, heterocycloalkyl, heteroaryl, aryl, alkoxy, alkoxyalkyl, —$N(R_{c'})(R_{d'})$, or —$(C(R_{g'})_2)_q$—$N(R_{c'})(R_{d'})$;
each $R_{g'}$ is independently H or alkyl;
$R_{c'}$ and $R_{d'}$ are each independently H, alkyl, heterocycloalkyl, alkoxy or alkoxyalkyl; or
$R_{c'}$ and $R_{d'}$ taken together with the atom to which they are attached, form a substituted or unsubstituted heterocycloalkyl, each $R_b$ is independently H, halo, hydroxyl, nitro, or cyano; or is alkyl, alkoxy, alkoxyalkyl, amino, haloalkyl, aryl, heteroaryl, heterocycloalkyl or cycloalkyl, which is unsubstituted or substituted;

each $R_b$ is independently H, halo, hydroxyl, nitro, or cyano, or is alkyl, alkoxy, alkoxyalkyl, amino, haloalkyl, aryl, heteroaryl, heterocycloalkyl, cycloalkyl or —$NR_hR_j$, which is unsubstituted or substituted;

$R_h$ and $R_j$ are each independently H, alkyl, —$N(R_{h'})(R_{j'})$, —$(C(R_g)_2)_q$—$N(R_{h'})(R_{j'})$, or heterocycloalkyl, $R_{h'}$ and $R_{j'}$ are each independently H or alkyl; or $R_{h'}$ and $R_{j'}$ taken together with the atom to which they are attached, form an unsubstituted or substituted heterocycloalkyl; and m and n are integers each independently selected from 1 to 4.

In preferred embodiments, the ring A may be 6- to 10-membered aryl; 5- or 6-membered heteroaryl containing 1 to 4 heteroatoms independently selected from the group consisting of N, O, and S; or 5- or 6-membered heterocycloalkyl containing 1 to 4 heteroatoms independently selected from the group consisting of N, O, and S. More preferably, the ring A may be phenyl, pyridinyl, pyrazinyl, pyrazolyl, thiophenyl, thiazolyl, or piperidinyl.

In preferred embodiments, the ring B may be 6- to 10-membered aryl; 5- or 6-membered heteroaryl containing 1 to 4 heteroatoms independently selected from the group consisting of N, O, and S; or 5- or 6-membered heterocycloalkyl containing 1 to 4 heteroatoms independently selected from the group consisting of N, O, and S. More preferably, the ring B may be phenyl, pyridinyl, pyrimidinyl, pyrazinyl, pyridazinyl, pyrazolyl, imidazolyl, thiazolyl, tetrahydropyridinyl, piperidinyl, or piperazinyl.

In preferred embodiments, the $R_1$ may be halo, $C_1$-$C_6$ alkyl, $C_3$-$C_7$ cycloalkyl, $C_1$-$C_6$ haloalkyl, cyano, —$SR_{c'}$—$C(O)R_{c'}$—$C(O)OR_{c'}$—$N(R_c)(R_d)$, —$OR_{c'}$ or —$C(R_g)_2$—$OR_c$; $R_c$ and $R_{d'}$ may be each independently H or $C_1$-$C_6$ alkyl; and $R_g$ may be H or $C_1$-$C_6$ alkyl.

In preferred embodiments, the $R_{2V}$ and $R_{2w}$ may be each independently H, halo, or $C_1$-$C_6$ alkyl; or $R_{2V}$ and $R_{2w}$, taken together with the atom to which they are attached, form a $C_3$-$C_7$ cycloalkyl.

In preferred embodiments, $L_1$ may be absent, —$N(R_e)$—, or —$CH_2N(R_e)$—, where $R_e$ may be H or $C_1$-$C_6$ alkyl; or $R_e$ may be covalently bound to an atom on ring B, thereby forming 5- or 6-membered heteroaryl containing 1 to 4 heteroatoms independently selected from the group consisting of N, O, and S; or 5- or 6-membered heterocycloalkyl containing 1 to 4 heteroatoms independently selected from the group consisting of N, O, and S, where the heteroaryl or heterocycloalkyl may be unsubstituted or substituted with $C_1$-$C_6$ alkyl.

More preferably, $L_1$ may be absent, —$N(R_e)$—, or —$CH_2N(R_e)$—, where $R_e$ may be H or $C_1$-$C_6$ alkyl; or $R_e$ may be covalently bound to an atom on ring B, thereby forming pyrrolidine or pyrrole which is unsubstituted or substituted with $C_1$-$C_6$ alkyl.

In preferred embodiments, $R_3$ may be

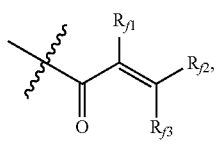 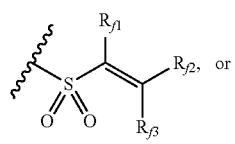

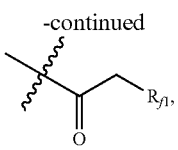

wherein $R_{f1}$ may be H, $C_1$-$C_6$ alkyl or cyano;

$R_{f2}$ and $R_{f3}$ may be each independently H, $C_1$-$C_6$ alkyl, $C_3$-$C_7$ cycloalkyl, —$N(R_{c'})(R_{d'})$, or —$(CH_2)N(R_{c'})(R_{d'})$;

$R_{c'}$ and $R_{d'}$ may be each independently H, or $C_1$-$C_6$ alkyl; or $R_{c'}$ and $R_{d'}$, taken together with the atom to which they are attached, form a 4- to 7-membered heterocycloalkyl containing 1 to 3 heteroatoms independently selected from the group consisting of N, O, and S, wherein heterocycloalkyl may be unsubstituted or substituted with halo, hydroxy, $C_1$-$C_6$ alkyl or $C_1$-$C_6$ alkoxy-$C_1$-$C_6$ alkyl. More preferably, $R_3$ may be

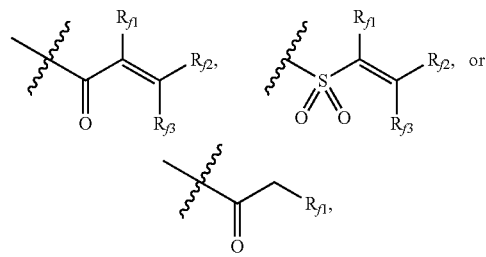

wherein $R_{f1}$ may be H, $C_1$-$C_6$ alkyl, or cyano;

$R_{f2}$ and $R_{f3}$ may be each independently H, $C_1$-$C_6$ alkyl, $C_3$-$C_7$ cycloalkyl, —$N(CH_3)_2$, or —$(CH_2)N(R_{c'})(R_{d'})$ $R_{c'}$ and $R_{d'}$ may be each independently $C_1$-$C_6$ alkyl; or $R_{c'}$ and $R_{d'}$, taken together with the atom to which they are attached, form azetidinyl; piperidinyl; morpholinyl; piperazinyl which is unsubstituted or substituted with $C_1$-$C_6$ alkyl; 2,5-diazabicyclo[2.2.1]heptanyl which is unsubstituted or substituted with $C_1$-$C_6$ alkyl; 2-oxa-5-azabicyclo[2.2.1]heptanyl; or pyrrolidinyl which is unsubstituted or substituted with halo, hydroxy or $C_1$-$C_6$ alkoxy-$C_1$-$C_6$ alkyl.

In preferred embodiments, each $R_a$ may be independently H, halo, or $C_1$-$C_6$ alkyl;

each $R_b$ may be independently H, halo, $C_1$-$C_6$ alkyl, $C_3$-$C_7$ cycloalkyl, $C_1$-$C_6$ alkoxy, cyano, $C_1$-$C_6$ haloalkyl, —$NR_hR_j$, or a 5- to 6-membered heterocycloalkyl containing 1 to 4 heteroatoms independently selected from the group consisting of N, O, and S where the heterocycloalkyl may be unsubstituted or substituted with $C_1$-$C_6$ alkyl, $R_h$ and $R_{j'}$ may be each independently $C_1$-$C_6$ alkyl, —$CH_2CH_2N(R_{h'})(R_{j'})$; and $R_{h'}$ and $R_{j'}$ may be each independently H or $C_1$-$C_6$ alkyl. More preferably, each $R_a$ may be independently H, halo, or $C_1$-$C_6$ alkyl;

each $R_b$ may be independently H, halo, $C_1$-$C_6$ alkyl, $C_3$-$C_7$ cycloalkyl, $C_1$-$C_6$ alkoxy, cyano, $C_1$-$C_6$ haloalkyl, —$N(CH_3)$—$CH_2CH_2$—$N(CH_3)_2$, or piperazinyl which is unsubstituted or substituted with $C_1$-$C_6$ alkyl.

In preferred embodiments, the m and n may be 1.

In preferred embodiments within Formula I, ring A is aryl or heteroaryl, for example, pyrrolidinyl, furanyl, thiophenyl, pyrrolyl, thiazolyl, oxazolyl, thiadiazolyl, oxadiazolyl, pyrazolyl, triazolyl, phenyl, pyridinyl, pyrazinyl, pyridazinyl, pyrimidinyl, piperidinyl, piperazinyl, cyclohexyl, azetidinyl, benzimidazolyl, benzthiazolyl, or quinolinyl.

In certain preferred such embodiments, ring A is phenyl. In other preferred such embodiments, ring A is pyridinyl. In still other preferred such embodiments, ring A is thiophenyl. In yet other preferred such embodiments, ring A is pyrazolyl.

In a second representative embodiment, the compound of Chemical Formula (I) may be a compound of the following Chemical Formula (Ia).

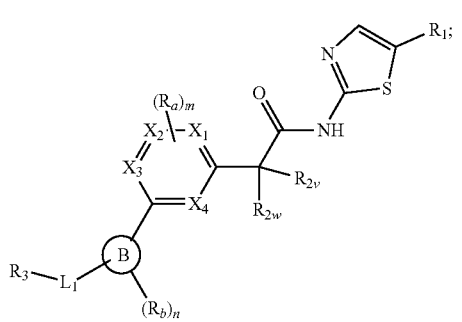

(Ia)

wherein $X_1$, $X_2$, $X_3$ and $X_4$ are each independently CH or N.

In a third representative embodiment, the compound of Chemical Formula (I) may be a compound of the following Chemical Formula (Iai).

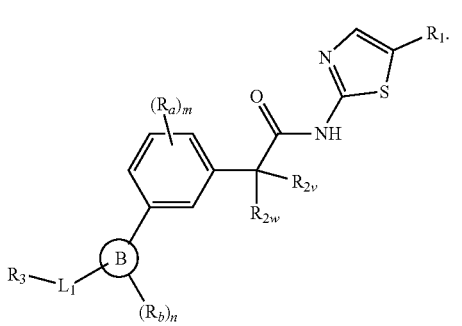

(Iai)

In a fourth representative embodiment, the compound of Chemical Formula (I) may be a compound of the following Chemical Formula (Iaii).

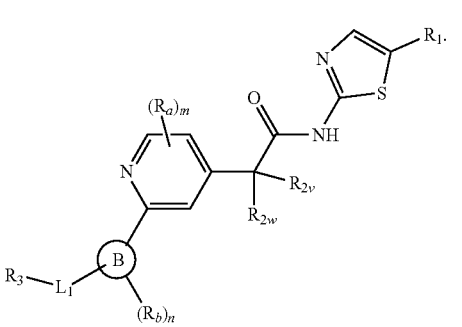

(Iaii)

In a fifth representative embodiment, the compound of Chemical Formula (I) may be a compound of the following Chemical Formula (Iaiii).

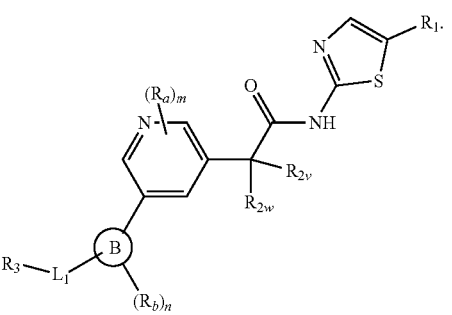

(Iaiii)

In a sixth representative embodiment, the compound of Chemical Formula (I) may be a compound of the following Chemical Formula (Ib).

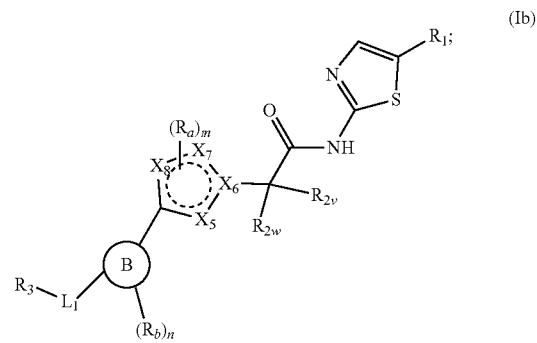

(Ib)

wherein $X_1$, $X_2$, $X_3$ and $X_4$ are each independently CH, O, S, or N.

In a seventh representative embodiment, the compound of Chemical Formula (I) may be a compound of the following Chemical Formula (Ibi).

(Ibi)

In an eighth representative embodiment, the compound of Chemical Formula (I) may be a compound of the following Chemical Formula (Thii).

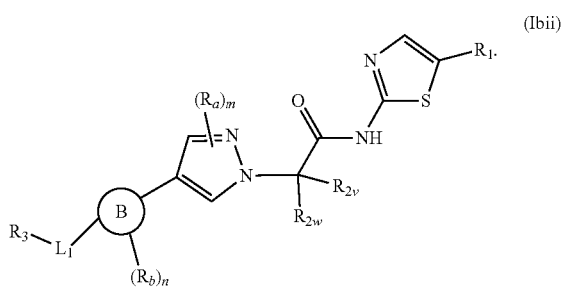

(Ibii)

In certain preferred embodiments, the ring B of formula (I), (Ia), (Iai), (Iaii), (Iaiii), (Ib), (Ibi), or (Ibii) is aryl or heteroaryl, such as phenyl, pyridinyl, pyrimidinyl, pyrazinyl, pyridazinyl, pyrazolyl, imidazolyl, thiazolyl, tetrahydropyridinyl, piperidinyl, or piperazinyl.

In a ninth representative embodiment, the compound of Chemical Formula (I) may be a compound of the following Chemical Formula (Ic).

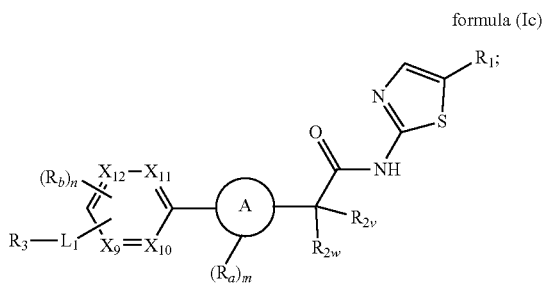

formula (Ic)

wherein $X_9$, $X_{10}$, $X_{11}$, and $X_{12}$ are each independently CH or N.

In a tenth representative embodiment, the compound of Chemical Formula (I) may be a compound of the following Chemical Formula (Ici).

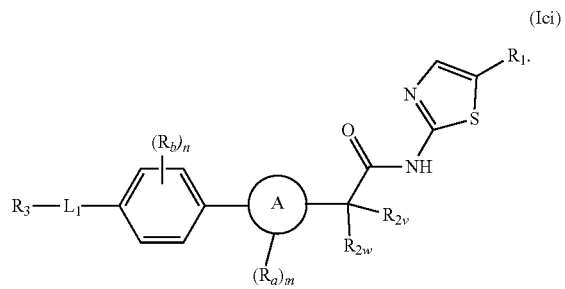

(Ici)

In an eleventh representative embodiment, the compound of Chemical Formula (I) may be a compound of the following Chemical Formula (Ibcii).

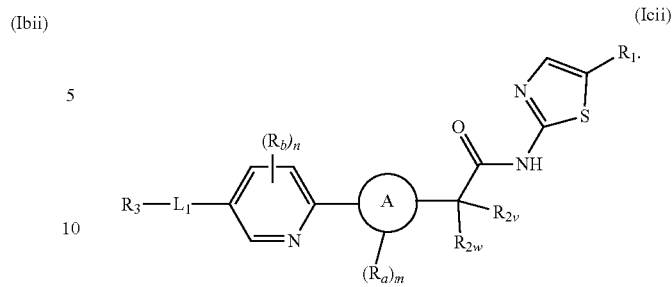

(Icii)

In a twelfth representative embodiment, the compound of Chemical Formula (I) may be a compound of the following Chemical Formula (Iciii).

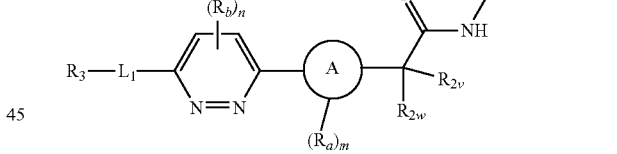

(Iciii)

In a thirteenth representative embodiment, the compound of Chemical Formula (I) may be a compound of the following Chemical Formula (Iciv).

(Iciv)

In a fourteenth representative embodiment, the compound of Chemical Formula (I) may be a compound of the following Chemical Formula (Icy).

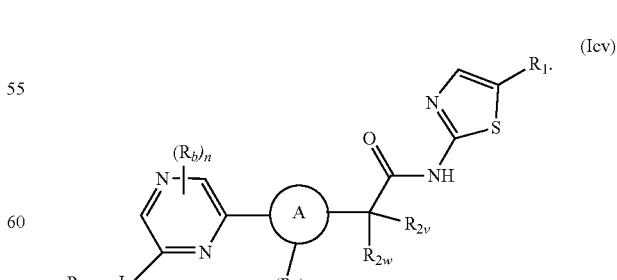

(Icv)

In a fifteenth representative embodiment, the compound of Chemical Formula (I) may be a compound of the following Chemical Formula (Icvi).

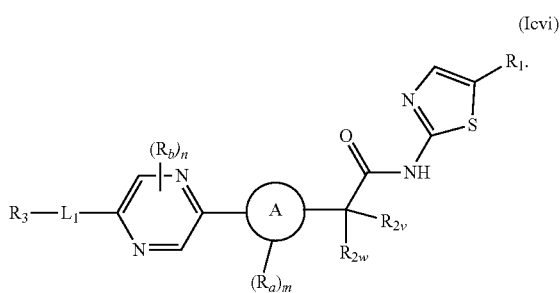

(Icvi)

In a sixteenth representative embodiment, the compound of Chemical Formula (I) may be a compound of the following Chemical Formula (Icvii).

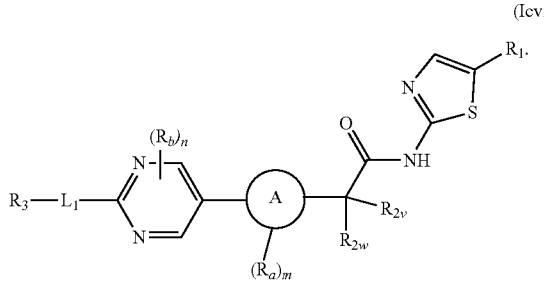

(Icvii)

In seventeenth representative embodiment, in formula (I), (Ia), (Iai), (Iaii), (Iaiii), (Ib), (Ibi), (Ibii), (Ici), (Icii), (Iciii) (Iciv), (Icv), (Icvi), or (Icvii) as defined in any of the representative embodiments above, $R_1$ is halo, alkyl, cycloalkyl, haloalkyl, cyano, —$SR_{c'}$—$C(O)R_{c'}$—$C(O)OR_{c'}$—$N(R_c)(R_d)$, —$OR_{c'}$ or —$C(R_g)_2$—$OR_c$; $R_c$ is independently H or alkyl.

In an eighteenth representative embodiment, in formula (I), (Ia), (Iai), (Iaii), (Iaiii), (Ib), (Ibi), (Ibii), (Ici), (Icii), (Iciii) (Iciv), (Icv), (Icvi), or (Icvii) as defined in any of the representative embodiments above, $R_{2V}$ and $R_{2w}$ are each independently H, halo, or alkyl.

In a nineteenth representative embodiment, in formula (I), (Ia), (Iai), (Iaii), (Iaiii), (Ib), (Ibi), (Ibii), (Ici), (Icii), (Iciii) (Iciv), (Icv), (Icvi), or (Icvii) as defined in any of the representative embodiments above, one of $R_{2V}$ and $R_{2w}$ is H and the other is alkyl or $R_{2V}$ and $R_{2w}$ taken together with the atom to which they are attached, form a C3-C7 cycloalkyl.

In a twentieth representative embodiment, in formula (I), (Ia), (Iai), (Iaii), (Iaiii), (Ib), (Ibi), (Ibii), (Ici), (Icii), (Iciii) (Iciv), (Icv), (Icvi), or (Icvii) as defined in any of the representative embodiments above, one of $R_{2V}$ and $R_{2w}$ is H and the other is methyl.

In a twenty-first representative embodiment, in formula (I), (Ia), (Iai), (Iaii), (Iaiii), (Ib), (Ibi), (Ibii), (Ici), (Icii), (Iciii) (Iciv), (Icv), (Icvi), or (Icvii) as defined in any of the representative embodiments above, $L_1$ is absent or —$N(R_e)$—.

In a twenty-second representative embodiment, in formula (I), (Ia), (Iai), (Iaii), (Iaiii), (Ib), (Ibi), or (Ibii) as defined in any of the representative embodiments above, the ring B is heterocycloayl and

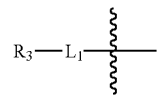

is attached to a nitrogen atom in the ring B heterocycloalkyl, then $L_1$ is absent.

In a twenty-third representative embodiment, in formula (I), (Ia), (Iai), (Iaii), (Iaiii), (Ib), (Ibi), (Ibii), (Ici), (Icii), (Iciii), (Iciv), (Icv), (Icvi), or (Icvii) as defined in any of the representative embodiments above, $L_1$ is —$N(R_e)$—.

In a twenty-fourth representative embodiment, in formula (I), (Ia), (Iai), (Iaii), (Iaiii), (Ib), (Ibi), (Ibii), (Ici), (Icii), (Iciii), (Iciv), (Icv), (Icvi), or (Icvii) as defined in any of the representative embodiments above, $R_e$ is H.

In a twenty-fifth representative embodiment, in formula (I), (Ia), (Iai), (Iaii), (Iaiii), (Ib), (Ibi), (Ibii), (Ici), (Icii), (Iciii), (Iciv), (Icv), (Icvi), or (Icvii) as defined in any of the representative embodiments above, $R_3$ is

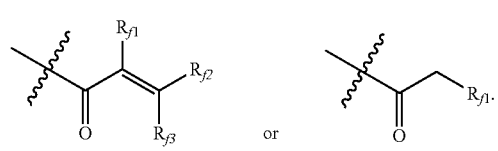

In a twenty-sixth representative embodiment, in formula (I), (Ia), (Iai), (Iaii), (Iaiii), (Tb), (Ibi), (Ibii), (Ici), (Icii), (Iciii), (Iciv), (Icv), (Icvi), or (Icvii) as defined in any of the representative embodiments above, $R_3$ is

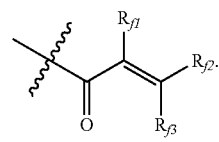

In a twenty-seventh representative embodiment, in formula (I), (Ia), (Iai), (Iaii), (Iaiii), (Ib), (Ibi), (Ibii), (Ici), (Icii), (Iciii), (Iciv), (Icv), (Icvi), or (Icvii) as defined in any of the representative embodiments above, $R_{f1}$ is H; and $R_{f2}$ and $R_{f3}$ are each independently H, alkyl, cycloalkyl, heterocycloalkyl, —$N(R_{c'})(R_{d'})$, or —$(C(R_{j'})_2)_q$—$N(R_{c'})(R_{d'})$.

In a twenty-eighth representative embodiment, in formula (I), (Ia), (Iai), (Iaii), (Iaiii), (Tb), (Ibi), (Ibii), (Ici), (Icii), (Iciii), (Iciv), (Icv), (Icvi), or (Icvii) as defined in any of the representative embodiments above, $R_{f3}$ is or

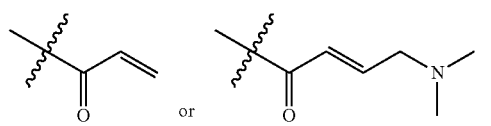

In a twenty-ninth representative embodiment, in formula (I), (Ia), (Iai), (Iaii), (Iaiii), (Tb), (Ibi), (Ibii), (Ici), (Icii), (Iciii), (Iciv), (Icv), (Icvi), or (Icvii) as defined in any of the representative embodiments above, $R_{d'}$ is H or halo.

In a thirtieth representative embodiment, in formula (I), (Ia), (Iai), (Iaii), (Iaiii), (Tb), (Ibi), (Ibii), (Ici), (Icii), (Iciii), (Iciv), (Icv), (Icvi), or (Icvii) as defined in any of the representative embodiments above, $R_b$ is H, halo, alkyl, or heterocycloalkyl.

A thirty-first representative embodiment contemplates a pharmaceutical composition comprising a compound as defined in any of the above embodiments.

A thirty-second representative embodiment contemplates a method of inhibiting CDK7, comprising administering a compound as defined in any of the first to thirtieth representative embodiments, or a pharmaceutical composition of the thirty-second representative embodiment.

A thirty-third representative embodiment contemplates a method of treating or preventing a disease in a subject, comprising administering a compound as defined in any of the first to thirtieth representative embodiments, or a pharmaceutical composition of the thirty-second representative embodiment. The disease may be any of the diseases discussed herein, and is preferably a disease associated with unwanted activity of CDK7.

In particularly preferred embodiments, the compound of Chemical Formula (I) is a compound represented by Formula (Id), or a pharmaceutically acceptable salt thereof.

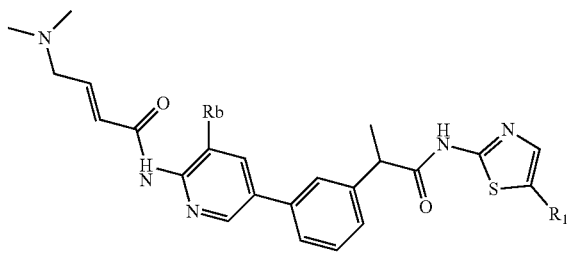

(Id)

wherein $R_1$ is C1-C3 alkyl, which is unsubstituted or substituted with halogen; and Rb is CN or halogen.

Representative compounds of Chemical Formulas (I)-(Icvii) include compounds selected from compounds 1) to 149), but are not limited thereto.

1) N-(5-(3-(1-((5-methylthiazol-2-yl)amino)-1-oxopropan-2-yl)phenyl)pyridin-2-yl)acrylamide;
2) N-(5-(3-(1-((5-cyclopropylthiazol-2-yl)amino)-1-oxopropan-2-yl)phenyl)pyridin-2-yl)acrylamide;
3) (R)-N-(5-(3-(1-((5-cyclopropylthiazol-2-yl)amino)-1-oxopropan-2-yl)phenyl)pyridin-2-yl)acrylamide;
4) N-(5-(3-(1-((5-ethylthiazol-2-yl)amino)-1-oxopropan-2-yl)phenyl)pyridin-2-yl)acrylamide;
5) (E)-4-(dimethylamino)-N-(5-(3-(1-((5-methylthiazol-2-yl)amino)-1-oxopropan-2-yl)phenyl)pyridin-2-yl)but-2-enamide;
6) (E)-N-(5-(3-(1-((5-cyclopropylthiazol-2-yl)amino)-1-oxopropan-2-yl)phenyl)pyridin-2-yl)-4-(dimethylamino)but-2-enamide;
7) (E)-4-(dimethylamino)-N-(5-(3-(1-((5-methylthiazol-2-yl)amino-1-oxopropan-2-yl)phenyl)pyridin-2-yl)but-2-enamide hydrochloride;
8) N-(3-fluoro-3'-(1-((5-methylthiazol-2-yl)amino-1-oxopropan-2-yl)-[1,1'-biphenyl]-4-yl)a crylamide;
9) 2-(3-(1-acryloylindolin-5-yl)phenyl)-N-(5-methylthiazol-2-yl)propanamide;
10) (E)-N-(5-(3-(1,1-difluoro-2-((5-methylthiazol-2-yl)amino)-2-oxoethyl)phenyl)pyridin-2-yl)-4-(dimethylamino)but-2-enamide;
11) N-(6-(3-(1-((5-cyanothiazol-2-yl)amino)-1-oxopropane-2-yl)-4-fluorophenyl)pyridazin-3-yl)acrylamide;
12) 2-(3-(6-acrylamidopyridazin-3-yl)phenyl)-N-(5-cyanothiazol-2-yl)-3-methylbutanamide;
13) N-(6-(5-(1-((5-cyanothiazol-2-yl)amino)-1-oxopropan-2-yl)-2-fluorophenyl)pyridazin-3-yl)acrylamide;
14) (S)-N-(5-(3-(1-(5-cyclopropylthiazol-2-yl)amino)-1-oxopropane-2-yl)phenyl)pyridin-2-yl)acrylamide;
15) (S,E)-N-(5-(3-(1-(5-cyclopropylthiazol-2-yl)amino)-1-oxopropan-2-yl)phenyl)pyridin-2-yl)-4-(dimethylamino)but-2-enamide;
16) (S)-N-(6-(3-(1-(5-cyclopropylthiazol-2-yl)amino)-1-oxopropan-2-yl)phenyl)pyrazin-2-yl)acrylamide;
17) (S,E)-4-(dimethylamino)-N-(5-(3-(1-((5-ethylthiazol-2-yl)amino)-1-oxopropan-2-yl)phenyl)pyridin-2-yl)but-2-enamide;
18) (S)-N-(5-(3-(1-((5-cyanothiazole-2-yl)amino)-1-oxopropan-2-yl)phenyl)pyridin-2-yl)a crylamide;
19) (S)-2-(3-(6-acrylamidopyridin-3-yl)phenyl)-N-(5-ethylthiazol-2-yl)butanamide;
20) (S)-2-(4'-acrylamido-3'-fluoro-[1,1'-biphenyl]-3-yl)-N-(5-ethylthiazol-2-yl)butanamide
21) (S,E)-N-(5-(3-(1-((5-cyanothiazol-2-yl)amino)-1-oxopropan-2-yl)phenyl)pyridin-2-yl)4-(dimethylamino)but-2-enamide;
22) (S)-N-(5-(3-(1-(5-cyclopropylthiazol-2-yl)amino)-1-oxopropan-2-yl)phenyl)pyrazin-2-yl)acrylamide;
23) (S)-N-(3'-(1-((5-cyclopropylthiazol-2-yl)amino)-1-oxopropan-2-yl)-[1,1'-biphenyl]-4-yl)acrylamide;
24) (S)-N-(3'-(1-((5-cyclopropylthiazol-2-yl)amino)-1-oxopropan-2-yl)-3-fluoro-[1,1'-biphenyl]-4-yl)acrylamide;
25) (S)-N-(5-(3-(1-((5-cyanothiazol-2-yl)amino)-1-oxopropan-2-yl)phenyl)pyrazin-2-yl)acrylamide;
26) (S)-N-(6-(3-(1-((5-cyanothiazol-2-yl)amino)-1-oxopropan-2-yl)phenyl)pyrazin-2-yl)acrylamide;
27) (S)-N-(5-(3-(1-(5-cyclopropylthiazol-2-yl)amino)-1-oxopropan-2-yl)phenyl)pyrimidin-2-yl)acrylamide;
28) (S)-N-(6-(3-(1-(5-cyclopropylthiazol-2-yl)amino)-1-oxopropan-2-yl)phenyl)pyridazin-3-yl)acrylamide;
29) (S)-N-(5-(3-(1-(5-cyclopropylthiazol-2-yl)amino)-1-oxopropan-2-yl)phenyl)-3-fluoropyridin-2-yl)acrylamide;
30) (S)-N-(3-cyano-3'-(1-((5-ethylthiazol-2-yl)amino)-1-oxopropan-2-yl)-[1,1'-biphenyl]-4-yl)acrylamide;
31) (S)-N-(5-(3-(1-((5-ethylthiazol-2-yl)amino)-1-oxopropan-2-yl)phenyl)-6-fluoropyridin-2-yl)acrylamide;
32) (S)-N-(6-(3-(1-((5-cyanothiazol-2-yl)amino)-1-oxopropan-2-yl)phenyl)pyridazin-3-yl) acrylamide;
33) (S)-N-(5-(3-(1-((5-cyanothiazol-2-yl)amino)-1-oxopropan-2-yl)phenyl)-3-fluoropyridin-2-yl)acrylamide;
34) (S)-N-(5-(3-(1-((5-cyanothiazol-2-yl)amino)-1-oxopropan-2-yl)phenyl)-3-methylpyrazin-2-yl)acrylamide;
35) (S)-N-(5-(3-(1-((5-isopropylthiazol-2-yl)amino)-1-oxopropan-2-yl)phenyl)pyridin-2-yl)acrylamide;
36) (S)-N-(5-(3-(1-((5-isopropylthiazol-2-yl)amino)-1-oxopropan-2-yl)phenyl)pyrazin-2-yl)acrylamide;
37) (S)-N-(5-(3-(1-oxo-1-((5-(trifluoromethyl)thiazol-2-yl)amino)propan-2-yl)phenyl)pyrazin-2-yl)acrylamide;
38) (S)-N-(5-(3-(1-oxo-1-((5-(trifluoromethyl)thiazol-2-yl)amino)propan-2-yl)phenyl)pyridin-2-yl)acrylamide;
39) (S)-N-(6-(3-(1-oxo-1-((5-(trifluoromethyl)thiazol-2-yl)amino)propan-2-yl)phenyl)pyridazin-3-yl)acrylamide;
40) (S)-N-(6-(3-(1-((5-isopropylthiazol-2-yl)amino)-1-oxopropan-2-yl)phenyl)pyridazin-3-yl)acrylamide;
41) N-(5'-(1-((5-cyanothiazol-2-yl)amino)-1-oxopropane-2-yl)-[3,3'-bipyridin]-6-yl)acrylamide;
42) N-(4-(1-((5-cyanothiazole-2-yl)amino)-1-oxopropan-2-yl)-[2,3'-bipyridine]-6'-yl)acrylamide;

43) N-(5-(5-(1-((5-cyclopropylthiazol-2-yl)amino)-1-oxopropan-2-yl)pyridin-3-yl)pyrazin-2-yl)acrylamide;
44) N-(5-(5-(1-((5-cyanothiazol-2-yl)amino)-1-oxopropan-2-yl)pyridin-3-yl)pyrazin-2-yl)acrylamide;
45) N-(5-(5-(1-oxo-1-((5-(trifluoromethyl)thiazol-2-yl)amino)propan-2-yl)pyridin-3-yl)pyrazin-2-yl)acrylamide;
46) N-(5-(5-(1-((5-ethylthiazol-2-yl)amino)-1-oxopropan-2-yl)pyridin-3-yl)pyrazin-2-yl)acryl amide;
47) N-(5-(5-(1-((5-isopropylthiazol-2-yl)amino)-1-oxopropan-2-yl)pyridin-3-yl)pyrazin-2-yl) acrylamide;
48) N-(5-(5-(1-((5-acetylthiazol-2-yl)amino)-1-oxopropan-2-yl)pyridin-3-yl)pyrazin-2-yl)acrylamide;
49) N-(6-(5-(1-oxo-1-((5-(trifluoromethyl)thiazol-2-yl)amino)propan-2-yl)pyridin-3-yl)pyridazin-3-yl)acrylamide;
50) N-(4-(1-((5-cyclopropylthiazol-2-yl)amino)-1-oxopropan-2-yl)-[2,3'-bipyridine]-6'-yl)acrylamide;
51) (R)-N-(5-(5-(1-oxo-1-((5-(trifluoromethyl)thiazol-2-yl)amino)propan-2-yl)pyridin-3-yl)pyrazin-2-yl)acrylamide;
52) (S)-N-(5-(5-(1-oxo-1-((5-(trifluoromethyl)thiazol-2-yl)amino)propan-2-yl)pyridin-3-yl)pyrazin-2-yl)acrylamide;
53) N-(5-(5-(1-oxo-1-((5-(trifluoromethyl)thiazol-2-yl)amino)propan-2-yl)thiophen-3-yl)pyridin-2-yl)acrylamide;
54) N-(5-(3-(1-((5-cyclopropylthiazol-2-yl)amino)-1-oxopropan-2-yl)-5-fluorophenyl)pyridin-2-yl)acrylamide;
55) N-(5-(5-(2-methyl-1-oxo-1-((5-(trifluoromethyl)thiazol-2-yl)amino)propan-2-yl)pyridin-3-yl)pyrazin-2-yl)acrylamide;
56) (S)-2-(3-(5-(2-cyanoacetamido)pyrazin-2-yl)phenyl)-N-(5-(trifluoromethyl)thiazol-2-yl)propanamide;
57) N-(5-(5-(1-oxo-1-((5-(trifluoromethyl)thiazol-2-yl)amino)propan-2-yl)thiophen-3-yl)pyrazin-2-yl)acrylamide;
58) (S)-2-(3-(5-(2-cyanoacetamido)pyrazin-2-yl)phenyl)-N-(5-cyanothiazol-2-yl)propanamide;
59) N-(5-(3-methyl-1-(1-oxo-1-((5-(trifluoromethyl)thiazol-2-yl)amino)propan-2-yl)-1H-pyrazol-4-yl)pyridin-2-yl)acrylamide;
60) 2-(1'-acryloyl-1',2',3',6'-tetrahydro-[3,4'-bipyridine]-5-yl)-N-(5-cyanothiazol-2-yl)propanamide;
61) N-(5-(5-(1-((5-chlorothiazol-2-yl)amino)-1-oxopropan-2-yl)pyridin-3-yl)pyrazine-2-yl)acrylamide;
62) (S)-N-(6-(3-(1-((5-cyclopropylthiazol-2-yl)amino)-1-oxopropan-2-yl)phenyl)pyridin-3-yl)acrylamide;
63) (E)-4-(dimethylamino)-N-(5-(5-(1-oxo-1-((5-(trifluoromethyl)thiazol-2-yl)amino)propan-2-yl)pyridin-3-yl)pyrazin-2-yl)but-2-enamide;
64) 2-(5-(5-(2-cyanoacetamido)pyrazin-2-yl)pyridin-3-yl)-N-(5-(trifluoromethyl)thiazol-2-yl)propanamide;
65) (E)-2-cyano-3-cyclopropyl-N-(5-(5-(1-oxo-1-((5-(trifluoromethyl)thiazol-2-yl)amino)propan-2-yl)pyridin-3-yl)pyrazin-2-yl)acrylamide;
66) N-(5-(5-(1-((5-methoxythiazol-2-yl)amino)-1-oxopropan-2-yl)pyridin-3-yl)pyrazin-2-yl)a crylamide;
67) N-(5-(5-(1-((5-fluorothiazol-2-yl)amino)-1-oxopropan-2-yl)pyridin-3-yl)pyrazin-2-yl)acrylamide;
68) N-(2-(4-methylpiperazin-1-yl)-4-(5-(1-oxo-1-((5-(trifluoromethyl)thiazol-2-yl)amino)propan-2-yl)pyridin-3-yl)phenyl)acrylamide;
69) (E)-2-cyano-3-(dimethylamino)-N-(5-(5-(1-oxo-1-((5-(trifluoromethyl)thiazol-2-yl)amino)propan-2-yl)pyridin-3-yl)pyrazin-2-yl)acrylamide;
70) N-(1-(5-(1-oxo-1-((5-(trifluoromethyl)thiazol-2-yl)amino)propan-2-yl)pyridin-3-yl)piperidin-4-yl)acrylamide;
71) N-(5-(5-(1-((5-(methylthio)thiazol-2-yl)amino)-1-oxopropan-2-yl)pyridin-3-yl)pyrazin-2-yl)acrylamide;
72) ethyl 2-(2-(5-(5-acrylamidopyrazin-2-yl)pyridin-3-yl)propanamido)thiazole-5-carboxylate;
73) (E)-N-(5-(5-(1-((5-chlorothiazol-2-yl)amino)-1-oxopropan-2-yl)pyridin-3-yl)pyrazin-2-yl)-4-(dimethylamino)but-2-enamide;
74) (E)-4-morpholino-N-(5-(5-(1-oxo-1-((5-(trifluoromethyl)thiazol-2-yl)amino)propan-2-yl)pyridin-3-yl)pyrazin-2-yl)but-2-enamide;
75) (E)-N-(5-(5-(1-oxo-1-((5-(trifluoromethyl)thiazol-2-yl)amino)propan-2-yl)pyridin-3-yl)pyrazin-2-yl)but-2-enamide;
76) N-(5-(5-(1-((5-chlorothiazol-2-yl)amino)-1-oxopropan-2-yl)thiophen-3-yl)pyridin-2-yl)acrylamide;
77) N-(5-(5-(1-((5-ethylthiazol-2-yl)amino)-1-oxopropan-2-yl)thiophen-3-yl)pyridin-2-yl)acrylamide;
78) N-(5-(5-(1-((5-acetylthiazol-2-yl)amino)-1-oxopropan-2-yl)thiophen-3-yl)pyridin-2-yl)acrylamide;
79) 2-(5-(5-propionamidopyrazin-2-yl)pyridin-3-yl)-N-(5-(trifluoromethyl)thiazol-2-yl)propanamide;
80) (E)-4-(5-methyl-2,5-diazabicyclo[2.2.1]heptan-2-yl)-N-(5-(5-(1-oxo-1-((5-(trifluoromethyl)thiazol-2-yl)amino)propan-2-yl)pyridin-3- yl)pyrazin-2-yl)but-2-enamide;
81) (S,E)-4-(dimethylamino)-N-(5-(3-(1-oxo-1-((5-(trifluoromethyl)thiazol-2-yl)amino)propan-2-yl)phenyl)pyrazin-2-yl)but-2-enamide;
82) N-(5'-(1-oxo-1-((5-(trifluoromethyl)thiazol-2-yl)amino)propan-2-yl)-[3,3'-bipyridin]-6-yl)acrylamide;
83) (E)-4-(2-oxa-5-azabicyclo[2.2.1]heptan-5-yl)-N-(5-(5-(1-oxo-1-((5-(trifluoromethyl)thiazol-2-yl)amino)propan-2-yl)pyridin-3- yl)pyrazin-2-yl)but-2-enamide;
84) N-(4-fluoro-5'-(1-oxo-1-((5-(trifluoromethyl)thiazol-2-yl)amino)propan-2-yl)-[3,3'-bipyridin]-6-yl)acrylamide;
85) 2-(5-(4-acryloylpiperazin-1-yl)pyridin-3-yl)-N-(5-(trifluoromethyl)thiazol-2-yl)propan amide;
86) 2-(5-(4-acryloylpiperazin-1-yl)pyridin-3-yl)-N-(5-ethylthiazol-2-yl)propanamide;
87) N-(6-(5-(1-((5-ethylthiazol-2-yl)amino)-1-oxopropan-2-yl)thiophen-3-yl)pyridin-3-yl)acrylamide;
88) N-(5-cyano-5'-(1-oxo-1-((5-(trifluoromethyl)thiazol-2-yl)amino)propan-2-yl)-[3,3'-bipyridin]-6-yl)acrylamide;
89) N((5'-(1-oxo-1-((5-(trifluoromethyl)thiazol-2-yl)amino)propan-2-yl)-[3,3'-bipyridin]-6-yl)methyl)acrylamide;
90) N-(5'-(1-oxo-1-((5-(trifluoromethyl)thiazol-2-yl)amino)propan-2-yl)-[2,3'-bipyridin]-5-yl)acrylamide;
91) (S,E)-4-(dimethylamino)-N-(5-(3-(1-oxo-1-((5-(trifluoromethyl)thiazol-2-yl)amino)propan-2-yl)phenyl)pyrazin-2-yl)but-2-enamide;
92) (S,E)-4-morpholino-N-(5-(3-(1-oxo-1-((5-(trifluoromethyl)thiazol-2-yl)amino)propan-2-yl)phenyl)pyrazin-2-yl)but-2-enamide;
93) (S,E)-N-(5-(3-(1-((5-chlorothiazol-2-yl)amino)-1-oxopropan-2-yl)phenyl)pyrazin-2-yl)-4-(dimethylamino)but-2-enamide;
94) (E)-4-(2-oxa-5-azabicyclo[2.2.1]heptan-5-yl)-N-(5-(3-((S)-1-((5-chlorothiazol-2-yl)amino)-1-oxopropan-2-yl)phenyl)pyrazin-2-yl)but-2-enamide;
95) (S,E)-4-(4-methylpiperazin-1-yl)-N-(5-(3-(1-oxo-1-((5-(trifluoromethyl)thiazol-2-yl)a mino)propan-2-yl)phenyl)pyrazin-2-yl)but-2-enamide;
96) (E)-4-(2-oxa-5-azabicyclo[2.2.1]heptan-5-yl)-N-(5-(3-((S)-1-oxo-1-((5-(trifluoromethyl)thiazol-2-yl)amino)propan-2-yl)phenyl)pyrazin-2-yl)but-2-enamide;

97) (S,E)-N-(5-(3-(1-((5-chlorothiazol-2-yl)amino)-1-oxopropan-2-yl)phenyl)pyrazin-2-yl)-4-(4-methylpiperazin-1-yl)but-2-enamide;
98) (S,E)-N-(5-(3-(1-((5-chlorothiazol-2-yl)amino)-1-oxopropan-2-yl)phenyl)pyrazin-2-yl)-4-morpholinobut-2-enamide;
99) (S,E)-4-(dimethylamino)-N-(3-fluoro-5-(3-(1-oxo-1-((5-(trifluoromethyl)thiazol-2-yl)amino)propan-2-yl)phenyl)pyridin-2-yl)but-2-enamide;
100) (S,E)-4-(dimethylamino)-N-(3-methoxy-5-(3-(1-oxo-1-((5-(trifluoromethyl)thiazol-2-yl)amino)propan-2-yl)phenyl)pyridin-2-yl)but-2-enamide;
101) (S,E)-N-(3-cyano-5-(3-(1-oxo-1-((5-(trifluoromethyl)thiazol-2-yl)amino)propan-2-yl)phenyl)pyridin-2-yl)-4-(dimethylamino)but-2-enamide;
102) (S,E)-N-(5-(3-(1-oxo-1-((5-(trifluoromethyl)thiazol-2-yl)amino)propan-2-yl)phenyl)pyrazin-2-yl)-4-(pyrrolidin-1-yl)but-2-enamide;
103) (S,E)-4-(azetidin-1-yl)-N-(5-(3-(1-oxo-1-((5-(trifluoromethyl)thiazol-2-yl)amino)propan-2-yl)phenyl)pyrazin-2-yl)but-2-enamide;
104) (S,E)-N-(5-(3-(1-((5-cyclobutylthiazol-2-yl)amino)-1-oxopropan-2-yl)phenyl)pyrazin-2-yl)-4-(dimethylamino)but-2-enamide;
105) (S,E)-4-(dimethylamino)-N-(5-(3-(1-((5-(2-hydroxypropan-2-yl)thiazol-2-yl)amino)-1-oxopropan-2-yl)phenyl)pyrazin-2-yl)but-2-enamide;
106) (S,E)-4-(dimethylamino)-N-(5-(3-(1-((5-(dimethylamino)thiazol-2-yl)amino)-1-oxopropan-2-yl)phenyl)pyrazin-2-yl)but-2-enamide;
107) (E)-4-(dimethylamino)-N-(5'-(1-oxo-1-((5-(trifluoromethyl)thiazol-2-yl)amino)propan-2-yl)-[3,3'-bipyridin]-6-yl)but-2-enamide;
108) (E)-N-(5-cyano-5'-(1-oxo-1-((5-(trifluoromethyl)thiazol-2-yl)amino)propan-2-yl)-[3,3'-bipyridin]-6-yl)-4-(dimethylamino)but-2-enamide;
109) (S,E)-4-(dimethylamino)-N-(3-methoxy-5-(3-(1-oxo-1-((5-(trifluoromethyl)thiazol-2-yl)amino)propan-2-yl)phenyl)pyrazin-2-yl)but-2-enamide;
110) (S,E)-2-(3-(1-(4-(dimethylamino)but-2-enoyl)-2,3-dihydro-1H-pyrrolo[2,3-b]pyridin-5-yl)phenyl)-N-(5-(trifluoromethyl)thiazol-2-yl)propanamide;
111) (S,E)-4-(dimethylamino)-N-(5-(3-(1-oxo-1-((5-(trifluoromethyl)thiazol-2-yl)amino)propan-2-yl)phenyl)-3-(trifluoromethyl)pyridin-2-yl)but-2-enamide;
112) (S,E)-4-(dimethylamino)-N-(3-methyl-5-(3-(1-oxo-1-((5-(trifluoromethyl)thiazol-2-yl)amino)propan-2-yl)phenyl)pyridin-2-yl)but-2-enamide;
113) (S,E)-N-(3-chloro-5-(3-(1-oxo-1-((5-(trifluoromethyl)thiazol-2-yl)amino)propan-2-yl)phenyl)pyridin-2-yl)-4-(dimethylamino)but-2-enamide;
114) (S,E)-4-(diethylamino)-N-(5-(3-(1-oxo-1-((5-(trifluoromethyl)thiazol-2-yl)amino)propan-2-yl)phenyl)pyrazin-2-yl)but-2-enamide;
115) (E)-4-((R)-3-fluoropyrrolidin-1-yl)-N-(5-(3-((S)-1-oxo-1-((5-(trifluoromethyl)thiazol-2-yl)amino)propan-2-yl)phenyl)pyrazin-2-yl)but-2- enamide;
116) (S,E)-4-(dimethylamino)-N-(5-(3-(1-oxo-1-((5-(trifluoromethyl)thiazol-2-yl)amino)propan-2-yl)phenyl)pyridin-2-yl)but-2-enamide;
117) (E)-4-((S)-3-fluoropyrrolidin-1-yl)-N-(5-(3-((S)-1-oxo-1-((5-(trifluoromethyl)thiazol-2-yl)amino)propan-2-yl)phenyl)pyrazin-2-yl)but-2-enamide;
118) (E)-4-((S)-2-(methoxymethyl)pyrrolidin-1-yl)-N-(5-(3-((S)-1-oxo-1-((5-(trifluoromethyl)thiazol-2-yl)amino)propan-2-yl)phenyl)pyrazin-2-yl)but-2-enamide;
119) (E)-4-(3-hydroxypyrrolidin-1-yl)-N-(5-(3-((S)-1-oxo-1-((5-(trifluoromethyl)thiazol-2-yl)amino)propan-2-yl)phenyl)pyrazin-2-yl)but-2-enamide;
120) (S,E)-N-(5-(3-(1-oxo-1-((5-(trifluoromethyl)thiazol-2-yl)amino)propan-2-yl)phenyl)pyrazin-2-yl)-4-(piperidin-1-yl)but-2-enamide;
121) (S,E)-N-(3-cyano-5-(3-(1-((5-ethylthiazol-2-yl)amino)-1-oxopropan-2-yl)phenyl)pyridin-2-yl)-4-(dimethylamino)but-2-enamide;
122) (S,E)-2-(3-(1-(4-(dimethylamino)but-2-enoyl)-2,3-dihydro-1H-pyrrolo[2,3-b]pyridin-5-yl)phenyl)-N-(5-ethylthiazol-2-yl)propanamide;
123) (E)-4-(2-oxa-5-azabicyclo[2.2.1]heptan-5-yl)-N-(3-cyano-5-(3-((S)-1-((5-ethylthiazol-2-yl)amino)-1-oxopropan-2-yl)phenyl)pyridin-2-yl)but-2-enamide;
124) (S)-N-(3-cyano-5-(3-(1-oxo-1-((5-(trifluoromethyl)thiazol-2-yl)amino)propan-2-yl)phenyl)pyridin-2-yl)acrylamide;
125) (S,E)-4-(dimethylamino)-N-(5-(3-(1-((5-ethylthiazol-2-yl)amino)-1-oxopropan-2-yl)phenyl)-3-methyl)pyridin-2-yl)but-2-enamide;
126) (S,E)-2-(3-(1-(4-(dimethylamino)but-2-enoyl)-2-methyl-1H-pyrrolo[2,3-b]pyridin-5-yl)phenyl)-N-(5-ethylthiazol-2-yl)propanamide;
127) (S,E)-2-(3-(1-(4-(dimethylamino)but-2-enoyl)-1H-pyrrolo[2,3-b]pyridin-5-yl)phenyl)N-(5-ethylthiazol-2-yl)propanamide;
128) (E)-1-(3-(5-cyano-6-(4-(dimethylamino)but-2-enamido)pyridin-3-yl)phenyl)-N-(5-ethylthiazol-2-yl)cyclopropane-1-carboxamide;
129) (S,E)-4-(dimethylamino)-N-(5-(3-(1-((5-ethylthiazol-2-yl)amino)-1-oxopropan-2-yl)phenyl)pyridin-2-yl)-N-methylbut-2-enamide;
130) (S,E)-4-(dimethylamino)-N-(5-(3-(1-((5-ethylthiazol-2-yl)amino)-1-oxopropan-2-yl)phenyl)-3-fluoropyridin-2-yl)but-2-enamide;
131) (E)-4-(dimethylamino)-N-(6-(3-(1-((5-ethylthiazol-2-yl)amino)-1-oxobutan-2-yl)phenyl)pyridin-3-yl)but-2-enamide;
132) (S,E)-N-(3-cyano-5-(3-(1-((5-ethylthiazol-2-yl)amino)-1-oxopropan-2-yl)phenyl)pyridin-2-yl)-4-(dimethylamino)-N-methylbut-2-enamide;
133) (E)-1-(3-(1-(4-(dimethylamino)but-2-enoyl)-2,3-dihydro-1H-pyrrolo[2,3-b]pyridin-5-yl)phenyl)-N-(5-ethylthiazol-2-yl)cyclopropane-1- carboxamide;
134) (E)-1-(3-(6-(4-(dimethylamino)but-2-enamido)-5-fluoropyridin-3-yl)phenyl)-N-(5-ethylthiazol-2-yl)cyclopropane-1-carboxamide;
135) (S,E)-N-(3-cyano-5-(3-(1-((5-ethylthiazol-2-yl)amino)-1-oxopropan-2-yl)phenyl)pyridin-2-yl)-4-morpholinobut-2-enamide;
136) (S,E)-N-(3-cyano-5-(3-(1-((5-ethylthiazol-2-yl)amino)-1-oxopropan-2-yl)phenyl)pyridin-2-yl)-4-(4-methylpiperazin-1-yl)but-2-enamide;
137) (E)-N-(5-cyano-5'-(1-((5-ethylthiazol-2-yl)amino)-1-oxopropan-2-yl)-[3,3'-bipyridin]-6-yl)-4-(dimethylamino)but-2-enamide;
138) (E)-N-(3-cyano-5-(3-(1-((5-ethylthiazol-2-yl)amino)-1-oxobutan-2-yl)phenyl)pyridin-2-yl)-4-(dimethylamino)but-2-enamide;
139) (S)-2-(3-(5-cyano-6-(2-cyanoacetamido)pyridin-3-yl)phenyl)-N-(5-ethylthiazol-2-yl)propanamide;
140) N-(5-(6-(1-((5-methylthiazol-2-yl)amino)-1-oxopropan-2-yl)pyridin-2-yl)pyridin-2-yl)acrylamide;
141) N-(2'-(1-((5-methylthiazol-2-yl)amino)-1-oxopropan-2-yl)-[3,4'-bipyridin]-6-yl)acrylamide;

142) N-(4-(3-(1-((5-methylthiazol-2-yl)amino)-1-oxopropan-2-yl)piperidin-1-yl)phenyl)acrylamide;
143) N-(5-(2-(1-((5-methylthiazol-2-yl)amino)-1-oxopropan-2-yl)thiazol-4-yl)pyridin-2-yl)acrylamide;
144) (S)-N-(3-cyclopropyl-5-(3-(1-((5-ethylthiazol-2-yl)amino)-1-oxopropan-2-yl)phenyl)pyridin-2-yl)acrylamide;
145) (S)-N-(3-((2-(dimethylamino)ethyl)(methyl)amino)-3'-(1-((5-ethylthiazol-2-yl)amino)1-oxopropan-2-yl)-[1,1'-biphenyl]-4-yl)acrylamide;
146) (S)-N-(5-ethylthiazol-2-yl)-2-(3-(6-(vinylsulfonamido)pyridin-3-yl)phenyl)propanamide;
147) (S)-N-(3-(3-(1-((5-ethylthiazol-2-yl)amino)-1-oxopropan-2-yl)phenyl)-1-methyl-1H-pyrazol-5-yl)acrylamide;
148) (S)-N-(4-(3-(1-((5-ethylthiazol-2-yl)amino)-1-oxopropan-2-yl)phenyl)-1H-imidazol-2-yl)acrylamide; and
149) (S)-N-(4-(3-(1-((5-ethylthiazol-2-yl)amino)-1-oxopropan-2-yl)phenyl)thiazol-2-yl)acrylamide.

Unless otherwise stated hereinafter, the compounds of the formulas above as active ingredients of therapeutic agents includes any pharmaceutically acceptable salt thereof, and all thereof must be construed as being included within the scope of the present invention. For the convenience of description, they may be simply abbreviated as compounds of the formulas above or compounds of the invention.

The compounds of the present invention may exist in the form of a salt, particularly a pharmaceutically acceptable salt. As the salt, salts commonly used in the art, such as acid addition salts formed by pharmaceutically acceptable free acids, can be used without limitation. The term "pharmaceutically acceptable salt" used herein refers to any organic or inorganic addition salt of the compounds of the invention, in which the adverse effect caused by the salt does not impair the beneficial effect of the compounds at a concentration exhibiting relatively non-toxic and non-harmful effective activity to a patient.

Organic acids and inorganic acids can be used as the free acids. The pharmaceutically acceptable salt includes acid addition salts formed by inorganic acids such as hydrochloric acid, sulfuric acid, nitric acid, phosphoric acid, hydrobromic acid, hydroiodic acid, etc.; organic carbonic acids such as tartaric acid, formic acid, citric acid, acetic acid, trichloroacetic acid, trifluoroacetic acid, gluconic acid, benzoic acid, lactic acid, mandelic acid, fumaric acid, maleic acid, salicylic acid, etc.; or sulfonic acids such as methanesulfonic acid, ethanesulfonic acid, benzenesulfonic acid, ptoluenesulfonic acid, etc. Examples of pharmaceutically acceptable carboxylic acid salts include metal salts or alkaline earth metal salts formed by lithium, sodium, potassium, calcium, magnesium, etc., amino acid salts such as lysine, arginine, guanidine, etc., organic salts such as dicyclohexylamine, N-methyl-D-glucamine, tris(hydroxymethyl)methylamine, diethanolamine, choline, triethylamine, etc. The compounds according to the present invention may also be converted into their salts by conventional methods.

In addition, the compounds of the present invention include not only pharmaceutically acceptable salts thereof, but also all possible optical isomers, without limitation. The stereoisomers of the compounds of the invention may be prepared using methods known in the art.

Further, the compounds of the present invention may be prepared either in a crystalline form or in a non-crystalline form. When the compounds are prepared in a crystalline form, they may be optionally hydrated or solvated. Hydrates of the compounds of the invention include stoichiometric hydrates (i.e., 1:1 ratio of compound molecule to water molecule), and non-stoichiometric hydrates (i.e., ratios of compound molecule to water molecule other than 1:1). Similarly, solvates of the compound of of the present invention includes both stoichiometric solvates and nonstoichiometric solvates.

Other terms have the same meaning as generally understood in the art to which the present invention pertains.

Methods of Treatment

The thiazole derivatives according to the invention, pharmaceutically acceptable salts, optical isomers, solvates or hydrates thereof inhibit activities of the cyclindependent kinase, preferably CDK7, thereby exhibiting prophylactic or therapeutic effects of proliferative disorders or diseases associated with these activities, and infectious diseases.

Accordingly, the present invention also relates to a pharmaceutical composition for preventing or treating disorder or disease associated with CDK activity, or infectious disease comprising a compound of the invention, or a pharmaceutically acceptable salt or optical isomer thereof as an active ingredient.

Further, the present invention relates to a method for preventing or treating disorder or disease associated with the CDK activity, or infectious diseases comprising a step of administering a compound of the invention, or a pharmaceutically acceptable salt or optical isomer thereof.

Furthermore, the present invention relates to a use of a compound of the invention, or a pharmaceutically acceptable salt or optical isomer thereof for preventing or treating disorder or disease related to CDK activity, or infectious disease. Specifically, the pharmaceutical composition of the present invention may prevent or treat disease or disorder related to CDK activity such as proliferative diseases or infectious diseases by inhibiting one or more cyclin dependent kinases. The proliferative disease means, for example, cancer, benign neoplasm, angiogenesis, inflammatory diseases, autoinflammatory diseases or autoimmune diseases, and the infectious disease means, for example, bacterial diseases or viral diseases. The proliferative disorders to be treated or prevented using the thiazole derivative compounds according to the present invention may be typically be associated with the aberrant activity of CDK7. Aberrant activity of CDK7 may be an elevated and/or an inappropriate (e.g., aberrant) activity of the CDK7.

A proliferative disease may also be associated with inhibition of apoptosis of a cell in a biological sample or subject. Inhibition of CDK7 activity is expected to result in cytotoxicity through induction of apoptosis. Compounds of the invention, and pharmaceutically acceptable salts and/or optical isomers thereof according to the present invention may induce apoptosis, and therefore, be useful in treating and/or preventing proliferative diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone Bcell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemial-lymphoma as described above); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma also known as Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) also known as myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, agerelated macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, beryl)iosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behcet's disease.

The novel thiazole derivatives according to the present invention have remarkable inhibitory activity against CDK in comparison with the compounds known in the art. Specifically, the compounds of the present invention have not only highly selective inhibitory activity against CDK7 compared with any known compounds in the art, but also have reduced side effects and toxicity, which results in exerting remarkable prophylactic or therapeutic effects on proliferative diseases or infectious diseases associated with CDK7.

In some embodiments, the compounds of the present invention are at least 2 times more selective for CDK7 than other types of CDKs, especially CDK2 or CDK5. For example, the compounds may be at least 2 times, at least 3 times at least 5 times, or even at least 10 times more selective for CDK7 than other types of CDKs, such as CDK2 or CDK5. In some embodiments, the compounds of the present invention may be at least 100 times more selective for CDK7 than other types of CDKs, especially CDK2 or CDK5.

Similarly, the CDK7-inhibitory activity (quantified as $IC_{50}$) of the compounds of the present invention is less than 1000 nM. In some embodiments, the CDK7-inhibitory activity ($IC_{50}$) of the compounds of present invention is less than 500 nM. In preferred embodiments, the CDK7-inhibitory activity ($IC_{50}$) of the compounds of present invention is less than 100 nM.

General Synthesis Method of Thiazole Derivative Compound

The thiazole derivative compounds according to the present invention can be prepared from readily available starting materials using modifications to the specific synthesis protocols set forth below that would be well known to those of skill in the art.

As a specific embodiment, intermediates 1-b and 1-c of the compound of the present invention may be prepared according to Scheme 1 below.

[Scheme 1]

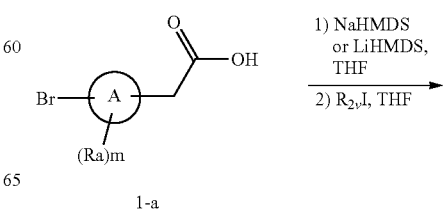

1-a

-continued

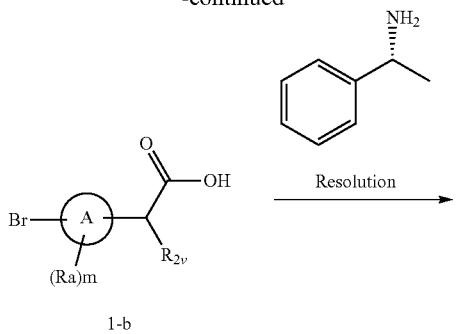

1-b

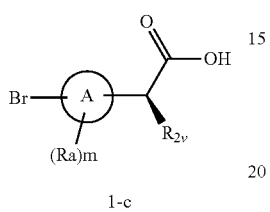

1-c wherein ring A, $R_{2v}$, $R_a$ and m are as defined above.

Compound 1-a is dissolved in a solvent, e.g., THF, and reacted with in an appropriate amount of a base, e.g., NaHMDS or LiHMDS, followed by adding halogenated alkyl ($R_{2v}$-I) to obtain compound 1-b substituted with different alkyl groups. Compound 1-c in (S)-form is then separated from compound 1-b in racemic acid form. Specifically, compound 1-b is dissolved in a suitable solvent, e.g., ACN, adding a base in (R)-form that is able to form a salt with an acid compound, e.g., (R)-1-phenylethan-1-amine, precipitating a salt, and filtering. The recrystallization with ACN is repeated twice, extracted under acid conditions, and dried, to obtain intermediate Compound 1-c in (S)-form.

As a specific embodiment, intermediate 2-b of the compound of the present invention may be prepared according to Scheme 2-1 below.

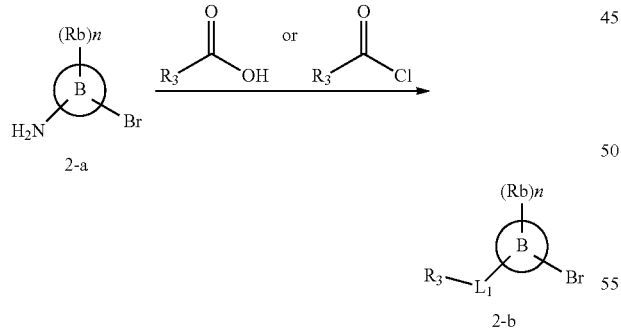

wherein ring B, $R_3$, $R_b$, L, and n are as defined above.

Compound 2-a is reacted with an acid chloride or carboxylic acid, which is commercially available, under appropriate reaction condition (e.g., $SOCl_2$ or $(COCl)_2$, DMF (catalytic amount), room temperature), and then under suitable base condition (e.g., triethylamine, diisopropylamine, pyridine, etc.), to obtain Compound 2-b. Otherwise, Compound 2-a is reacted with carboxylic acid in the presence of an appropriate coupling agent comprising, for example, HATU, HBTU, TBTU, EDC/HOBt, or $T_3P$, under suitable base condition (e.g., pyridine, triethylamine, diisopropylethylamine, etc.), to obtain Compound 2-b.

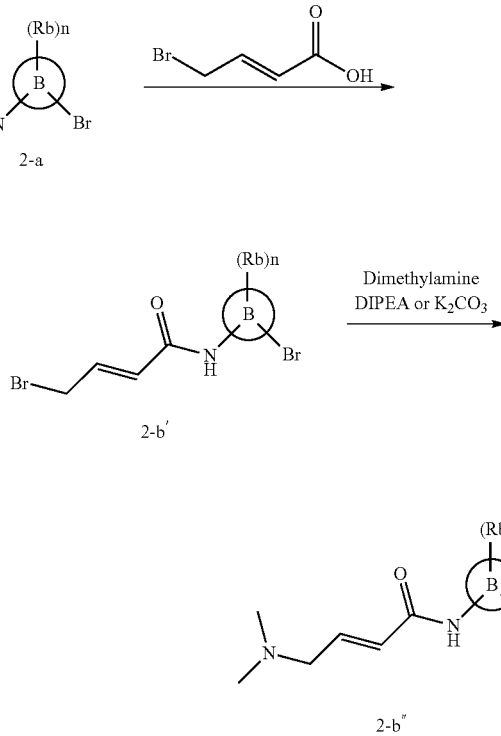

In the scheme, Compound 2-b' is obtained under the condition of Scheme 2-1, and reacted with dimethylamine under suitable solvent (e.g., ACN or THF) and base condition ($K_2CO_3$ or DPIEA) at an appropriate temperature, to obtain compound 2-b".

The compound of the present invention may be prepared according to Scheme 3 below.

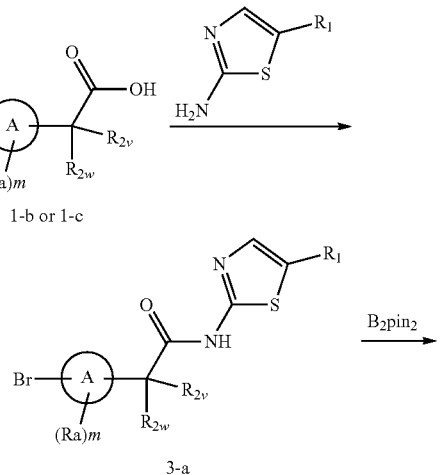

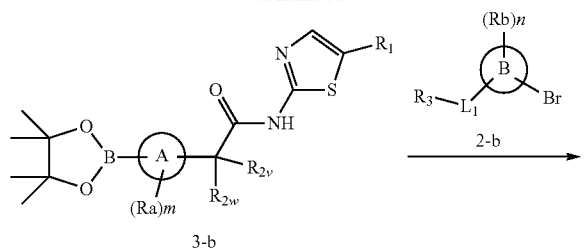

3-c

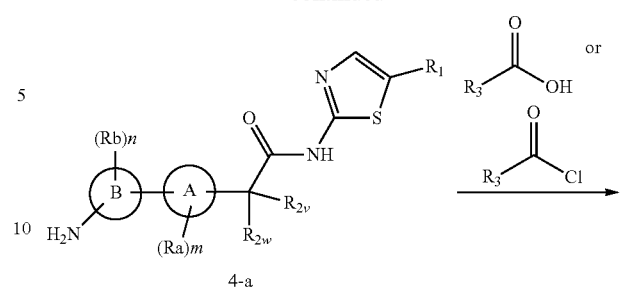

4-b wherein ring A, ring B, $R_1$, $R_{2v}$, $R_{2w}$, $R_3$, $R_a$, $R_b$, $L_1$, m and n are as defined above.

Intermediate 1-b or 1-c, which is commercially available or synthesized, is reacted with an acid chloride under appropriate reaction condition (e.g., $SOCl_2$ or $(COCl)_2$, DMF (catalytic amount), room temperature) and then under suitable base condition (e.g., pyridine, triethylamine, diisopropylethylamine, etc.) to obtain compound 3-a. Otherwise, intermediate 1-b or 1-c is reacted in the presence of an appropriate coupling agent to obtain compound 3-a. The coupling agent may comprise HATU, HBTU, TBTU, EDC/HOBt, or $T_3P$, where the reaction may be conducted under suitable base condition. The base may comprise pyridine, triethylamine, diisopropylethylamine, etc. Intermediate 3-b is synthesized by using Miyaura reaction in the presence of a catalyst such as pd(dppf)$Cl_2$.DCM, a base such as $Na_2CO_3$, and in a solvent such as 1,4-dioxane. The desired compound 3-c can be synthesized under Suzuki condition in the presence of a catalyst such as pd(dppf)$Cl_2$.DCM or Pd(PPh$_3$)$_4$, a base such as $Na_2CO_3$, $NaHCO_3$ or $Cs_2CO_3$, and a solvent such as 1,4-dioxane/water.

The compound of the present invention may be prepared according to Scheme 4 below.

[Scheme 4]

wherein ring A, ring B, $R_1$, $R_{2v}$, $R_{2w}$, $R_3$, $R_a$, $R_b$, $L_1$, m and n are as defined above.

Compound 4-a is synthesized from compound 3-b in the presence of a catalyst such as pd(dppf)$Cl_2$.DCM or Pd(PPh$_3$)$_4$, a base such as $Na_2CO_3$ or $Cs_2CO_3$, and a solvent such as 1,4-dioxane/water, and then the desired compound 4-b can be synthesized under the condition of Scheme 2.

The compound of the present invention may be prepared according to Scheme 5 below.

[Scheme 5]

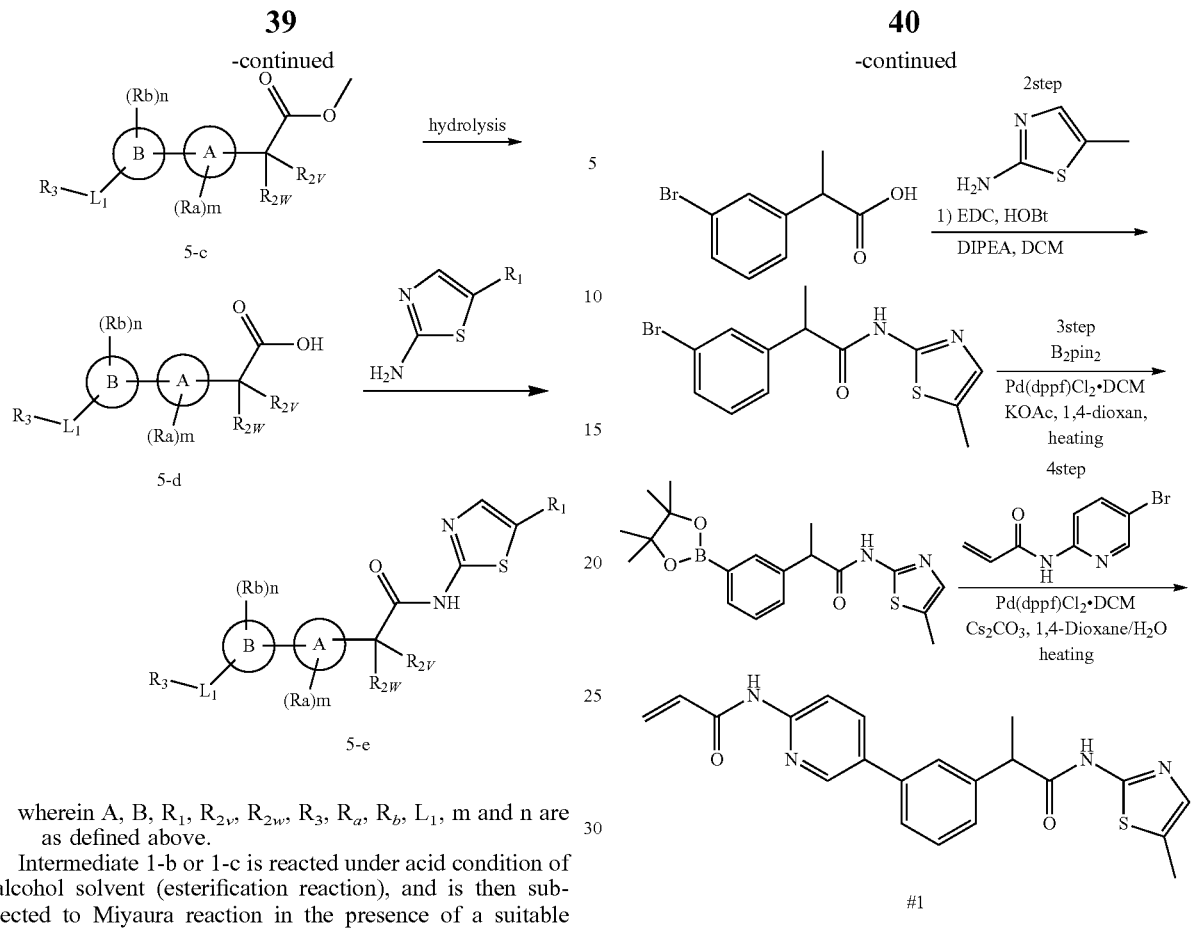

wherein A, B, $R_1$, $R_{2V}$, $R_{2W}$, $R_3$, $R_a$, $R_b$, $L_1$, m and n are as defined above.

Intermediate 1-b or 1-c is reacted under acid condition of alcohol solvent (esterification reaction), and is then subjected to Miyaura reaction in the presence of a suitable catalyst such as pd(dppf)Cl$_2$.DCM, a base such as Na$_2$CO$_3$, and a solvent such as 1,4-dioxane to obtain intermediate 5-b. Compound 5-c is then synthesized by using Suzuki reaction in a catalyst such as pd(dppf)Cl$_2$.DCM or Pd(PPh$_3$)$_4$, a base such as Na$_2$CO$_3$ or Cs$_2$CO$_3$, and a solvent such as 1,4-dioxane/water. The hydrolysis is then conducted with a base such as LiGH or NaOH to obtain Compound 5-d, followed by using an appropriate coupling agent to obtain Compound 5-e. The coupling agent may comprise HATU, HBTU, TBTU, EDC/HOBt, or T$_3$P, where the reaction may be conducted under suitable base condition (e.g., pyridine, triethylamine, diisopropylethylamine, etc.).

EXAMPLES

The present invention will be described in detail with reference to the following Examples and Experimental Examples, but the scope of the present invention is not limited thereby. In the examples, the contents of methods for synthesizing intermediates for making final compounds and methods for synthesizing final compounds using the compounds of the examples are described.

Example 1. Synthesis of N-(5-(3-(1-((5-methylthiazol-2-yl)amino)-1-oxopropan-2-yl)phenyl)pyridin-2-yl)acryl amide

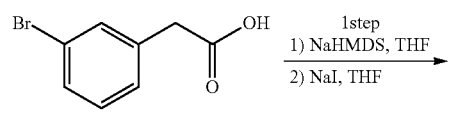

Step 1) Preparation of 2-(3-bromophenyl)propanoic acid 2-(3-bromophenyl) acetic acid (21 g, 97.56 mmol) was dissolved in THF (200 ml, 0.5 M) and then 1 M NaHMDS (200 ml, 200 mmol) was added dropwise at 0° C. After stirring for 30 minutes, MeI (6.07 ml, 97.56 mmol) was added, followed by stirring at room temperature for 2 hours. The mixture was diluted with EtOAc, washed with 1N HCl, and then the organic layer was dried (MgSO$_4$), filtered and dried under reduced pressure. The residue was purified by using a Combi-flash column (100% gradient in EA/Hex 10) to give the title compound (19.6 g, 92%).

Step 2) Preparation of 2-(3-bromophenyl)-N-(5-methylthiazol-2-yl)propanamide

To 2-(3-bromophenyl)propanoic acid (2 g, 8.73 mmol), HOBt (1.77 g, 13.1 mmol), DIPEA (4.6 ml, 26.2 mmol) and EDCI (2.5 g, 13.1 mmol) were added DCM (50 ml, 0.2M). The mixture was stirred at room temperature for 30 minutes, then 5-methylthiazol-2-amine (1 g, 8.73 mmol) was added thereto and stirred at room temperature for 15 hours. This mixture was diluted with EtOAc, washed with 1N HCl, washed with saturated NaHCO$_3$ solution, then dried (MgSO$_4$), filtered and then dried under reduced pressure. The residue was purified by a Combi-flash column (EA/Hex 10 to 100% gradient) to give the title compound (2.27 g, 80%) as a white solid.

¹H NMR (400 MHz, CDCl3) δ 7.46 (s, 1H), 7.40 (d, J=5.7 Hz, 1H), 7.23-7.17 (m, 2H), 7.03 (m, 1H), 3.75 (q, J=5.1 Hz, 1H), 2.41 (s, 3H), 1.60 (d, J=5.1 Hz, 3H); MS (m/z): 326.0 [M+1]

Step 3) Preparation of N-(5-methylthiazol-2-yl)-2-(3-(4,4,5,5-tetramethyl-1,3,2-dioxaborolan-2-yl)phenyl)propanamide To 2-(3-bromophenyl)-N-(5-methylthiazol-2-yl)propanamide (1.0 g, 3.07 mmol) and KOAc (904 mg, 9.21 mmol) were added anhydrous 1,4-dioxane (15 ml, 0.2 M), and the reaction mixture was stirred and degassed. Bis(pinacolato)diboron (0.94 g, 3.69 mmol) and Pd (dppf)Cl₂.DCM (253 mg, 0.31 mmol) were added and stirred at 85° C. for 15 hours. This mixture was diluted with EtOAc, washed with water, then dried (MgSO 4), filtered and then dried under reduced pressure. The residue was purified by a Combi-flash column (EA/Hex 20 to 100% gradient) to give the title compound (704 mg, 62%) as a white solid.

¹H NMR (400 MHz, CDCl3) δ 9.80 (s, 1H), 7.78-7.71 (2H), 7.43 (d, J=6.0 Hz, 1H), 7.36 (t, J=5.7 Hz, 1H), 7.02 (s, 1H), 3.81 (q, J=5.1 Hz, 1H), 2.39 (s, 3H), 1.62 (d, J=5.4 Hz, 3H), 1.34 (s, 12H); MS (m/z): 373.0 [M+1]

Step 4) Preparation of N-(5-(3-(1-((5-methylthiazol-2-yl)amino)-1-oxopropan-2-yl)phenyl)pyridin-2-yl)acryl amide To N-(5-methylthiazol-2-yl)-2-(3-(4,4,5,5-tetramethyl-1,3,2-dioxaborolan-2-yl)phenyl)propa namide (372 mg, 1 mmol), N-(5-bromopyridin-2-yl)acrylamide (227 mg, 1 mmol) and Cs₂CO₃ (815 mg, 2.5 mmol) were added H₂O (4 ml) and 1,4-dioxane (15 ml), and the reaction mixture was stirred and degassed. Then, Pd(dppf)Cl₂.DCM(253 mg, 0.31 mmol) was added thereto and stirred at 100° C. for 4 hours. This mixture was diluted with EtOAc, washed with water, further washed with brine, then dried (MgSO₄), filtered and then dried under reduced pressure. The residue was purified by a Combiflash column (EA/Hex 50 to 100% gradient) to give the title compound (118 mg, 30%) as a white solid.

¹H NMR (400 MHz, CDCl3) δ 10.96 (s, 1H), 9.36 (s, 1H), 8.34 (d, J=6.6 Hz, 1H), 8.19 (s, 1H), 7.82 (d, J=6.6 Hz, 1H), 7.39-7.37 (m, 3H), 7.30-7.29 (m, 1H), 7.06 (s, 1H), 6.50 (d, J=13.2 Hz, 1H), 6.29 (dd, J=12.9, 7.5 Hz, 1H), 5.81 (d, J=7.5 Hz, 1H), 3.90-3.86 (m, 1H), 2.40 (s, 3H), 1.64 (d, J=5.4 Hz, 3H); MS (m/z): 393.0 [M+1]

Example 2. Synthesis of N-5-(3-(1-((5-cyclopropylthiazol-2-yl)amino)-1-oxopropan-2-yl)phenyl)pyridin-2-yl)acrylamide

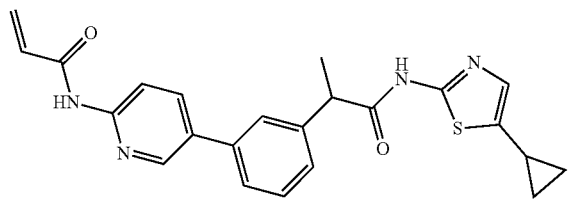 [SMILES: C=CC(=O)Nc1ccc(-c2cccc(C(C)C(=O)Nc3ncc(C4CC4)s3)c2)cn1]

The title compound was prepared in the same manner as in Example 1, except for using 5-cyclopropylthiazol-2-amine instead of 5-methylthiazol-2-amine.

1H NMR (400 MHz, CDCl3) δ 9.45 (s, 1H), 8.57 (s, 1H), 8.37-8.34 (m, 2H), 7.87 (dd, J=8.8, 2.4 Hz, 1H), 7.45-7.44 (m, 3H), 7.33-7.32 (m, 1H), 7.04 (s, 1H), 6.50 (d, J=16.8 Hz, 1H), 6.29 (dd, J=16.8, 10.0 Hz, 1H), 5.84 (d, J=10.0 Hz, 1H), 3.88-3.83 (m, 1H), 1.98-1.94 (m, 1H), 1.65 (d, J=7.2 Hz, 3H), 0.99-0.95 (m, 2H), 0.72-0.69 (m, 2H); MS (m/z): 419.0 [M+1]

Example 3. Separation of (R)-N-(5-(3-(1-((5-cyclopropylthiazol-2-yl)amino)-1-oxopropan-2-yl)phenyl)pyridi n-2-yl)acrylamide

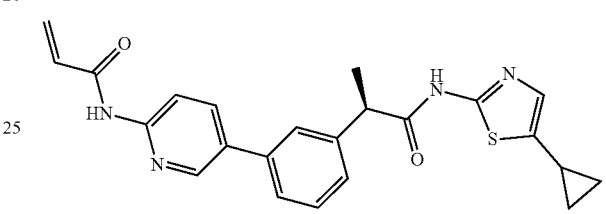

Only R-form was separated from the compound of Example 2 using a chiral column.

1H NMR (400 MHz, CDCl₃) δ 9.63 (s, 1H), 8.73 (s, 1H), 8.36 (d, J=8.8 Hz, 1H), 8.31 (s, 1H), 7.87 (dd, J=8.4, 2.4 Hz, 1H), 7.45-7.43 (m, 3H), 7.33-7.31 (m, 1H), 7.05 (s, 1H), 6.50 (d, J=16.8 Hz, 1H), 6.29 (dd, J=16.8, 10.4 Hz, 1H), 5.84 (d, J=10.4 Hz, 1H), 3.88-3.86 (m, 1H), 1.98-1.94 (m, 1H), 1.66 (d, J=7.2 Hz, 3H), 0.99-0.96 (m, 2H), 0.71-0.69 (m, 2H); MS (m/z): 419.0 [M+1]

Example 4. Synthesis of N-(5-(3-(1-((5-ethylthiazol-2-yl)amino)-1-oxopropan-2-yl)phenyl)pyridin-2-yl)acrylamide

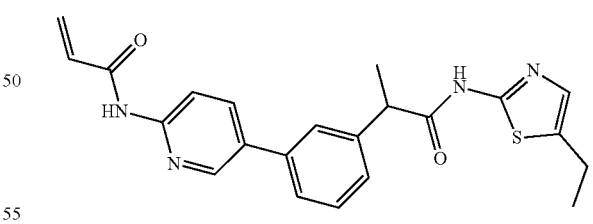

The title compound was prepared in the same manner as in Example 1, except for using 5-ethylthiazol-2-amine instead of 5-methylthiazol-2-amine.

1H NMR (400 MHz, CDCl₃) δ 10.12 (s, 1H), 8.93 (s, 1H), 8.36 (d, J=8.8 Hz, 1H), 8.28 (s, 1H), 7.86 (dd, J=8.4, 2.4 Hz, 1H), 7.43-7.41 (m, 3H), 7.33-7.31 (m, 1H), 7.06 (s, 1H), 6.50 (d, J=16.8 Hz, 1H), 6.29 (dd, J=16.8, 10.4 Hz, 1H), 5.83 (d, J=10.0 Hz, 1H), 3.88 (q, J=7.2 Hz, 1H), 2.78 (q, J=6.8 Hz, 2H), 1.65 (d, J=7.2 Hz, 3H), 1.29 (t, J=7.6 Hz, 3H); MS (m/z): 407.2 [M+1]

Example 5. Synthesis of (E)-4-(dimethylamino)-N-(5-(3-(1-((5-methylthiazol-2-yl)amino)-1-oxopropan-2-yl)phenyl)pyridin-2-yl)but-2-enamide

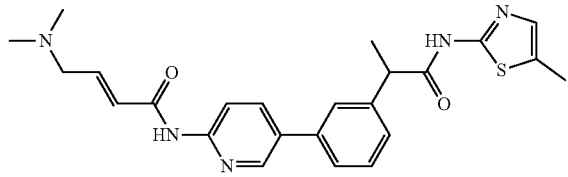

The title compound was prepared in the same manner as in Example 1, except for using (E)-N-(5-bromopyridin-2-yl)-4-(dimethylamino)but-2-enamide instead of acryloyl chloride (see International Patent Publication No. WO 2015/154038).

1H NMR (400 MHz, CDCl3) δ 9.56 (s, 1H), 8.51 (s, 1H), 8.37-8.34 (m, 2H), 7.87 (dd, J=8.8, 2.4 Hz, 1H), 7.46-7.43 (m, 3H), 7.33-7.32 (m, 1H), 7.07-6.99 (m, 2H), 6.17 (d, J=15.6 Hz, 1H), 3.87-3.86 (m, 1H), 3.16 (d, J=5.6 Hz, 2H), 2.39 (s, 3H), 2.31 (s, 6H), 1.64 (d, J=7.2 Hz, 3H); MS (m/z): 450.5[M+1]

Example 6. Synthesis of (E)-N-(5-(3-(1-((5-cyclopropylthiazol-2-yl)amino)-1-oxopropan-2-yl)phenyl)pyridin-2-yl)-4-(dimethylamino)but-2-enamide

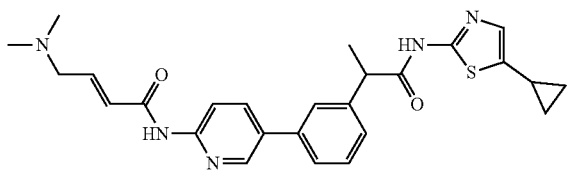 [SMILES: CC(C(=O)Nc1ncc(C2CC2)s1)c1cccc(-c2ccc(NC(=O)/C=C/CN(C)C)nc2)c1]

The title compound was prepared in the same manner as in Example 1, except for using 5-cyclopropylthiazole-2-amine instead of 5-methylthiazol-2-amine, and using (E)-N-(5-bromopyridin-2-yl)-4-(dimethylamino)but-2-enamide instead of acryloyl chloride.

1H NMR (400 MHz, CDCl3) δ 9.88 (s, 1H), 8.69 (s, 1H), 8.36-8.32 (m, 2H), 7.86 (dd, J=8.4, 2.4 Hz, 1H), 7.43-7.42 (m, 3H), 7.32-7.26 (m, 1H), 7.06-7.00 (m, 2H), 6.15 (d, J=15.6 Hz, 1H), 3.89-3.84 (m, 1H), 3.13 (d, J=6.0 Hz, 2H), 2.29 (s, 6H), 1.99-1.92 (m, 1H), 1.65 (d, J=7.2 Hz, 3H), 0.99-0.96 (m, 2H), 0.71-0.67 (m, 2H); MS (m/z): 476.0 [M+1]

Example 7. Synthesis of (E)-4-(dimethylamino)-N-(5-(3-(1-((5-methylthiazol-2-yl)amino)-1-oxopropan-2-yl)phenyl)pyridin-2-yl)but-2-enamide salt

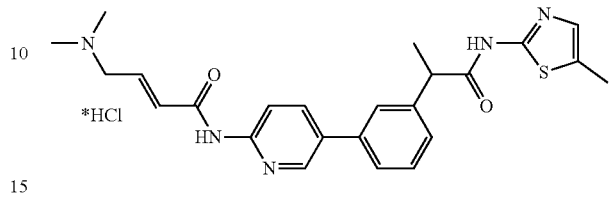

After the compound of Example 5 (30 mg, 0.06 mmol) was dissolved in DCM (1 ml), cHCl (2.5 uL) was added thereto at 0° C. and stirred for 5 minutes. The precipitated solid is filtered and washed with MC/Hex.

1H NMR (400 MHz, CDCl3) δ 9.45 (s, 1H), 8.57 (s, 1H), 8.37-8.34 (m, 2H), 7.87 (dd, J=8.8, 2.4 Hz, 1H), 7.45-7.44 (m, 3H), 7.33-7.32 (m, 1H), 7.04 (s, 1H), 6.50 (d, J=16.8 Hz, 1H), 6.29 (dd, J=16.8, 10.0 Hz, 1H), 5.84 (d, J=10.0 Hz, 1H), 3.88-3.83 (m, 1H), 1.98-1.94 (m, 1H), 1.65 (d, J=7.2 Hz, 3H), 0.99-0.95 (m, 2H), 0.72-0.69 (m, 2H); MS (m/z): 450.5 [M+1]

Example 8. Synthesis of N-(3-fluoro-3'-(1-((5-methylthiazol-2-yl)amino-1-oxopropan-2-yl)-[11'-biphenyl]-4-yl)acrylamide

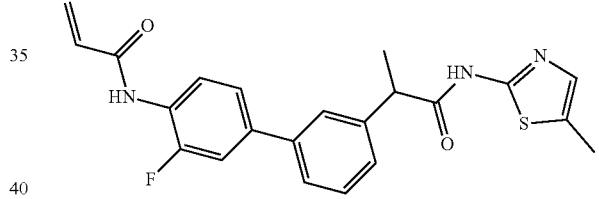

The title compound was prepared in the same manner as in Example 1, except for using N-(4-bromo-2-fluorophenyl)acrylamide instead of N-(5-bromopyridin-2-yl)acrylamide.

1H NMR (400 MHz, DMSO-d6) δ 12.12 (s, 1H), 10.05 (s, 1H), 8.14 (t, J=8.4 Hz, 1H), 7.70 (s, 1H), 7.61-7.57 (m, 2H), 7.49 (d, J=7.6 Hz, 1H), 7.42 (t, J=7.6 Hz, 1H), 7.35 (d, J=7.6 Hz, 1H), 7.10 (s, 1H), 6.65 (dd, J=17.0, 10.4 Hz, 1H), 6.30 (d, J=16.8 Hz, 1H), 5.79 (d, J=10.0 Hz, 1H), 4.02-4.00 (m, 1H), 2.31 (s, 3H), 1.49 (d, J=6.8 Hz, 3H); MS (m/z): 410.0 [M+1]

Example 9. Synthesis of 2-(3-(1-acryloylindolin-5-yl)phenyl)-N-(5-methylthiazol-2-yl)propanamide

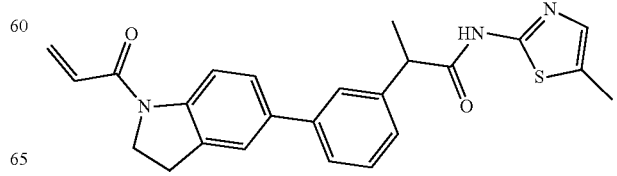

The title compound was prepared in the same manner as in Example 1, except for using 1-(5-bromoindolan-1-yl)prop-2-en-1-one instead of N-(5-bromopyridin-2-yl)acrylamide.

¹H NMR (400 MHz, DMSO-d6) δ 12.08 (s, 1H), 8.22 (d, J=7.6 Hz, 1H), 7.65 (s, 1H), 7.54-7.47 (m, 3H), 7.39 (t, J=7.6 Hz, 1H), 7.30 (d, J=7.6 Hz, 1H), 7.09 (s, 1H), 6.77 (dd, J=16.4, 10.4 Hz, 1H), 6.32 (d, J=16.4 Hz, 1H), 5.84 (d, J=10.4 Hz, 1H), 4.27 (t, J=8.4 Hz, 2H), 4.00 (q, J=6.8 Hz, 1H), 3.24 (t, J=8.8 Hz, 2H), 2.30 (s, 3H), 1.48 (d, J=6.8 Hz, 3H); MS (m/z): 418.0 [M+1]

Example 10. Synthesis of (E)-N-(5-(3-(1,1-difluoro-2-((5-methylthiazol-2-yl)amino)-2-oxoethyl)phenyl)pyridin-2-yl)-4-(dimethylamino)but-2-enamide

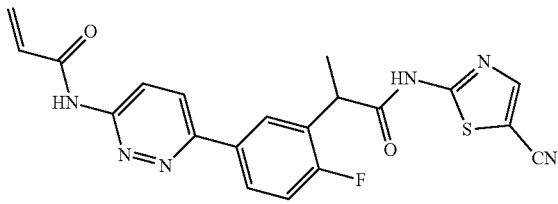 [SMILES: C=CC(=O)Nc1ccc(-c2ccc(F)c(C(C)C(=O)Nc3ncc(C#N)s3)c2)nn1]

The title compound was prepared in the same manner as in Example 1, except for using 2-(3-bromophenyl)-2,2-difluoro acetic acid instead of 2-(3-bromophenyl)propanoic acid, and using (E)-N-(5-bromopyridin-2-yl)-4-(dimethylamino)but-2-enamide instead of N-(5-bromopyridin-2-yl)acrylamide.

¹H NMR (400 MHz, DMSO-d6) δ 10.77 (s, 1H), 8.64 (s, 1H), 8.28 (d, J=8.7 Hz, 1H), 8.10 (d, J=11.4 Hz, 1H), 7.86 (s, 1H), 7.82-7.80 (m, 1H), 7.60-7.55 (m, 1H), 6.98 (s, 1H), 6.78 (d, J=16.2 Hz, 1H), 6.45 (d, J=16.2 Hz, 1H), 3.05 (d, J=6 Hz, 2H), 2.23 (s, 3H), 2.16 (s, 6H); MS (m/z): 472.0 [M+1]

Example 11. Synthesis of N-6-(3-(1-((5-cyanothiazol-2-yl)amino)-1-oxopropane-2-yl)-4-fluorophenyl)pyridazin-3-yl)acrylamide

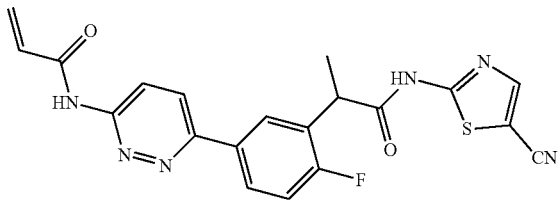 [SMILES: C=CC(=O)Nc1ccc(-c2ccc(F)c(C(C)C(=O)Nc3ncc(C#N)s3)c2)nn1]

The title compound was prepared in the same manner as in Example 1, except for using 2-(5-bromo-2-fluorophenyl)acetic acid instead of 2-(3-bromophenyl)acetic acid, using 5-cyanothiazol-2-amine instead of 5-methylthiazol-2-amine, and using N-(6-bromopyridazin-3-yl)acrylamide instead of N-(5-bromopyridin-2-yl)acrylamide.

¹H NMR (400 MHz, DMSO) δ 13.25 (br, 1H), 11.45 (s, 1H), 8.50 (d, J=9.6 Hz, 1H), 8.36 (s, 1H), 8.26 (d, J=9.6 Hz, 1H), 8.17 (dd, J=7.2, 2.4 Hz, 1H), 8.02-8.03 (m, 1H), 7.40-7.36 (m, 1H), 6.68 (dd, J=16.8, 10.0 Hz, 1H), 6.38 (dd, J=16.8, 1.2 Hz, 1H), 5.88 (dd, J=10.0, 1.2 Hz, 1H), 4.38-4.32 (m, 1H), 1.58 (d, J=7.2 Hz, 3H); MS (m/z): 423.0 [M+1]

Example 12. Synthesis of 2-(3-(6-acrylamidopyridazin-3-yl)phenyl)-N-(5-cyanothiazol-2-yl)-3-methylbutanamide

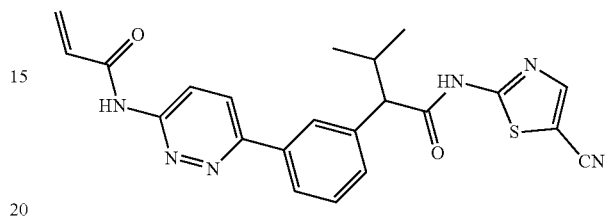

The title compound was prepared in the same manner as in Example 1, except for using 2-iodopropane instead of isodomethane, using 5-cyanothiazol-2-amine instead of 5-methylthiazol-2-amine, and using N-(6-bromopyridazin-3-yl)acrylamide instead of N-(5-bromopyridin-2-yl)acrylamide.

¹H NMR (400 MHz, CDCl3) δ 13.68 (br, 1H), 11.32 (s, 1H), 8.84 (d, J=9.2 Hz, 1H), 8.36 (s, 1H), 8.01 (s, 1H), 7.89-7.87 (m, 2H), 7.59 (d, J=5.2 Hz, 1H), 6.59 (dd, J=16.8, 1.2 Hz, 1H), 6.44 (dd, J=16.8, 10.0 Hz, 1H), 5.97 (dd, J=10.0, 1.2 Hz, 1H), 4.61 (d, J=10.0, 1H), 2.52-2.46 (m, 1H), 0.79 (d, J=6.4 Hz, 3H), 0.52 (d, J=6.4 Hz, 3H); MS (m/z): 433.0 [M+1]

Example 13. Synthesis of N-(6-(5-(1-((5-cyanothiazol-2-yl)amino)-1-oxopropan-2-yl)-2-fluorophenyl)pyridazin-3-yl)acrylamide

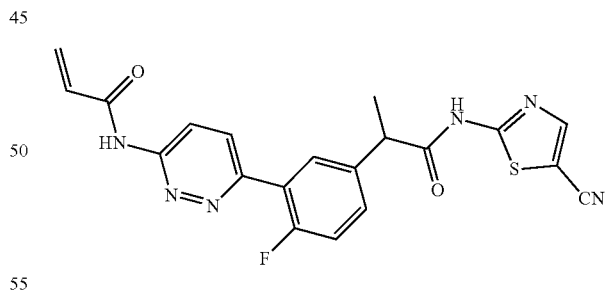

The title compound was prepared in the same manner as in Example 1, except for using 2-(3-bromo-4-fluorophenyl)acetic acid instead of 2-(3-bromophenyl)acetic acid, using 5-cyanothiazol-2-amine instead of 5-methylthiazol-2-amine and using N-(6-bromopyridazin-3-yl)acrylamide instead of N-(5-bromopyridin-2-yl)acrylamide.

¹H NMR (400 MHz, DMSO-d6) δ 13.21 (s, 1H), 11.52 (s, 1H), 8.54-8.52 (m, 1H), 8.34 (s, 1H), 8.09-7.95 (m, 2H), 7.55-7.51 (m, 1H), 7.41-7.38 (m, 1H), 6.71-6.66 (m, 1H), 6.41-6.37 (m, 1H), 5.90-5.87 (m, 1H), 4.15-4.10 (m, 1H), 1.55-1.48 (m, 3H); MS (m/z): 423.0 [M+1]

Example 14. Synthesis of (S)-N-(5-(3-(1-((5-cyclopropylthiazol-2-yl)amino)-1-oxopropane-2-yl)phenyl)pyridin-2-yl)acrylamide

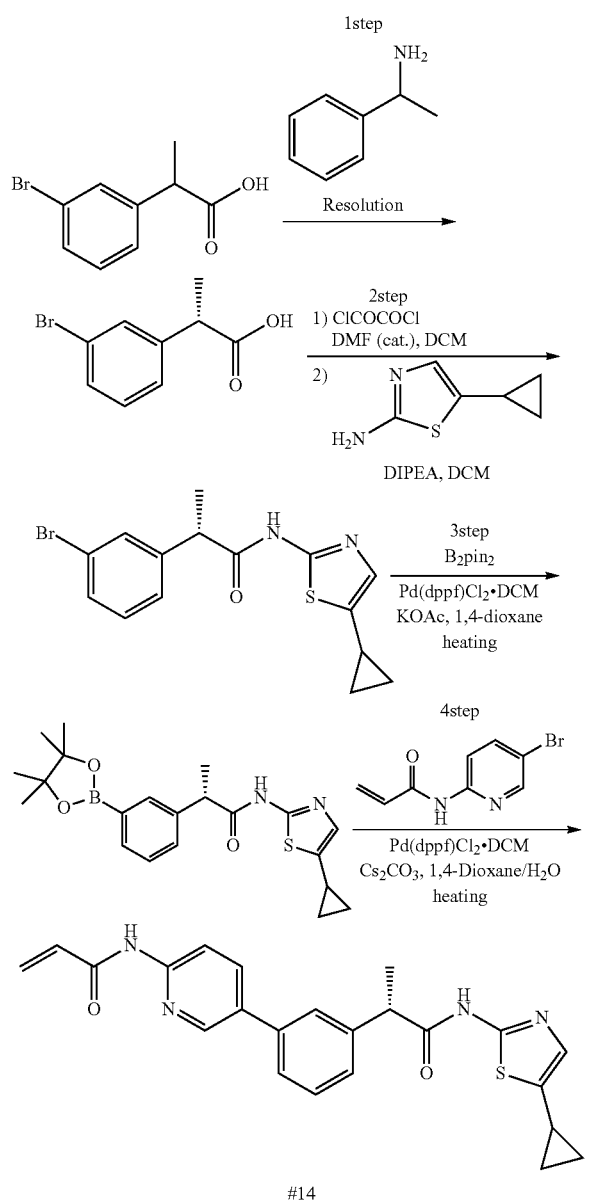

14

Step 1) Preparation of (S)-2-(3-bromophenyl) propanoic acid

ACN (165 ml) was added to racemic form 2-(3-bromophenyl) propanoic acid (33.13 g, 144.63 mmol), followed by adding (R)-1-phenylethan-1-amine thereinto and stirred at 30-35° C. After stirring for 2 hours at 20~ 25° C., the reactant was filtered, washed with ACN (100 ml) of 0~ 5° C. and dried. ACN (165 ml) was added to the dried compound, and the mixture was stirred at 80° C. to 85° C. for 1 hour. Then the mixture was cooled to 30~ 35° C., and stirred for 1 hour. After cooling to 20~ 25° C., the mixture was stirred for 3 hours, filtered and dried with ACN (100 ml) cooled to 0~ 5° C. This process was repeated twice. MC (265 ml) and 1N HCl (132 ml) were added to the obtained solid, and the solid was extracted, dried over MgSO$_4$, filtered, and concentrated to obtain 6.6 g of the title compound.

$^1$H NMR (400 MHz, CDCl$_3$) δ 9.85 (br, 1H), 7.45-7.44 (m, 1H), 7.43-7.40 (m, 1H), 7.23-7.20 (m, 2H), 7.05-7.04 (m, 1H), 3.76-3.71 (m, 1H), 2.00-1.94 (m, 1H), 1.60(d, J=6.8, Hz, 3H), 1.01-0.96 (m, 2H), 0.75-0.69 (m, 2H); MS (m/z): 352.0 [M+1]; 99.6 ee %

Step 2) Preparation of (S)-2-(3-bromophenyl)-N-(5-cyclopropylthiazol-2-yl)propanamide After (S)-2-(3-bromophenyl)propanoic acid (2.6 g, 11.35 mmol) was dissolved in DCM (113 ml, 0.1M), oxalyl chloride (1.09 ml, 12.97 mmol) was added and 2~ 3 drops of DMF was added. The mixture was stirred at room temperature for 1 hour and then concentrated. The concentrated mixture was dissolved in DCM (113 ml, 0.1 M) and 5-cyclopropylthiazol-2-amine (1.51 g, 10.81 mmol) was added. DIPEA (2.1 ml, 12.28 mmol) was slowly added and stirred at room temperature for 3 hours. The reaction mixture was diluted with DCM, washed with water, dried (MgSO4), filtrated and dried under reduced pressure. The residue was purified by a Combi-flash column (EA/Hex 0 to 60% gradient) to give the title compound (2.97 g, 78%) as a white solid.

$^1$H NMR (400 MHz, CDCl3) δ 9.85 (br, 1H), 7.45-7.44 (m, 1H), 7.43-7.40 (m, 1H), 7.23-7.20 (m, 2H), 7.05-7.04 (m, 1H), 3.76-3.71 (m, 1H), 2.00-1.94 (m, 1H), 1.60(d, J=6.8, Hz, 3H), 1.01-0.96 (m, 2H), 0.75-0.69 (m, 2H); MS (m/z): 352.0 [M+1]

Step 3) Preparation of (S)-N-(5-cyclopropylthiazol-2-yl)-2-(3-(4.4.5.5-tetramethyl-1,3,2-dioxaborolan-2-yl)nhenyl)propanamide To (S)-2-(3-bromophenyl)-N-(5-cyclopropylthiazol-2-yl)propanamide(2.97 g, 8.46 mmol) and KOAc (1.66 g, 16.91 mmol) were added anhydrous 1,4-dioxane (42 ml, 0.2 M) and the reaction mixture was stirred and degassed. Then, bis(pinacolato)diboron (2.79 g, 10.99 mmol) and Pd(dppf)Cl$_2$.DCM(690 mg, 0.85 mmol) were added and stirred at 85° C. for 15 hours. This mixture was diluted with EtOAc, washed with water, then dried (MgSO$_4$), filtered and then dried under reduced pressure. The residue was purified by a Combi-flash column (EA/Hex 0 to 60% gradient) to give the title compound (2.12 g, 63%) as a white solid.

$^1$H NMR (400 MHz, CDCl3) δ 8.96 (br, 1H), 7.75-7.73 (m, 2H), 7.41-7.37 (m, 2H), 7.02-7.01 (m, 21), 3.82-3.77 (m, 1H), 1.97-1.91 (m, 1H), 1.62 (d, J=7.2, Hz, 3H), 0.97-0.93 (m, 2H), 0.71-0.69 (m, 2H); MS (m/z): 399.0 [M+1]

Step 4) Preparation of (S)-N-(5-(3-(1-((5-cyclopropylthiazol-2-yl)amino)-1-oxopropane-2-yl)phenyl)pyridin-2-yl)acrylamide To (S)-N-(5-cyclopropylthiazol-2-yl)-2-(3-(4,4,5,5-tetramethyl-1,3,2-dioxaborolan-2-yl)phenyl)propanamide(1.2 g, 3.0 mmol), N-(5-bromopyridin-2-yl)acrylamide (680 mg, 3.0 mmol) and Cs₂CO₃ (2.44 g, 7.5 mmol) were added H₂O (15 ml) and 1,4-dioxane (45 ml), and the reaction mixture was stirred and degassed. Then, Pd(dppf)Cl₂·DCM (244 mg, 0.30 mmol) was added and stirred at 100° C. for 3 hours. This mixture was diluted with EtOAc, washed with water, further washed with brine, then dried (MgSO₄), filtered and then dried under reduced pressure. The residue was purified by a Combiflash column (EA/Hex 50 to 100% gradient) to give the title compound (474 mg, 38%) as a white solid.

¹H NMR (400 MHz, CDCl₃) δ 9.47 (s, 1H), 8.63 (s, 1H), 8.36 (d, J=8.4 Hz, 1H), 8.34 (s, 1H), 7.87 (dd, J=8.4, 2.4 Hz, 1H), 7.45-7.44 (m, 3H), 7.33-7.31 (m, 1H), 7.05 (s, 1H), 6.50 (d, J=16.8 Hz, 1H), 6.29 (dd, J=16.8, 10.4 Hz, 1H), 5.84 (d, J=10.4 Hz, 1H), 3.89-3.84 (m, 1H), 1.99-1.94 (m, 1H), 1.66 (d, J=7.2 Hz, 3H), 0.99-0.95 (m, 2H), 0.72-0.69 (m, 2H); MS (m/z): 419.0 [M+1]; 78 ee %

Example 15. Synthesis of (S,E)-N-(5-(3-(1-((5-cyclopropylthiazol-2-yl)amino)-1-oxopropan-2-yl)phenyl)pyridin-2-yl)-4-(dimethylamino)but-2-enamide

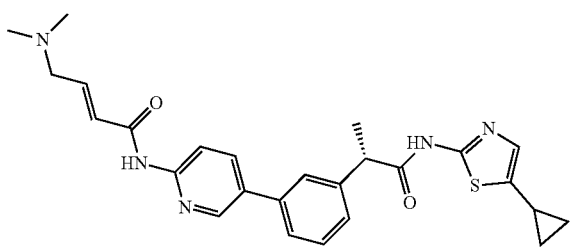 [SMILES: C[C@H](C(=O)Nc1ncc(C2CC2)s1)c1cccc(-c2ccc(NC(=O)/C=C/CN(C)C)nc2)c1]

The title compound was prepared in the same manner as in Example 14, except for using (E)-N-(5-bromopyridin-2-yl)-4-(dimethylamino)but-2-enamide instead of N-(5-bromopyridin-2-yl)acrylamide.

¹H NMR (400 MHz, CDCl3) δ 9.85 (br, 1H), 8.74 (s, 1H), 8.37-8.33 (m, 2H), 7.87-7.84 (m, 1H), 7.44-7.43 (m, 3H), 7.33-7.32 (m, 1H), 7.05-7.00 (m, 2H), 6.15 (d, J=15.6 Hz, 1H), 3.88-3.84 (m, 1H), 3.13 (d, J=6.0, Hz, 2H), 2.28 (s, 6H), 1.98-1.93 (m, 1H), 1.65 (d, J=6.8 Hz, 3H), 0.99-0.96 (m, 2H), 0.72-0.68 (m, 2H); MS (m/z): 476.0 [M+1]; 76 ee %

Example 16. Synthesis of (S)-N-(6-(3-(1-((5-cyclopropylthiazol-2-yl)amino)-1-oxopropan-2-yl)phenylpyrazin-2-yl)acrylamide

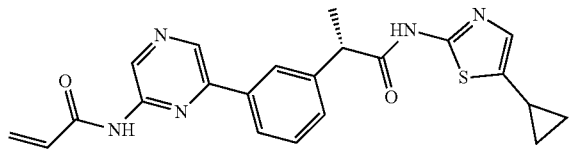 [SMILES: C=CC(=O)Nc1cncc(-c2cccc([C@H](C)C(=O)Nc3ncc(C4CC4)s3)c2)n1]

The title compound was prepared in the same manner as in Example 14, except for using N-(6-bromopyrazin-2-yl)acrylamide instead of N-(5-bromopyridin-2-yl)acrylamide.

¹H NMR (400 MHz, CDCl3) δ 9.71 (br, 1H), 9.54 (s, 1H), 8.69 (s, 1H), 8.29 (s, 1H), 7.74 (s, 1H), 7.72-7.71 (m, 1H), 7.33-7.32 (m, 2H), 7.07 (s, 1H), 6.61-6.52 (m, 2H), 5.93 (d, J=10.0 Hz, 1H), 3.77-3.78 (m, 1H), 1.94-1.93 (m, 1H), 1.65 (d, J=6.8 Hz, 3H), 0.98-0.96 (m, 2H), 0.69-0.68 (m, 2H); MS (m/z): 420.0 [M+1]; 74 ee %

Example 17. Synthesis of (S,E)-4-(dimethylamino)-N-(5-(3-(1-((5-ethylthiazol-2-yl)amino)-1-oxopropan-2-yl)phenyl)pyridin-2-yl)but-2-enamide

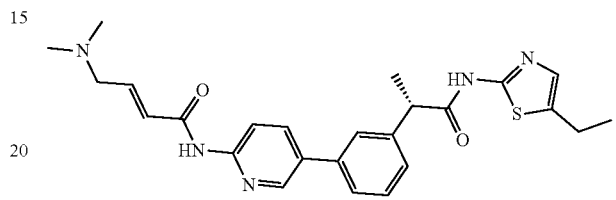

The title compound was prepared in the same manner as in Example 14, except for using 5-ethylthiazole-2-amine instead of 5-cyclopropylthiazol-2-amine, and using (E)-N-(5-bromopyridin-2-yl)-4-(dimethylamino)but-2-enamide instead of N-(5-bromopyridin-2-yl)acrylamide.

¹H NMR (400 MHz, DMSO) δ 12.12 (s, 1H), 10.75 (s, 1H), 8.63 (d, J=2.4 Hz, 1H), 8.28 (d, J=8.8 Hz, 1H), 8.09 (dd, J=8.4, 2.4 Hz, 1H), 7.71 (s, 1H), 7.60 (d, J=7.6 Hz, 1H), 7.46-7.43 (m, 1H), 7.36 (d, J=8.0 Hz, 1H), 7.13 (s, 1H), 6.85-6.78 (m, 1H), 6.46 (d, J=15.6 Hz, 1H), 4.04-4.02 (m, 1H), 3.05 (d, J=4.8, Hz, 2H), 2.73-2.67 (m, 2H), 2.17 (s, 6H), 1.49 (d, J=6.8 Hz, 3H), 1.23-1.17 (m, 3H); MS (m/z): 464.0 [M+1]; 80 ee %

Example 18. Synthesis of (S)-N-(5-(3-(1-((5-cyanothiazole-2-yl)amino)-1-oxopropan-2-yl)phenyl)pyridin-2-yl-acrylamide

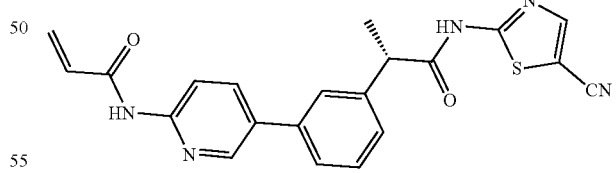

The title compound was prepared in the same manner as in Example 14, except for using 2-cyanothiazol-2-amine instead of 5-cyclopropylthiazol-2-amine.

¹H NMR (400 MHz, DMSO-d6) δ 13.14 (s, 1H), 10.86 (s, 1H), 8.66 (d, J=2.0 Hz, 1H), 8.34 (s, 1H), 8.30 (d, J=8.4 Hz, 1H), 8.11 (dd, J=8.4, 2.4 Hz, 1H), 7.72 (s, 1H), 7.62 (d, J=7.6 Hz, 1H), 7.48-7.44 (m, 1H), 7.36 (d, J=8.0 Hz, 1H), 6.64 (dd, J=16.8, 10.0 Hz, 1H), 6.33 (dd, J=16.8, 1.2 Hz, 1H), 5.80 (dd, J=10.0, 1.2 Hz, 1H), 4.11-4.09 (m, 1H), 1.53 (d, J=7.2 Hz, 3H); MS (m/z): 404.0 [M+1]; 75 ee %

Example 19. Synthesis of (S)-2-(3-(6-acrylamidopyridin-3-yl)phenyl)-N-(5-ethylthiazol-2-yl)butanamide

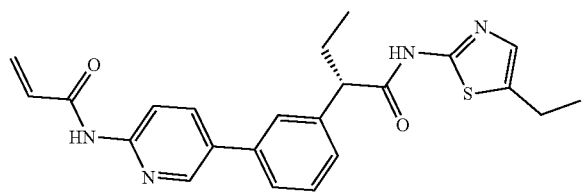 [SMILES: C=CC(=O)Nc1ccc(-c2cccc([C@H](CC)C(=O)Nc3ncc(CC)s3)c2)cn1]

The title compound was prepared in the same manner as in Example 14, except for using 5-ethylthiazol-2-amine instead of 5-cyclopropylthiazol-2-amine, and using (S)-2-(3-bromophenyl)butanoic acid instead of (S)-2-(3-bromophenyl)propanoic acid.

$^1$H NMR (400 MHz, CDCl3) δ 10.67 (br, 1H), 9.17 (s, 1H), 8.38 (s, 1H), 8.35 (d, J=2.4 Hz, 1H), 7.85 (dd, J=8.8, 2.4 Hz, 1H), 7.44-7.37 (m, 4H), 7.09 (s, 1H), 6.49 (dd, J=16.8, 0.8 Hz, 1H), 6.31 (dd, J=16.8, 10.0 Hz, 1H), 5.82 (dd, J=10.0, 0.8 Hz, 1H), 3.63-3.59 (m, 1H), 2.82-2.77 (m, 2H), 2.34-2.28 (m, 1H), 1.98-1.90 (m, 1H), 1.33-1.24 (m, 6H); MS (m/z): 421.0 [M+1]; 72 ee %

Example 20. Synthesis of (S)-2-(4'-acrylamido-3'-fluoro-[11'-biphenyl)-3-yl)-N-(5-ethylthiazol-2-yl)butanamide

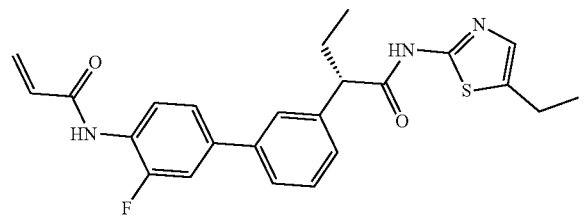 [SMILES: C=CC(=O)Nc1ccc(-c2cccc([C@H](CC)C(=O)Nc3ncc(CC)s3)c2)cc1F]

The title compound was prepared in the same manner as in Example 14, except for using 5-ethylthiazol-2-amine instead of 5-cyclopropylthiazol-2-amine, using (S)-2-(3-bromophenyl)butanoic acid instead of (S)-2-(3-bromophenyl)propanoic acid and using N-(4-bromo-2-fluorophenyl)acrylamide instead of N-(5-bromopyridin-2-yl)acrylamide.

$^1$H NMR (400 MHz, CDCl3) δ 8.43 (br, 1H), 7.53 (br, 1H), 7.44-7.42 (m, 2H), 7.37-7.33 (m, 1H), 7.30-7.26 (m, 1H), 7.22-7.29 (m, 1H), 7.12-7.09 (m, 2H), 6.80-6.68 (m, 1H), 6.48 (dd, J=16.8, 1.2 Hz, 1H), 6.30 (dd, J=16.8, 10.0 Hz, 1H), 5.83 (dd, J=10.0, 1.2 Hz, 1H), 3.58-3.55 (m, 1H), 2.82-2.74 (m, 2H), 2.35-2.22 (m, 1H), 1.99-1.89 (m, 1H), 1.31-1.24 (m, 6H); MS (m/z): 438.0 [M+1]; 7lee %

Example 21. Synthesis of (S,E)-N-(5-(3-(1-((5-cyanothiazol-2-yl)amino)-1-oxopropan-2-yl)phenyl)pyridin-2-yl)-4-(dimethylamino)but-2-enamide

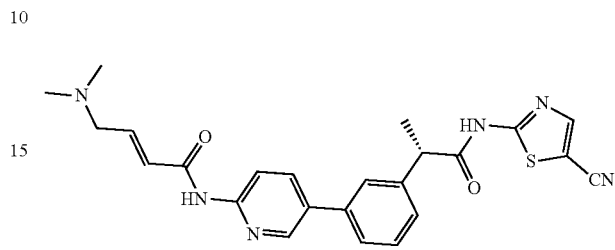

The title compound was prepared in the same manner as in Example 14, except for using 5-cyanothiazol-2-amine instead of 5-cyclopropylthiazole-2-amine, and using (E)-N-(5-bromopyridin-2-yl)-4-(dimethylamino)but-2-enamide instead of N-(5-bromopyridin-2-yl)acrylamide.

$^1$H NMR (400 MHz, DMSO-d6) δ 13.05 (br, 1H), 10.75 (s, 1H), 8.64 (dd, J=2.4, 0.8 Hz, 1H), 8.34 (s, 1H), 8.28 (dd, J=8.8, 0.8 Hz, 1H), 8.09 (dd, J=8.8, 2.4 Hz, 1H), 7.71 (s, 1H), 7.61 (d, J=8.0, 1H), 7.47-7.44 (m, 1H), 7.37-7.34 (m, 1H), 6.85-6.78 (m, 1H), 6.49-6.45 (m, 1H), 4.11-4.09 (m, 1H), 3.09-3.08 (m, 2H), 2.19 (s, 6H), 1.53 (d, J=7.2, 3H)

MS (m/z): 461.0 [M+1]; 75 ee %

Example 22. Synthesis of (S)-N-(5-(3-(1-((5-cyclopropylthiazol-2-yl)amino)-1-oxopropan-2-yl)phenyl)pyrazin-2-yl)acrylamide

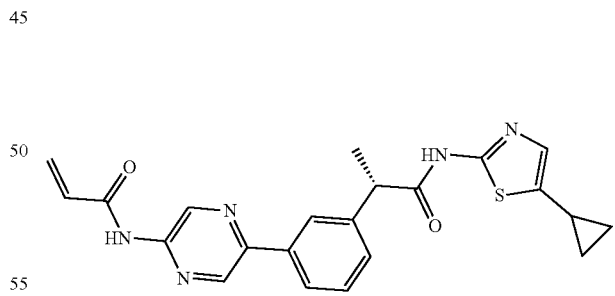

The title compound was prepared in the same manner as in Example 14, except for using N-(5-bromopyrazin-2-yl)acrylamide instead of N-(5-bromopyridin-2-yl)acrylamide.

$^1$H NMR (400 MHz, CDCl3) δ 9.81 (br, 1H), 9.62 (s, 1H), 8.68 (s, 1H), 8.38 (s, 1H), 7.90 (s, 1H), 7.78-7.76 (m, 1H), 7.46-7.42 (m, 1H), 7.38-7.36 (m, 1H), 7.06 (s, 1H), 6.54 (dd, J=16.8, 1.2 Hz, 1H), 6.31 (dd, J=16.8, 10.0 Hz, 1H), 5.88 (dd, J=10.0, 1.2 Hz, 1H), 3.91-3.89 (m, 1H), 1.96-1.95 (m, 1H), 1.66 (d, J=7.2 Hz, 3H), 0.99-0.95 (m, 2H), 0.72-0.69 (m, 2H); MS (m/z): 420.0 [M+1]; 73 ee %

Example 23. Synthesis of (S)-N-(3'-(1-((5-cyclopropylthiazol-2-yl)amino)-1-oxopropan-2-yl)-[1,1'-biphenyl]4-yl)acrylamide

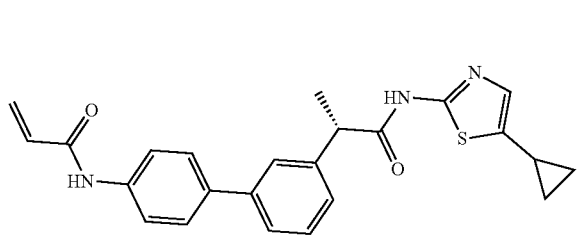 [SMILES: C=CC(=O)Nc1ccc(-c2cccc([C@H](C)C(=O)Nc3ncc(C4CC4)s3)c2)cc1]

The title compound was prepared in the same manner as in Example 14, except for using N-(4-bromophenyl)acrylamide instead of N-(5-bromopyridin-2-yl)acrylamide.

¹H NMR (400 MHz, CDCl3) δ 9.56 (br, 1H), ), 7.63 (d, J=8.0 Hz, 2H), 7.52-7.45 (m, 4H), 7.41-7.37 (m, 2H), 7.24 (s, 1H), 7.04 (s, 1H), 6.46 (dd, J=16.8, 1.2 Hz, 1H), 6.27 (dd, J=16.8, 10.8 Hz, 1H), 5.80 (dd, J=10.8, 1.2 Hz, 1H), 3.87-3.81 (m, 1H), 1.96-1.92 (m, 1H), 1.66 (d, J=7.2 Hz, 3H), 0.98-0.95 (m, 2H), 0.69-0.67 (m, 2H); MS (m/z): 418.0 [M+1]; 78 ee %

Example 24. Synthesis of (S)-N-(3'-(1-((5-cyclopropylthiazol-2-yl)amino)-1-oxopropan-2-yl)-3-fluoro-[1.1'-biphenyl)-4-yl)acrylamide

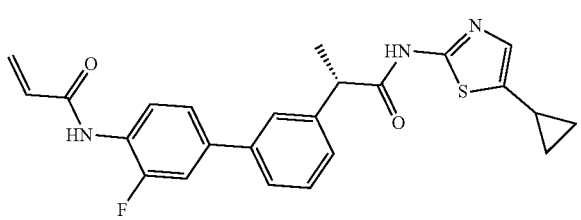 [SMILES: C=CC(=O)Nc1ccc(-c2cccc([C@H](C)C(=O)Nc3ncc(C4CC4)s3)c2)cc1F]

The title compound was prepared in the same manner as in Example 14, except for using N-(4-bromo-2-fluorophenyl)acrylamide instead of N-(5-bromopyridin-2-yl)acrylamide.

¹H NMR (400 MHz, CDCl3) δ 9.26 (s, 1H), ), 8.49 (br, 1H), 7.49-7.48 (m, 2H), 7.47-7.46 (m, 1H), 7.43-7.39 (m, 1H), 7.36-7.31 (m, 1H), 7.29-7.27 (m, 2H), 7.04 (s, 1H), 6.48 (dd, J=16.8, 1.2 Hz, 1H), 6.30 (dd, J=16.8, 10.0 Hz, 1H), 5.84 (dd, J=10.0, 1.2 Hz, 1H), 3.86-3.81 (m, 1H), 1.96-1.92 (m, 1H), 1.66 (d, J=7.2 Hz, 3H), 0.98-0.95 (m, 2H), 0.72-0.65 (m, 2H); MS (m/z): 436.0 [M+1]; 72 ee %

Example 25. Synthesis of (S)-N-(5-(3-(1-((5-cyanothiazol-2-yl)amino)-1-oxopropan-2-yl)phenyl)pyrazin-2-yl)acrylamide

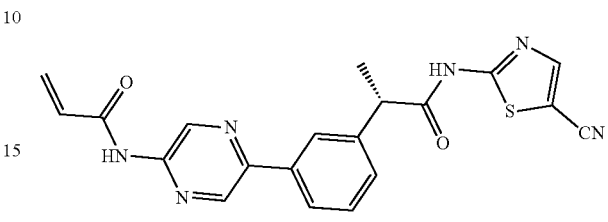

The title compound was prepared in the same manner as in Example 14, except for using 5-cyanothiazol-2-amine instead of 5-cyclopropylthiazol-2-amine, and using N-(5-bromopyrazin-2-yl)acrylamide instead of N-(5-bromopyridin-2-yl)acrylamide.

¹H NMR (400 MHz, CDCl3) δ 9.65 (dd, J=4.8, 1.6 Hz, 1H), 9.42 (br, 1H), 8.65 (dd, J=10.0, 1.6 Hz, 1H), 8.13 (s, 1H), 7.99 (s, 1H), 7.90-7.88 (m, 2H), 7.54-7.50 (m, 1H), 7.38 (d, J=10.0 Hz, 1H), 6.54 (dd, J=16.8, 0.8 Hz, 1H), 6.31 (dd, J=16.8, 10.0 Hz, 1H), 5.91 (dd, J=10.0, 0.8 Hz, 1H), 3.99-3.94 (m, 1H), 1.70 (d, J=7.2 Hz, 3H); MS (m/z): 405.0 [M+1]; 72 ee %

Example 26. Synthesis of (S)-N-(6-(3-(1-((5-cyanothiazol-2-yl)amino)-1-oxopropan-2-yl)phenyl)pyrazin-2-yl)acrylamide

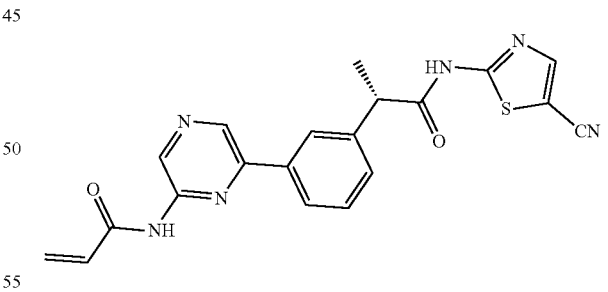

The title compound was prepared in the same manner as in Example 14, except for using 5-cyanothiazol-2-amine instead of 5-cyclopropylthiazole-2-amine, and using N-(6-bromopyrazin-2-yl)acrylamide instead of N-(5-bromopyridin-2-yl)acrylamide.

¹H NMR (400 MHz, CDCl3) δ 9.58 (s, 1H), 9.46 (br, 1H), 8.78 (d, J=2.4 Hz, 1H), 8.08 (s, 1H), 7.92-7.89 (m, 3H), 7.54-7.50 (m, 1H), 7.41 (d, J=7.6 Hz, 1H), 6.56 (dd, J=16.8, 0.8 Hz, 1H), 6.36 (dd, J=16.8, 10.0 Hz, 1H), 5.93 (dd, J=10.0, 0.8 Hz, 1H), 3.98-3.89 (m, 1H), 1.69 (d, J=7.2 Hz, 3H); MS (m/z): 405.0 [M+1]; 75 ee %

Example 27. Synthesis of (S)-N-(5-(3-(1-((5-cyclopropylthiazol-2-yl)amino)-1-oxopropan-2-yl)phenyl)pyrimidin-2-yl)acrylamide

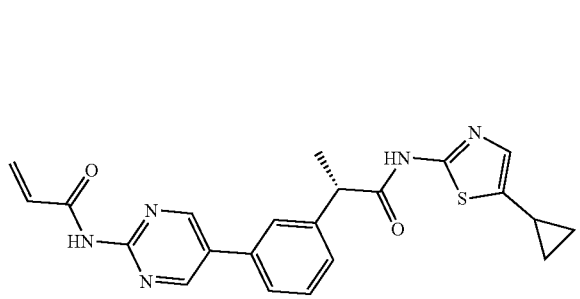 [SMILES: C=CC(=O)Nc1ncc(-c2cccc([C@H](C)C(=O)Nc3ncc(C4CC4)s3)c2)cn1]

The title compound was prepared in the same manner as in Example 14, except for using N-(5-bromopyrimidin-2-yl)acrylamide instead of N-(5-bromopyridin-2-yl)acrylamide.

$^1$H NMR (400 MHz, DMSO-d$_6$) δ 12.10 (s, 1H), 10.96 (s, 1H), 8.99 (s, 2H), 7.75 (s, 1H), 7.66 (d, J=8.0 Hz, 1H), 7.48 (t, J=8.0 Hz, 1H), 7.41 (d, J=8.0 Hz, 1H), 7.13 (s, 1H), 6.69 (dd, J=16.8 Hz, 10.0 Hz, 1H), 6.32 (dd, J=17.0 Hz, 2.0 Hz, 1H), 5.81 (dd, J=10.0 Hz, 1.6 Hz, 1H), 4.03 (q, J=6.8 Hz, 2H), 2.00-1.97 (m, 1H), 1.49 (d, J=6.8 Hz, 3H), 0.94-0.89 (m, 2H), 0.62-0.60 (m, 2H); MS (m/z): 420.0 [M+1]; 77 ee %

Example 28. Synthesis of (S)-N-(6-(3-(1-((5-cyclopropylthiazol-2-yl)amino)-1-oxopropan-2-yl)phenyl)pyridazin-3-yl)acrylamide

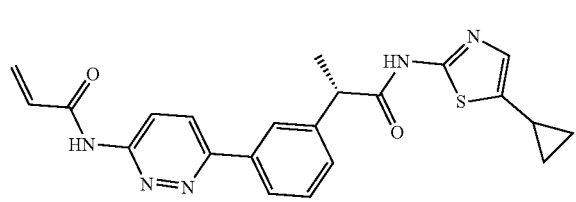

The title compound was prepared in the same manner as in Example 14, except for using N-(6-bromopyridazin-3-yl)acrylamide instead of N-(5-bromopyridin-2-yl)acrylamide.

$^1$H NMR (400 MHz, CDCl$_3$) δ 12.64 (s, 1H), ), 11.89 (s, 1H), 8.73 (d, J=9.6 Hz, 1H), 8.54 (s, 1H), 7.86 (d, J=9.6 Hz, 1H), 7.68 (d, J=8.0 Hz, 1H), 7.58 (d, J=8.0 Hz, 1H), 7.52-7.48 (m, 1H), 7.12 (s, 1H), 6.56 (s, 1H), 6.54 (d, J=2.4 Hz, 1H), 5.92-5.89 (m, 1H), 4.90-4.88 (m, 1H), 2.02-1.98 (m, 1H), 1.60 (d, J=7.2 Hz, 3H), 1.03-0.98 (m, 2H), 0.76-0.72 (m, 2H); MS (m/z): 420.0 [M+1]; 78 ee %

Example 29. Synthesis of (S)-N-(5-(3-(1-((5-cyclopropylthiazol-2-yl)amino)-1-oxopropan-2-yl)phenyl)-3-fluoropyridin-2-yl)acrylamide

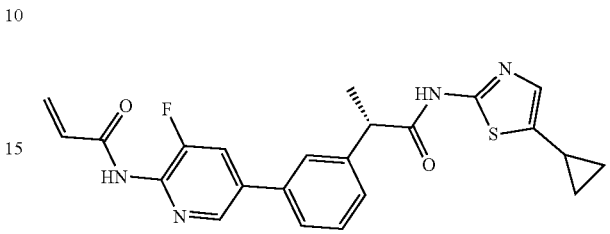

The title compound was prepared in the same manner as in Example 14, except for using N-(5-bromo-3-fluoropyridin-2-yl)acrylamide instead of N-(5-bromopyridin-2-yl)acrylamide.

$^1$H NMR (400 MHz, CDCl$_3$) δ 8.33 (s, 1H), 8.22 (s, 1H), 7.64 (d, J=10.4 Hz, 1H), 7.46-7.36 (m, 5H), 7.05 (s, 1H), 6.55-6.50 (m, 2H), 5.87-5.84 (m, 1H), 3.88 (q, J=7.2 Hz, 1H), 1.97-1.93 (m, 1H), 1.66 (d, J=6.8 Hz, 3H), 1.00-0.95 (m, 2H), 0.71-0.68 (m, 2H); MS (m/z): 437.0 [M+1]; 78 ee %

Example 30. Synthesis of (S)-N-(3-cyano-3'-(1-((5-ethylthiazol-2-yl)amino)-1-oxopropan-2-yl)-[1,1'-biphenyl]-4-yl)acrylamide

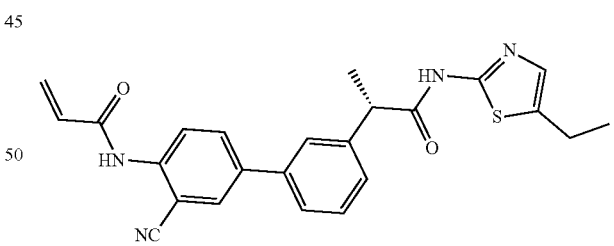

The title compound was prepared in the same manner as in Example 14, except for using 5-ethylthiazole-2-amine instead of 5-cyclopropylthiazole-2-amine, and using N-(4-bromo-2-cyanophenyl)acrylamide instead of N-(5-bromopyridin-2-yl)acrylamide.

$^1$H NMR (400 MHz, CDCl3) δ 9.11 (br, 1H), 8.61 (d, J=8.8 Hz, 1H), 7.81-7.77 (m, 3H), 7.48-7.46 (m, 3H), 7.35-7.33 (m, 1H), 7.05-7.04 (m, 1H), 6.52 (dd, J=16.8, 0.8 Hz, 1H), 6.34 (dd, J=16.8, 10.0 Hz, 1H), 5.91 (dd, J=10.0, 0.8 Hz, 1H), 3.88-3.82 (m, 1H), 2.80-2.75 (m, 1H), 1.67 (d, J=6.4 Hz, 3H), 1.31-1.27 (m, 3H); MS (m/z): 431.0 [M+1]; 73 ee %

Example 31. Synthesis of (S)-N-(5-(3-(1-((5-ethylthiazol-2-yl)amino)-1-oxo-propan-2-yl)phenyl)-6-fluoropyridin-2-yl)acrylamide

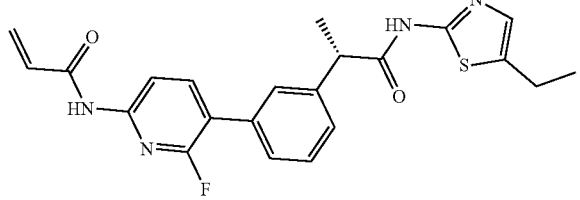

The title compound was prepared in the same manner as in Example 14, except for using 5-ethylthiazole-2-amine instead of 5-cyclopropylthiazole-2-amine, and using N-(5-bromo-6-fluoropyridin-2-yl)acrylamide instead of N-(5-bromopyridin-2-yl)acrylamide.

$^1$H NMR (400 MHz, DMSO-d$_6$) δ 12.10 (s, 1H), 11.03 (s, 1H), 8.22 (dd, J=8.0 Hz, 1.6 Hz, 1H), 8.13 (dd, J=10.0 Hz, 8.0 Hz, 1H) 7.61 (s, 1H), 7.50-7.39 (m, 3H), 7.13 (s, 1H), 6.59 (dd, J=16.8 Hz, 10.0 Hz, 1H), 6.35 (dd, J=17.0 Hz, 2.0 Hz, 1H), 5.84 (dd, J=10.4 Hz, 2.0 Hz, 1H), 4.02 (q, J=6.8 Hz, 1H), 2.71 (q, J=7.2 Hz, 2H), 1.47 (d, J=6.8 Hz, 3H), 1.18 (t, J=7.2 Hz, 3H); MS (m/z): 425.0 [M+1]; 78 ee %

Example 32. Synthesis of (S)-N-(6-(3-(1-((5-cyanothiazol-2-yl)amino)-1-oxo-propan-2-yl)phenyl)pyridazin-3-yl)acrylamide

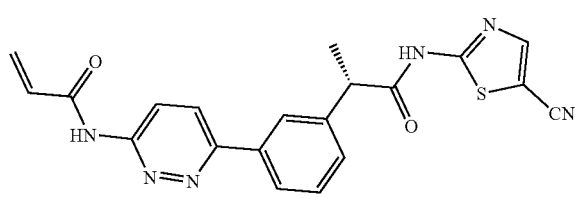 [SMILES: C=CC(=O)Nc1ccc(-c2cccc([C@H](C)C(=O)Nc3ncc(C#N)s3)c2)nn1]

The title compound was prepared in the same manner as in Example 14, except for using 5-cyanothiazol-2-amine instead of 5-cyclopropylthiazole-2-amine, and using N-(6-bromopyridazin-3-yl)acrylamide instead of N-(5-bromopyridin-2-yl)acrylamide.

$^1$H NMR (400 MHz, CDCl3) δ 13.28 (br, 1H), 11.17 (s, 1H), 8.70 (dd, J=9.6, 4.8 Hz, 1H), 8.49 (d, J=17.2 Hz, 1H), 7.99 (d, J=4.0, 1H), 7.91 (d, J=9.2, 1H), 7.66-7.63 (m, 2H), 7.58-7.54 (m, 1H), 6.58 (d, J=17.2, 1H), 6.43 (dd, J=17.2, 10.0 Hz, 1H), 5.96 (d, J=10.0, 1H), 4.98-4.97 (m, 1H), 1.62 (d, J=6.8 Hz, 3H); MS (m/z): 405.0 [M+1]; 75 ee %

Example 33. Synthesis of (S)-N-(5-(3-(1-((5-cyanothiazol-2-yl)amino)-1-oxo-propan-2-yl)phenyl)-3-fluoropyridin-2-yl)acrylamide

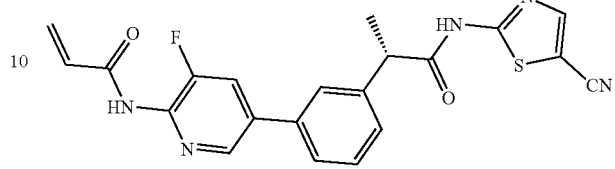

The title compound was prepared in the same manner as in Example 14, except for using 5-cyanothiazol-2-amine instead of 5-cyclopropylthiazole-2-amine, and using N-(5-bromo-3-fluoropyridin-2-yl)acrylamide instead of N-(5-bromopyridin-2-yl)acrylamide.

$^1$H NMR (400 MHz, CDCl3) δ 9.66 (br, 1H), 8.30-8.29 (m, 1H), 8.00 (s, 1H), 7.91 (s, 1H), 7.64 (dd, J=10.4, 2.0 Hz, 1H), 7.52-7.47 (m, 2H), 7.43 (s, 1H), 7.39-7.37 (m, 1H), 6.57-6.51 (m, 2H), 5.90-5.87 (m, 1H), 3.98-3.93 (m, 1H), 1.69 (d, J=7.2 Hz, 3H); MS (m/z): 422.0 [M+1]; 75 ee %

Example 34. Synthesis of (S)-N-(5-(3-(1-((5-cyanothiazol-2-yl)amino)-1-oxo-propan-2-yl)phenyl)-3-methylpyrazin-2-yl)acrylamide

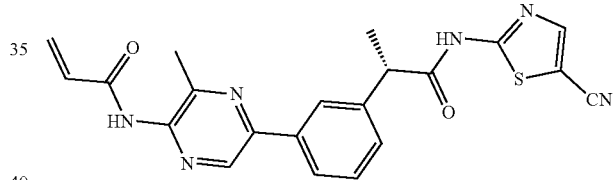

The title compound was prepared in the same manner as in Example 14, except for using 5-cyanothiazol-2-amineinstead of 5-cyclopropylthiazole-2-amine, and using N-(5-bromo-3-methylpyrazin-2-yl)acrylamide instead of N-(5-bromopyridin-2-yl)acrylamide.

$^1$H NMR (400 MHz, DMSO-d$_6$) δ 13.15 (s, 1H), 10.61 (s, 1H), 8.91 (s, 1H), 8.31 (s, 1H), 8.11 (s, 1H), 8.80 (d, J=7.2 Hz, 1H), 7.51-7.45 (m, 2H), 6.54 (dd, J=17.0 Hz, 10.4 Hz, 1H), 6.32 (dd, J=17.0 Hz, 2.0 Hz, 1H), 5.84 (dd, J=10.4 Hz, 2.0 Hz, 1H), 4.12-4.08 (m, 1H), 2.48 (s, 3H), 1.53 (d, J=7.2 Hz, 3H); MS (m/z): 419.0 [M+1]; 78 ee %

Example 35. Synthesis of (S)-N-(5-(3-(1-((5-isopropylthiazol-2-yl)amino)-1-oxopropan-2-Y)phenyl)pyridin-2-yl)acrylamide

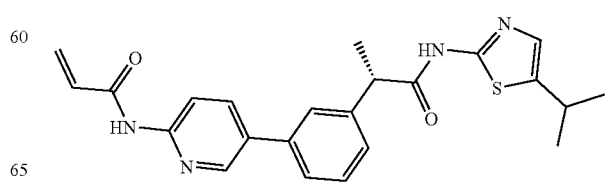

The title compound was prepared in the same manner as in Example 14, except for using 5-isopropylthiazol-2-amine instead of 5-cyclopropylthiazole-2-amine.

¹H NMR (400 MHz, DMSO-d₆) δ 12.13 (s, 1H), 10.88 (s, 1H), 8.66 (s, 1H), 8.31 (d, J=9.6 Hz, 1H), 8.11 (dd, J=8.4 Hz, 2.4 Hz, 1H), 7.73 (s, 1H), 7.61 (d, J=7.6 Hz, 1H), 7.45 (t, J=7.6 hz, 1H), 7.38 (d, J=7.6 Hz, 1H), 7.14 (s, 1H), 6.65 (dd, J=16.8 Hz, 10.0 Hz, 1H), 6.34 (dd, J=16.8 Hz, 2.0 Hz, 1H), 5.81 (dd, J=10.0 Hz, 2.0 Hz, 1H), 4.03 (q, J=6.8 Hz, 1H), 3.10-3.05 (m, 1H), 1.50 (d, J=6.8 Hz, 3H), 1.23 (d, J=6.8 Hz, 6H); MS (m/z): 421.0 [M+1]; 73 ee %

Example 36. Synthesis of (S)-N-(5-(3-(1-((5-isopropylthiazol-2-yl)amino)-1-oxopropan-2-Y)phenyl)pyrazin-2-yl)acrylamide

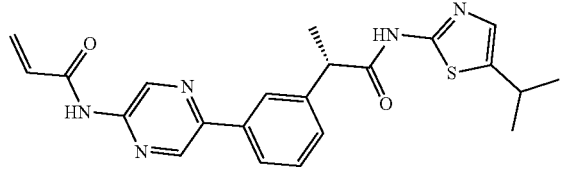 [SMILES: C=CC(=O)Nc1cnc(-c2cccc([C@H](C)C(=O)Nc3ncc(C(C)C)s3)c2)cn1]

The title compound was prepared in the same manner as in Example 14, except for using 5-isopropylthiazol-2-amine instead of 5-cyclopropylthiazole-2-amine, and using N-(5-bromopyrazin-2-yl)acrylamide instead of N-(5-bromopyridin-2-yl)acrylamide.

¹H NMR (400 MHz, DMSO-d₆) δ 12.18 (s, 1H), 11.16 (s, 1H), 9.52 (s, 1H), 9.02 (s, 1H), 8.16 (s, 1H), 8.00 (d, J=7.6 Hz, 1H), 7.51-7.45 (m, 2H), 7.14 (s, 1H), 6.65 (dd, J=16.8 Hz, 10.0 Hz, 1H), 6.39 (dd, J=17.0 Hz, 2.0 Hz, 1H), 5.88 (dd, J=10.0 Hz, 2.0 Hz, 1H), 4.12-4.05 (m, 1H), 3.13-3.07 (m, 1H), 1.50 (d, J=7.2 Hz, 3H), 1.24 (d, J=6.8 Hz, 6H); MS (m/z): 422.0 [M+1]; 72 ee %

Example 37. Synthesis of (S)-N-(5-(3-(1-oxo-1-((5-(trifluoromethyl)thiazol-2-yl)amino)propan-2-yl)phenyl)pyrazin-2-yl)acrylamide

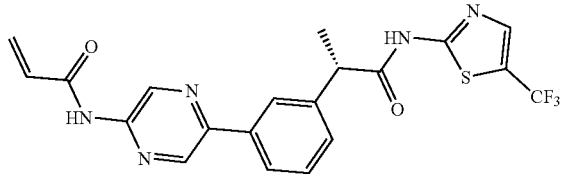 [SMILES: C=CC(=O)Nc1cnc(-c2cccc([C@H](C)C(=O)Nc3ncc(C(F)(F)F)s3)c2)cn1]

The title compound was prepared in the same manner as in Example 14, except for using 5-(trifluoromethyl)thiazol-2-amine instead of 5-cyclopropylthiazole-2-amine, and using N-(5-bromopyrazin-2-yl)acrylamide instead of N-(5-bromopyridin-2-yl)acrylamide.

¹H NMR (400 MHz, CDCl3) δ 9.66 (dd, J=4.0, 1.2 Hz, 1H), 9.15 (br, 1H), 8.64 (dd, J=14.8, 1.6 Hz, 1H), 8.14 (br, 1H), 8.00-7.99 (m, 1H), 7.90-7.88 (m, 1H), 7.69 (d, J=1.2 Hz, 1H), 7.54-7.50 (m, 1H), 7.39 (d, J=8.0, 1H), 6.55 (dd, J=16.8, 1.2 Hz, 1H), 6.32 (dd, J=16.8, 10.0 Hz, 1H), 5.91 (dd, J=10.0, 1.2 Hz, 1H), 3.97-3.92 (m, 1H), 1.70 (d, J=7.2 Hz, 3H); MS (m/z): 448.0 [M+1]; 70 ee %

Example 38. Synthesis of (S)-N-(5-(3-(1-oxo-1-((5-(trifluoromethyl)thiazol-2-yl)amino)propan-2-yl)phenyl)pyridin-2-yl)acrylamide

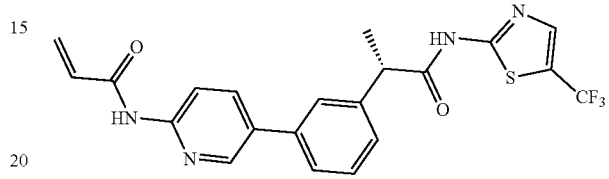

The title compound was prepared in the same manner as in Example 14, except for using 5-(trifluoromethyl)thiazol-2-amine instead of 5-cyclopropylthiazole-2-amine.

¹H NMR (400 MHz, CDCl3) δ 9.76 (s, 1H), 8.63 (s, 1H), 8.37 (d, J=8.8, 1H), 8.30 (d, J=1.6 Hz, 1H), 7.87 (dd, J=8.8, 2.4 Hz, 1H), 7.10 (d, J=1.2 Hz, 1H), 7.49-7.45 (m, 2H), 7.44 (s, 1H), 7.34-7.31 (m, 1H), 6.50 (dd, J=16.8, 1.2 Hz, 1H), 6.27 (dd, J=16.8, 10.0 Hz, 1H), 5.85 (dd, J=10.0, 1.2 Hz, 1H), 3.96-3.91 (m, 1H), 1.68 (d, J=7.2 Hz, 3H); MS (m/z): 447.0 [M+1]; 69 ee %

Example 39. Synthesis of (S)-N-(6-(3-(1-oxo-1-((5-(trifluoromethyl)thiazol-2-yl)amino)propan-2-yl)phenyl)pyridazin-3-yl)acrylamide

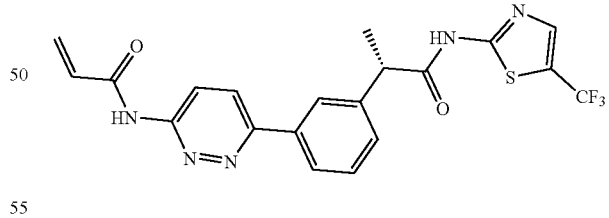

The title compound was prepared in the same manner as in Example 14, except for using 5-(trifluoromethyl)thiazol-2-amine instead of 5-cyclopropylthiazole-2-amine, and using N-(6-bromopyridazin-3-yl)acrylamide instead of N-(5-bromopyridin-2-yl)acrylamide.

¹H NMR (400 MHz, CDCl3) δ 12.75 (br, 1H), 11.16 (br, 1H), 8.76 (d, J=9.6 Hz, 1H), 8.51 (s, 1H), 7.90 (d, J=9.2 Hz, 1H), 7.76 (d, J=1.2 Hz, 1H), 7.65 (d, J=7.2 Hz, 2H), 7.52-7.51 (m, 1H), 6.58 (dd, J=16.8, 1.2 Hz, 1H), 6.46 (dd, J=16.8, 10.0 Hz, 1H), 5.95 (dd, J=10.0, 1.2 Hz, 1H), 4.89-4.88 (m, 1H), 1.63 (d, J=7.2 Hz, 3H); MS (m/z): 448.0 [M+1]; 68 ee %

Example 40. Synthesis of (S)-N-(6-(3-(1-((5-isopropylthiazol-2-yl))amino)-1-oxopropan-2-yl)phenyl)pyridazin-3-yl)acrylamide

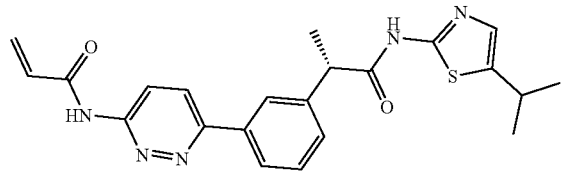 [SMILES: C=CC(=O)Nc1ccc(-c2cccc([C@H](C)C(=O)Nc3ncc(C(C)C)s3)c2)nn1]

The title compound was prepared in the same manner as in Example 14, except for using 5-isopropylthiazol-2-amine instead of 5-cyclopropylthiazole-2-amine, and using N-(6-bromopyridazin-3-yl)acrylamide instead of N-(5-bromopyridin-2-yl)acrylamide.

$^1$H NMR (400 MHz, DMSO-d$_6$) δ 12.20 (s, 1H), 11.47 (s, 1H), 8.52 (d, J=9.6 Hz, 1H), 8.25 (d, J=9.6 Hz, 1H), 8.19 (s, 1H), 7.96-7.94 (m, 1H), 7.54-7.50 (m, 2H), 7.14 (s, 1H), 6.70 (dd, J=16.8 Hz, 10.0 Hz, 1H), 6.39 (dd, J=17.0 Hz, 2.0 Hz, 1H), 5.88 (dd, J=10.0 Hz, 2.0 Hz, 1H), 4.12-4.06 (m, 1H), 3.12-3.05 (m, 1H), 1.51 (d, J=6.8 Hz, 3H), 1.24 (d, J=6.8 Hz, 6H); MS (m/z): 422.0 [M+1]; 70 ee %

Example 41. Synthesis of N-5'-(1-((5-cyanothiazol-2-yl)amino)-1-oxopropane-2-yl)-[3,3'-bipyridin]-6-yl)acryl amide

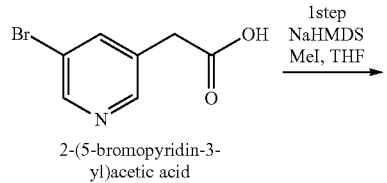

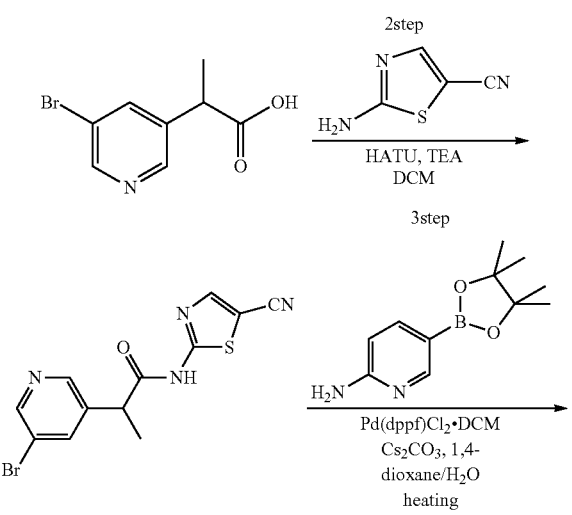

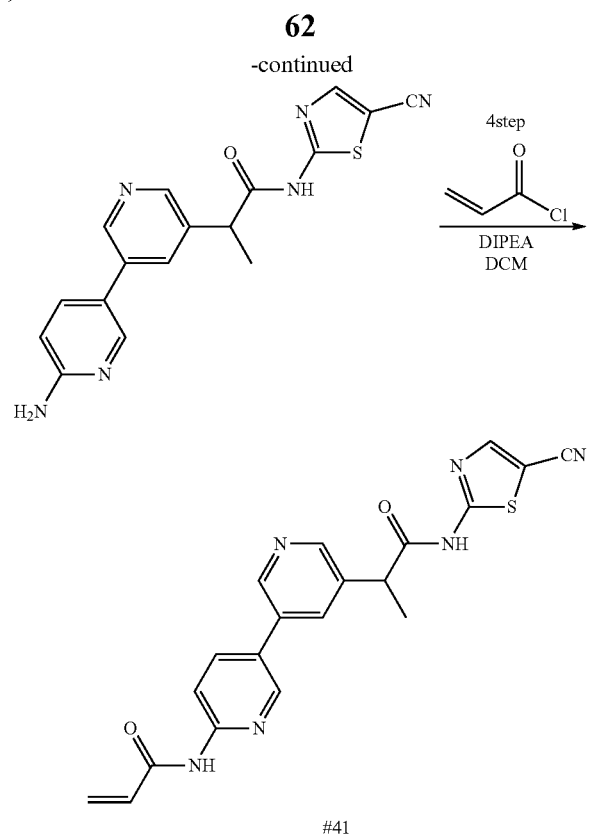

Step 1) Preparation of 2-(5-bromopyridin-3-yl) propanoic acid 2-(5-bromopyridin-3-yl) acetic acid (5 g, 23.144 mmol) was dissolved in THF (65 ml), then added 1 M NaHMDS (50.9 ml, 50.9 mmol) thereto dropwise at 0° C. After stirring for 30 minutes, MeI (1.7 ml, 27.77 mmol) was added and the mixture was stirred at room temperature for 3 hours. The mixture was diluted with EtOAc, washed with 4N HCl, and the organic layer was dried (MgSO$_4$), filtered and dried under reduced pressure. The residue was purified by using a Combi-flash column (100% gradient in EA/Hex 10) to obtain the title compound (3.4 g, 63%).

Step 2) Preparation of 2-(5-bromopyridin-3-yl)-N-(5-cyanothiazol-2-yl)propanamide To 2-(5-bromopyridin-3-yl)propanoic acid (500 mg, 2.173 mmol) and 5-cyanothiazol-2-amine (306 mg, 2.39 mmol) were added DCM (11 ml, 0.2 M), and TEA was added thereto and stirred at room temperature for 5 minutes. Then, HATU was added and stirred at room temperature for 5 hours. This mixture was diluted with EtOAc, washed with saturated NaHCO$_3$ solution, then dried (MgSO$_4$), filtered and then dried under reduced pressure. The residue was purified by a Combi-flash column (EA/Hex 10 to 100% gradient) to give the title compound (2.27 g, 80%) as a white solid.

$^1$H NMR (400 MHz, DMSO-d6) δ13.23 (s, 1H), 8.64 (s, 1H), 8.56 (s, 1H), 8.38 (s, 1H), 8.04 (s, 1H), 4.11-4.08 (m, 1H), 1.53 (d, J=5.4 Hz, 3H); MS (m/z): 338.0 [M+1]

Step 3) Preparation of 2-(6'-amino-[3,3'-bipyridine]-5-yl)-N-(5-cyanothiazol-2-yl)propanamide To 2-(5-bromopyridin-3-yl)-N-(5-cyanothiazol-2-yl)propanamide (100 mg, 0.29 mmol) and $Cs_2CO_3$ (815 mg, 2.5 mmol) were added $H_2O$ (0.7 ml) and 1,4-dioxane (2 ml), and the reaction mixture was stirred and degassed. Then, 5-(4,4,5,5-tetramethyl-1,3,2-dioxaborolane-2-yl)pyridin-2-amine and Pd(dppf)Cl2.DCM (24 mg, 0.03 mmol) were added thereto and stirred at 100° C. for 3 hours. This mixture was diluted with EtOAc, washed with water, further washed with brine, then dried ($MgSO_4$), filtered and then dried under reduced pressure. The residue was purified by a Combi-flash column (EA/Hex 50 to 100% gradient) to give the title compound (21 mg, 20%) as a white solid.

$^1$H NMR (400 MHz, DMSO-d6) δ13.21 (s, 1H), 8.72 (s, 1H), 8.46 (s, 1H), 8.37 (s, 1H), 8.30 (s, 1H), 7.92 (s, 1H), 7.76 (d, J=6.6 Hz, 1H), 6.56 (d, J=6.6 Hz, 1H), 6.22 (s, 2H), 4.13-4.09 (m, 1H), 1.56 (d, J=5.1 Hz, 3H); MS (m/z): 351.0 [M+1]

Step 4) Preparation of N-(5'-(1-((5-cyanothiazol-2-yl)amino)-1-oxopropane-2-yl)-[3,3'-bipyridin]-6-yl) acryl amide To 2-(6'-amino-[3,3'-bipyridine]-5-yl)-N-(5-cyanothiazol-2-yl)propanamide (20 mg, 0.057 mmol) was added THF, and then DIPEA (30 uL, 0.17 mmol) was added, and acryloyl chloride (4.6 uL, 0.057 mol) was slowly added at 0° C. The mixture was stirred at 0° C. for 30 minutes, then diluted with EtOAc, washed with saturated $NaHCO_3$ solution, then dried ($MgSO_4$), filtered and then dried under reduced pressure. The residue was purified by preparative TLC (MC: MeOH=15: 1) to give the title compound (1.3 mg, 6%) as a white solid.

$^1$H NMR (400 MHz, DMSO-$d_6$) δ 10.92 (s, 1H), 8.82 (s, 1H), 8.73 (s, 1H), 8.55 (s, 1H), 8.32 (d, J=8.8 Hz, 1H), 8.21-8.18 (m, 2H), 8.07 (s, 1H), 6.64 (dd, J=16.8 Hz, 10.0 Hz, 1H), 6.34 (dd, J=16.8 Hz, 2.0 Hz, 1H), 5.81 (dd, J=10.0 Hz, 1.6 Hz, 1H), 4.04 (q, J=7.6 Hz, 1H), 1.55 (d, J=7.2 Hz, 3H); MS (m/z): 405.0 [M+1]

Example 42. Synthesis of N-4-(1-((5-cyanothiazole-2-yl)amino)-1-oxopropan-2-yl)-[2,3'-bipyridine]-6'-yl)acrylamide

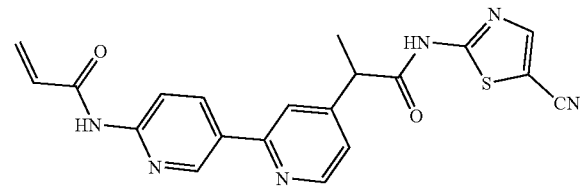 [SMILES: C=CC(=O)Nc1ccc(-c2cc(C(C)C(=O)Nc3ncc(C#N)s3)ccn2)cn1]

The title compound was prepared in the same manner as in Example 41, except for using 2-(5-bromopyridin-3-yl) acetic acid instead of 2-(2-bromopyridin-4-yl)acetic acid. ; MS (m/z): 405.0 [M+1]

Example 43. Synthesis of N-5-(5-(1-((5-cyclopropylthiazol-2-yl)amino)-1-oxopropan-2-yl)pyridin-3-yl)pyrazin-2-ylWacrylamide

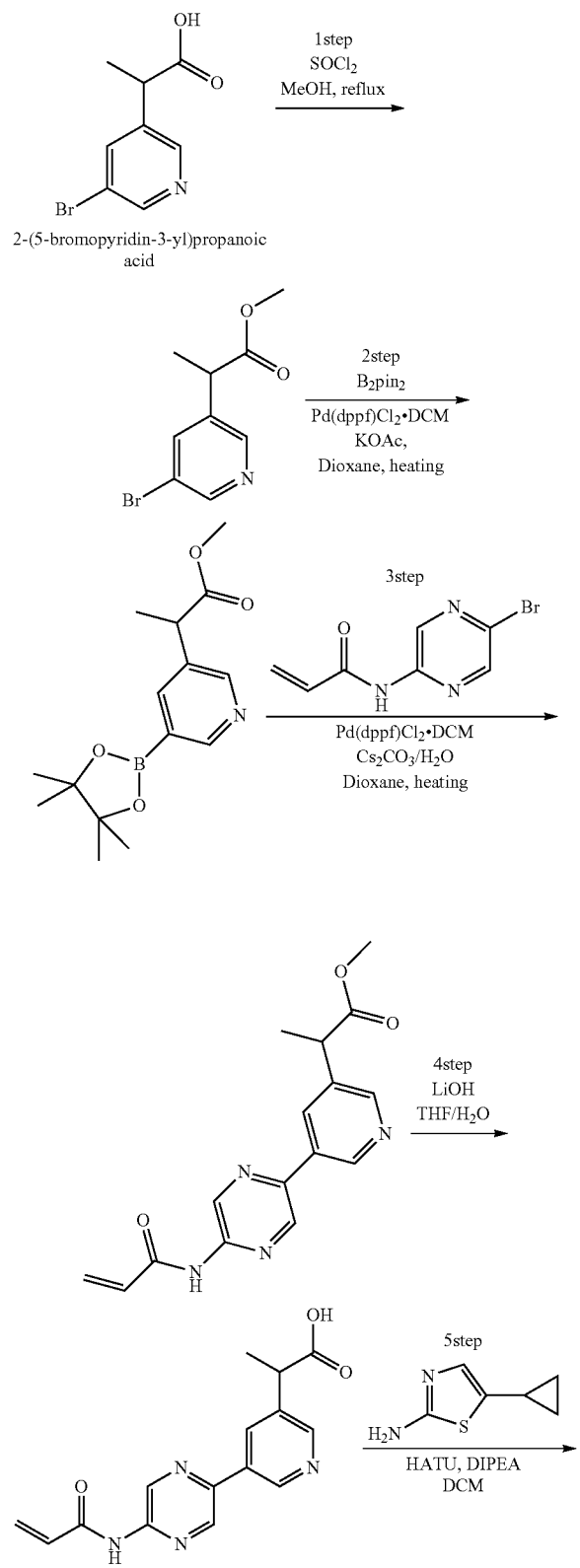

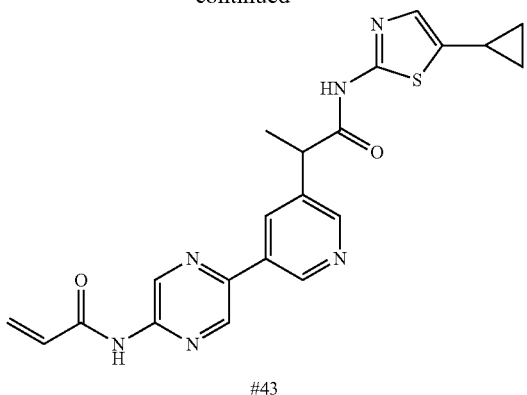

43

Step 1) Preparation of methyl 2-(5-bromopyridin-3-yl)propanoate

To 2-(5-bromopyridin-3-yl)propanoic acid (1.5 g, 6.548 mmol) was added MeOH (40 ml, 0.15M), and SOCl$_2$ was slowly added. The reaction mixture was stirred at 60° C. for 18 hours and then concentrated under reduced pressure. This mixture was diluted with EtOAc, washed with saturated NaHCO$_3$ solution, then dried (MgSO$_4$), filtered and then dried under reduced pressure. The residue was purified by a Combi-flash column (MC/MEOH 5 to 10% gradient) to give the title compound (1.27 g, 79%).

Step 2) Preparation of methyl 2-(5-(4,4,5,5-tetramethyl-1,3,2-dioxaborolan-2-yl)pyridin-3-yl)propanoate To methyl 2-(5-bromopyridin-3-yl)propanoate (200 mg, 0.819 mmol) and KOAc (196 mg, 2.047 mmol) were added anhydrous 1,4-dioxane (4 ml, 0.2 M), and the reaction mixture was stirred and degassed. Bis(pinacolato)diboron (250 mg, 0.983 mmol) and Pd(dppf)Cl$_2$.DCM (33 mg, 0.041 mmol) were added and stirred at 85° C. for 2 hours. This mixture was diluted with EtOAc, filtered through celite, and dried under reduced pressure to give the crude title compound as a black oil.
MS (m/z): 210.0 [M+1]

Step 3) Preparation of methyl 2-(5-(5-acrylamidopyrazin-2-yl)pyridin-3-yl)propanoate To methyl 2-(5-(4,4,5,5-tetramethyl-1,3,2-dioxaborolan-2-yl)pyridin-3-yl)propanoate(crude, 0.819 mmol), N-(5-bromopyrazin-2-yl)acrylamide (143 mg, 0.63 mmol) and Cs$_2$CO$_3$ (513 mg, 1.57 mmol) were added H$_2$O (3 ml) and 1,4-dioxane (9 ml), and the reaction mixture was stirred and degassed. Then, Pd(dppf)Cl$_2$.DCM(51 mg, 0.082 mmol) was added and stirred at 100° C. for 1.5 hours. This mixture was diluted with EtOAc, washed with water, further washed with brine, then dried (MgSO$_4$), filtered and then dried under reduced pressure. The residue was purified by a Combi-flash column (EA/Hex 50 to 100% gradient) to give the title compound (116 mg, 45%) as a white solid.

$^1$H NMR (400 MHz, CDCl$_3$) δ 9.71 (s, 1H), 9.09 (s, 1H), 8.73 (s, 1H), 8.62 (s, 1H), 8.29 (s, 1H), 8.02 (s, 1H), 5.56 (d, J=17.2 Hz, 1H), 6.34 (dd, J=17.2 Hz, 10.4 Hz, 1H), 5.92 (d, J=10.4 Hz, 1H), 3.86 (q, J=7.2 Hz, 1H), 3.71 (s, 3H), 1.61 (d, J=7.2 Hz, 3H); MS (m/z): 312.0 [M+1]

Step 4) Preparation of 2-(5-(5-acrylamidopyrazin-2-yl)pyridin-3-yl)propanoic acid To methyl 2-(5-(5-acrylamidopyrazin-2-yl)pyridin-3-yl)propanoate (116 mg, 0.373 mmol) was added THF(2.7 ml), and then a solution of LiGH (18 mg, 0.75 mmol) in H$_2$O (0.9 ml) was added. This mixture was stirred at room temperature for 2 hours, diluted with EtOAc, washed with water, further washed with 1N HCl, and extracted three times with EA. The extracts were then dried (MgSO$_4$), filtered and then dried under reduced pressure to give the title compound (80 mg, 72%) as an apricot-colored solid.
MS (m/z): 298.0 [M+1]

Step 5) Preparation of N-(5-(5-(1-((5-cyclopropylthiazol-2-yl)amino)-1-oxopropan-2-yl)pyridin-3-yl)pyrazin-2-yl)acrylamide After 2-(5-(5-acrylamidopyrazin-2-yl)pyridin-3-yl)propanoic acid (15 mg, 0.05 mmol) and 5-cyclopropylthiazol-2-amine (7 mg, 0.05 mmol) were dissolved in DCM (0.5 ml, 0.1 M) and then DIPEA (26 ul, 0.15 mol) was added. HATU (21 mg, 0.06 mmol) was added with stirring at room temperature, followed by stirring at room temperature for 20 minutes. The mixture was diluted with EtOAc, washed with water, dried (MgSO$_4$), filtered and then dried under reduced pressure. The residue was purified by preparative TLC (MC: MeOH=20: 1) to give the title compound (4.5 mg, 21%) as an off-white solid.

$^1$H NMR (400 MHz, DMSO-d$_6$) δ 12.23 (s, 1H), 11.22 (s, 1H), 9.55 (s, 1H), 9.20 (s, 1H), 9.14 (s, 1H), 8.64 (s, 1H), 8.44 (s, 1H), 7.16 (s, 1H), 6.66 (dd, J=17.2 Hz, 10.0 Hz, 1H), 6.40 (dd, J=17.2 Hz, 2.0 Hz, 1H), 5.89 (dd, J=10.0 Hz, 2.0 Hz, 1H), 4.14-4.08 (m, 1H), 2.03-1.96 (m, 1H), 1.54 (d, J=6.8 Hz, 3H), 0.95-0.92 (m, 2H), 0.63-0.61 (m, 2H); MS (m/z): 421.0 [M+1]

Example 44. Synthesis of N-5-(5-(1-((5-cyanothiazol-2-yl)amino)-1-oxopropan-2-yl)pyridin-3-yl)pyrazin-2-yl)acrylamide

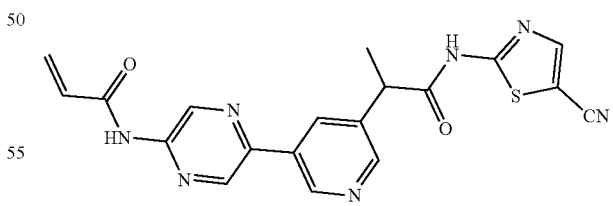

The title compound was prepared in the same manner as in Example 43, except for using 5-cyanothiazol-2-amine instead of 5-cyclopropylthiazol-2-amine.

$^1$H NMR (400 MHz, DMSO-d$_6$) δ 13.27 (s, 1H), 11.22 (s, 1H), 9.55 (s, 1H), 9.21 (s, 1H), 9.14 (s, 1H), 8.65 (s, 1H), 8.45 (s, 1H), 8.36 (s, 1H), 6.66 (dd, J=17.2 Hz, 10.0 Hz, 1H), 6.40 (dd, J=17.2 Hz, 2.0 Hz, 1H), 5.89 (dd, J=10.0 Hz, 1.6 Hz, 1H), 4.22-4.16 (m, 1H), 1.59 (d, J=7.2 Hz, 3H); MS (m/z): 406.0 [M+1]

Example 45. Synthesis of N-(5-(5-(1-oxo-1-((5-(trifluoromethyl)thiazol-2-yl)amino)propan-2-yl)pyridin-3-yl)pyrazin-2-yl)acrylamide

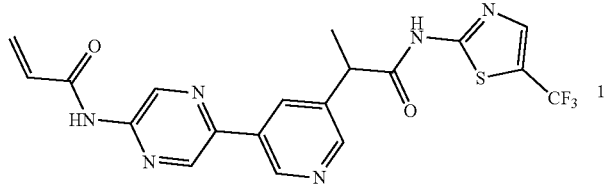

The title compound was prepared in the same manner as in Example 43, except for using 5-(trifluoromethyl)thiazol-2-amine instead of 5-cyclopropylthiazol-2-amine.

¹H NMR (400 MHz, DMSO-d₆) δ 11.22 (s, 1H), 9.55 (s, 1H), 9.21 (s, 1H), 9.14 (s, 1H), 8.65 (s, 1H), 8.45 (s, 1H), 8.10 (s, 1H), 6.65 (dd, J=17.2 Hz, 10.0 Hz, 1H), 6.40 (dd, J=17.2 Hz, 2.0 Hz, 1H), 5.89 (dd, J=10.0 Hz, 2.0 Hz, 1H) 4.19 (q, J=7.2 Hz, 1H), 1.59 (d, J=7.2 Hz, 3H); MS (m/z): 449.0 [M+1]

Example 46. Synthesis of N-5-(5-(1-((5-ethylthiazol-2-yl)amino)-1-oxopropan-2-yl)pyridin-3-yl)pyrazin-2-yl)acrylamide

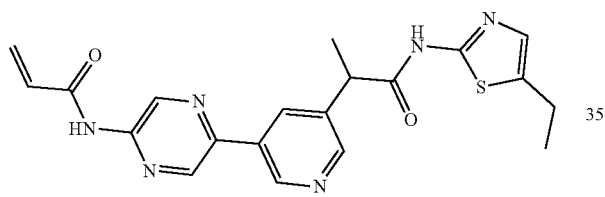

The title compound was prepared in the same manner as in Example 43, except for using 5-ethylthiazol-2-amine instead of 5-cyclopropylthiazol-2-amine.

¹H NMR (400 MHz, DMSO-d₆) δ 12.26 (s, 1H), 11.22 (s, 1H), 9.55 (s, 1H), 9.20 (s, 1H), 9.14 (s, 1H), 8.64 (s, 1H), 8.45 (s, 1H), 7.16 (s, 1H), 6.65 (dd, J=17.2 Hz, 10.0 Hz, 1H), 6.40 (dd, J=17.2 Hz, 2.0 Hz, 1H), 5.89 (dd, J=10.0 Hz, 2.0 Hz, 1H), 4.16-4.08 (q, J=8.8 Hz, 2H), 1.55 (d, J=7.2 Hz, 3H), 1.18 (t, J=8.8 Hz, 3H); MS (m/z): 409.0 [M+1]

Example 47. Synthesis of N-5-(5-(1-((5-isopropylthiazol-2-yl)amino)-1-oxopropan-2-yl)pyridin-3-yl)pyrazin-2-yl)acrylamide

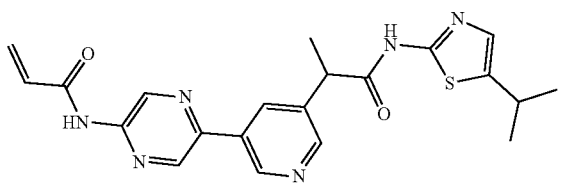 [SMILES: C=CC(=O)Nc1cnc(-c2cncc(C(C)C(=O)Nc3ncc(C(C)C)s3)c2)cn1]

The title compound was prepared in the same manner as in Example 43, except for using 5-isopropyl-thiazol-2-amine instead of 5-cyclopropylthiazol-2-amine.

¹H NMR (400 MHz, DMSO-d₆) δ 12.26 (s, 1H), 11.22 (s, 1H), 9.55 (s, 1H), 9.20 (s, 1H), 9.14 (s, 1H), 8.64 (s, 1H), 8.46 (s, 1H), 7.16 (s, 1H), 6.65 (dd, J=17.2 Hz, 10.0 Hz, 1H), 6.40 (dd, J=17.2 Hz, 2.0 Hz, 1H), 5.89 (dd, J=10.0 Hz, 2.0 Hz, 1H), 4.12 (q, J=6.8 Hz, 1H), 3.17-3.08 (m, 1H), 1.55 (d, J=6.8 Hz, 3H), 1.24 (d, J=6.8 Hz, 6H); MS (m/z): 423.0 [M+1]

Example 48. Synthesis of N-5-(5-(1-((5-acetylthiazol-2-yl)amino)-1-oxopropan-2-yl)pyridin-3-yl)pyrazin-2-yl)acrylamide

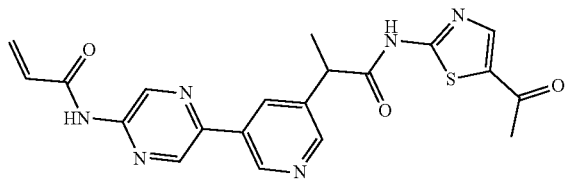 [SMILES: C=CC(=O)Nc1cnc(-c2cncc(C(C)C(=O)Nc3ncc(C(C)=O)s3)c2)cn1]

The title compound was prepared in the same manner as in Example 43, except for using 1-(2-aminothiazol-5-yl)ethan-1-one instead of 5-cyclopropylthiazol-2-amine.

1H NMR (400 MHz, DMSO-d6) δ 11.20 (s, 1H), 9.55 (s, 1H), 9.20 (s, 1H), 9.14 (s, 1H), 8.65 (s, 1H), 8.45 (s, 1H), 8.34 (s, 1H), 6.65 (dd, J=17.2 Hz, 10.0 Hz, 1H), 6.40 (dd, J=17.2 Hz, 2.0 Hz, 1H), 5.89 (dd, J=10.0 Hz, 2.0 Hz, 1H), 4.17 (q, J=7.2 Hz, 1H), 2.49 (s, 3H), 1.57 (d, J=7.2 Hz, 3H); MS (m/z): 423.0 [M+1]

Example 49. Synthesis of N-6-(5-(1-oxo-1-((5-(trifluoromethyl)thiazol-2-yl)amino)propan-2-yl)pyridin-3-yl)pyridazin-3-yl)acrylamide

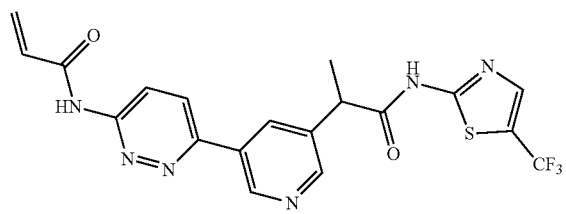 [SMILES: C=CC(=O)Nc1ccc(-c2cncc(C(C)C(=O)Nc3ncc(C(F)(F)F)s3)c2)nn1]

The title compound was prepared in the same manner as in Example 43, except for using 5-(trifluoromethyl)thiazol-2-amine instead of 5-cyclopropylthiazol-2-amine and using N-(6-bromopyridazin-3-yl)acrylamide instead of N-(5-bromopyrazin-2-yl)acrylamide.

¹H NMR (400 MHz, DMSO-d₆) δ 11.53 (s, 1H), 9.17 (s, 1H), 8.70 (s, 1H), 8.55 (d, J=9.6 Hz, 1H), 8.51 (s, 1H), 8.38 (d, J=9.2 Hz, 1H), 8.11 (s, 1H), 6.70 (dd, J=16.8 Hz, 10.0 Hz, 1H), 6.40 (dd, J=16.8 Hz, 2.0 Hz, 1H), 5.90 (dd, J=10.0 Hz, 2.0 Hz, 1H), 4.22 (q, J=6.8 Hz, 1H), 1.60 (d, J=6.8 Hz, 3H); MS (m/z): 449.0 [M+1]

Example 50. Synthesis of N-4-(1-((5-cyclopropylthiazol-2-yl)amino)-1-oxopropan-2-yl)-[2,3'-bipyridine]-6'-yl)acrylamide

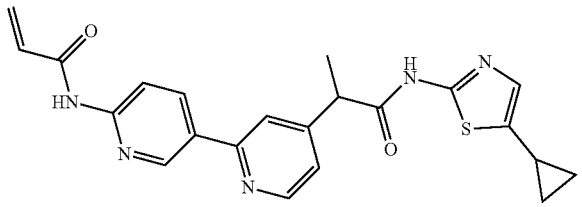 [SMILES: C=CC(=O)Nc1ccc(-c2cc(C(C)C(=O)Nc3ncc(C4CC4)s3)ccn2)cn1]

The title compound was prepared in the same manner as in Example 43, except for using 2-(2-bromopyridin-4-yl)acetic acid instead of 2-(5-bromopyridin-3-yl)acetic acid.

$^1$H NMR (400 MHz, DMSO-d$_6$) δ 10.96 (s, 1H), 9.04 (s, 1H), 8.61 (d, J=5.2 Hz, 1H), 8.47 (d, J=8.8 Hz, 2.4 Hz, 1H), 8.33 (d, J=8.8 Hz, 1H), 7.98 (s, 1H), 7.32 (d, J=4.8 Hz, 1H), 7.15 (s, 1H), 6.65 (dd, J=17.2 Hz, 10.0 Hz, 1H), 6.35 (dd, J=17.2 Hz, 2.0 Hz, 1H), 5.82 (dd, J=10.0 Hz, 2.0 Hz, 1H), 4.06-4.00 (m, 1H), 2.04-1.96 (m, 1H), 1.52 (d, J=7.2 Hz, 3H), 0.96-0.91 (m, 2H), 0.64-0.61 (m, 2H); MS (m/z): 420.0 [M+1]

Example 51. Synthesis of (R)-N-(5-(5-(1-oxo-1-((5-(trifluoromethyl)thiazol-2-yl)amino)propan-2-yl)pyridin-3-yl)pyrazin-2-yl)acrylamide Only R-form was separated from the compound of Example 45 using a chiral column.

$^1$H NMR (400 MHz, DMSO-d6) δ 11.22 (s, 1H), 9.55 (s, 1H), 9.21 (s, 1H), 9.14 (s, 1H), 8.65 (s, 1H), 8.45 (s, 1H), 8.10 (s, 1H), 6.65 (dd, J=12.9 Hz, 7.5 Hz, 1H), 6.40 (dd, J=12.9 Hz, 1.5 Hz, 1H), 5.89 (dd, J=7.5 Hz, 1.5 Hz, 1H) 4.19 (q, J=5.4 Hz, 1H), 1.59 (d, J=5.4 Hz, 3H); MS (m/z): 449.0 [M+1]

Example 52. Synthesis of (S)-N-(5-(5-(1-oxo-1-((5-(trifluoromethyl))thiazol-2-yl))amino)propan-2-yl)pyridin-3-yl)pyrazin-2-yl)acrylamide Only S-form was separated from the compound of Example 45 using a chiral column.

$^1$H NMR (400 MHz, DMSO-d6) δ 11.22 (s, 1H), 9.55 (s, 1H), 9.21 (s, 1H), 9.14 (s, 1H), 8.65 (s, 1H), 8.45 (s, 1H), 8.10 (s, 1H), 6.65 (dd, J=12.9 Hz, 7.5 Hz, 1H), 6.40 (dd, J=12.9 Hz, 1.5 Hz, 1H), 5.89 (dd, J=7.5 Hz, 1.5 Hz, 1H) 4.19 (q, J=5.4 Hz, 1H), 1.59 (d, J=5.4 Hz, 3H); MS (m/z): 449.0 [M+1]

Example 53. Synthesis of N-5-(5-(1-oxo-1-((5-(trifluoromethyl)thiazol-2-yl)amino)propan-2-yl)thiophen-3-yl)pyridin-2-yl)acrylamide

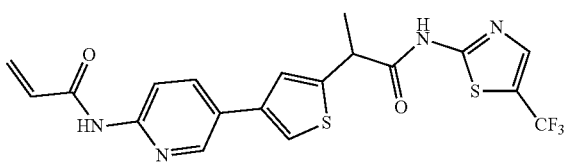 [SMILES: C=CC(=O)Nc1ccc(-c2csc(C(C)C(=O)Nc3ncc(C(F)(F)F)s3)c2)cn1]

The title compound was prepared in the same manner as in Example 41, except for using 2-(4-bromothiophen-2-yl)acetic acid instead of 2-(5-bromopyridin-3-yl)acetic acid, and using 5-(trifluoromethyl)thiazol-2-amine instead of 5-cyanothiazol-2-amine.

MS (m/z): 453.0 [M+1]

Example 54. Synthesis of N-5-(3-(1-((5-cyclopropylthiazol-2-yl)amino)-1-oxopropan-2-yl)-5-fluorophenyl)pyridin-2-yl)acrylamide

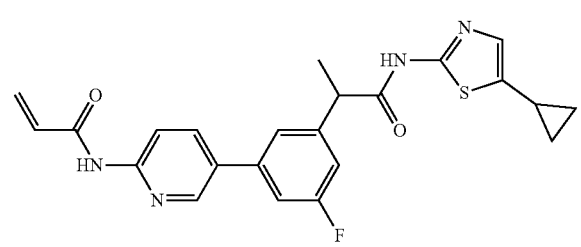 [SMILES: C=CC(=O)Nc1ccc(-c2cc(F)cc(C(C)C(=O)Nc3ncc(C4CC4)s3)c2)cn1]

The title compound was prepared in the same manner as in Example 1, except for using 5-cyclopropylthiazol-2-amine instead of 5-methylthiazol-2-amine, and using 2-(3-bromo-5-fluorophenyl)acetic acid instead of 2-(3-bromophenyl)acetic acid.

1H NMR (400 MHz, DMSO-d6) δ 10.90 (s, 1H), 8.30 (d, J=8.4 Hz, 1H), 8.15 (d, J=8.8 Hz, 1H), 7.57 (s, 1H), 7.51 (d, J=9.2 Hz, 1H), 7.18 (d, J=11.2 Hz, 1H), 7.12 (s, 1H), 6.64 (dd, J=16.0 Hz, 9.6 Hz, 1H), 6.34 (d, J=16.0 Hz, 1H), 5.81 (d, J=9.6 Hz, 1H), 4.04-4.02 (m, 1H), 1.98 (m, 1H), 1.49 (d, J=7.2 Hz, 3H), 0.93-0.86 (m, 2H), 0.62-0.61 (m, 2H); MS (m/z): 437.0 [M+1]

Example 55. Synthesis of N-5-(5-(2-methyl-1-oxo-1-((5-(trifluoromethyl))thiazol-2-yl))amino)propan-2-yl)pyridin-3-ylpyrazin-2-yl)acrylamide

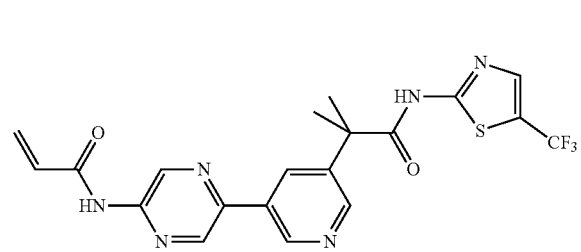 [SMILES: C=CC(=O)Nc1cnc(-c2cncc(C(C)(C)C(=O)Nc3ncc(C(F)(F)F)s3)c2)cn1]

The title compound was prepared in the same manner as in Example 43, except for using 5-(trifluoromethyl)thiazol-2-amine instead of 5-cyclopropylthiazol-2-amine, and using 2-(5-bromopyridin-3-yl)-2-methyl)propanoic acid instead of 2-(5-bromopyridin-3-yl)propanoic acid.

1H NMR (400 MHz, DMSO-d$_6$) δ 11.21 (s, 1H), 9.54 (s, 1H), 9.17 (s, 1H), 9.15 (s, 1H), 8.59 (s, 1H), 8.37 (t, J=2.0 Hz, 1H), 7.98 (s, 1H), 6.66 (dd, J=16.0 Hz, 10.0 Hz, 1H), 6.40 (dd, J=16.0 Hz, 2.0 Hz, 1H), 5.89 (dd, J=10.0 Hz, 2.0 Hz, 1H), 1.71 (s, 6H)

MS (m/z): 463.0 [M+1]

Example 56. Synthesis of (S)-2-(3-(5-(2-cyanoacetamido)pyrazin-2-yl)phenyl)-N-(5-(trifluoromethyl))thiazol-2-yl)propanamide

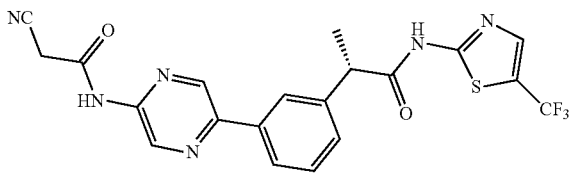 [SMILES: C[C@H](C(=O)Nc1ncc(C(F)(F)F)s1)c1cccc(-c2cnc(NC(=O)CC#N)cn2)c1]

The title compound was prepared in the same manner as in Example 14, except for using 5-(trifluoromethyl)thiazol-2-amine instead of 5-cyclopropylthiazole-2-amine, and using N-(5-bromopyrazin-2-yl)-2-cyanoacetamide instead of N-(5-bromopyridin-2-yl)acrylamide.

$^1$H NMR (400 MHz, CDCl3) δ 9.49 (s, 1H), 9.18 (s, 1H), 8.69 (d, J=1.6 Hz, 1H), 8.51 (s, 1H), 8.00 (t, J=1.6 Hz, 1H), 7.90 (dd, J=8.0, 1.6 Hz, 1H), 7.69 (d, J=1.6 Hz, 1H), 7.53-7.51 (m, 1H), 7.42 (d, J=8.0 Hz, 1H), 3.97-3.92 (m, 1H), 3.66 (s, 2H), 1.70 (d, J=7.2 Hz, 3H); MS (m/z): 461.0 [M+1]

Example 57. Synthesis of N-5-(5-(1-oxo-1-((5-(trifluoromethyl)thiazol-2-yl)amino)propan-2-yl)thiophen-3-yl)pyrazin-2-yl)acrylamide

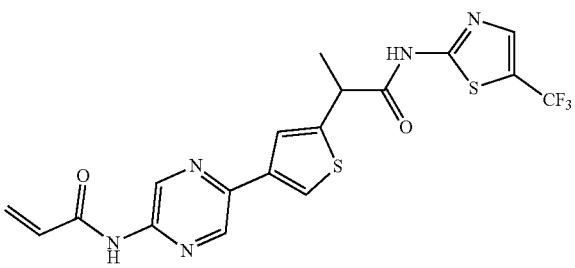 [SMILES: C=CC(=O)Nc1cnc(-c2csc(C(C)C(=O)Nc3ncc(C(F)(F)F)s3)c2)cn1]

The title compound was prepared in the same manner as in Example 43, except for using 5-(trifluoromethyl)thiazol-2-amine instead of 5-cyclopropylthiazol-2-amine, and using 2-(4-bromothiophen-2-yl)acetic acid instead of 2-(5-bromopyridin-3-yl)propanoic acid.

1H NMR (400 MHz, DMSO-d$_6$) δ 11.04 (s, 1H), 9.40 (s, 1H), 7.98 (s, 1H), 7.61 (s, 1H), 7.54 (s, 1H), 6.63 (dd, J=16.8, 10.0 Hz, 1H), 6.36 (dd, J=16.8, 1.8 Hz, 1H), 5.85 (dd, J=10.0, 1.8 Hz, 1H), 3.99-3.94 (m, 1H), 1.68 (d, J=6.8 Hz, 3H); MS (m/z): 454.0 [M+1]

Example 58. Synthesis of (S)-2-(3-(5-(2-cyanoacetamido)pyrazin-2-yl)phenyl)-N-(5-cyanothiazol-2-yl)propanamide

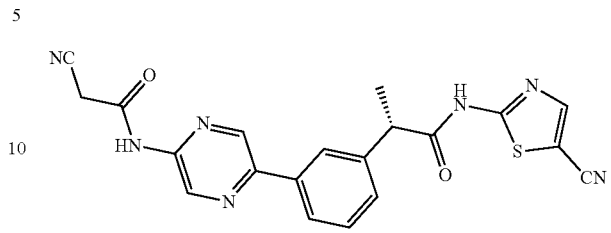

The title compound was prepared in the same manner as in Example 14, except for using 5-cyanothiazol-2-amine instead of 5-cyclopropylthiazole-2-amine, and using N-(5-bromopyrazin-2-yl)-2-cyanoacetamide instead of N-(5-bromopyridin-2-yl)acrylamide.

$^1$H NMR (400 MHz, DMSO-d6) δ 9.34 (s, 1H), 9.03 (s, 1H), 8.33 (s, 1H), 8.14 (s, 1H), 8.00 (d, J=7.2, 1.6 Hz, 1H), 7.52-7.47 (m, 2H), 4.06 (s, 2H), 4.04-4.00 (m, 1H), 1.53 (dd, J=6.8 Hz, 3H); MS (m/z): 418.1 [M+1]

Example 59. Synthesis of N-5-(3-methyl-1-(1-oxo-1-((5-(trifluoromethyl)thiazol-2-yl)amino)propan-2-yl)-1H-pyrazol-4-yl)pyridin-2-yl)acrylamide

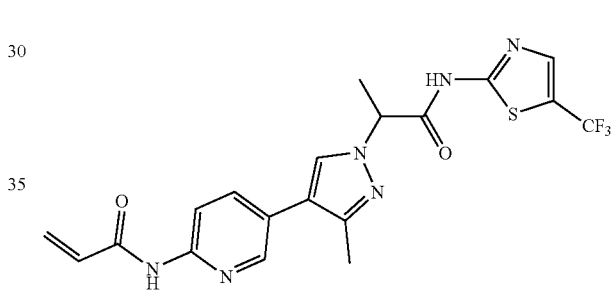

The title compound was prepared in the same manner as in Example 41, except for using 5-(trifluoro)thiazoleamine instead of 5-cyanothiazole amine, and using 2-(4-bromo-3-methyl-1H-pyrazol-1-yl)acetic acid instead of 2-(5-bromopyridin-3-yl)acetic acid.

MS (m/z): 451.0 [M+1]

Example 60. Synthesis of 2-(1'-acryloyl-1',2',3',6'-tetrahydro-[3,4'-bipyridine]-5-yl)-N-(5-cyanothiazol-2-yl)propanamide

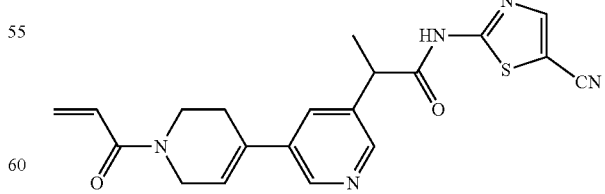

The title compound was prepared in the same manner as in Example 41, except for using t-butyl-4-(4,4,5,5-tetramethyl-1,3,2-dioxaborolane-2-yl)-3,6-dihydropyridin-1(2H)-carboxylate instead of 5-(4,4,5,5-tetramethyl-1,3,2-dioxaborolan-2- yl)pyridin-2-amine.

1H NMR (400 MHz, DMSO-d$_6$) δ 8.57 (s, 1H), 8.46 (s, 1H), 8.29 (s, 1H), 7.79 (s, 1H), 6.95-6.75 (m, 1H), 6.30-6.27 (m, 1H), 6.15 (d, J=16.0 Hz, 1H), 5.72 (dd, J=10.4 Hz, 2.4 Hz, 1H), 4.29 (s, 1H), 4.20 (s, 1H), 4.04-4.02 (m, 2H), 3.78-3.75 (m, 3H), 1.52 (d, J=7.2 Hz, 3H); MS (m/z): 394.0 [M+1]

Example 61. Synthesis of N-5-(5-(1-((5-chlorothiazol-2-yl)amino)-1-oxopropan-2-yl)pyridin-3-yl)pyrazine-2-yl)acrylamide

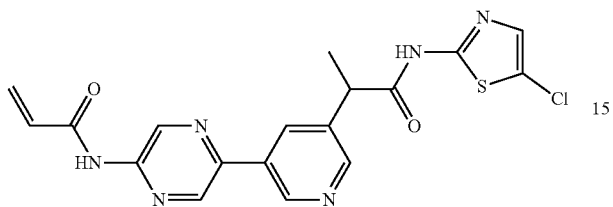

The title compound was prepared in the same manner as in Example 43, except for using 5-chlorothiazol-2-amine instead of 5-cyclopropylthiazole-2-amine.

1H NMR (400 MHz, DMSO-d$_6$) δ 11.21 (s, 1H), 9.55 (d, J=1.6 Hz, 1H), 9.20 (d, J=2.0 Hz, 1H), 9.13 (d, J=1.6 Hz, 1H), 8.64 (d, J=2.0 Hz, 1H), 8.44 (t, J=2.0 Hz, 1H), 7.49 (s, 1H), 6.66 (dd, J=17.2 Hz, 7.5 Hz, 1H), 6.40 (dd, J=16.8 Hz, 1.6 Hz, 1H), 5.89 (dd, J=10.0 Hz, 1.6 Hz, 1H), 4.12 (q, J=7.2 Hz, 1H), 1.56 (d, J=7.2 Hz, 1H); MS (m/z): 415.5 [M+1]

Examples 62-149

The compounds of the following Examples 62-149 were prepared according to the reaction described in the example shown in Table 1 below, and the NMR results thereof are shown in Table 1.

TABLE 1

| Example | Structure | ¹H NMR | Example # |
|---|---|---|---|
| 62 | 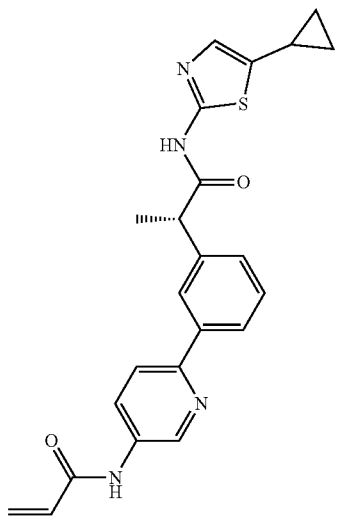 [SMILES: C=CC(=O)Nc1ccc(-c2cccc([C@H](C)C(=O)Nc3ncc(C4CC4)s3)c2)nc1] | ¹H NMR (400 MHz, DMSO-d$_6$) δ 12.16 (brs, 1H), 10.51 (s, 1H), 8.89 (d, J = 2.4 Hz, 1H), 8.25 (dd, J = 8.8 Hz, 2.8 Hz, 1H), 8.11 (s, 1H), 7.94 (d, J = 8.8 Hz, 1H), 7.90 (d, J = 7.6 Hz, 1H), 7.45-7.38 (m, 2H), 7.13 (s, 1H), 6.48 (dd, J = 16.8 Hz, 10.0 Hz, 1H), 6.32 (dd, J = 16.8 Hz, 1.6 Hz, 1H), 5.83 (dd, J = 10.0 Hz, 2.0 Hz, 1H), 4.03 (q, J = 7.2 Hz, 1H), 2.01-1.96 (m, 1H), 1.48 (d, J = 7.2 Hz, 3H), 0.95-0.90 (m, 2H), 0.64-0.60 (m, 2H); MS (m/z): 419.0 [M + 1]; 75 ee % | Example 14 |

TABLE 1-continued

| Example | Structure | ¹H NMR | Example # |
|---|---|---|---|
| 63 | 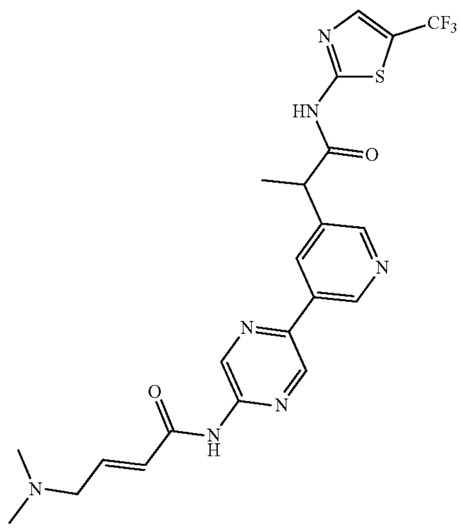 [SMILES: CC(C(=O)Nc1ncc(C(F)(F)F)s1)c1cncc(-c2cnc(NC(=O)/C=C/CN(C)C)cn2)c1] | ¹H NMR (400 MHz, DMSO-d₆) δ 13.02 (brs, 1H), 11.09 (s, 1H), 9.54 (d, J = 1.6 Hz, 1H), 9.20 (d, J = 2.0 Hz, 1H), 9.12 (d, J = 1.6 Hz, 1H), 8.65 (d, J = 2.0 Hz, 1H), 8.45 (t, 2.0 Hz, 1H), 8.08 (s, 1H), 6.89 (dt, J = 15.6 Hz, 6.0 Hz, 1H), 6.49 (d, J = 15.2 Hz, 1H), 4.18 (q, J = 6.8 Hz, 1H), 3.09 (d, J = 5.6 Hz, 2H), 2.19 (s, 6H), 1.58 (d, J = 7.2 Hz, 3H); MS (m/z): 506.0 [M + 1] | Example43 |
| 64 | 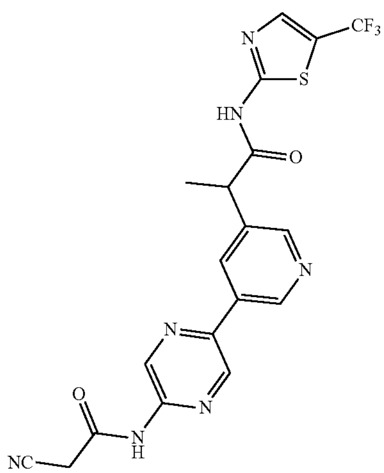 [SMILES: CC(C(=O)Nc1ncc(C(F)(F)F)s1)c1cncc(-c2cnc(NC(=O)CC#N)cn2)c1] | ¹H NMR (400 MHz, DMSO-d₆) δ 13.06 (br, 1H), 11.33 (s, 1H), 9.38 (s, 1H), 9.21 (d, J = 2.4 Hz, 1H), 9.14 (d, J = 1.6 Hz, 1H), 8.66 (d, J = 2.0 Hz, 1H), 8.45 (t, J = 2.0 Hz, 1H), 8.11 (d, J = 1.2 Hz, 1H), 4.21 (m, 1H), 4.08 (s, 2H), 1.58 (d, J = 7.2 Hz, 1H); MS (m/z): 463.0 [M + 1] | Example41 |
| 65 | 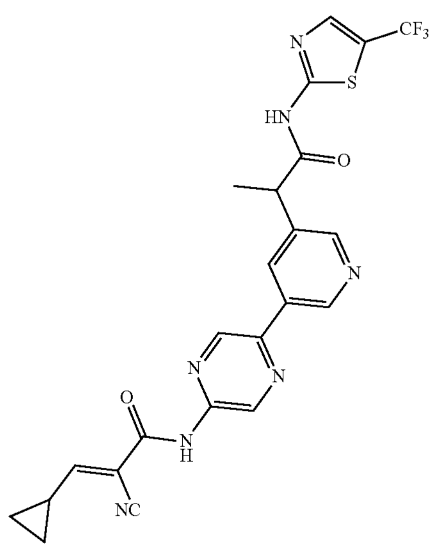 [SMILES: CC(C(=O)Nc1ncc(C(F)(F)F)s1)c1cncc(-c2cnc(NC(=O)/C(C#N)=C/C3CC3)cn2)c1] | ¹H NMR (400 MHz, DMSO-d₆) δ 13.01 (br, 1H), 11.13 (s, 1H), 9.36 (d, J = 1.2 Hz, 1H), 9.22 (d, J = 2.0 Hz, 1H), 9.17 (d, J = 2.0 Hz, 1H), 8.66 (d, J = 2.0 Hz, 1H), 8.46 (t, J = 2.0 Hz, 1H), 8.10 (d, J = 1.2 Hz, 1H), 4.19 (m, 1H), 2.00 (m, 1H), 1.59 (d, J = 7.2 Hz, 1H), 1.33 (m, 1H), 1.07 (m, 1H); MS (m/z): 514.0 [M + 1] | Example41 |

TABLE 1-continued

| Example | Structure | ¹H NMR | Example # |
|---|---|---|---|
| 66 | 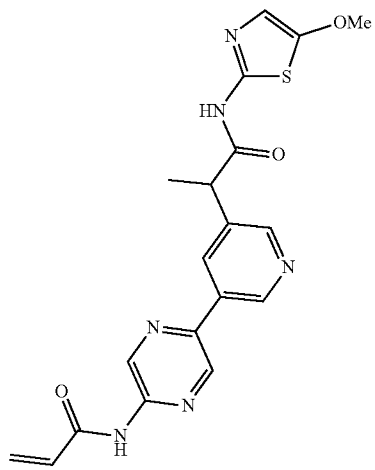 [SMILES: C=CC(=O)Nc1cnc(-c2cncc(C(C)C(=O)Nc3ncc(OC)s3)c2)cn1] | ¹H NMR (400 MHz, DMSO-d₆) δ 12.17(s, 1H), 11.22(s, 1H), 9.55(d, J = 1.6 Hz, 1H), 9.20(d, J = 2.0 Hz, 1H), 9.14(d, J = 1.2 Hz, 1H), 8.64(d, J = 2.0 Hz, 1H), 8.45(t, J = 2.0 Hz, 1H), 6.84(s, 1H), 6.66(dd, J = 17.2, 10.0 Hz, 1H), 6.40(dd, J = 16.8, 1.6 Hz, 1H), 5.90(dd, J = 10.4, 1.6 Hz, 1H), 4.09(q, J = 7.2 Hz, 1H), 3.83(s, 3H), 1.54(d, J = 7.2 Hz, 3H); MS (m/z): 411.0 [M + 1] | Example43 |
| 67 | 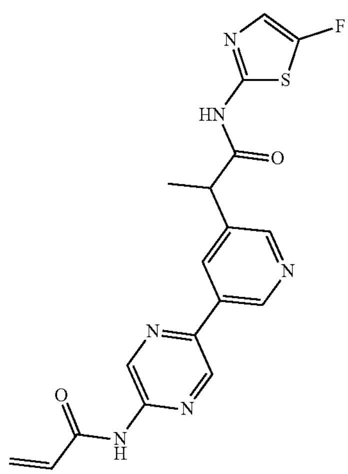 [SMILES: C=CC(=O)Nc1cnc(-c2cncc(C(C)C(=O)Nc3ncc(F)s3)c2)cn1] | ¹H NMR (400 MHz, DMSO-d₆) δ 12.50(s, 1H), 11.21(s, 1H), 9.55(d, J = 1.2 Hz, 1H), 9.20(d, J = 2.0 Hz, 1H), 9.14(d, J = 1.6 Hz, 1H), 8.64(d, J = 2.0 Hz, 1H), 8.45-8.44(m, 1H), 6.66(dd, J = 16.8, 10.0 Hz, 1H), 6.40(dd, J = 16.8, 1.6 Hz, 1H), 5.89(dd, J = 10.0, 1.6 Hz, 1H), 4.11 (q, J = 7.2 Hz, 1H), 1.56(d, J = 7.2 Hz, 3H); MS (m/z): 399.0 [M + 1] | Example43 |
| 68 | 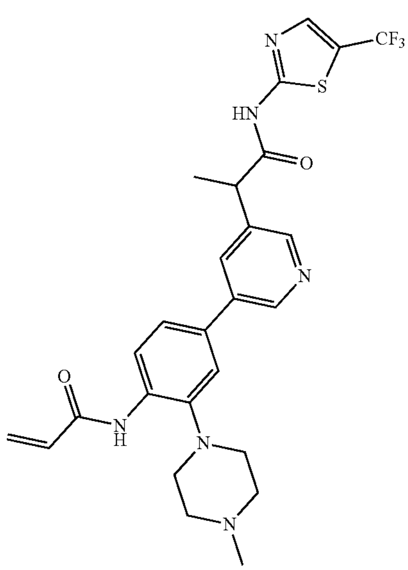 [SMILES: C=CC(=O)Nc1ccc(-c2cncc(C(C)C(=O)Nc3ncc(C(F)(F)F)s3)c2)cc1N1CCN(C)CC1] | ¹H NMR (400 MHz, DMSO-d₆) δ 9.13 (s, 1H), 8.75 (s, 1H), 8.51 (d, J = 1.6 Hz, 1H), 8.09 (d, J = 8.0 Hz, 1H), 7.99 (s, 1H), 7.89 (s, 1H), 7.45-7.41 (m, 2H), 6.67 (dd, J = 16.8 Hz, 10.4 Hz, 1H), 6.27 (dd, J = 16.8 Hz, 1.6 Hz, 1H), 5.79 (dd, J = 10.4 Hz, 1.6 Hz, 1H), 4.04-3.97 (m, 1H), 2.92 (t, J = 4.8 Hz, 4H), 2.58-2.55 (m, 4H) 2.27 (s, 3H), 1.54 (d, J = 6.8 Hz, 3H); MS (m/z): 545.0 [M + 1] | Example1 |

TABLE 1-continued

| Example | Structure | ¹H NMR | Example # |
|---|---|---|---|
| 69 | 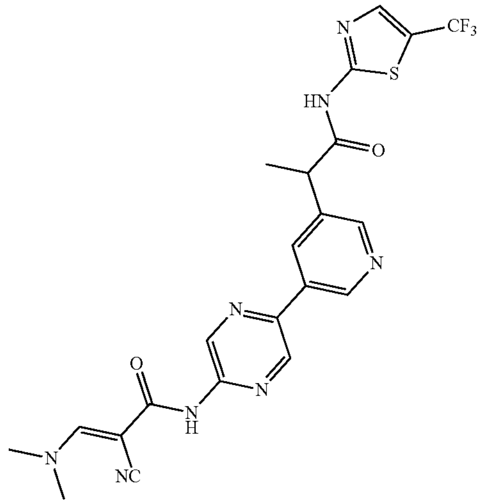 [SMILES: CC(C(=O)Nc1ncc(C(F)(F)F)s1)c1cncc(-c2cnc(NC(=O)/C(C#N)=C/N(C)C)cn2)c1] | ¹H NMR (400 MHz, DMSO-d₆) δ 13.10 (br, 1H), 9.74 (s, 1H), 9.35 (d, J = 1.2 Hz, 1H), 9.19 (d, J = 2.0 Hz, 1H), 9.08 (d, J = 1.2 Hz, 1H), 8.64 (d, J = 2.0 Hz, 1H), 8.44 (t, J = 2.0 Hz, 1H), 8.09 (d, J = 1.2 Hz, 1H), 8.00(s, 1H), 4.18 (m, 1H), 3.32(s, 6H), 1.58 (d, J = 7.2 Hz, 1H); MS (m/z): 517.0 [M + 1] | Example41 |
| 70 | 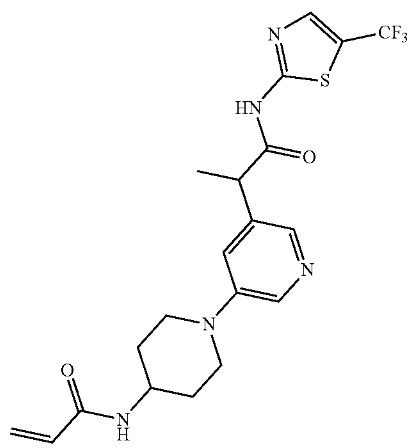 [SMILES: C=CC(=O)NC1CCN(c2cncc(C(C)C(=O)Nc3ncc(C(F)(F)F)s3)c2)CC1] | ¹H NMR (400 MHz, DMSO-d₆) δ 12.95(s, 1H), 8.22(d, J = 2.8 Hz, 1H), 8.10-8.08(m, 2H), 7.96(d, J = 1.6 Hz, 1H), 7.30-7.29(m, 1H), 6.21(dd, J = 17.2, 10.0 Hz, 1H), 6.09(dd, J = 17.2, 2.4 Hz, 1H), 5.59(dd, J = 10.0, 2.4 Hz, 1H), 3.99(q, J = 7.2 Hz, 1H), 3.86-3.38(m, 2H), 3.74-3.71(m, 3H), 2.92-2.86(m, 2H), 1.87-1.85(m, 2H), 1.49(d, J = 7.2 Hz, 3H); MS (m/z): 454.0 [M + 1] | Example41 |
| 71 | 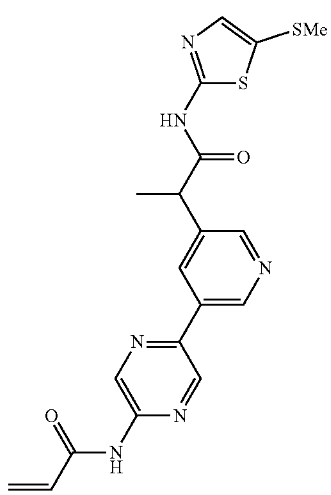 [SMILES: C=CC(=O)Nc1cnc(-c2cncc(C(C)C(=O)Nc3ncc(SC)s3)c2)cn1] | ¹H NMR (400 MHz, DMSO-d₆) δ 12.58(s, 1H), 11.22(s, 1H), 9.55(d, J = 1.2 Hz, 1H), 9.21(d, J = 2.0 Hz, 1H), 9.14(d, J = 1.6 Hz, 1H), 8.65(d, J = 2.4 Hz, 1H), 8.46-8.45(m, 1H), 8.17(s, 1H), 7.49(s, 1H), 6.66(dd, J = 16.8, 10.0 Hz, 1H), 6.40(dd, J = 16.8, 1.6 Hz, 1H), 5.89(dd, J = 10.0, 1.6 Hz, 1H), 4.15(q, J = 7.2 Hz, 2H), 2.34(s, 3H), 1.56(d, J = 7.2 Hz, 3H); MS (m/z): 427.0 [M + 1] | Example43 |

TABLE 1-continued

| Example | Structure | ¹H NMR | Example # |
|---|---|---|---|
| 72 | 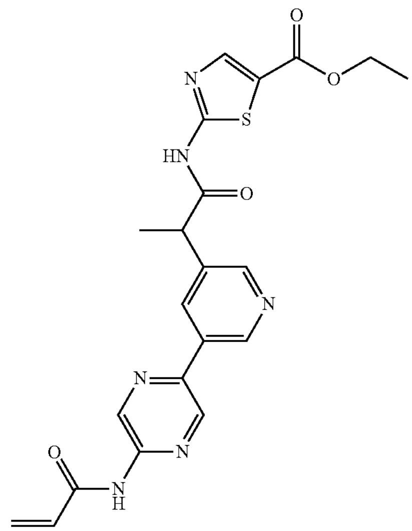 [SMILES: C=CC(=O)Nc1cnc(-c2cncc(C(C)C(=O)Nc3ncc(C(=O)OCC)s3)c2)cn1] | ¹H NMR (400 MHz, DMSO-d$_6$) δ 12.94(s, 1H), 11.21(s, 1H), 9.55(d, J = 1.2 Hz, 1H), 9.21(s, 1H), 9.13(d, J = 1.2 Hz, 1H), 8.65(s, 1H), 8.46-8.45(m, 1H), 8.14(s, 1H), 6.65(dd, J = 17.2, 10.0 Hz, 1H), 6.40(dd, J = 17.2, 1.6 Hz, 1H), 5.89(dd, J = 10.0, 1.6 Hz, 1H), 4.26(q, J = 7.2 Hz, 2H), 4.19(q, J = 6.8 Hz, 1H), 1.58(d, J = 7.2 Hz, 3H), 1.28(t, J = 6.8 Hz, 3H); MS (m/z): 453.0 [M + 1] | Example43 |
| 73 | 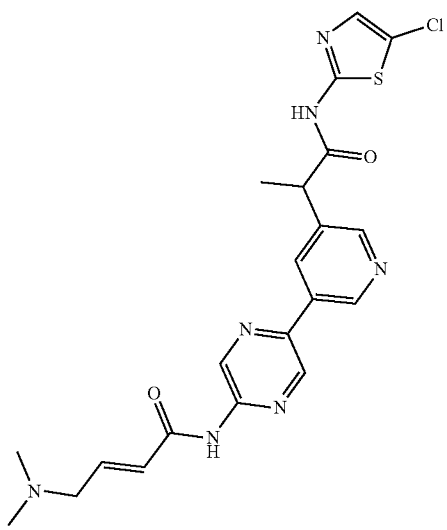 [SMILES: CC(C(=O)Nc1ncc(Cl)s1)c1cncc(-c2cnc(NC(=O)/C=C/CN(C)C)cn2)c1] | ¹H NMR (400 MHz, DMSO-d$_6$) δ12.71 (brs, 1H), 11.10 (s, 1H), 9.54 (d, J = 1.6 Hz, 1H), 9.20 (d, J = 2.0 Hz, 1H), 9.12 (d, J = 1.6 Hz, 1H), 8.64 (d, J = 2.4 Hz, 1H), 8.44 (t, J = 2.0 Hz, 1H), 7.52 (s, 1H), 6.89 (dt, J = 15.6 Hz, 6.0 Hz, 1H), 6.49 (d, J = 15.6 Hz, 1H), 4.15 (q, J = 6.8 Hz, 1H), 3.09 (d, J = 6.0 Hz, 2H), 2.19 (s, 6H), 1.57 (d, J = 7.2 Hz, 3H); MS (m/z): 472.5 [M + 1] | Example1 |
| 74 | 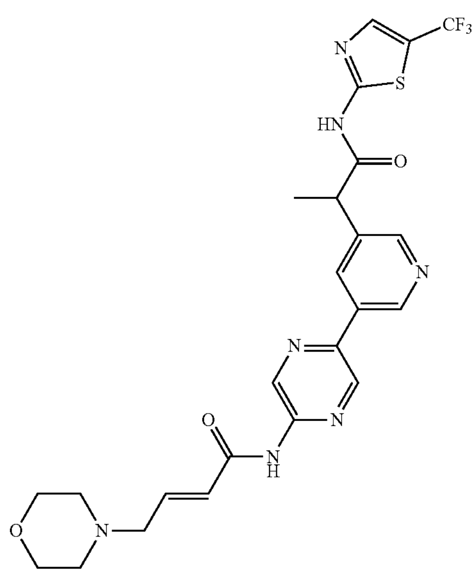 [SMILES: CC(C(=O)Nc1ncc(C(F)(F)F)s1)c1cncc(-c2cnc(NC(=O)/C=C/CN3CCOCC3)cn2)c1] | ¹H NMR (400 MHz, DMSO-d$_6$) δ 13.06 (s, 1H), 11.11 (s, 1H), 9.53 (d, J = 1.2 Hz, 1H), 9.21 (d, J = 2.0 Hz, 1H), 9.12 (d, J = 1.2 Hz, 1H), 8.65 (d, J = 1.6 Hz, 1H), 8.45 (t, J = 1.6 Hz, 1H), 8.11 (d, J = 1.2 Hz, 1H), 6.89 (dt, J = 15.6 Hz, 6.0 Hz, 1H), 6.52 (d, J = 15.6 Hz, 1H), 4.20 (q, J = 7.2 Hz, 1H), 3.63-3.58 (m, 4H), 3.17 (s, 2H), 2.43-2.36 (m, 4H), 1.59 (d, J = 7.2 Hz, 3H); MS (m/z): 548.0 [M + 1] | Example1 |

TABLE 1-continued

| Example | Structure | ¹H NMR | Example # |
|---|---|---|---|
| 75 | 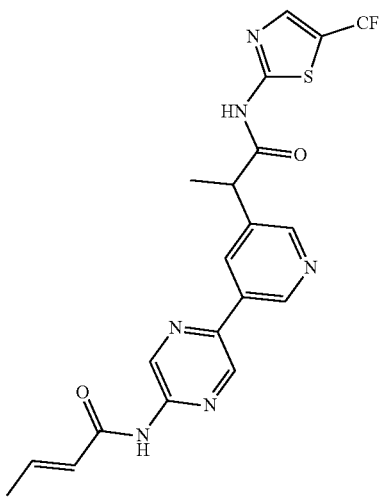 | ¹H NMR (400 MHz, DMSO-d₆) 13.06 (s, 1H), 11.02 (s, 1H), 9.53 (d, J = 1.6 Hz, 1H), 9.20 (d, J = 2.0 Hz, 1H), 9.12 (d, J = 1.2 Hz, 1H), 8.65 (d, J = 1.6 Hz, 1H), 8.45 (t, J = 2.0 Hz, 1H), 8.11 (d, J = 1.6 Hz, 1H), 7.00-6.91 (m, 1H), 6.35 (dd, J = 16.8 Hz, 1.6 Hz, 1H), 4.20 (q, J = 6.8 Hz, 1H), 1.90 (dd, J = 6.8 Hz, 1.2 Hz, 3H), 1.59 (d, J = 7.2 Hz, 3H); MS (m/z): 463.0 [M + 1] | Example1 |
| 76 | 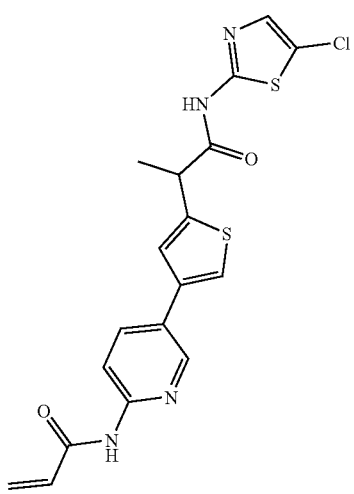 [SMILES: C=CC(=O)Nc1ccc(-c2csc(C(C)C(=O)Nc3ncc(Cl)s3)c2)cn1] | ¹H NMR (400 MHz, DMSO-d₆) δ 12.70(s, 1H), 10.81(s, 1H), 8.70(d, J = 2.0 Hz, 1H), 8.23(d, J = 8.4 Hz, 1H), 8.12(d, J = 2.4 Hz, 1H), 8.10(d, J = 2.4 Hz, 1H), 7.83(d, J = 1.2 Hz, 1H), 7.54-7.52(m, 2H), 6.63(dd, J = 16.8, 10.0 Hz, 1H), 6.32(dd, J = 17.2, 2.0 Hz, 1H), 5.80(dd, J = 10.4, 2.0 Hz, 1H), 4.32(q, J = 6.8 Hz, 1H), 1.56(d, J = 19.2 Hz, 3H); MS (m/z): 419.5 [M + 1] | Example41 |
| 77 | 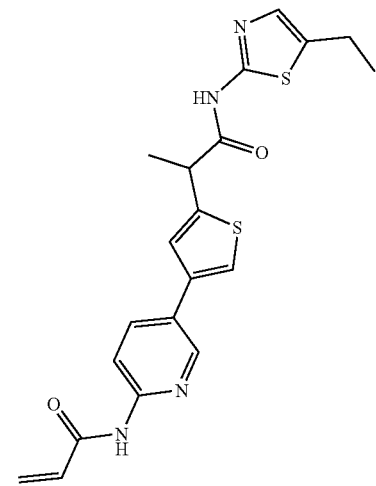 [SMILES: C=CC(=O)Nc1ccc(-c2csc(C(C)C(=O)Nc3ncc(CC)s3)c2)cn1] | ¹H NMR (400 MHz, DMSO-d₆) δ 12.25(s, 1H), 10.81(s, 1H), 8.70(d, J = 2.0 Hz, 1H), 8.23(d, J = 8.4 Hz, 1H), 8.11(dd, J = 8.8, 2.4 Hz, 1H), 7.82(d, J = 1.2 Hz, 1H), 7.51(s, 1H), 7.17(s, 1H), 6.63(dd, J = 16.8, 10.0 Hz, 1H), 6.32(dd, J = 17.2, 2.0 Hz, 1H), 5.80(dd, J = 10.0, 2.0 Hz, 1H), 4.30(q, J = 7.2 Hz, 1H), 2.74(q, J = 7.6 Hz, 2H), 1.54(d, J = 6.8 Hz, 3H), 1.21 (t, J = 7.6 Hz, 3H); MS (m/z): 413.0 [M + 1] | Example41 |

TABLE 1-continued

| Example | Structure | ¹H NMR | Example # |
|---|---|---|---|
| 78 | 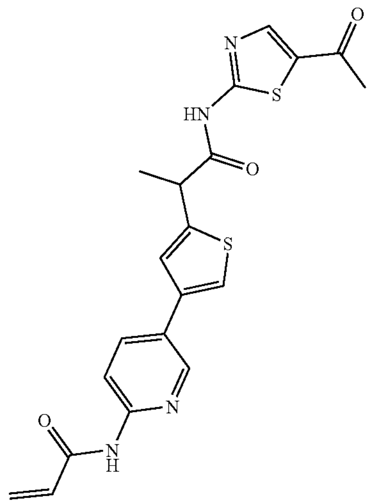 [SMILES: C=CC(=O)Nc1ccc(-c2csc(C(C)C(=O)Nc3ncc(C(C)=O)s3)c2)cn1] | ¹H NMR (400 MHz, DMSO-d₆) δ 12.89(s, 1H), 10.82(s, 1H), 8.70(dd, J = 2.4, 0.4 Hz, 1H), 8.37(s, 1H), 8.23(dd, J = 8.8, 0.4 Hz, 1H), 8.11(dd, J = 8.8, 2.4 Hz, 1H), 7.84(d, J = 1.2 Hz, 1H), 7.53(d, J = 1.2 Hz, 1H), 6.63(dd, J = 17.2, 10.0 Hz, 1H), 6.32(dd, J = 17.2, 2.0 Hz, 1H), 5.80(dd, J = 10.4, 2.0 Hz, 1H), 4.36(q, J = 6.8 Hz, 1H), 2.70(s, 3H), 1.57(d, J = 6.8 Hz, 3H); MS (m/z): 427.0 [M + 1] | Example41 |
| 79 | 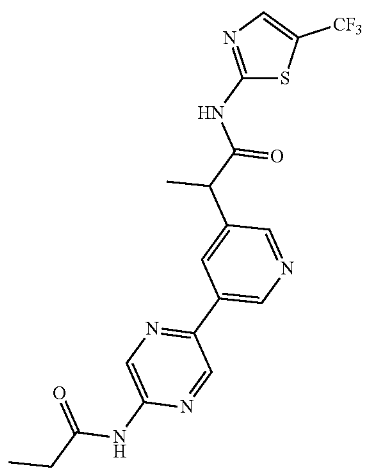 [SMILES: CCC(=O)Nc1cnc(-c2cncc(C(C)C(=O)Nc3ncc(C(F)(F)F)s3)c2)cn1] | ¹H NMR (400 MHz, DMSO-d₆) δ 13.05 (s, 1H), 10.92 (s, 1H), 9.45 (d, J = 1.6 Hz, 1H), 9.19 (d, J = 1.6 Hz, 1H), 9.10 (d, J = 1.6 Hz, 1H), 8.64 (d, J = 1.6 Hz, 1H), 8.44 (t, J = 2.0 Hz, 1H), 8.09 (d J = 1.2 Hz, 1H), 4.18 (q, J = 6.8 Hz, 1H), 2.48 (q, J = 7.6 Hz, 2H), 1.58 (d, J = 6.8 Hz, 3H), 1.11 (t, J = 7.6 Hz, 3H); MS (m/z): 451.0 [M + 1]; | Example1 |
| 80 | 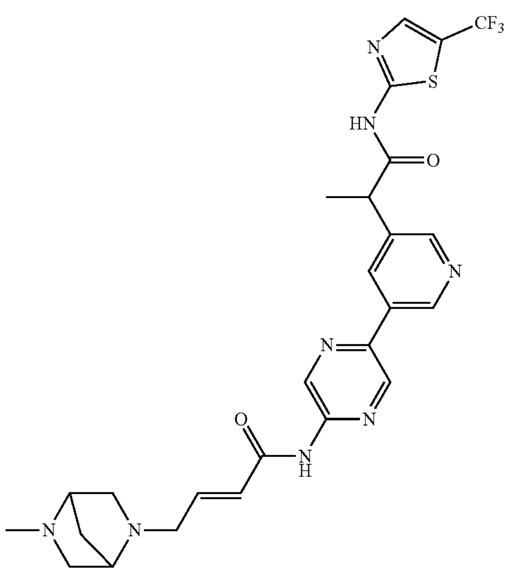 [SMILES: CC(C(=O)Nc1ncc(C(F)(F)F)s1)c1cncc(-c2cnc(NC(=O)/C=C/CN3CC4CC3CN4C)cn2)c1] | MS (m/z): 573.0 [M + 1] | Example1 |

TABLE 1-continued

| Example | Structure | 1H NMR | Example # |
|---|---|---|---|
| 81 | 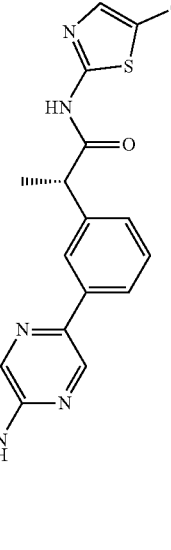 | 1H NMR (400 MHz, DMSO-d6) δ13.01 (s, 1H), 11.02 (s, 1H), 9.50 (d, J = 1.2 Hz, 1H), 9.01 (d, J = 1.6 Hz, 1H), 8.14 (s, 1H), 8.05 (s, 1H), 7.99 (dt, J = 7.6 Hz, 2.0 Hz, 1H), 7.51-7.44 (m, 2H), 6.88 (dt, J = 15.6 Hz, 2.0 Hz, 1H), 6.48 (d, J = 15.6 Hz, 1H), 4.11 (q, J = 6.8 Hz, 1H), 3.08 (d, J = 6.0 Hz, 2H), 2.19 (s, 6H), 1.53 (d, J = 7.2 Hz, 3H); MS (m/z): 505.0 [M + 1]; 70 ee % | Example14 |
| 82 | 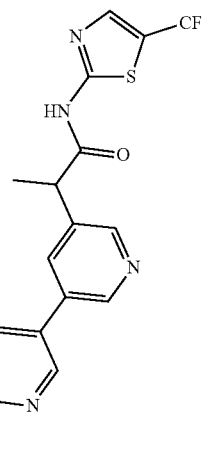 | 1H NMR (400 MHz, DMSO-d6) δ10.93 (s, 1H), 8.85 (d, J = 2.4 Hz, 1H), 8.74 (d, J = 2.4 Hz, 1H), 8.58 (d, J = 2.0 Hz, 1H), 8.33 (d, J = 8.4 Hz, 1H), 8.21 (dd, J = 8.8 Hz, 2.4 Hz, 1H), 8.10 (t, J = 2.0 Hz, 1H), 8.03 (s, 1H), 6.65 (dd, J = 16.8 Hz, 10.4 Hz, 1H), 6.35 (dd, J = 16.8 Hz, 1.6 Hz, 1H), 5.82 (dd, J = 8.0 Hz, 2.0 Hz, 1H), 4.18-4.08 (m, 1H), 1.58 (d, J = 7.2 Hz, 3H); MS (m/z): 448.0 [M + 1] | Example1 |
| 83 | 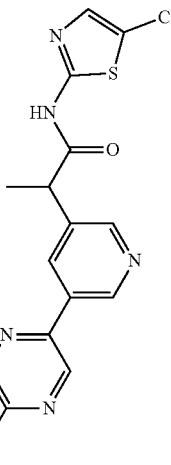 | 1H NMR (400 MHz, DMSO-d6) δ 13.01 (brs, 1H), 11.08 (s, 1H), 9.54 (d, J = 1.2 Hz, 1H), 9.19 (d, J = 2.0 Hz, 1H), 9.12 (d, J = 1.2 Hz, 1H), 8.65 (d, J = 2.0 Hz, 1H), 8.44 (t, J = 2.0 Hz, 1H), 8.07 (s, 1H), 6.90 (dt, J = 15.2 Hz, 8.8 Hz, 1H), 6.53 (d, J = 15.2 Hz, 1H), 4.37 (s, 1H), 4.18-4.15 (m, 1H), 3.86 (d, J = 7.2 Hz, 1H), 3.56-3.49 (m, 2H), 3.41-3.38 (m, 1H), 3.32-3.31 (m, 2H), 2.80-2.76 (m, 1H), 1.79-1.74 (m, 1H), 1.62-1.56 (m, 4H); MS (m/z): 560.0 [M + 1] | Example1 |

TABLE 1-continued

| Example | Structure | ¹H NMR | Example # |
|---|---|---|---|
| 84 | 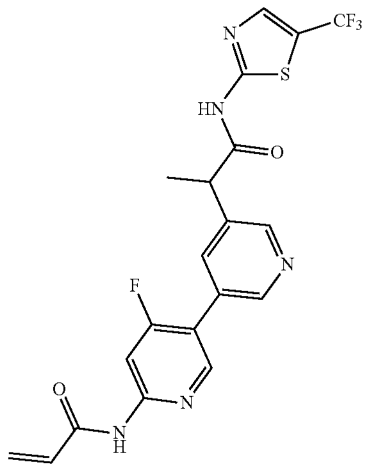 [SMILES: C=CC(=O)Nc1cc(F)c(-c2cncc(C(C)C(=O)Nc3ncc(C(F)(F)F)s3)c2)cn1] | ¹H NMR (400 MHz, DMSO-d₆) δ 13.03 (brs, 1H), 11.20 (s, 1H), 8.71 (s, 1H), 8.62-8.60 (m, 2H), 8.17 (d, J = 13.2 Hz, 1H), 8.02-7.09 (m, 1H), 6.64 (dd, J = 17.2 Hz, 6.8 Hz, 1H), 6.37 (dd, J = 17.2 Hz, 2.0 Hz, 1H), 5.86 (dd, J = 10.4 Hz, 2.0 Hz, 1H), 4.12-4.07 (m, 1H), 1.56 (d, J = 7.2 Hz, 3H); MS (m/z): 466.0 [M + 1] | Example1 |
| 85 | 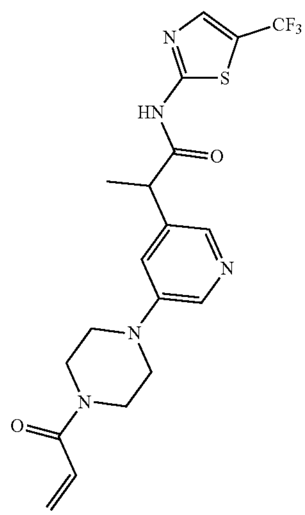 [SMILES: C=CC(=O)N1CCN(c2cncc(C(C)C(=O)Nc3ncc(C(F)(F)F)s3)c2)CC1] | ¹H NMR (400 MHz, DMSO-d₆) δ 12.96(s, 1H), 8.23(d, J = 2.8 Hz, 1H), 8.11-8.10(m, 1H), 8.02(d, J = 1.6 Hz, 1H), 7.31(t, J = 2.4 Hz, 1H), 6.86(dd, J = 16.4, 10.4 Hz, 1H), 6.15(dd, J = 16.8, 2.4 Hz, 1H), 5.72(dd, J = 10.4, 2.4 Hz, 1H), 4.02(q, J = 6.8 Hz, 1H), 3.73-3.66(m, 4H), 3.23-3.22(m, 4H), 1.50(d, J = 6.8 Hz, 3H); MS (m/z): 440.0 [M + 1] | Example41 |
| 86 | 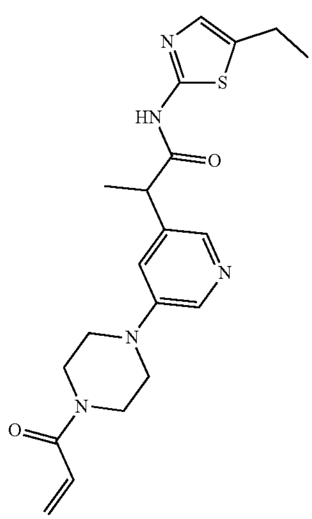 [SMILES: C=CC(=O)N1CCN(c2cncc(C(C)C(=O)Nc3ncc(CC)s3)c2)CC1] | ¹H NMR (400 MHz, DMSO-d₆) δ 12.12(s, 1H), 8.22(d, J = 2.8 Hz, 1H), 8.02(d, J = 1.6 Hz, 1H), 7.31(d, J = 2.0 Hz, 1H), 7.45(s, 1H), 6.86(dd, J = 16.8, 10.4 Hz, 1H), 6.15(dd, J = 16.8, 2.4 Hz, 1H), 5.72(dd, J = 10.4, 2.4 Hz, 1H), 3.94(q, J = 7.2 Hz, 1H), 3.72-3.69(m, 4H), 3.23-3.22(m, 4H), 2.73(q, J = 7.6 Hz, 2H), 1.46(d, J = 7.2 Hz, 3H), 1.20(t, J = 7.6 Hz, 3H); MS (m/z): 400.0 [M + 1] | Example41 |

TABLE 1-continued

| Example | Structure | ¹H NMR | Example # |
|---|---|---|---|
| 87 | 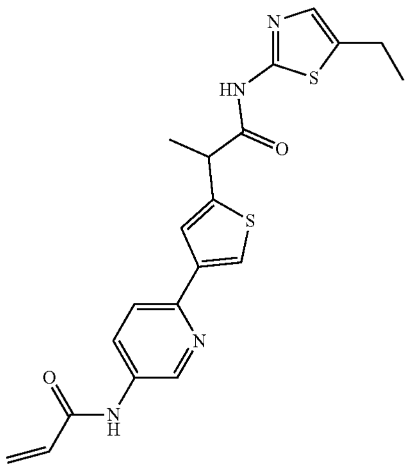 [SMILES: C=CC(=O)Nc1ccc(-c2csc(C(C)C(=O)Nc3ncc(CC)s3)c2)nc1] | ¹H NMR (400 MHz, DMSO-d₆) δ 12.25(s, 1H), 10.42(s, 1H), 8.79(d, J = 2.0 Hz, 1H), 8.16(dd, J = 8.8, 2.4 Hz, 1H), 7.94(d, J = 1.2 Hz, 1H), 7.82(d, J = 8.0 Hz, 1H), 7.64(d, J = 0.8 Hz, 1H), 7.18-7.17(m, 1H), 6.46(dd, J = 16.8, 10.0 Hz, 1H), 6.30(dd, J = 17.2, 2.0 Hz, 1H), 5.82(dd, J = 10.0, 2.0 Hz, 1H), 4.29(q, J = 7.2 Hz, 1H), 2.60(q, J = 7.6 Hz, 3H), 1.53(d, J = 7.2 Hz, 3H), 1.21(t, J = 7.6 Hz, 3H); MS (m/z): 413.0 [M + 1]; | Example43 |
| 88 | 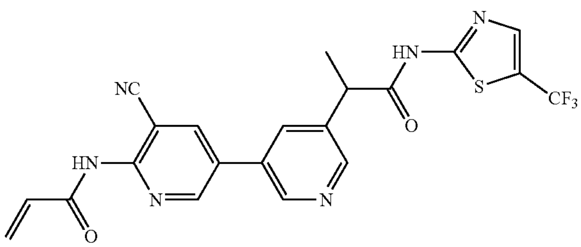 [SMILES: C=CC(=O)Nc1ncc(-c2cncc(C(C)C(=O)Nc3ncc(C(F)(F)F)s3)c2)cc1C#N] | MS (m/z): 473.0 [M + 1]; | Example1 |
| 89 | 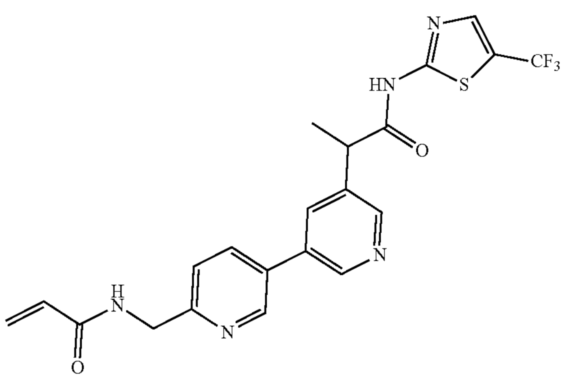 [SMILES: C=CC(=O)NCc1ccc(-c2cncc(C(C)C(=O)Nc3ncc(C(F)(F)F)s3)c2)cn1] | MS (m/z): 462.0 [M + 1]; | Example1 |
| 90 | 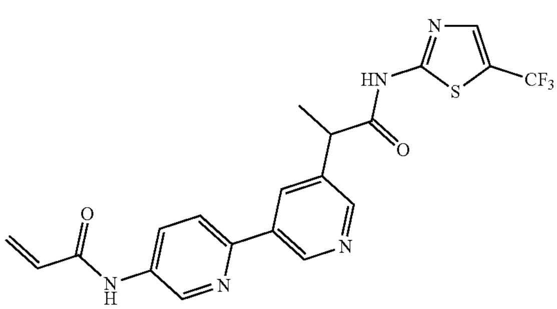 [SMILES: C=CC(=O)Nc1ccc(-c2cncc(C(C)C(=O)Nc3ncc(C(F)(F)F)s3)c2)nc1] | MS (m/z): 448.0 [M + 1] | Example1 |

TABLE 1-continued

| Example | Structure | $^1$H NMR | Example # |
|---|---|---|---|
| 91 | 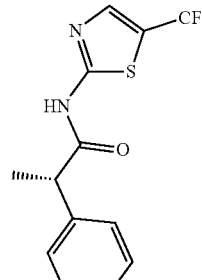 | $^1$H NMR (400 MHz, DMSO-$d_6$) δ13.00 (s, 1H), 11.05 (s, 1H), 9.51 (d, J = 1.2 Hz, 1H), 9.02 (d, J = 1.6 Hz, 1H), 8.15 (s, 1H), 8.08 (s, 1H), 8.00 (dt, J = 7.6 Hz, 1H), 7.50 (t, J = 8.0 Hz, 1H), 7.45 (d, J = 7.6 Hz, 1H), 6.87 (dt, J = 15.6 Hz, 5.6 Hz, 1H), 6.48 (d, J = 15.6 Hz, 1H), 4.11 (q, J = 6.8 Hz, 1H), 3.08 (d, J = 4.8 Hz, 2H), 2.18 (s, 6H), 1.53 (d, J = 7.2 Hz, 3H); MS (m/z): 505.0 [M + 1]; 70 ee % | Example14 |
| 92 | 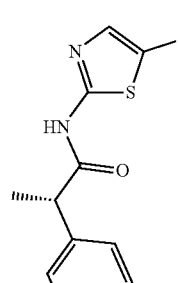 | $^1$H NMR (400 MHz, DMSO-$d_6$) δ 12.94 (s, 1H), 11.06 (s, 1H), 9.50 (d, J = 1.2 Hz, 1H), 9.01 (d, J = 1.6 Hz, 1H), 8.14 (s, 1H), 8.05 (s, 1H), 7.99 (d, J = 6.8 Hz, 1H), 7.51-7.44 (m, 2H), 6.86 (dt, J = 15.6 Hz, 5.6 Hz, 1H), 6.51 (d, J = 15.6 Hz, 1H), 4.15-4.08 (m, 1H), 3.61 (t, J = 4.4 Hz, 4H), 3.15 (d, J = 5.6 Hz, 2H), 2.43-2.38 (m, 4H), 1.52 (d, J = 6.8 Hz, 3H); MS (m/z): 547.0 [M + 1]; 72 ee % | Example14 |
| 93 | 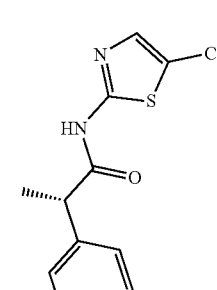 | $^1$H NMR (400 MHz, DMSO-$d_6$) δ 12.60(s, 1H), 11.03(s, 1H), 9.50(d, J = 1.2 Hz, 1H), 9.01(d, J = 1.2 Hz, 1H), 8.14(s, 1H), 8.00(d, J = 7.6 Hz, 1H), 7.56-7.44(m, 3H), 6.88(dt, J = 15.2, 6.0 Hz, 1H), 6.48(d, J = 18.8 Hz, 1H), 4.09(q, J = 7.2 Hz, 1H), 3.08(d, J = 4.4 Hz, 2H), 2.19(s, 6H), 1.52(d, J = 7.2 Hz, 3H); MS (m/z): 471.5 [M + 1]; 75 ee % | Example14 |

TABLE 1-continued
| Example | Structure | ¹H NMR | Example # |
|---|---|---|---|
| 94 | 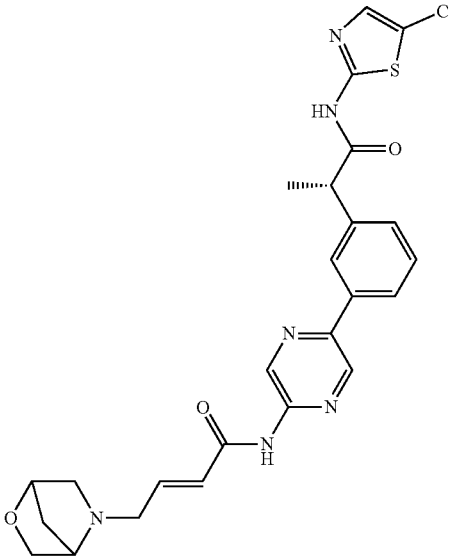 | ¹H NMR (400 MHz, DMSO-d₆) δ 12.60(s, 1H), 11.01(s, 1H), 9.50(d, J = 1.2 Hz, 1H), 9.00(d, J = 2.0 Hz, 1H), 8.13(s, 1H), 7.99(d, J = 11.2 Hz, 1H), 7.51-7.44(m, 3H), 6.89(dt, J = 15.6, 4.8 Hz, 1H), 6.52(d, J = 15.6 Hz, 1H), 4.37(s, 1H), 4.08(q, J = 6.8 Hz, 1H), 3.86(d, J = 7.6 Hz, 1H), 3.54(dd, J = 7.6, 1.6 Hz, 1H), 3.50(s, 6H), 3.40-3.36(m, 3H), 2.78(dd, J = 10.0, 1.6 Hz, 1H), 1.77(dd, J = 8.0, 1.6 Hz, 1H), 1.62-1.59(m, 1H), 1.52(d, J = 7.2 Hz, 3H); MS (m/z): 526.0 [M + 1]; 70 ee % | Example14 |
| 95 | 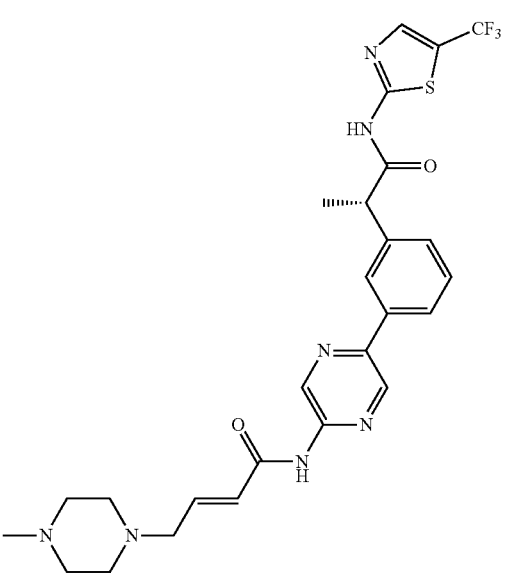 [SMILES: C[C@H](C(=O)Nc1ncc(C(F)(F)F)s1)c1cccc(-c2cnc(NC(=O)/C=C/CN3CCN(C)CC3)cn2)c1] | ¹H NMR (400 MHz, DMSO-d₆) δ 13.00 (s, 1H), 11.04 (s, 1H), 9.49 (d, J = 1.2 Hz, 1H), 9.01 (d, J = 1.2 Hz, 1H), 8.14 (s, 1H), 8.05 (s, 1H), 7.99 (d, J = 7.6 Hz, 1H), 7.51-7.44 (m, 2H), 6.86 (dt, J = 15.6, 6.0 Hz, 1H), 6.49 (d, J = 15.6 Hz, 1H), 4.13-4.09 (m, 1H), 3.14 (d, J = 6.0 Hz, 2H), 2.50-2.30 (m, 8H), 2.17 (s, 3H), 1.53 (d, J = 7.2 Hz, 3H); MS (m/z): 560.0 [M + 1]; 70 ee % | Example14 |

TABLE 1-continued
| Example | Structure | ¹H NMR | Example # |
|---|---|---|---|
| 96 | 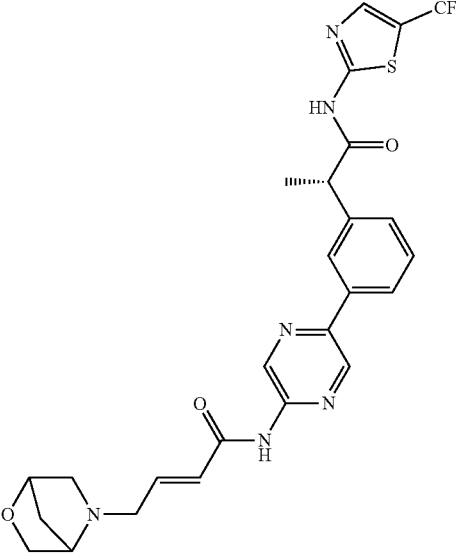 | ¹H NMR (400 MHz, DMSO-d₆) δ 13.01 (s, 1H), 11.02 (s, 1H), 9.50 (s, 1H), 9.01 (s, 1H), 8.14 (s, 1H), 8.07 (s, 1H), 7.99 (d, J = 7.2 Hz, 1H), 7.51-7.44 (m, 2H), 6.89 (dt, J = 15.2 Hz, 4.8 Hz, 1H), 6.52 (d, J = 15.2 Hz, 1H), 4.37 (s, 1H), 4.15-4.10 (m, 1H), 3.86 (d, J = 7.6 Hz, 1H), 3.54 (d, J = 7.6 Hz, 1H), 3.50 (s, 1H), 3.17 (d, J = 5.2 Hz, 2H), 2.78 (d, J = 9.6 Hz, 1H), 2.50-2.48 (m, 1H), 1.77 (d, J = 6.4 Hz, 1H); MS (m/z): 559.0 [M + 1]; 68 ee % | Example14 |
| 97 | 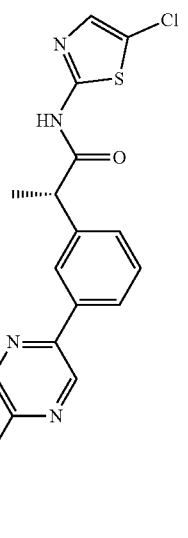 | ¹H NMR (400 MHz, DMSO-d₆) δ 12.61(s, 1H), 11.04(s, 1H), 9.50(d, J = 1.6 Hz, 1H), 9.01(d, J = 1.6 Hz, 1H), 8.14(s, 1H), 8.00(dt, J = 6.0, 1.2 Hz, 1H), 7.51-7.44(m, 3H), 6.86(dt, J = 15.6, 5.6 Hz, 1H), 6.49(d, J = 15.2 Hz, 1H), 4.09(q, J = 7.2 Hz, 1H), 3.14(d, J = 4.8 Hz, 2H), 2.41-2.36(m, 8H), 2.18(s, 3H), 1.52(d, J = 7.2 Hz, 3H); MS (m/z): 527.0 [M + 1]; 73 ee % | Example14 |

TABLE 1-continued

| Example | Structure | ¹H NMR | Example # |
|---|---|---|---|
| 98 | 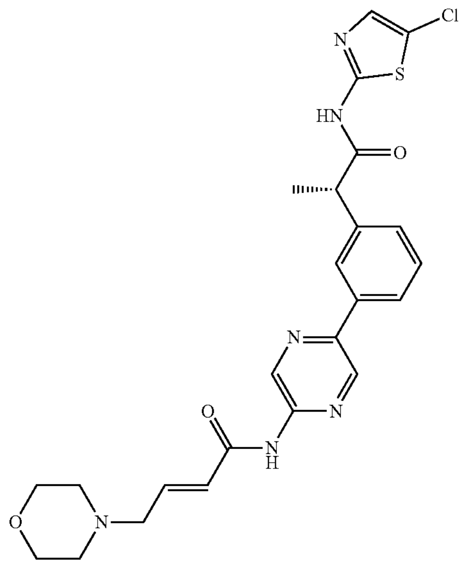 [SMILES: C[C@H](C(=O)Nc1ncc(Cl)s1)c1cccc(-c2cnc(NC(=O)/C=C/CN3CCOCC3)cn2)c1] | ¹H NMR (400 MHz, DMSO-$d_6$)) δ 12.61(s, 1H), 11.05(s, 1H), 9.50(d, J = 1.6 Hz, 1H), 9.01(d, J = 1.6 Hz, 1H), 8.14(s, 1H), 7.99(dt, J = 7.6, 1.6 Hz, 1H), 7.51-7.44(m, 3H), 6.87(dt, J = 15.6, 5.6 Hz, 1H), 6.51(d, J = 15.2 Hz, 1H), 4.09(q, J = 6.8 Hz, 1H), 3.61(t, J = 4.8 Hz, 4H), 3.15(dd, J = 6.0, 1.2 Hz, 1H), 2.41(t, J = 4.8 Hz, 4H), 1.51(d, J = 6.8 Hz, 3H); MS (m/z): 514.0 [M + 1]; 73 ee % | Example14 |
| 99 | 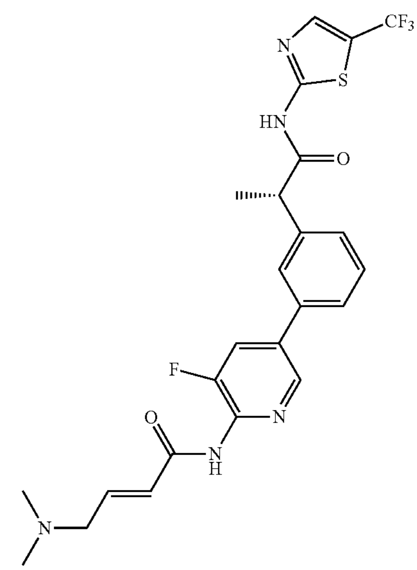 [SMILES: C[C@H](C(=O)Nc1ncc(C(F)(F)F)s1)c1cccc(-c2cnc(NC(=O)/C=C/CN(C)C)c(F)c2)c1] | ¹H NMR (400 MHz, DMSO-$d_6$) δ 10.40 (s, 1H), 8.60 (s, 1H), 8.11 (dd, J = 11.2 Hz, 2.0 Hz, 1H), 8.15-7.98 (m, 1H), 7.78 (s, 1H), 7.67 (d, J = 8.0 Hz, 1H), 7.49-7.40 (m, 2H), 6.80 (dt, J = 15.6 Hz, 6.0 Hz, 1H), 6.35 (d, J = 15.6 Hz, 1H) 4.07-4.02 (m, 1H), 3.08 (d, J = 7.2 Hz, 2H), 12.19 (s, 6H), 1.53 (d, J = 6.8 Hz, 3H); MS (m/z): 522.0 [M + 1]; 70 ee % | Example14 |

TABLE 1-continued
| Example | Structure | ¹H NMR | Example # |
|---|---|---|---|
| 100 | 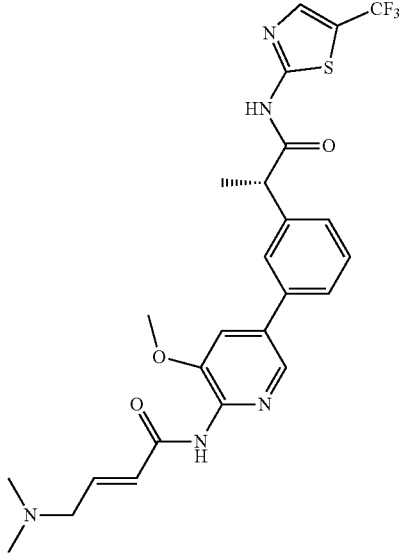 [SMILES: COc1cc(-c2cccc([C@H](C)C(=O)Nc3ncc(C(F)(F)F)s3)c2)cnc1NC(=O)/C=C/CN(C)C] | ¹H NMR (400 MHz, DMSO-d₆) δ 9.88 (s, 1H), 8.25 (d, J = 2.0 Hz, 1H), 7.99 (s, 1H), 7.73 (s, 1H), 7.67-7.64 (m, 2H), 7.49-7.39 (m, 2H), 6.72 (dt, J = 15.6 Hz, 2.0 Hz, 1H), 6.37 (d, J = 15.6 Hz, 1H), 4.09-4.03 (m, 1H), 3.92 (s, 3H), 3.05 (d, J = 6.0 Hz, 2H), 2.18 (s, 6H), 1.53 (d, J = 7.2 Hz, 3H); MS (m/z): 534.0 [M + 1]; 71 ee % | Example14 |
| 101 | 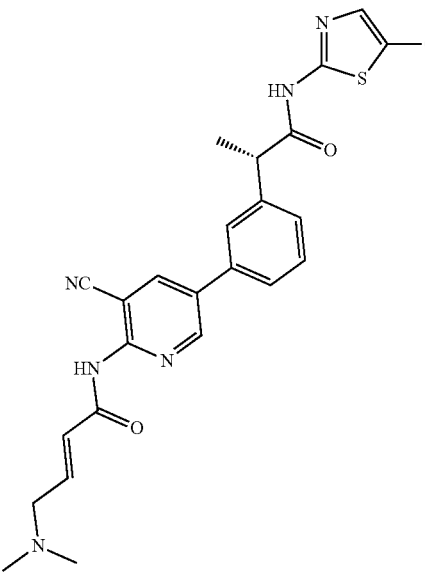 | ¹H NMR (400 MHz, DMSO-d₆) δ 12.91 (brs, 1H), 11.04 (s, 1H), 9.03 (d, J = 2.4 Hz, 1H), 8.67 (d, J = 2.4 Hz, 1H), 8.10 (t, J = 1.6 Hz, 1H), 7.84 (s, 1H), 7.75 (d, J = 7.6 Hz, 1H), 7.52 (t, J = 7.6 Hz, 1H), 7.46 (d, J = 8.0 Hz, 1H), 6.90 (dt, J = 15.6 Hz, 6.0 Hz, 1H), 6.40 (dt, J = 15.6 Hz, 1.6 Hz, 1H), 4.13 (q, J = 6.8 Hz, 1H), 3.12 (dd, J = 6.0 Hz, 1.2 Hz, 2H), 2.22 (s, 6H), 1.57 (d, J = 6.8 Hz, 3H); MS (m/z): 529.0 [M + 1]; 70 ee % | Example14 |

TABLE 1-continued
| Example | Structure | ¹H NMR | Example # |
|---|---|---|---|
| 102 | 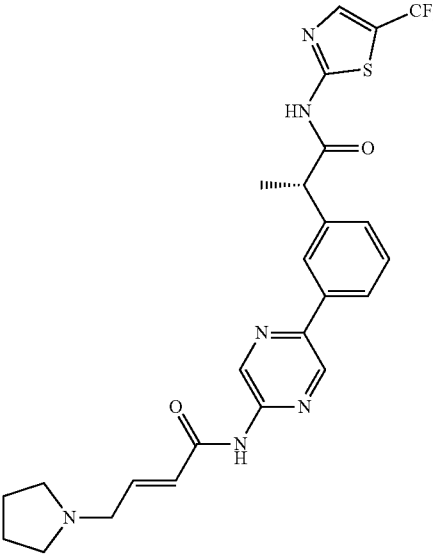 | ¹H NMR (400 MHz, DMSO-d₆) δ 11.01 (s, 1H), 9.50 (d, J = 1.6 Hz, 1H), 9.00 (d, J = 1.6 Hz, 1H), 8.14 (s, 1H), 8.03 (s, 1H), 7.99 (d, J = 7.2 Hz, 1H), 7.51-7.43 (m, 2H), 6.92 (dt, J = 15.2 Hz, 6.0 Hz, 1H), 6.50 (d, J = 15.6 Hz, 1H), 4.10 (q, J = 7.2 Hz, 1H), 3.40-3.30 (m, 4H), 3.26 (d, J = 5.6 Hz, 2H), 1.74-1.68 (m, 4H), 1.53 (d, J = 7.2 Hz, 3H); MS (m/z): 531.0 [M + 1]; 71 ee % | Example14 |
| 103 | 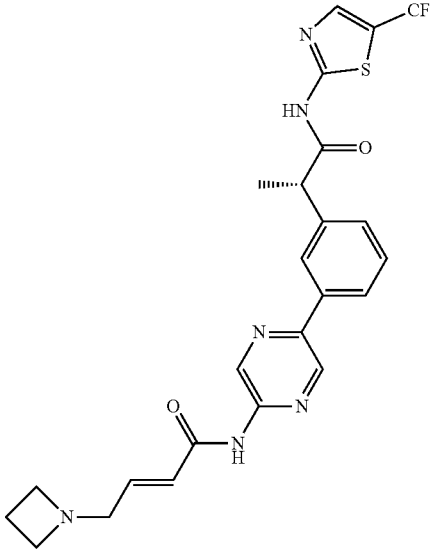 | ¹H NMR (400 MHz, DMSO-d₆) δ 10.99 (s, 1H), 9.49 (d, J = 1.6 Hz, 1H), 8.99 (d, J = 1.6 Hz, 1H), 8.12 (s, 1H), 7.98-7.92 (m, 2H), 7.49-7.43 (m, 2H), 7.81-6.75 (m, 1H), 6.44 (d, J = 15.6 Hz, 1H), 4.06-4.01 (m, 1H), 3.20-3.16 (m, 6H), 2.05-1.98 (m, 2H), 1.51 (d, J = 7.2 Hz, 3H); MS (m/z): 517.0 [M + 1]; 68 ee % | Example14 |

TABLE 1-continued
| Example | Structure | ¹H NMR | Example # |
|---|---|---|---|
| 104 | 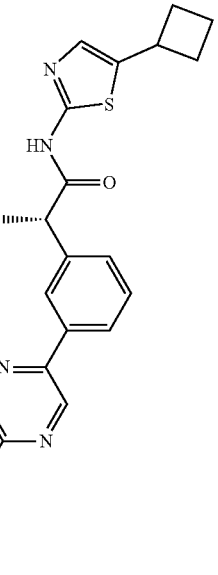 | ¹H NMR (400 MHz, DMSO-d₆) δ 12.18(s, 1H), 11.02(s, 1H), 9.50(d, J = 1.6 Hz, 1H), 9.00(d, J = 1.6 Hz, 1H), 8.15(s, 1H), 7.98(dt, J = 7.2, 2.0 Hz, 1H), 7.51-7.44(m, 2H), 7.15(d, J = 0.8 Hz, 1H), 6.88(dt, J = 15.6, 5.6 Hz, 1H), 6.48(dt, J = 15.6, 1.6 Hz, 1H), 4.07(q, J = 6.8 Hz, 1H), 3.63(qui, J = 8.4 Hz, 1H), 3.09(dd, J = 6.4, 1.6 Hz, 2H), 2.37-2.29(m, 2H), 2.19(s, 6H), 2.09-2.02(m, 2H), 1.97-1.90(m, 1H), 1.87-1.82(m, 1H), 1.50(d, J = 6.8 Hz, 3H); MS (m/z): 491.0 [M + 1]; ; 72 ee % | Example14 |
| 105 | 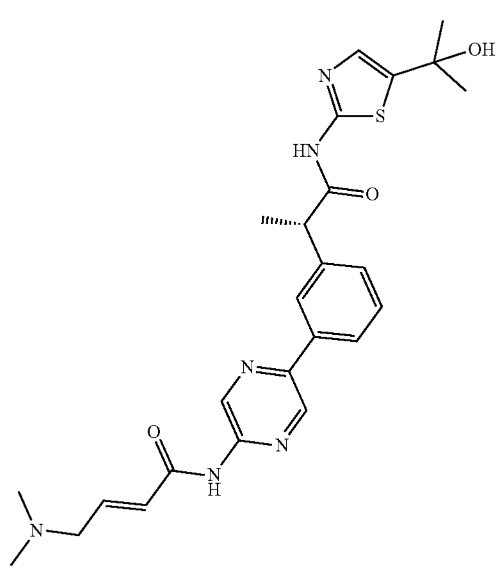 [SMILES: C[C@H](C(=O)Nc1ncc(C(C)(C)O)s1)c1cccc(-c2cnc(NC(=O)/C=C/CN(C)C)cn2)c1] | ¹H NMR (400 MHz, CDCl3) δ 10.51(s, 1H), 9.59-9.58(m, 1H), 8.57-8.39(m, 2H), 7.95-7.76(m, 2H), 7.42-7.38(m, 2H), 7.26-7.22(m, 2H), 7.05-7.00(m, 1H), 6.18(d, J = 15.6 Hz, 1H), 3.93(q, J = 7.2 Hz, 1H), 3.16(dd, J = 5.6, 1.2 Hz, 2H), 2.30(s, 6H), 1.67-1.65(m, 9H); MS (m/z): 495.0 [M + 1]; 66 ee % | Example14 |

TABLE 1-continued
| Example | Structure | ¹H NMR | Example # |
|---|---|---|---|
| 106 | 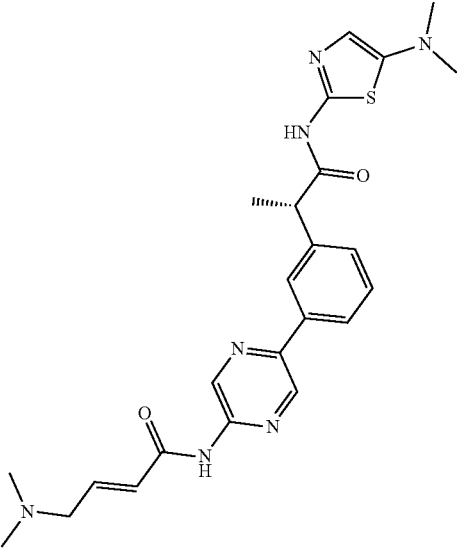 | ¹H NMR (400 MHz, DMSO-d₆) δ 11.91(s, 1H), 11.03(s, 1H), 9.51(s, 1H), 9.00(s, 1H), 8.14(s, 1H), 7.98(d, J = 7.6 Hz, 1H), 7.50-7.43(m, 2H), 6.88(dt, J = 15.2, 6.0 Hz, 1H), 6.48(d, J = 15.2 Hz, 1H), 6.42(s, 1H), 4.04-4.00(m, 1H), 3.08(d, J = 5.2 Hz, 2H), 2.75(s, 6H), 2.19(s, 6H), 1.48(d, J = 6.8 Hz, 3H); MS (m/z): 480.0 [M + 1]; 66 ee % | Example14 |
| 107 | 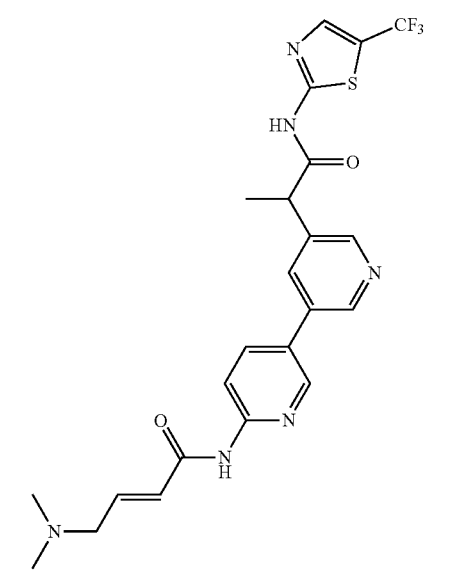 [SMILES: CC(C(=O)Nc1ncc(C(F)(F)F)s1)c1cncc(-c2ccc(NC(=O)/C=C/CN(C)C)nc2)c1] | ¹H NMR (400 MHz, DMSO-d₆) 8.82 (d, J = 2.4 Hz, 1H), 8.60 (d, J = 2.0 Hz, 1H), 8.49 (d, J = 2.4 Hz, 1H), 8.44 (d, J = 8.4 Hz, 1H), 8.19 (s, 1H), 7.93 (dd, J = 8.8 Hz, 1.8 Hz, 1H), 7.85 (t, J = 2.4 Hz, 1H), 7.75 (d, J = 1.6 Hz, 1H), 7.09-6.99 (m, 1H), 6.16 (d, J = 15.2 Hz, 1H), 3.93 (q, J = 7.2 Hz, 1H), 3.14 (dd, J = 6.0 Hz, 1.6 Hz, 2H), 2.29 (s, 6H), 1.72 (d, J = 6.8 Hz, 3H); MS (m/z): 505.0 [M + 1] | Example1 |

TABLE 1-continued

| Example | Structure | ¹H NMR | Example # |
|---|---|---|---|
| 108 | 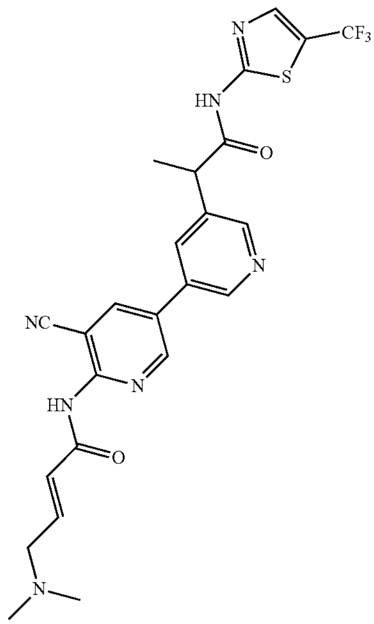 [SMILES: CC(C(=O)Nc1ncc(C(F)(F)F)s1)c1cncc(-c2cnc(NC(=O)/C=C/CN(C)C)c(C#N)c2)c1] | ¹H NMR (400 MHz, DMSO-d₆) δ 11.08 (s, 1H), 9.11 (d, J = 2.4 Hz, 1H), 8.95 (d, J = 2.4 Hz, 1H), 8.80 (d, J = 2.4 Hz, 1H), 8.66 (d, J = 2.0 Hz, 1H), 8.24 (t, J = 2.0 Hz, 1H), 8.04 (s, 1H), 6.92 (dt, J = 15.6 Hz, 5.6 Hz, 1H), 6.41 (dt, J = 15.2 Hz, 1.6 Hz, 1H), 4.15 (q, J = 7.6 Hz, 1H), 3.13 (d, J = 6.0 Hz, 2H), 2.21 (s, 6H), 1.62 (d, J = 7.2 Hz, 3H); MS (m/z): 530.0 [M + 1] | Example1 |
| 109 | 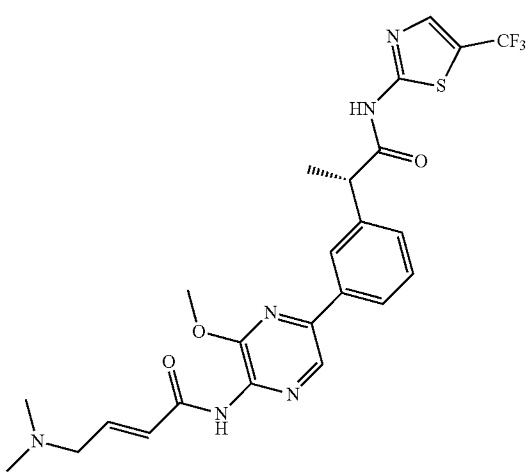 [SMILES: COc1nc(-c2cccc([C@H](C)C(=O)Nc3ncc(C(F)(F)F)s3)c2)cnc1NC(=O)/C=C/CN(C)C] | ¹H NMR (400 MHz, DMSO-d₆) δ 12.95(s, 1H), 10.21(s, 1H), 8.60(s, 1H), 8.10-8.08(m, 2H), 8.01(d, J = 7.2 Hz, 1H), 7.52-7.44(m, 2H), 6.77(dt, J = 15.6, 6.0 Hz, 1H), 6.41(d, J = 15.2 Hz, 1H), 4.14(q, J = 6.8 Hz, 1H), 4.03(s, 3H), 3.07(dd, J = 6.0, 1.2 Hz, 2H), 2.19(s, 6H), 1.54(d, J = 7.2 Hz, 3H); MS (m/z): 535.0 [M + 1]; 68 ee % | Example14 |

TABLE 1-continued
| Example | Structure | ¹H NMR | Example # |
|---|---|---|---|
| 110 | 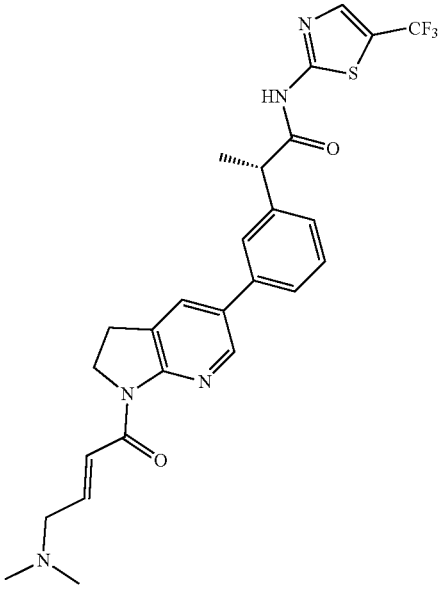 [SMILES: C[C@H](C(=O)Nc1ncc(C(F)(F)F)s1)c1cccc(-c2cnc3c(c2)CCN3C(=O)/C=C/CN(C)C)c1] | ¹H NMR (400 MHz, DMSO-$d_6$) δ 8.44 (s, 1H), 7.96-7.91 (m, 3H), 7.69 (s, 1H), 7.57 (d, J = 7.6 Hz, 1H), 7.43 (t, J = 7.6 Hz, 1H), 7.36 (d, J = 7.6 Hz, 1H), 6.87 (dd, J = 15.6 Hz, 6.0 Hz, 1H), 4.12-4.02 (m, 3H), 3.13-3.11 (m, 4H), 2.20 (s, 6H), 1.51 (d, J = 7.2 Hz, 3H); MS (m/z): 530.0 [M + 1]; 69 ee % | Example14 |
| 111 | 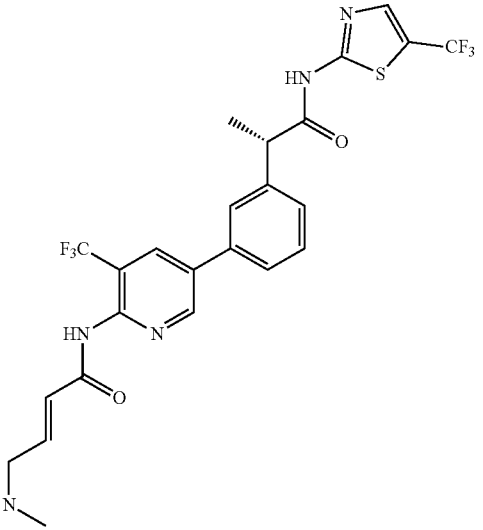 | ¹H NMR (400 MHz, DMSO-$d_6$) δ 10.38 (s, 1H), 9.04 (s, 1H), 8.41 (s, 1H), 7.08-7.70 (m, 2H), 7.51-7.46 (m, 2H), 6.80-6.75 (m, 2H), 6.32 (d, J = 15.2 Hz, 1H), 4.10-4.00 (m, 1H), 3.08 (d, J = 7.2 Hz, 2H), 2.19 (s, 6H), 1.52 (d, J = 7.2 Hz, 3H); MS (m/z): 572.0 [M + 1]; 70 ee % | Example14 |
| 112 | 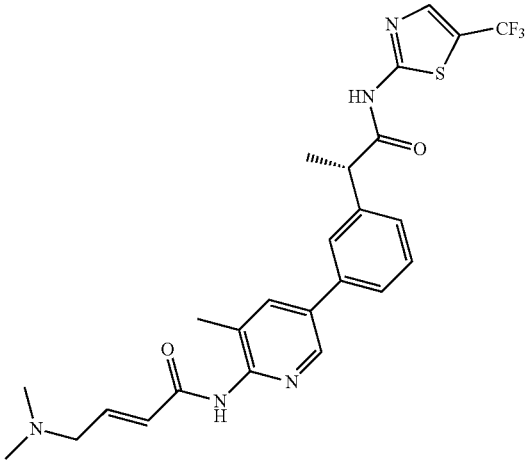 [SMILES: Cc1cc(-c2cccc([C@H](C)C(=O)Nc3ncc(C(F)(F)F)s3)c2)cnc1NC(=O)/C=C/CN(C)C] | ¹H NMR (400 MHz, DMSO-$d_6$) δ10.21 (s, 1H), 8.54 (d, J = 2.0 Hz, 1H), 7.97 (d, J = 1.6 Hz, 2H), 7.71 (s, 1H), 7.61 (d, J = 8.0 Hz, 1H), 7.45 (t, J = 7.6 Hz, 1H), 7.39 (d, J = 8.0 Hz, 1H), 6.76 (dt, J = 15.6 Hz, 6.0 Hz, 1H), 6.34 (d, J = 15.6 Hz, 1H), 4.11 (q, J = 5.2 Hz, 1H), 3.07 (d, J = 6.0 Hz, 2H), 2.24 (s, 3H), 2.19 (s, 6H), 1.52 (d, J = 7.2 Hz, 3H); MS (m/z): 518.0 [M + 1]; 70 ee % | Example14 |

TABLE 1-continued

| Example | Structure | ¹H NMR | Example # |
|---|---|---|---|
| 113 | 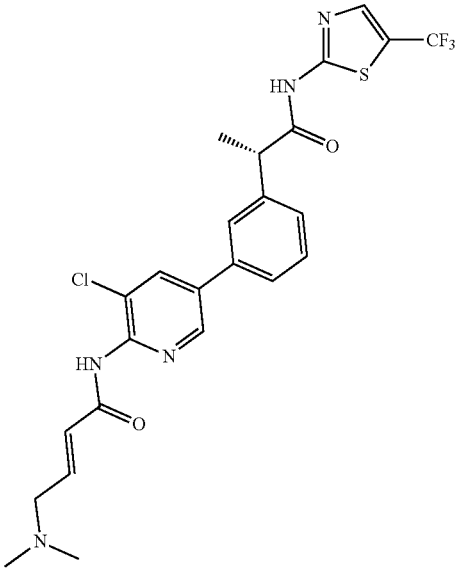 | ¹H NMR (400 MHz, DMSO-d₆) δ 10.41 (s, 1H), 8.72 (d, J = 2.0 Hz, 1H), 8.29 (d, J = 2.0 Hz, 1H), 7.99 (s, 1H), 7.78 (s, 1H), 7.68 (d, J = 7.6 Hz, 1H), 7.48 (t, J = 7.6 Hz, 1H), 7.42 (d, J = 8.0 Hz, 1H), 6.79 (dt, J = 15.6 Hz, 6.0 Hz, 1H), 6.34 (d, J = 15.6 Hz, 1H), 4.11 (q, 5.2 Hz, 1H), 3.08 (dd, J = 6.0 Hz, 2H), 2.19 (s, 6H), 1.53 (d, J = 7.2 Hz, 3H); MS (m/z): 538.5 [M + 1]; 68 ee % | Example14 |
| 114 | 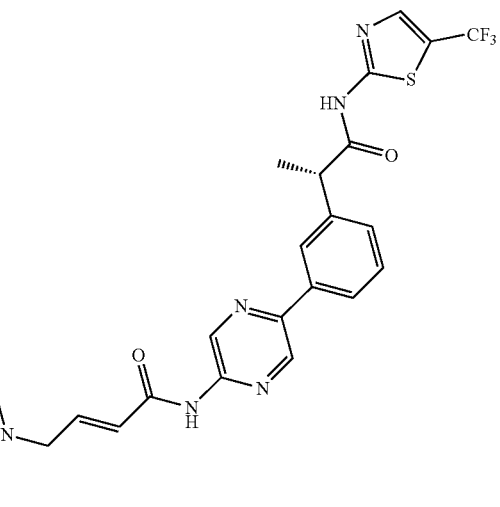 | ¹H NMR (400 MHz, DMSO-d₆) δ 12.97(s, 1H), 11.03(s, 1H), 9.50(d, J = 1.2 Hz, 1H), 9.01(d, J = 1.2 Hz, 1H), 8.15(s, 1H), 8.09(d, J = 1.2 Hz, 1H), 8.00(d, J = 7.6 Hz, 1H), 7.52-7.44(m, 2H), 6.91 (dt, J = 15.2, 6.0 Hz, 1H), 6.50(d, J = 15.6 Hz, 1H), 4.14(q, J = 6.8 Hz, 1H), 3.24(d, J = 4.4 Hz, 2H), 2.50-2.46(m, 4H), 1.54(d, J = 7.2 Hz, 3H), 0.99(t, J = 6.8 Hz, 6H); MS (m/z): 533.0 [M + 1]; 67 ee % | Example14 |
| 115 | 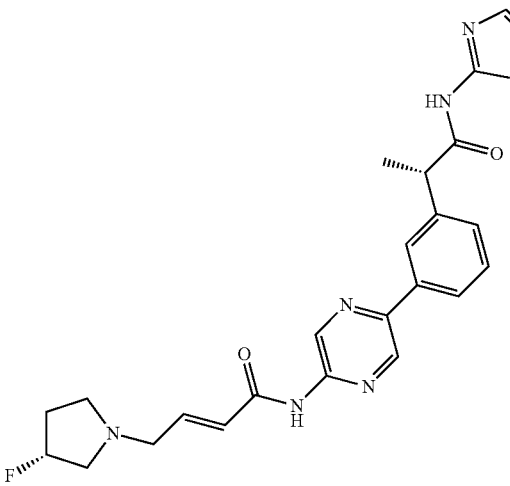 | ¹H NMR (400 MHz, DMSO-d₆) δ 12.99(s, 1H), 11.05(s, 1H), 9.50(d, J = 1.6 Hz, 1H), 9.01(d, J = 1.6 Hz, 1H), 8.15(s, 1H), 8.09-8.08(m, 1H), 8.00(dt, J = 7.6, 1.6 Hz, 1H), 7.52-7.45 (m, 2H), 6.91 (dt, J = 15.2, 5.6 Hz, 1H), 6.52(d, J = 15.2 Hz, 1H), 5.31-5.14(m, 1H), 4.14(q, J = 7.2 Hz, 1H), 3.31-3.29(m, 2H), 2.91-2.81(m, 2H), 2.72-2.60(m, 1H), 2.40-2.34(m, 1H), 2.23-2.08(m, 1H), 1.98-1.83(m, 1H), 1.54(d, J = 6.8 Hz, 3H); MS (m/z): 549.0 [M + 1]; 68 ee % | Example14 |

TABLE 1-continued
| Example | Structure | ¹H NMR | Example # |
|---|---|---|---|
| 116 | 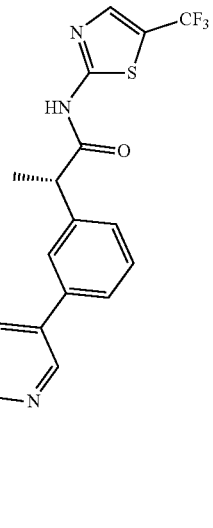 | ¹H NMR (400 MHz, DMSO-d₆) δ 10.75 (s, 1H), 8.65 (d, J = 2.0 Hz, 1H), 8.29 (d, J = 8.8 Hz, 1H), 8.10 (m, 1H), 8.04 (m, 1H), 7.72 (m, 1H), 7.61 (d, J = 7.2 Hz, 1H), 7.48(m, 1H), 7.44(m, 1H), 7.38(m, 1H), 7.29(m, 1H), 6.81(m, 1H), 6.46(m, 1H), 4.10 (m, 1H), 3.06 (d, J = 6.4 Hz, 1H), 2.18(s, 6H), 1.53 (d, J = 6.8 Hz, 1H); MS (m/z): 504.0 [M + 1]; 70 ee % | Example14 |
| 117 | 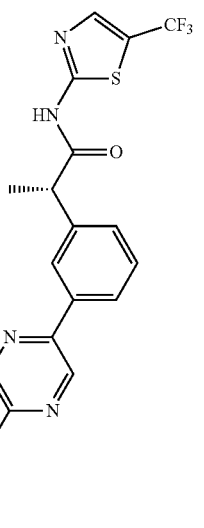 | ¹H NMR (400 MHz, DMSO-d₆) δ 12.97(s, 1H), 11.04(s, 1H), 9.50(d, J = 1.2 Hz, 1H), 9.01(d, J = 1.6 Hz, 1H), 8.15(s, 1H), 8.10-8.09(m, 1H), 8.00(dt, J = 7.6, 1.6 Hz, 1H), 7.52-7.45(m, 2H), 6.91(dt, J = 15.6, 5.6 Hz, 1H), 6.52(dt, J = 15.6, 1.6 Hz, 1H), 5.31-5.14(m, 1H), 4.14(q, J = 6.8 Hz, 1H), 3.31-3.29(m, 2H), 2.91-2.81(m, 2H), 2.72-2.60(m, 1H), 2.40-2.34(m, 1H), 2.23-2.08(m, 1H), 1.98-1.83(m, 1H), 1.54(d, J = 7.2 Hz, 3H); MS (m/z): 549.0 [M + 1]; 65 ee % | Example14 |

TABLE 1-continued
| Example | Structure | ¹H NMR | Example # |
|---|---|---|---|
| 118 | 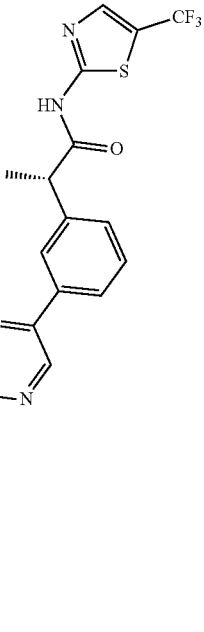 | ¹H NMR (400 MHz, DMSO-d₆) δ 13.02(s, 1H), 11.01(s, 1H), 9.50(d, J = 1.6 Hz, 1H), 9.01(d, J = 1.6 Hz, 1H), 8.14(s, 1H), 8.07(s, 1H), 8.00(d, J = 7.2 Hz, 1H), 7.51-7.44(m, 2H), 6.95-6.89(m, 1H), 6.48(d, J = 15.2 Hz, 1H), 4.24-4.22(m, 1H), 4.15(q, J = 6.8 Hz, 1H), 4.04-3.99(m, 1H), 3.73-3.52(m, 4H), 3.36(s, 3H), 3.34-3.16(m, 1H), 2.34-2.15(m, 1H), 2.09-2.01(m, 1H), 1.94-1.87(m, 1H), 1.76-1.72(m, 1H), 1.54(d, J = 6.8 Hz, 3H); MS (m/z): 575.0 [M + 1]; 65 ee % | Example14 |
| 119 | 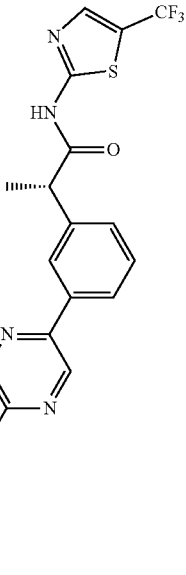 | ¹H NMR (400 MHz, DMSO-d₆) δ 12.96(s, 1H), 11.03(s, 1H), 9.50(d, J = 1.6 Hz, 1H), 9.07(d, J = 1.6 Hz, 1H), 8.15(s, 1H), 8.09(t, J = 1.2 Hz, 1H), 8.02-7.99(m, 1H), 7.52-7.44(m, 2H), 6.87(dt, J = 15.6, 6.0 Hz, 1H), 6.48(d, J = 15.6 Hz, 1H), 4.14(q, J = 7.2 Hz, 1H), 3.11(dd, J = 5.6, 1.2 Hz, 1H), 2.36(s, 4H), 1.55-1.50(m, 4H), 1.41-1.40(m, 2H); MS (m/z): 547.0 [M + 1]; 65 ee % | Example14 |

TABLE 1-continued
| Example | Structure | ¹H NMR | Example # |
|---|---|---|---|
| 120 | 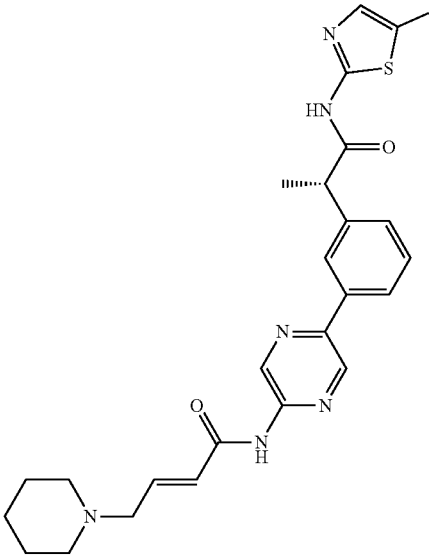 | ¹H NMR (400 MHz, DMSO-d₆) δ 12.97(s, 1H), 11.02(s, 1H), 9.50(d, J = 1.2 Hz, 1H), 9.01(d, J = 1.6 Hz, 1H), 8.15(s, 1H), 8.08(s, 1H), 8.00(d, J = 7.6 Hz, 1H), 7.52-7.44(m, 2H), 6.90(dt, J = 15.6, 5.2 Hz, 1H), 6.50(d, J = 15.6 Hz, 1H), 4.73-4.72(m, 1H), 4.21-4.20(m, 1H), 4.13(q, J = 6.8 Hz, 1H), 3.25(d, J = 5.6 Hz, 1H), 2.77-2.74(m, 1H), 2.63-2.51(m, 2H), 2.51-2.50(m, 1H), 2.37-2.34(m, 1H), 2.02-1.92(m, 1H), 2.09-2.01(m, 1H), 2.55-1.53(m, 5H); MS (m/z): 545.0 [M + 1]; 65 ee % | Example14 |
| 121 | 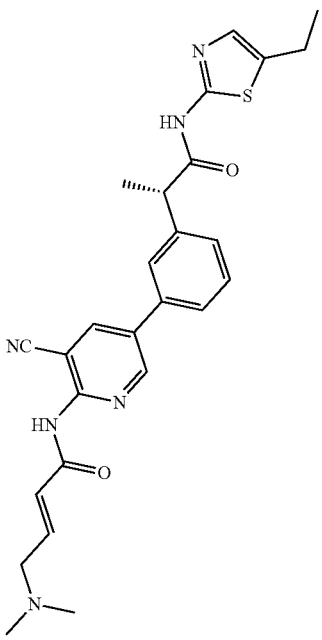 [SMILES: CCc1cnc(NC(=O)[C@@H](C)c2cccc(-c3cnc(NC(=O)/C=C/CN(C)C)c(C#N)c3)c2)s1] | ¹H NMR (400 MHz, DMSO-d₆) δ 12.10 (brs, 1H), 11.03 (brs, 1H), 9.01 (d, J = 2.4 Hz, 1H), 8.65 (d, J = 2.4 Hz, 1H), 7.82 (s, 1H), 7.72 (d, J = 7.6 Hz, 1H), 7.51-7.43 (m, 2H), 7.14 (s, 1H), 6.89 (dt, J = 15.6 Hz, 6.0 Hz, 1H), 6.38 (d, J = 15.6 Hz, 1H), 4.05 (q, J = 6.8 Hz, 1H), 3.10 (dd, J = 5.6 Hz, 1.2 Hz, 2H), 2.72 (q, J = 7.2 Hz, 2H), 2.20 (s, 6H), 1.52 (d, J = 7.2 Hz, 3H), 1.19 (t, J = 7.2 Hz, 3H); MS (m/z): 489.0 [M + 1]; 75 ee % | Example14 |

TABLE 1-continued

| Example | Structure | ¹H NMR | Example # |
|---|---|---|---|
| 122 | 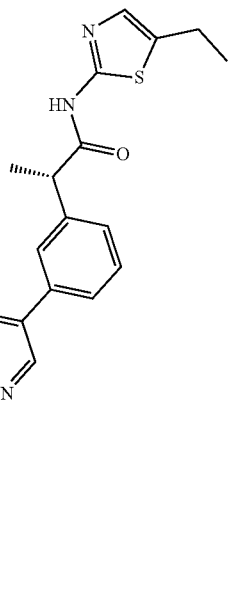 | ¹H NMR (400 MHz, DMSO-d₆) δ 12.10 (s, 1H), 8.44 (d, J = 2.0 Hz, 1H), 7.96-7.92 (m, 2H), 7.70 (s, 1H), 7.58 (d, J = 7.6 Hz, 1H), 7.43 (t, J = 7.6 Hz, 1H), 7.36 (d, J = 7.6 Hz, 1H), 7.12 (s, 1H), 6.87 (dd, J = 15.2 Hz, 6.4 Hz, 1H), 4.13-4.06 (m, 2H), 4.04-3.98 (m, 1H), 3.15-3.10 (m, 4H), 2.74-2.67 (m, 2H), 2.20 (s, 6H), 1.50 (d, J = 7.2 Hz, 3H), 1.19 (t, J = 7.6 Hz, 3H); MS (m/z): 490.0 [M + 1]; 72 ee % | Example14 |
| 123 | 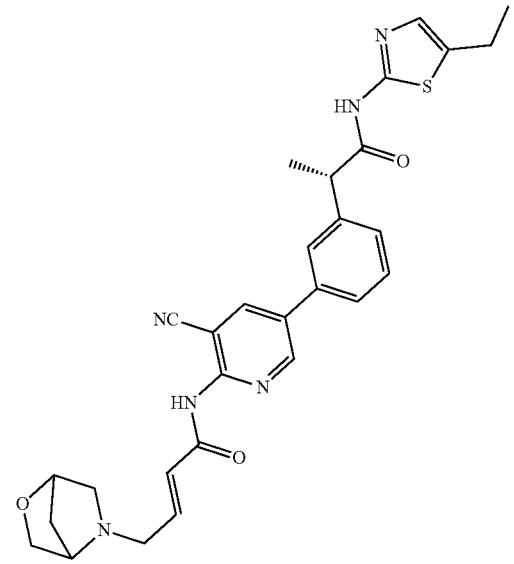 [SMILES: CCc1cnc(NC(=O)[C@@H](C)c2cccc(-c3cnc(NC(=O)/C=C/CN4CC5CC4CO5)c(C#N)c3)c2)s1] | ¹H NMR (400 MHz, DMSO-d₆) δ 12.11 (brs, 1H), 11.05 (brs, 1H), 9.00 (d, J = 2.4 Hz, 1H), 8.64 (d, J = 2.4 Hz, 1H), 7.82 (s, 1H), 7.71 (d, J = 8.0 Hz, 1H), 7.51-7.43 (m, 2H), 7.13 (s, 1H), 6.89 (dt, J = 15.6 Hz, 5.2 Hz, 1H), 6.41 (d, J = 15.2 Hz, 1H), 4.38 (s, 1H), 4.04 (q, J = 6.8 Hz, 1H), 3.86 (d, J = 7.6 Hz, 1H), 3.57-4.90 (m, 2H), 3.43-3.37 (m, 2H), 2.82-2.67 (m, 4H), 1.77 (d, J = 7.6 Hz, 1H), 1.61 (d, J = 10.2 Hz, 1H), 1.51 (d, J = 7.2 Hz, 3H), 1.19 (t, J = 7.2 Hz, 3H); MS (m/z): 543.0 [M + 1]; 73 ee % | Example14 |
| 124 | 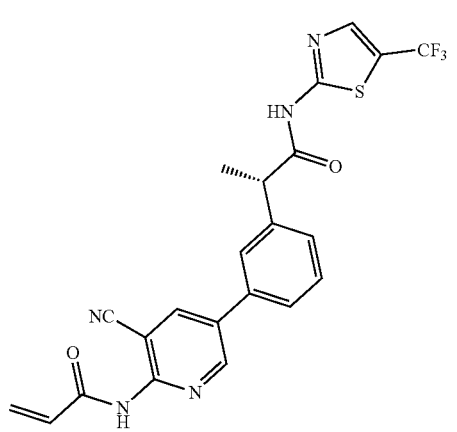 [SMILES: C=CC(=O)Nc1ncc(-c2cccc([C@H](C)C(=O)Nc3ncc(C(F)(F)F)s3)c2)cc1C#N] | ¹H NMR (400 MHz, CDCl3) δ 9.08 (s, 1H), 8.70 (d, J = 2.4 Hz, 1H), 8.19 (s, 1H), 8.17 (d, J = 2.4 Hz, 1H), 7.72 (d, J = 1.2 Hz, 1H), 7.57-7.41 (m, 3H), 6.60 (dd, J = 17.2 Hz, 1.2 Hz, 1H), 6.46 (dd, J = 16.8 Hz, 10.4 Hz, 1H), 5.95 (dd, J = 10.4 Hz, 1.2 Hz, 1H), 3.93 (q, J = 7.2 Hz, 1H), 1.70 (d, J = 7.2 Hz, 3H); MS (m/z): 472.0 [M + 1]; 71 ee % | Example14 |

TABLE 1-continued
| Example | Structure | ¹H NMR | Example # |
|---|---|---|---|
| 125 | 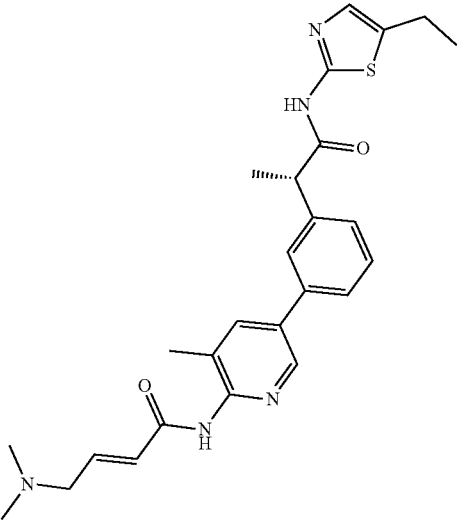 [SMILES: CCc1cnc(NC(=O)[C@@H](C)c2cccc(-c3cnc(NC(=O)/C=C/CN(C)C)c(C)c3)c2)s1] | ¹H NMR (400 MHz, DMSO-d₆) δ 12.13(s, 1H), 10.21(s, 1H), 8.54(d, J = 2.4 Hz, 1H), 7.96(d, J = 1.6 Hz, 1H), 7.73(s, 1H), 7.62(d, J = 8.0 Hz, 1H), 7.46(t, J = 7.6 Hz, 1H), 7.39(d, J = 7.6 Hz, 1H), 7.14(s, 1H), 6.76(dt, J = 15.2, 6.0 Hz, 1H), 6.34(d, J = 15.6 Hz, 1H), 4.04(q, J = 7.2 Hz, 1H), 3.07(d, J = 4.8 Hz, 2H), 2.72(q, J = 7.6 Hz, 2H), 2.24(s, 3H), 2.19(s, 6H), 1.50(d, J = 6.8 Hz, 3H), 1.19(t, J = 7.2 Hz, 3H); MS (m/z): 478.0 [M + 1]; 70 ee % | Example14 |
| 126 | 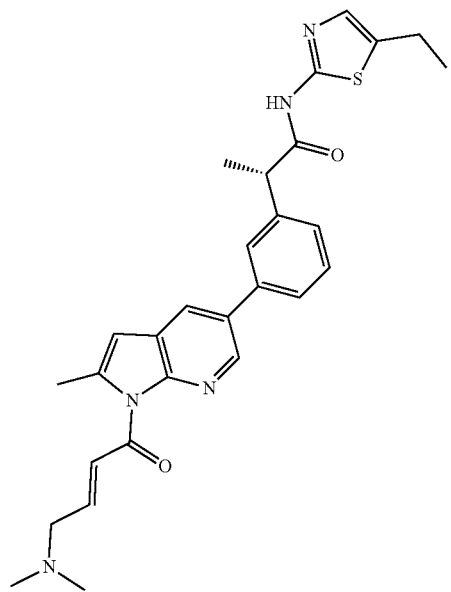 [SMILES: CCc1cnc(NC(=O)[C@@H](C)c2cccc(-c3cnc4c(c3)cc(C)n4C(=O)/C=C/CN(C)C)c2)s1] | ¹H NMR (400 MHz, DMSO-d₆) δ 12.12(s, 1H), 8.51(d, J = 1.2 Hz, 1H), 8.13(d, J = 1.6 Hz, 1H), 7.74(s, 1H), 7.61(d, J = 7.6 Hz, 1H), 7.45(t, J = 7.6 Hz, 1H), 7.35(d, J = 8.0 Hz, 1H), 7.14-7.09(m, 2H), 6.87-6.78(m, 1H), 6.43(s, 1H), 4.06-4.01(m, 1H), 3.36(d, J = 7.2 Hz, 1H), 3.07(s, 3H), 2.86(s, 3H), 2.72(q, J = 7.2 Hz, 2H), 2.52(s, 3H), 1.51(d, J = 7.2 Hz, 3H), 1.24(s, 3H), 1.21-1.17(m, 3H); MS (m/z): 502.0 [M + 1]; 70 ee % | Example14 |

TABLE 1-continued
| Example | Structure | ¹H NMR | Example # |
|---|---|---|---|
| 127 | 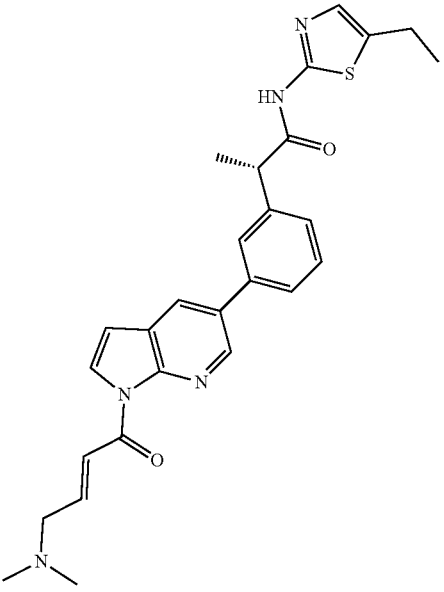 [SMILES: CCc1cnc(NC(=O)[C@@H](C)c2cccc(-c3cnc4c(ccn4C(=O)/C=C/CN(C)C)c3)c2)s1] | ¹H NMR (400 MHz, DMSO-d₆) δ 12.13(s, 1H), 8.58(d, J = 2.0 Hz, 1H), 8.26(d, J = 2.0 Hz, 1H), 8.02(d, J = 3.6 Hz, 1H), 7.74(s, 1H), 7.62(d, J = 7.6 Hz, 1H), 7.52-7.44(m, 2H), 7.37(d, J = 7.6 Hz, 1H), 7.14(s, 1H), 6.73(d, J = 3.6 Hz, 1H), 6.29-6.25(m, 1H), 4.06-4.04(m, 1H), 3.36-3.33(m, 2H), 3.06(s, 3H), 2.86(s, 3H), 2.71(q, J = 7.6 Hz, 2H), 1.51(d, J = 6.8 Hz, 3H), 1.18(d, J = 7.6 Hz, 3H); MS (m/z): 488.0 [M + 1]; 70 ee % | Example14 |
| 128 | 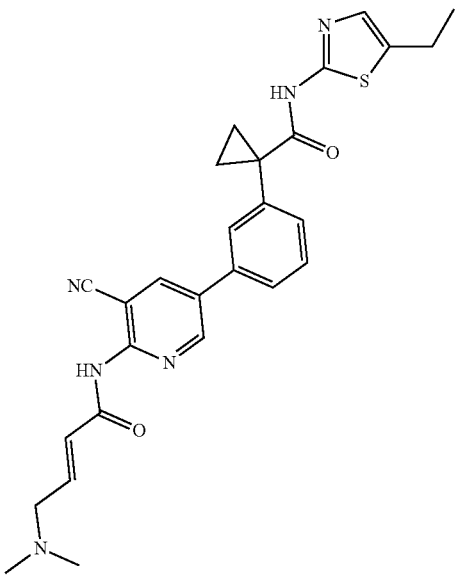 [SMILES: CCc1cnc(NC(=O)C2(c3cccc(-c4cnc(NC(=O)/C=C/CN(C)C)c(C#N)c4)c3)CC2)s1] | ¹H NMR (400 MHz, DMSO-d₆) δ 11.03(s, 1H), 9.06(d, J = 2.4 Hz, 1H), 8.72(d, J = 2.4 Hz, 1H), 7.85(s, 1H), 7.79-7.76(m, 1H), 7.52-7.47(m, 2H), 7.11(s, 1H), 6.88(dt, J = 15.6, 5.6 Hz, 1H), 6.38(d, J = 15.6 Hz, 1H), 3.11-3.10(m, 2H), 2.72(q, J = 7.2 Hz, 1H), 2.20(s, 6H), 1.56-1.55(m, 2H), 1.33-1.31(m, 2H), 1.20(t, J = 7.6 Hz, 3H); MS (m/z): 501.0 [M + 1]; 70 ee % | Example43 |

TABLE 1-continued
| Example | Structure | ¹H NMR | Example # |
|---|---|---|---|
| 129 | 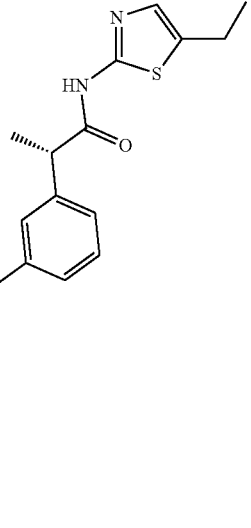 | ¹H NMR (400 MHz, DMSO-d₆) 12.13 (s, 1H), 8.78 (d, J = 2.4 Hz, 1H), 8.16 (dd, J = 8.4 Hz, 2.4 Hz, 1H), 7.75 (s, 1H), 7.65 (d, J = 7.6 Hz, 1H), 7.51-7.41 (m, 3H), 7.14 (s, 1H), 6.70 (dt, J = 15.2 Hz, 6.0 Hz, 1H), 6.16 (d, J = 14.8 Hz, 1H), 4.05 (q, J = 6.8 Hz, 1H), 2.96 (d, J = 5.2 Hz, 2H), 2.72 (q, J = 7.6 Hz, 2H), 2.09 (s, 9H), 1.51 (d, J = 7.2 Hz, 3H), 1.19 (t, J = 7.6 Hz, 3H); MS (m/z): 478.0 [M + 1]; 65 ee % | Example1 |
| 130 | 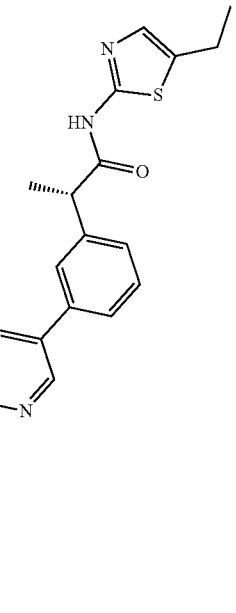 | ¹H NMR (400 MHz, DMSO-d₆) δ 12.10 (brs, 1H), 10.48 (s, 1H), 8.59 (s, 1H), 8.10 (dd, J = 11.2 Hz, 2.0 Hz, 1H), 7.78 (s, 1H), 7.68 (d, J = 7.6 Hz, 1H), 7.48 (t, J = 7.6 Hz, 1H), 7.42 (d, J = 8.0 Hz, 1H), 7.13 (s, 1H), 6.80 (dt, J = 15.2 Hz, 6.0 Hz, 1H), 6.35 (d, J = 15.6 Hz, 1H), 4.03 (q, J = 7.2 Hz, 1H), 3.07 (d, J = 5.2 Hz, 2H), 2.72 (q, J = 7.2 Hz, 2H), 2.19 (s, 6H), 1.51 (d, J = 6.8 Hz, 3H), 1.19 (t, J = 7.2 Hz, 3H); MS (m/z): 482.0 [M + 1]; 65 ee % | Example14 |

TABLE 1-continued
| Example | Structure | ¹H NMR | Example # |
|---|---|---|---|
| 131 | 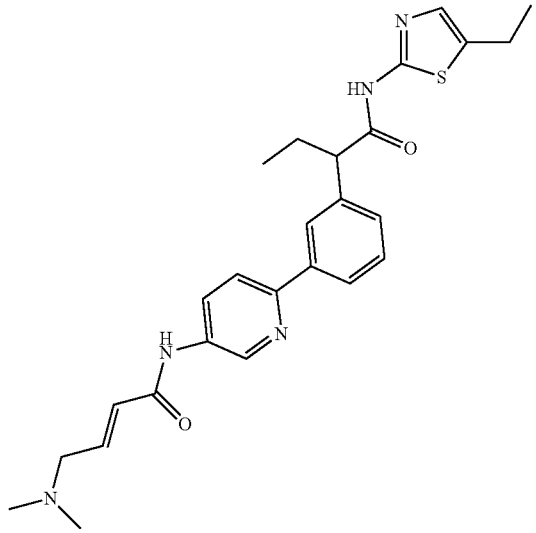 [SMILES: CCc1cnc(NC(=O)C(CC)c2cccc(-c3ccc(NC(=O)/C=C/CN(C)C)cn3)c2)s1] | ¹H NMR (400 MHz, DMSO-d₆) δ 12.17(s, 1H), 10.40(s, 1H), 8.88(d, J = 2.4 Hz, 1H), 8.23(dd, J = 8.8, 2.4 Hz, 1H), 8.11(s, 1H), 7.93-7.89(m, 2H), 7.14(s, 1H), 6.83-6.77(m, 1H), 6.31(d, J = 15.2 Hz, 1H), 3.81(t, J = 7.2 Hz, 1H), 3.09(d, J = 6.0 Hz, 2H), 2.72(t, J = 7.6 Hz, 2H), 2.20(s, 6H), 2.16-2.09(m, 1H), 1.84-1.77(m, 1H), 1.19(t, J = 7.6 Hz, 3H), 0.86(t, J = 7.2 Hz, 3H); MS (m/z): 478.0 [M + 1] | Example1 |
| 132 | 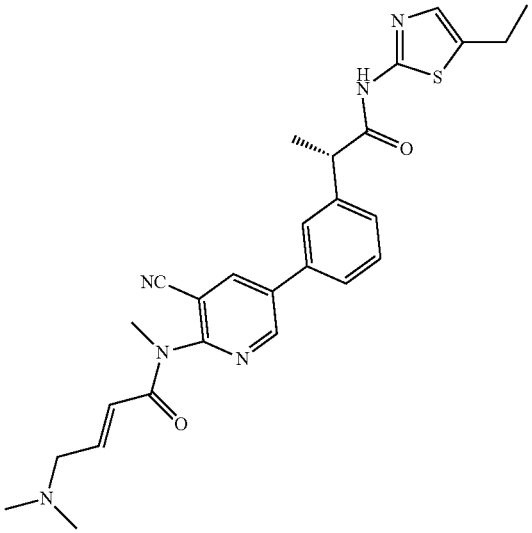 [SMILES: CCc1cnc(NC(=O)[C@@H](C)c2cccc(-c3cnc(N(C)C(=O)/C=C/CN(C)C)c(C#N)c3)c2)s1] | 1H NMR, 400 MHz, CDCl3, 8.87 (d, J = 2.4 Hz, 1H), 8.19 (d, J = 2.4 Hz, 1H), 7.56-7.45 (m, 4H), 7.04-6.99 (m, 2H), 6.13-6.09 (m, 1H), 3.75-3.67 (m, 1H), 3.52 (s, 3H), 3.16-3.11 (m, 2H), 2.78 (q, J = 7.6 Hz, 2H), 2.30 (s, 6H), 1.69 (d, J = 7.2 Hz, 3H), 1.29 (t, J = 7.6 Hz, 3H); MS (m/z): 503.0 [M + 1]; 72 ee % | Example14 |

TABLE 1-continued
| Example | Structure | ¹H NMR | Example # |
|---|---|---|---|
| 133 | 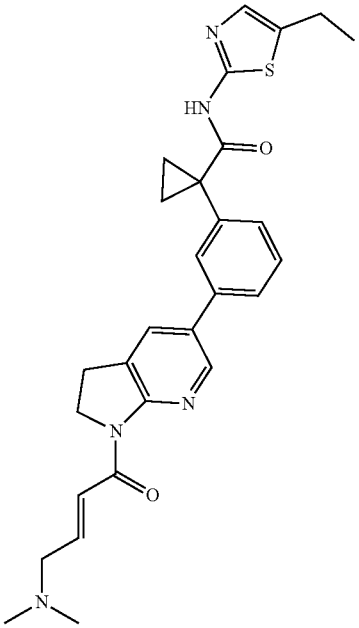 [SMILES: CCc1cnc(NC(=O)C2(c3cccc(-c4cnc5c(c4)CCN5C(=O)/C=C/CN(C)C)c3)CC2)s1] | ¹H NMR (400 MHz, DMSO-d₆) δ 11.09(s, 1H), 8.49(d, J = 2.0 Hz, 1H), 8.02(s, 1H), 7.94(d, J = 15.6 Hz, 1H), 7.72(s, 1H), 7.63(d, J = 8 Hz, 1H), 7.45(t, J = 7.6 Hz, 1H), 7.40(d, J = 7.6 Hz, 2H), 7.11(s, 1H), 6.87(dt, J = 15.6, 6.0 Hz, 1H), 4.09(t, J = 8.0 Hz, 2H), 3.15-3.10(m, 4H), 2.71(q, J = 7.2 Hz, 2H), 2.19(s, 6H), 1.55-1.52(m, 2H), 1.29-1.26(m, 2H), 1.21-1.16(m, 3H); MS (m/z): 502.0 [M + 1] | Example1 |
| 134 | 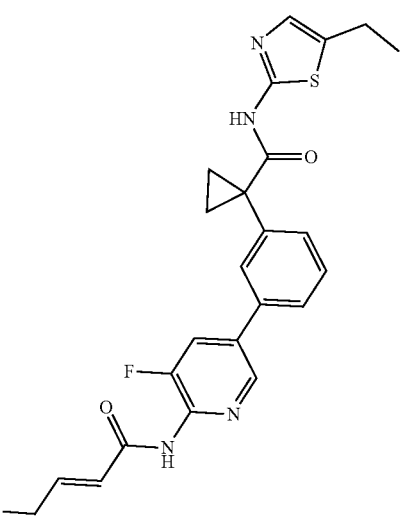 | ¹H NMR (400 MHz, DMSO-d₆) δ 8.63 (s, 1H), 8.16 (dd, J = 11.6 Hz, 2.0 Hz, 1H), 7.78 (s, 1H), 7.71 (d, J = 7.2 Hz, 1H), 7.49-7.43 (m, 2H), 7.08 (s, 1H), 6.80 (dt, J = 15.6, 6.0 Hz, 1H), 6.34 (d, J = 15.6 Hz, 1H), 3.07 (d, J = 6.0 Hz, 2H), 2.70 (q, J = 7.6 Hz, 2H), 2.19 (s, 6H), 1.55-1.51 (m, 2H), 1.28-1.24 (m, 2H), 1.20-1.16 (m, 3H); MS (m/z): 494.0 [M + 1] | Example1 |

TABLE 1-continued
| Example | Structure | ¹H NMR | Example # |
|---|---|---|---|
| 135 | 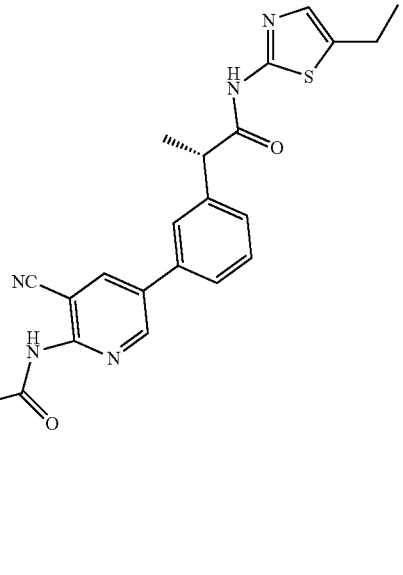 | ¹H NMR (400 MHz, DMSO-d₆) δ 12.12 (s, 1H), 11.06 (s, 1H), 9.03 (d, J = 2.4 Hz, 1H), 8.67 (d, J = 2.4 Hz, 1H) 7.84 (s, 1H), 7.74 (d, J = 8.0 Hz, 1H), 7.53-7.49 (m, 1H), 7.46 (d, J = 8.0 Hz, 1H), 7.16 (s, 1H), 6.93-6.86 (m, 1H), 6.43 (d, J = 15.6 Hz, 1H), 4.09-4.04 (m, 1H), 3.63 (t, J = 4.6 Hz, 4H), 3.19 (d, J = 5.2 Hz, 2H), 2.73 (q, J = 7.4 Hz, 2H), 2.44 (m, 4H), 1.53 (d, J = 6.8 Hz, 3H), 1.21 (t, J = 7.4 Hz, 3H); MS (m/z): 531.0 [M + 1]; 68 ee % | Example14 |
| 136 | 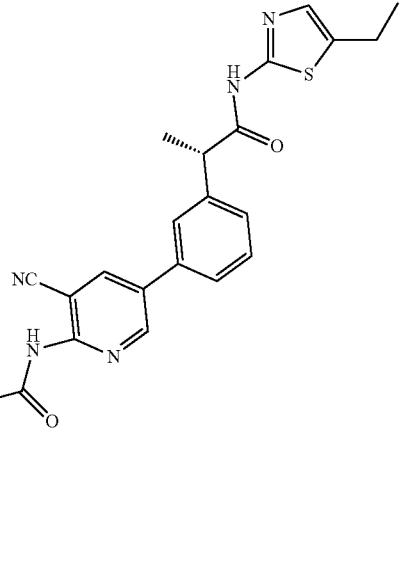 | ¹H NMR (400 MHz, DMSO-d₆) δ 12.12 (s, 1H), 11.04 (s, 1H), 9.02 (d, J = 2.4 Hz, 1H), 8.66 (d, J = 2.4 Hz, 1H), 7.84 (s, 1H), 7.74 (d, J = 7.6 Hz, 1H), 7.53-7.45 (m, 2H), 7.16 (s, 1H), 6.92-6.86 (m, 1H), 6.43 (d, J = 15.6 Hz, 1H), 4.09-4.04 (m, 1H), 3.18 (d, J = 4.8 Hz, 2H), 2.76-2.69 (m, 2H), 2.44-2.35 (m, 8H), 1.93 (s, 3H) 1.54 (d, J = 6.8 Hz, 3H), 1.21 (t, J = 7.4 Hz, 3H); MS (m/z): 544.0 [M + 1]; 66 ee % | Example14 |

TABLE 1-continued

| Example | Structure | ¹H NMR | Example # |
|---|---|---|---|
| 137 | 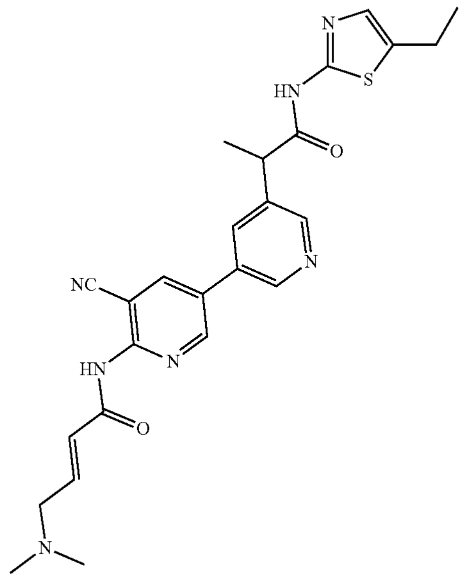 [SMILES: CCc1cnc(NC(=O)C(C)c2cncc(-c3cnc(NC(=O)/C=C/CN(C)C)c(C#N)c3)c2)s1] | ¹H NMR (400 MHz, DMSO-d₆) δ 12.25(s, 1H), 11.10(s, 1H), 9.10(d, J = 2.4 Hz, 1H), 8.95(d, J = 2.0 Hz, 1H), 8.79(d, J = 2.4 Hz, 1H), 8.65(d, J = 2.0 Hz, 1H), 8.23(t, J = 2.0 Hz, 1H), 7.17(t, J = 1.2 Hz, 1H), 6.91(dt, J = 15.6, 5.6 Hz, 1H), 6.40(dt, J = 15.6, 1.6 Hz, 1H), 4.12(q, J = 7.2 Hz, 1H), 3.12(dd, J = 6.0, 2.0 Hz, 2H), 2.76-2.72(m, 2H), 2.21 (s, 6H), 1.59(d, J = 7.2 Hz, 3H), 1.21(t, J = 7.6 Hz, 3H); MS (m/z): 490.0 [M + 1] | Example1 |
| 138 | 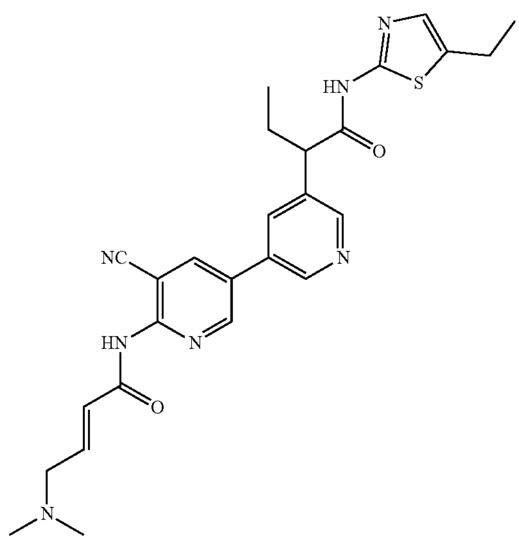 [SMILES: CCc1cnc(NC(=O)C(CC)c2cncc(-c3cnc(NC(=O)/C=C/CN(C)C)c(C#N)c3)c2)s1] | ¹H NMR (400 MHz, DMSO-d₆) δ 9.01 (d, J = 2.4 Hz, 1H), 8.65 (d, J = 2.4 Hz, 1H), 7.82 (s, 1H), 7.73 (d, J = 7.6 Hz, 1H), 7.51 (t, J = 7.6 Hz, 1H), 7.46 (d, J = 7.6 Hz, 1H), 7.15 (s, 1H), 6.89 (dt, J = 15.6 Hz, 6.0 Hz, 1H), 6.39 (d, J = 15.6 Hz, 1H), 3.83 (t, J = 7.2 Hz, 1H), 3.12 (d, J = 6.0 Hz, 2H), 2.73 (q, J = 7.2 Hz, 1H), 2.22 (s, 6H), 1.21 (t, J = 7.6 Hz, 3H), 0.89 (t, J = 7.2 Hz, 3H); MS (m/z): 503.0 [M + 1] | Example1 |
| 139 | 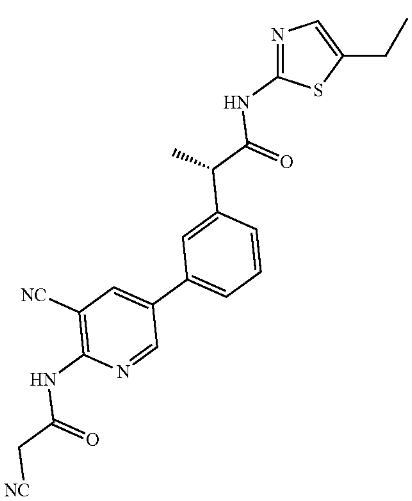 [SMILES: CCc1cnc(NC(=O)[C@@H](C)c2cccc(-c3cnc(NC(=O)CC#N)c(C#N)c3)c2)s1] | ¹H NMR (400 MHz, DMSO-d₆) δ 12.16 (br, 1H), 11.79 (br, 1H), 8.93 (s, 2H), 7.81 (s, 1H), 7.72 (d, J = 8.0 Hz, 1H), 7.51 (t, J = 7.6 Hz, 1H), 7.43 (d, J = 8.0 Hz, 1H), 7.15(s, 1H), 4.06 (m, 1H), 3.32(s, 2H), 1.55 (d, J = 7.2 Hz, 1H), 1.21 (m, 3H); MS (m/z): 445.0 [M + 1]; 70 ee % | Example14 |

TABLE 1-continued

| Example | Structure | ¹H NMR | Example # |
|---|---|---|---|
| 140 | 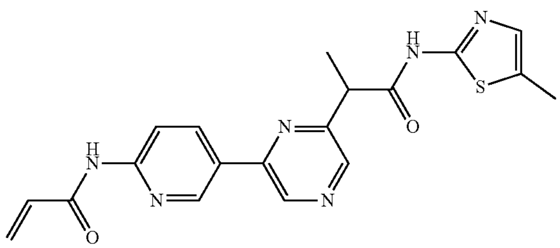 [SMILES: C=CC(=O)Nc1ccc(-c2cncc(C(C)C(=O)Nc3ncc(C)s3)n2)cn1] | MS (m/z): 395.0 [M + 1] | Example 41 |
| 141 | 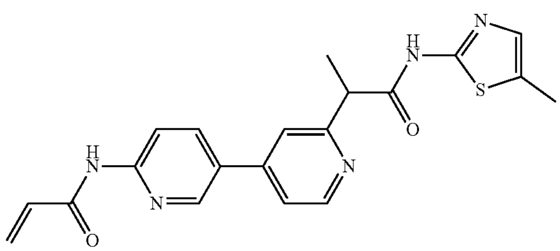 [SMILES: C=CC(=O)Nc1ccc(-c2ccnc(C(C)C(=O)Nc3ncc(C)s3)c2)cn1] | MS (m/z): 394.0 [M + 1] | Example 41 |
| 142 | 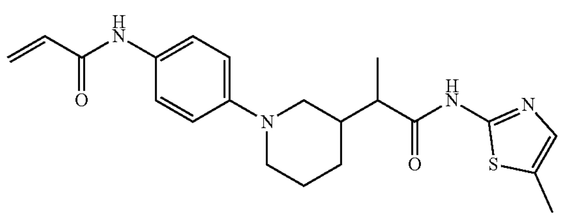 [SMILES: C=CC(=O)Nc1ccc(N2CCCC(C(C)C(=O)Nc3ncc(C)s3)C2)cc1] | MS (m/z): 399.0 [M + 1] | Example 41 |
| 143 | 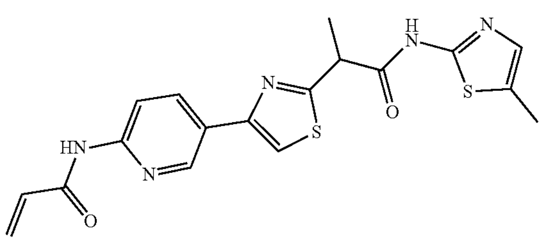 [SMILES: C=CC(=O)Nc1ccc(-c2csc(C(C)C(=O)Nc3ncc(C)s3)n2)cn1] | MS (m/z): 400.0 [M + 1] | Example 41 |
| 144 | 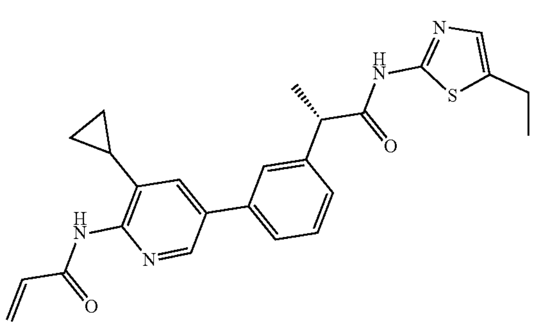 [SMILES: C=CC(=O)Nc1ncc(-c2cccc([C@H](C)C(=O)Nc3ncc(CC)s3)c2)cc1C1CC1] | MS (m/z): 447.0 [M + 1] | Example 14 |

TABLE 1-continued

| Example | Structure | ¹H NMR | Example # |
|---|---|---|---|
| 145 | 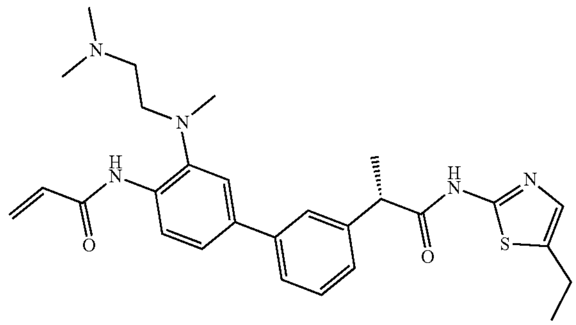 [SMILES: C=CC(=O)Nc1ccc(-c2cccc([C@H](C)C(=O)Nc3ncc(CC)s3)c2)cc1N(C)CCN(C)C] | MS (m/z): 506.0 [M + 1]; 6S ee % | Example 14 |
| 146 | 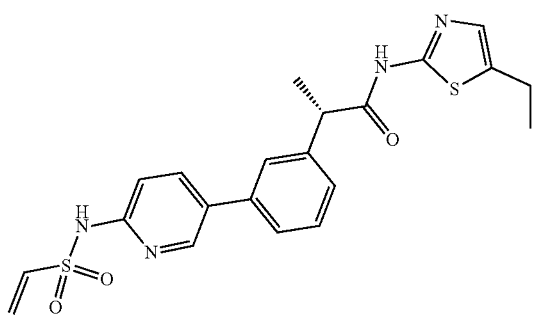 [SMILES: C=CS(=O)(=O)Nc1ccc(-c2cccc([C@H](C)C(=O)Nc3ncc(CC)s3)c2)cn1] | MS (m/z): 443.0 [M + 1]; 70 ee % | Example 14 |
| 147 | 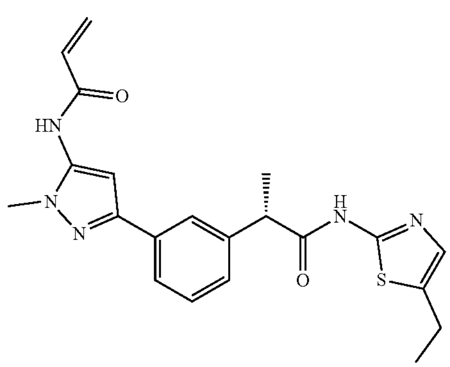 [SMILES: C=CC(=O)Nc1cc(-c2cccc([C@H](C)C(=O)Nc3ncc(CC)s3)c2)nn1C] | MS (m/z): 410.0 [M + 1]; 70 ee % | Example 14 |
| 148 | 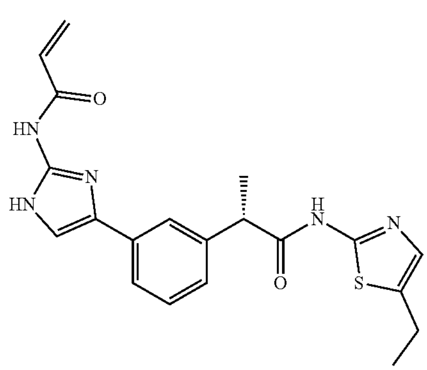 [SMILES: C=CC(=O)Nc1nc(-c2cccc([C@H](C)C(=O)Nc3ncc(CC)s3)c2)c[nH]1] | MS (m/z): 396.0 [M + 1]; 67 ee % | Example 14 |

TABLE 1-continued

| Example | Structure | ¹H NMR | Example # |
|---|---|---|---|
| 149 | 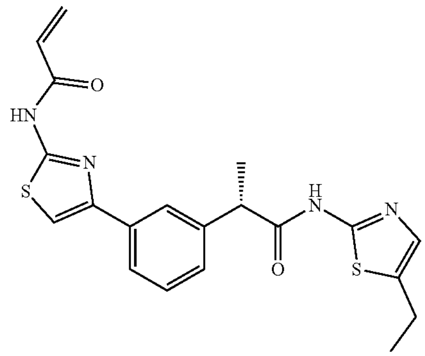 [SMILES: C=CC(=O)Nc1nc(-c2cccc([C@H](C)C(=O)Nc3ncc(CC)s3)c2)cs1] | MS (m/z): 413.0 [M + 1]; 68 ee % | Example 14 |

TEST EXAMPLE

The efficacies of the compounds prepared in Examples above were evaluated as follows, and the results are shown below.

Test Example 1: CDK7 Kinase Activity

Representative compounds of the present invention were assayed in vitro for CDK7 kinase-inhibitory activities using ADP-Glo platform. In detail, CDK7 kinase-inhibitory activity was measured using recombinant purified human CDK7 kinase (ThermoFisher, PV3868) and ADP Glo kinase assays kit (Promega, V9102). CDK7 kinase was diluted with 1× kinase reaction buffer (40 mM Tris-Cl, pH 7.5, 20 mM $MgCl_2$, 0.1 mg/ml BSA and 50 [M DTT) and added to 96 well plates (final concentration of CDK7 per reaction: 50 ng). The compound was finally treated to be a 1% DMSO aqueous solution, and a substrate cocktail containing ATP (final concentration of 90 [M) and 0.2 μg/μl of MBP (Myelin basic protein) in a total of 25 μl of reaction mass was added to 96 well plates, thereby initiating an enzymatic reaction. After 2 hours of incubation (30° C.), equivalent volume (25 μl per reaction) of ADP Glo was added and incubated (30° C.) at room temperature for 60 minutes. The kinase detection reagent (50 μl per reaction) was then added and incubated (30° C.) at room temperature for 30 minutes. The kinase activity was measured by chemiluminescence method according to ADP Glo Kanease Assay Kit instruction manual, and the CDK7-inhibitory activity of the compounds according to the present invention was calculated. The result analysis of each compound was performed using Microsoft Excel, and $IC_{50}$ values were calculated by Prism software. The CDK7 kinase-inhibitory $IC_{50}$ values were recorded for selected test compounds reported below in Table 2.

TABLE 2

CDK7 kinase-inhibitory activity of the compounds of the present invention

| Example | CDK7 inhibition(IC50 nM) |
|---|---|
| 2 | 40 |
| 6 | 35 |
| 14 | 28 |
| 15 | 11 |
| 17 | 11 |
| 37 | 17 |
| 45 | 22 |
| 52 | 19 |
| 63 | 17 |
| 73 | 43 |
| 74 | 77 |
| 76 | 92 |
| 81 | 6.4 |
| 82 | 36 |
| 83 | 23 |
| 84 | 68 |
| 88 | 16 |
| 91 | 8 |
| 92 | 42 |
| 93 | 93 |
| 94 | 14 |
| 95 | 80 |
| 96 | 7.6 |
| 98 | 87 |
| 99 | 7.6 |
| 100 | 9.8 |
| 101 | 7 |
| 102 | 13 |
| 103 | 13 |
| 104 | 9 |
| 106 | 71 |
| 107 | 31 |
| 108 | 10.5 |
| 109 | 8.2 |
| 110 | 5.9 |
| 111 | 9.5 |
| 112 | 17 |
| 113 | 8.5 |
| 114 | 12 |
| 115 | 17 |
| 116 | 13 |
| 117 | 15 |
| 118 | 20 |
| 119 | 9 |
| 120 | 16 |
| 121 | 7 |
| 122 | 6 |
| 123 | 5.3 |
| 124 | 4.5 |
| 125 | 13 |
| 128 | 50 |
| 129 | 17 |
| 130 | 8 |

TABLE 2-continued

CDK7 kinase-inhibitory activity of the compounds of the present invention

| Example | CDK7 inhibition(IC50 nM) |
|---|---|
| 131 | 59 |
| 132 | 6.6 |
| 133 | 47 |
| 135 | 13 |
| 136 | 33 |
| 137 | 13 |
| 138 | 8 |

Test Example 2: CDK7 Selectivity

The assay (scanMAX Kinase Assay Panel) was performed. ScanMAX Kinase Assay Panel contains a set of 468 kinases including CDK2, CDK5. The compounds were screened at 1 [M, and results for binding interactions are reported compared to control (%).

TABLE 3

Percent inhibition of various kinase of the compounds of the present invention

| | % inhibition at 1 uM | | |
|---|---|---|---|
| Example | CDK2 | CDK5 | CDK7 |
| 101 | 26 | 22 | 99 |
| 121 | 20 | 30 | 99 |

As shown in Table 3 above, the present compounds exerted the high inhibition to CDK7, and low inhibition of CDK 2 and CDK5. It was confirmed from the result that the present compounds highly selectively inhibit CDK7.

Test Example 3: Confirmation of Anti-Proliferative Effect of the Compound of the Present Invention on Cancer Cells (Inhibition Rate at 100 nM)

MDA-MB-468 Cells

MDA-MB-468 cells are one of the cells of triple-negative breast cancer (TNBC: negative for estrogen receptor, progesterone receptor, and HER2 expression) that is difficulty to be diagnosed at an early stage and is known as malignant tumors having high metastatic potential, and these cells are often used to test the inhibition of proliferation and survival of breast cancer cells.

Representative compounds of the present invention were tested at different concentrations (from 1000 nM to 25 nM) to assess their ability to inhibit the proliferation of MDA-MB-468 cells. Cells were grown in RPMI 1640 (Welgene)+ 10% FBS (Gibco)+1% penicillin/streptomycin (Gibco) and cultured at 37° C. in a humidified chamber in the presence of 5% $CO_2$.

MDA-MB-468 cells cultured in 96-well cell culture plates were treated with representative compounds of the present invention and cultured for 72 hours. Then, the antiproliferative effect of the compounds was assayed by MIT method using tetrazolium salt, and the results are shown in Table 3 below. The % values in Table 3 below represent the inhibition rate at a compound concentration of 100 nM.

TABLE 4

Inhibition rate of MDA-MB-468 cells at 100 nM

| Example | % Inhibition (@ 100 nM) |
|---|---|
| 1 | 54% |
| 2 | 50% |
| 4 | 56% |
| 6 | 66% |
| 11 | 53% |
| 14 | 74% |
| 15 | 73% |
| 16 | 53% |
| 17 | 70% |
| 22 | 72% |
| 25 | 71% |
| 27 | 74% |
| 28 | 74% |
| 29 | 75% |
| 33 | 59% |
| 36 | 64% |
| 37 | 60% |
| 38 | 64% |
| 39 | 67% |
| 40 | 64% |
| 45 | 59% |
| 47 | 72% |
| 49 | 67% |
| 50 | 66% |
| 52 | 72% |
| 53 | 51% |
| 61 | 73% |
| — | — |
| — | — |

MV4-11 Cells

MV4-11 cells are one of acute myelogenous leukemia cells with Fins-like tyrosine kinase (FLT3) gene mutation, and are often used to test the inhibition of proliferation and survival of leukemia cells.

Representative compounds of the present invention were tested at different concentrations (from 100 nM to 10 nM) to assess their ability to inhibit the proliferation of MV4-11 cells. Cells were grown in IMDM (Welgene)+10% FBS (Gibco)+1% penicillin/streptomycin (Gibco) and cultured at 37° C. in a humidified chamber in the presence of 5% $CO_2$.

MV4-11 cells cultured in 96-well cell culture plates were treated with representative compounds of the present invention and cultured for 72 hours. Then, the antiproliferative effect of the compounds was assayed by CCK-8 method using tetrazolium salt, and the results are shown in Table 4 below. The % values in Table 4 below represent the inhibition rate at a compound concentration of 100 nM.

TABLE 5

Inhibition rate of MV4-11 cells at 100 nM

| Example | % Inhibition (@ 100 nM) |
|---|---|
| 1 | 80% |
| 4 | 100% |
| 14 | 100% |
| 15 | 100% |
| 16 | 90% |
| 17 | 100% |
| 18 | 67% |
| 19 | 75% |
| 21 | 84% |
| 22 | 100% |
| 25 | 100% |
| 27 | 100% |

TABLE 5-continued

Inhibition rate of MV4-11 cells at 100 nM

| Example | % Inhibition (@ 100 nM) |
|---|---|
| 28 | 100% |
| 29 | 100% |
| 30 | 96% |
| 31 | 98% |
| 32 | 100% |
| 33 | 100% |
| 34 | 80% |
| 35 | 98% |
| 36 | 100% |
| 37 | 100% |
| 38 | 98% |
| 39 | 100% |
| 40 | 100% |
| 41 | 100% |
| 42 | 100% |
| 43 | 100% |
| 44 | 100% |
| 45 | 100% |
| 46 | 100% |
| 47 | 100% |
| 48 | 100% |
| 49 | 100% |
| 50 | 100% |
| — | — |

Test Example 4: Anti-Proliferative Effect of the Compound of the Present Invention on Cancer Cells MDA-MB-468 Cells The compounds of the present invention were tested at different concentrations (from 1000 nM to 1 nM) to assess their ability for inhibiting the proliferation of MDAMB-468 cells. Cells were cultivated in RPMI 1640 (Welgene)+10% FBS (Gibco)+1% penicillin/streptomycin (Gibco) and cultured at 37° C. in a humidified chamber in the presence of 5% C02.

MDA-MB-468 cells cultured in 96-well cell culture plates were treated with the compounds of the present invention and incubated for 72 hours. Then, the antiproliferative effect of the compounds was assayed by MTT method using tetrazolium salt, and the results are shown in Table 5 below.

TABLE 6

Inhibitory effect of the compounds of the present invention on the proliferation of MDA-MB-468 cells

| Example | MDA-MB-468($IC_{50}$ nM) |
|---|---|
| 2 | 104 |
| 6 | 86 |
| 14 | 63 |
| 15 | 46 |
| 17 | 26 |
| 37 | 40 |
| 45 | 10 |
| 63 | 20 |
| 73 | 35 |
| 74 | 65 |
| 81 | 39 |
| 82 | 32 |
| 83 | 21 |
| 88 | 54 |
| 91 | 38 |
| 92 | 52 |

TABLE 6-continued

Inhibitory effect of the compounds of the present invention on the proliferation of MDA-MB-468 cells

| Example | MDA-MB-468($IC_{50}$ nM) |
|---|---|
| 93 | 38 |
| 94 | 59 |
| 95 | 57 |
| 96 | 68 |
| 99 | 23 |
| 100 | 56 |
| 101 | 30 |
| 102 | 57 |
| 103 | 68 |
| 104 | 44 |
| 108 | 31 |
| 109 | 31 |
| 110 | 74 |
| 111 | 32 |
| 112 | 59 |
| 113 | 35 |
| 114 | 56 |
| 115 | 75 |
| 116 | 65 |
| 117 | 56 |
| 118 | 47 |
| 119 | 44 |
| 120 | 51 |
| 121 | 23 |
| 122 | 34 |
| 123 | 24 |
| 124 | 40 |
| 125 | 33 |
| 130 | 18 |
| 132 | 32 |
| 135 | 48 |
| 137 | 47 |
| 138 | 100 |
| — | — |

HepG2 Cells

The ability to inhibit the proliferation of HepG2 cells, which are human hepatocellular carcinoma cells, was measured through the in vitro cell viability assay. Cells were cultured at 37° C. in a humidified condition in the presence of 5% $CO_2$ using a culture medium of MEM (Welgene)+10% FBS (Gibco)+1% penicillin/streptomycin (Gibco). HepG2 cells cultured in 96-well cell culture plates were treated with the compounds and cultured for 72 hours. Cell viability was measured by CCK-8 method using tetrazolium salt, and the ability of the compounds according to the present invention to inhibit cancer cell proliferation was calculated. The result analysis of each compound was performed using Microsoft Excel and $IC_{50}$ values were calculated by Prism software and are shown in Table 7 below.

TABLE 7

Inhibitory effect of the compound of the present invention on the proliferation of HCC (HepG2) cells

| Example | HepG2($IC_{50}$ nM) |
|---|---|
| 2 | 15 |
| 6 | 22 |
| 14 | 5 |
| 37 | 8 |
| 45 | 8 |
| 63 | 2 |
| 81 | 11 |
| 82 | 4 |
| 83 | 3 |

TABLE 7-continued

Inhibitory effect of the compound of the present invention on the proliferation of HCC (HepG2) cells

| Example | HepG2(IC$_{50}$ nM) |
|---|---|
| 88 | 9 |
| 91 | 9.5 |
| 92 | 74 |
| 93 | 21 |
| 94 | 25 |
| 96 | 19 |
| 99 | 5 |
| 100 | 8 |
| 101 | 5 |
| 102 | 13 |
| 103 | 14 |
| 104 | 8 |
| 107 | 3.1 |
| 108 | 4.6 |
| 109 | 2.6 |
| 110 | 17.4 |
| 111 | 4 |
| 112 | 8.7 |
| 113 | 4.2 |
| 114 | 12 |
| 115 | 12 |
| 121 | 3 |
| 122 | 38 |
| 123 | 11 |
| 130 | 3.8 |
| 132 | 9.5 |
| 135 | 10 |
| 137 | 18 |
| 138 | 52 |

Test Example 5: Inhibitory Effect of the Compounds of the Present Invention on Gene Expression in Cancer Cells MDA-MB-468 Cells The compounds of the present invention were tested at different concentrations (from 250 nM to 100 nM) to assess their ability for inhibiting gene expression involving the proliferation of cancer cells of MDA-MB-468 cells, which are triple-negative breast cancers (TNBC: negative for estrogen receptor, progesterone receptor, and HER2 expression). Cells were cultivated in RPMI 1640 (Welgene)+10% FBS (Gibco)+1% penicillin/streptomycin (Gibco) and cultured at 37° C. in a humidified chamber in the presence of 5% C02.

MDA-MB-468 cells cultured in 96-well cell culture plates were treated with the compounds of the present invention and incubated for 24 hours. Then, proteins were extracted from the cells using RIPA (Radio immunoprecipitation assay) buffer comprising protease and phosphatase inhibitor. The proteins were separated depending on molecular weight by SDS-PAGE, and transferred to nitrocellulose membrane. RNAPII CTD p-Ser2, RNAPII CTD p-Ser5, RNAPII CTD p-Ser7, CDK7, c-Myc, and beta-Actin antibodies were reacted with the membrane at 4° C. for 18 hours and then the antibodies were reacted with ECL (enhanced chemiluminescence). The luminescence produced during the reaction was transmitted on X-Ray film and developed, and the results are shown in FIG. 1.

It can be seen that the compounds according to the present invention have excellent activity against proliferative diseases such as cancer by phosphorylating RNAPII CTD that plays important roles in gene transcription process, and effectively inhibiting MYC (a gene encoding a transcription factor) associated with proliferative diseases.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:
1. A compound represented by Formula (I), or a pharmaceutically acceptable salt thereof

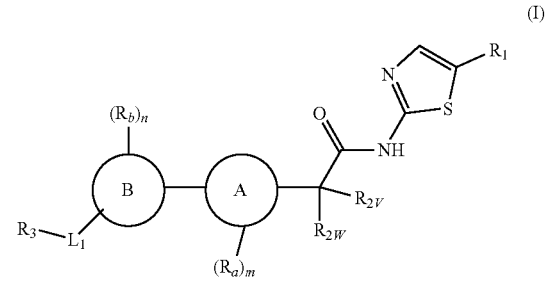

wherein:
ring A is phenyl, pyridinyl, pyrazinyl, pyrazolyl, thiophenyl, thiazolyl, or piperidinyl;
ring B is phenyl, pyridinyl, pyrimidinyl, pyrazinyl, pyridazinyl, pyrazolyl, imidazolyl, thiazolyl, tetrahydropyridinyl, piperidinyl, or piperazinyl;
$R_1$ is halo, $C_1$-$C_6$ alkyl, $C_3$-$C_7$ cycloalkyl, $C_1$-$C_6$ haloalkyl, cyano, —$SR_c$, —$C(O)R_c$, —$C(O)OR$, —$N(R_c)(R_d)$, —$OR_c$, or —$C(R_g)$—$OR_c$;
$R_c$ and $R_d$ are each independently H or $C_1$-$C_6$ alkyl;
$R_g$ is H or $C_1$-$C_6$ alkyl;
$R_{2V}$ and $R_{2W}$ are each independently H, halo, or $C_1$-$C_6$ alkyl or
$R_{2V}$ and $R_{2W}$, taken together with the atom to which they are attached, form a $C_3$-$C_7$ cycloalkyl;
$L_1$ is absent, —$N(R_e)$—, or —*$CH_2N(R_e)$—, * is the site in which $L_1$ is attached to ring B;
where $R_e$ is H or $C_1$-$C_6$ alkyl; or $R_e$ is bound to an atom on ring B, thereby forming ring B-fused pyrrole or pyrrolidine which is unsubstituted or substituted with $C_1$-$C_6$ alkyl;

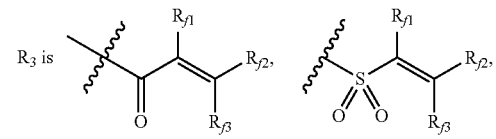

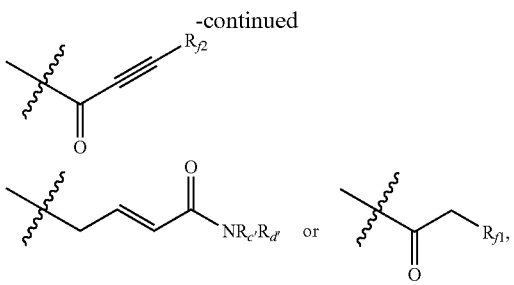

wherein $R_{f1}$ is H, halo, $C_1$-$C_6$ alkyl, or cyano;
$R_{f2}$ and $R_{f3}$ are each independently H, $C_1$-$C_6$ alkyl, $C_3$-$C_7$ cycloalkyl, —N($R_{c'}$ ($R_{d'}$), or —CH$_2$N($R_{c'}$)($R_{d'}$);
$R_{c'}$ and $R_{d'}$ are each independently $C_1$-$C_6$ alkyl; or
$R_{c'}$ and $R_{d'}$, taken together with the atom to which they are attached, form azetidinyl; piperidinyl; morpholinyl; piperazinyl which is unsubstituted or substituted with $C_1$-$C_6$ alkyl; 2,5-diazabicyclo[2.2.1]heptanyl which is unsubstituted or substituted with $C_1$-$C_6$ alkyl; 2-oxa-5-azabicyclo[2.2.1]heptanyl: or pyrrolidinyl which is unsubstituted or substituted with halo, hydroxy or $C_1$-$C_6$ alkoxy-$C_1$-$C_6$ alkyl;
$R_a$ is H, halo, or $C_1$-$C_6$ alkyl;
$R_b$ is H, halo, $C_1$-$C_6$ alkyl, $C_3$-$C_7$ cycloalkyl, $C_1$-$C_6$ alkoxy, cyano, $C_1$-$C_6$ haloalkyl, —N(CH$_3$)—CH$_2$CH—N(CH$_3$), or piperazinyl which is unsubstituted or substituted with $C_1$-$C_6$ alkyl;
m and n are each integer 1.

2. The compound of claim 1, wherein ring A is phenyl, pyridinyl, or thiophenyl.

3. The compound of claim 2, wherein ring A is phenyl.

4. The compound of claim 1, wherein ring B is pyridinyl, pyrimidinyl, pyrazinyl, pyridazinyl, or piperidinyl.

5. The compound of claim 4, wherein ring B is pyridinyl.

6. The compound of claim 1, wherein $R_1$ is halo, $C_1$-$C_6$ alkyl, $C_3$-$C_7$ cycloalkyl, $C_1$-$C_6$ haloalkyl, cyano, or —N($R_c$)($R_d$); and $R_c$ and $R_d$ are each independently H or $C_1$-$C_6$ alkyl.

7. The compound of claim 6, wherein $R_1$ is $C_1$-$C_6$ alkyl or $C_1$-$C_6$ haloalkyl.

8. The compound of claim 1, wherein $R_{2V}$ and $R_{2w}$ are each independently H or $C_1$-$C_6$ alkyl; or $R_{2V}$ and $R_{2w}$, taken together with the atom to which they are attached, form a $C_3$-$C_7$ cycloalkyl.

9. The compound of claim 8, wherein $R_{2V}$ and $R_{2w}$ are each independently H or $C_1$-$C_6$ alkyl.

10. The compound of claim 1, wherein $L_1$ is —N($R_e$)—; where $R_e$ is H or $C_1$-$C_6$ alkyl; or
$R_e$ is bound to an atom on ring B, thereby forming ring B-fused pyrrolidine which is unsubstituted or substituted with $C_1$-$C_6$ alkyl.

11. The compound of claim 10, wherein $R_e$ is H; or
$R_e$ is bound to an atom on ring B, thereby forming ring B-fused pyrrolidine which is unsubstituted or substituted with $C_1$-$C_6$ alkyl.

12. The compound of claim 1, wherein $R_3$ is

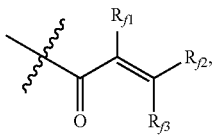

wherein $R_{f1}$ is H;
$R_{f2}$ and $R_{f3}$ are each independently H or —CH$_2$N($R_{c'}$)($R_{d'}$);
$R_{c'}$ and $R_{d'}$ are each independently $C_1$-$C_6$ alkyl; or
$R_{c'}$ and $R_{d'}$, taken together with the atom to which they are attached, form azetidinyl; piperidinyl; morpholinyl; piperazinyl which is unsubstituted or substituted with $C_1$-$C_6$ alkyl; 2,5-diazabicyclo[2.2.1]heptanyl which is unsubstituted or substituted with $C_1$-$C_6$ alkyl; 2-oxa-5-azabicyclo[2.2.1]heptanyl; or pyrrolidinyl which is unsubstituted or substituted with halo, hydroxy or $C_1$-$C_6$ alkoxy-$C_1$-$C_6$ alkyl.

13. The compound of claim 12, wherein $R_{c'}$ and $R_{d'}$ are each independently $C_1$-$C_6$ alkyl.

14. The compound of claim 1, wherein $R_a$ is H.

15. The compound of claim 1, wherein $R_b$ is H, halo, $C_1$-$C_6$ alkyl, $C_1$-$C_6$ alkoxy, cyano, or $C_1$-$C_6$ haloalkyl.

16. The compound of claim 15, wherein $R_b$ is halo or cyano.

17. A compound selected from the group consisting of
1) N-(5-(3-(1-((5-methylthiazol-2-yl)amino)-1-oxopropan-2-yl)phenyl)pyridin-2-yl)acrylamide;
2) N-(5-(3-(1-((5-cyclopropylthiazol-2-yl)amino)-1-oxopropan-2-yl)phenyl)pyridin-2-yl)acrylamide;
3) (R)-N-(5-(3-(1-((5-cyclopropylthiazol-2-yl)amino)-1-oxopropan-2-yl)phenyl)pyridin-2-yl)acrylamide;
4) N-(5-(3-(1-((5-ethylthiazol-2-yl)amino)-1-oxopropan-2-yl)phenyl)pyridin-2-yl)acrylamide;
5) (E)-4-(dimethylamino)-N-(5-(3-(1-((5-methylthiazol-2-yl)amino)-1-oxopropan-2-yl)phenyl)pyridin-2-yl)but-2-enamide;
6) (E)-N-(5-(3-(1-((5-cyclopropylthiazol-2-yl)amino)-1-oxopropan-2-yl)phenyl)pyridin-2-yl)-4-(dimethylamino)but-2-enamide;
7) (E)-4-(dimethylamino) -N-(5-(3-(1-(5-methylthiazol-2-yl)amino-1-oxopropan-2-yl)phenyl)pyridin-2-yl)but-2-enamide hydrochloride;
8) N-(3-fluoro-3'-(1-(5-methylthiazol-2-yl)amino-1-oxopropan-2-yl)-[1,1'-biphenyl]-4-yl)acrylamide
9) 2-(3-(1-acryloylindolin-5-yl)phenyl)-N-(5-methylthiazol-2-yl)propanamide;
10) (E)-N-(5-(3-(1,1-difluoro-2-((5-methylthiazol-2-yl)amino)-2-oxoethyl)phenyl)pyridin-2-yl)-4-(dimethylamino)but-2-enamide;
11) N-(6-(3-(1-((5-cyanothiazol-2-yl)amino)-1-oxopropane-2-yl)-4-fluorophenyl)pyridazin-3-yl)acrylamide;
12) 2-(3-(6-acrylamidopyridazin-3-yl)phenyl)-N-(5-cyanothiazol-2-yl)-3-methylbutanamide;
13) N-(6-(5-(1-((5-cyanothiazol-2-yl)amino)-1-oxopropan-2-yl)-2-fluorophenyl)pyridazin-3-yl)acrylamide;
14) (S)-N-((5-(3-(1-(5-cyclopropylthiazol-2-yl)amino)-1-oxopropane-2-yl)phenyl)pyridin-2-yl)acrylamide;
15) (S,E)-N-((5-(3-(1-(5-cyclopropylthiazol-2-yl)amino)-1-oxopropan-2-yl)phenyl)pyridin-2-yl)-4-(dimethylamino)but-2-enamide;
16) (S)-N-((6-(3-(1-(5-cyclopropylthiazol-2-yl)amino)-1-oxopropan-2-yl)phenyl) pyrazin-2-yl) acrylamide
17) (S,E)-4-(dimethylamino)-N-(5-(3-(1-((5-ethylthiazol-2-yl)amino)-1-oxopropan-2-yl)phenyl)pyridin-2-yl)but-2-enamide;
18) (S)-N-(5-(3-(1-((5-cyanothiazole-2-yl)amino)-1-oxopropan-2-yl)phenyl)pyridin-2-yl)acrylamide;
19) (S)-2-(3-(6-acrylamidopyridin-3-yl)phenyl)-N-(5-ethylthiazol-2-yl)butanamide;
20) (S)-2-(4'-acrylamido-3'-fluoro-[1,1'-biphenyl]-3-yl)-N-(5-ethylthiazol-2-yl)butanamide;

21) (S,E)-N-(5-(3-(1-((5-cyanothiazol-2-yl)amino)-1-oxopropan-2-yl)phenyl)pyridin-2-yl)-4-(dimethylamino)but-2-enamide;
22) (S)-N-(5-(3-(1-(5-cyclopropylthiazol-2-yl)amino)-1-oxopropan-2-yl)phenyl)pyrazin-2-yl)acrylamide;
23) (S)-N-(3'-(1-(5-cyclopropylthiazol-2-yl)amino-1-oxopropan-2-yl)-[1,1'-biphenyl]-4-yl)acrylamide;
24) (S)-N-(3'-(1-(5-cyclopropylthiazol-2-yl)amino-1-oxopropan-2-yl)-3-fluoro-[1,1'-biphenyl]-4-yl)acrylamide;
25) (S)-N-(5-(3-(1-(5-cyanothiazol-2-yl)amino-1-oxopropan-2-yl)phenyl)pyrazin-2-yl)acrylamide;
26) (S)-N-(6-(3-(1-(5-cyanothiazol-2-yl)amino-1-oxopropan-2-yl)phenyl) pyrazin-2-yl) acrylamide
27) (S)-N-(5-(3-(1-(5-cyclopropylthiazol-2-yl)amino-1-oxopropan-2-yl)phenyl)pyrimidin-2-yl)acrylamide;
28) (S)-N-(6-(3-(1-(5-cyclopropylthiazol-2-yl)amino-1-oxopropan-2-yl)phenyl)pyridazin-3-yl)acrylamide;
29) (S) -N-((5-(3-(1-(5-cyclopropylthiazol-2-yl)amino)-1-oxopropan-2-yl)phenyl)-3-fluoropyridin-2-yl) acrylamide
30) (S)-N-(3-cyano-3'-(1-((5-ethylthiazol-2-yl)amino)-1-oxopropan-2-yl)-[1,1'-biphenyl]-4-yl)acrylamide;
31) (S)-N-(5-(3-(1-((5-ethylthiazol-2-yl)amino)-1-oxopropan-2-yl)phenyl)-6-fluoropyridin-2-yl)acrylamide;
32) (S)-N-(6-(3-(1-((5-cyanothiazol-2-yl)amino)-1-oxopropan-2-yl)phenyl)pyridazin-3-yl)acrylamide;
33) (S)-N-(5-(3-(1-((5-cyanothiazol-2-yl)amino)-1-oxopropan-2-yl)phenyl)-3-fluoropyridin-2-yl)acrylamide;
34) (S)-N-(5-(3-(1-((5-cyanothiazol-2-yl)amino)-1-oxopropan-2-yl)phenyl)-3-methylpyrazin-2-yl)acrylamide;
35) (S)-N-(5-(3-(1-(5-isopropylthiazol-2-yl)amino)-1-oxopropan-2-yl)phenyl)pyridin-2-yl) acrylamide
36) (S)-N-(5-(3-(1-((5-isopropylthiazol-2-yl)amino)-1-oxopropan-2-yl)phenyl)pyrazin-2-yl)acrylamide;
37) (S)-N-(5-(3-(1-oxo-1-((5-(trifluoromethyl)thiazol-2-yl)amino)propan-2-yl)phenyl)pyrazin-2-yl)acrylamide;
38) (S)-N-(5-(3-(1-oxo-1-((5-(trifluoromethyl)thiazol-2-yl)amino)propan-2-yl)phenyl)pyrazin-2-yl)acrylamide;
39) (S)-N-(6-(3-(1-oxo-1-((5-(trifluoromethyl)thiazol-2-yl)amino)propan-2-yl)phenyl)pyridazin-3-yl)acrylamide;
40) (S)-N-(6-(3-(1-((5-isopropylthiazol-2-yl)amino)-1-oxopropan-2-yl)phenyl)pyridazin-3-yl)acrylamide;
41) N-(5'-(1-(5-cyanothiazol-2-yl)amino-1-oxopropane-2-yl)-[3,3'-bipyridin]-6-yl) acrylamide;
42) N-(4-(1-(5-cyanothiazole-2-yl)amino-1-oxopropan-2-yl)-[2,3'-bipyridine]-6'-yl) acrylamide;
43) N-(5-(5-(1-(5-cyclopropylthiazol-2-yl)amino-1-oxopropan-2-yl)pyridin-3-yl) pyrazin-2-yl) acrylamide
44) N-(5-(5-(1-((5-cyanothiazol-2-yl)amino)-1-oxopropan-2-yl)pyridin-3-yl)pyrazin-2-yl)acrylamide;
45) N-(5-(5-(1-oxo-1-((5-(trifluoromethyl)thiazol-2-yl)amino)propan-2-yl)pyridin-3-yl)pyrazin-2-yl)acrylamide;
46) N-(5-(5-(1-((5-ethylthiazol-2-yl)amino)-1-oxopropan-2-yl)pyridin-3-yl)pyrazin-2-yl)acrylamide;
47) N-(5-(5-(1-((5-isopropylthiazol-2-yl)amino)-1-oxopropan-2-yl)pyridin-3-yl)pyrazin-2-yl)acrylamide;
48) N-(5-(5-(1-((5-acetylthiazol-2-yl)amino)-1-oxopropan-2-yl)pyridin-3-yl)pyrazin-2-yl)acrylamide;
49) N-(6-(5-(1-oxo-1-((5-(trifluoromethyl)thiazol-2-yl)amino)propan-2-yl)pyridin-3-yl)pyridazin-3-yl)acrylamide;
50) N-(4-(1-((5-cyclopropylthiazol-2-yl)amino)-1-oxopropan-2-yl)-[2,3'-bipyridine]-6'-yl)acrylamide;
51) (R)-N-(5-(5-(1-oxo-1-((5-(trifluoromethyl)thiazol-2-yl)amino)propan-2-yl)pyridin-3-yl)pyrazin-2-yl)acrylamide;
52) (S)-N-(5-(5-(1-oxo-1-((5-(trifluoromethyl)thiazol-2-yl)amino)propan-2-yl)pyridin-3-yl)pyrazin-2-yl)acrylamide;
53) N-(5-(5-(1-oxo-1-((5-(trifluoromethyl)thiazol-2-yl)amino)propan-2-yl)thiophen-3-yl)pyridin-2-yl)acrylamide;
54) N-(5-(5-(1-(5-cyclopropylthiazol-2-yl)amino-1-oxopropan-2-yl)pyridin-3-yl) pyrazin-2-yl) acrylamide
55) N-(5-(5-(2-methyl-1-oxo-1-((5-(trifluoromethyl)thiazol-2-yl)amino)propan-2-yl)pyridin-3-yl)pyrazin-2-yl)acrylamide;
56) (S)-2-(3-(5-(2-cyanoacetamido)pyrazin-2-yl)phenyl)-N-(5-(trifluoromethyl)thiazol-2-yl)propanamide;
57) N-(5-(5-(1-oxo-1-((5-(trifluoromethyl)thiazol-2-yl)amino)propan-2-yl)thiophen-3-yl)pyrazin-2-yl)acrylamide;
58) (S)-2-(3-(5-(2-cyanoacetamido)pyrazin-2-yl)phenyl)-N-(5-cyanothiazol-2-yl)propanamide;
59) N-(5-(3-methyl-1-(1-oxo-1-((5-(trifluoromethyl)thiazol-2-yl)amino)propan-2-yl)-1H-pyrazol-4-yl)pyridin-2-yl)acrylamide;
60) 2-(1'-acryloyl-1',2',3',6'-tetrahydro-[3,4'-bipyridine]-5-yl)-N-(5-cyanothiazol-2-yl)propanamide;
61) N-(5-(5-(1-((5-chlorothiazol-2-yl)amino)-1-oxopropan-2-yl)pyridin-3-yl)pyrazine-2-yl)acrylamide;
62) (S)-N-(6-(3-(1-((5-cyclopropylthiazol-2-yl)amino)-1-oxopropan-2-yl)phenyl)pyridin-3-yl)acrylamide;
63) (E)-4-(dimethylamino)-N-(5-(5-(1-oxo-1-((5-(trifluoromethyl)thiazol-2-yl)amino)propan-2-yl)pyridin-3-yl)pyrazin-2-yl)but-2-enamide;
64) 2-(5-(5-(2-cyanoacetamido)pyrazin-2-yl)pyridin-3-yl)-N-(5-(trifluoromethyl)thiazol-2-yl)propanamide;
65) (E)-2-cyano-3-cyclopropyl-N-(5-(5-(1-oxo-1-((5-(trifluoromethyl)thiazol-2-yl)amino)propan-2-yl)pyridin-3-yl)pyrazin-2-yl)acrylamide;
66) N-(5-(5-(1-((5-methoxythiazol-2-yl)amino)-1-oxopropan-2-yl)pyridin-3-yl)pyrazin-2-yl)acrylamide;
67) N-(5-(5-(1-((5-fluorothiazol-2-yl)amino)-1-oxopropan-2-yl)pyridin-3-yl)pyrazin-2-yl)acrylamide;
68) N-(2-(4-methylpiperazin-1-yl)-4-(5-(1-oxo-1-((5-(trifluoromethyl)thiazol-2-yl)amino)propan-2-yl)pyridin-3-yl)phenyl)acrylamide;
69) (E)-2-cyano-3-(dimethylamino)-N-(5-(5-(1-oxo-1-((5-(trifluoromethyl)thiazol-2-yl)amino)propan-2-yl)pyridin-3-yl)pyrazin-2-yl)acrylamide;
70) N-(1-(5-(1-oxo-1-((5-(trifluoromethyl)thiazol-2-yl)amino)propan-2-yl)pyridin-3-yl)piperidin-4-yl)acrylamide;
71) N-(5-(5-(1-((5-(methylthio)thiazol-2-yl)amino)-1-oxopropan-2-yl)pyridin-3-yl)pyrazin-2-yl)acrylamide;
72) ethyl 2-(2-(5-(5-acrylamidopyrazin-2-yl)pyridin-3-yl)propanamido)thiazole-5-carboxylate;
73) (E)-N-(5-(5-(1-((5-chlorothiazol-2-yl)amino)-1-oxopropan-2-yl)pyridin-3-yl)pyrazin-2-yl)-4-(dimethylamino)but-2-enamide;
74) (E)-4-morpholino-N-(5-(5-(1-oxo-1-((5-(trifluoromethyl)thiazol-2-yl)amino)propan-2-yl)pyridin-3-yl)pyrazin-2-yl)but-2-enamide;
75) (E)-N-(5-(5-(1-oxo-1-((5-(trifluoromethyl)thiazol-2-yl)amino)propan-2-yl)pyridin-3-yl)pyrazin-2-yl)but-2-enamide;

76) N-(5-(5-(1-(((5-chlorothiazol-2-yl)amino)-1-oxopropan-2-yl)thiophen-3-yl)pyridin-2-yl)acrylamide;
77) N-(5-(5-(1-((5-ethylthiazol-2-yl)amino)-1-oxopropan-2-yl)thiophen-3-yl)pyridin-2-yl)acrylamide;
78) N-(5-(5-(1-((5-acetylthiazol-2-yl)amino)-1-oxopropan-2-yl)thiophen-3-yl)pyridin-2-yl)acrylamide;
79) 2-(5-(5-propionamidopyrazin-2-yl)pyridin-3-yl)-N-(5-(trifluoromethyl)thiazol-2-yl)propanamide;
80) (E)-4-(5-methyl-2,5-diazabicyclo[2.2.1]heptan-2-yl)-N-(5-(5-(1-oxo-1-((5-(trifluoromethyl)thiazol-2-yl)amino)propan-2-yl)pyridin-3-yl)pyrazin-2-yl)but-2-enamide;
81) (S,E)-4-(dimethylamino)-N-(5-(3-(1-oxo-1-((5-(trifluoromethyl)thiazol-2-yl)amino)propan-2-yl)phenyl)pyrazin-2-yl)but-2-enamide;
82) N-(5'-(1-oxo-1-((5-(trifluoromethyl)thiazol-2-yl)amino)propan-2-yl)-[3,3'-bipyridin]-6-yl)acrylamide;
83) (E)-4-(2-oxa-5-azabicyclo[2.2.1]heptan-5-yl)-N-(5-(5-(1-oxo-1-((5-(trifluoromethyl)thiazol-2-yl)amino)propan-2-yl)pyridin-3-yl)pyrazin-2-yl)but-2-enamide;
84) N-(4-fluoro-5'-(1-oxo-1-((5-(trifluoromethyl)thiazol-2-yl)amino)propan-2-yl)[3,3'-bipyridin]-6-yl)acrylamide;
85) 2-(5-(4-acryloylpiperazin-1-yl)pyridin-3-yl)-N-(5-(trifluoromethyl)thiazol-2-yl)propanamide;
86) 2-(5-(4-acryloylpiperazin-1-yl)pyridin-3-yl)-N-(5-ethylthiazol-2-yl)propanamide;
87) N-(6-(5-(1-((5-ethylthiazol-2-yl)amino)-1-oxopropan-2-yl)thiophen-3-yl)pyridin-3-yl)acrylamide;
88) N-(5-cyano-5'-(1-oxo-1-((5-(trifluoromethyl)thiazol-2-yl)amino)propan-2-yl)[3,3'-bipyridin]-6-yl)acrylamide;
89) N-((5'-(1-oxo-1-((5-(trifluoromethyl)thiazol-2-yl)amino)propan-2-yl)-[3,3'-bipyridin]-6-yl)methyl)acrylamide;
90) N-(5'-(1-oxo-1-((5-(trifluoromethyl)thiazol-2-yl)amino)propan-2-yl)-[2,3'-bipyridin]-5-yl)acrylamide;
91) (S,E)-4-(dimethylamino)-N-(5-(3-(1-oxo-1-((5-(trifluoromethyl)thiazol-2-yl)amino)propan-2-yl)phenyl)pyrazin-2-yl)but-2-enamide;
92) (S,E)-4-morpholino-N-(5-(3-(1-oxo-1-((5-(trifluoromethyl)thiazol-2-yl)amino)propan-2-yl)phenyl)pyrazin-2-yl)but-2-enamide;
93) (S,E)-N-(5-(3-(1-((5-chlorothiazol-2-yl)amino)-1-oxopropan-2-yl)phenyl)pyrazin-2-yl)-4-(dimethylamino)but-2-enamide;
94) (E)-4-(2-oxa-5-azabicyclo[2.2.1]heptan-5-yl)-N-(5-(3-((S)-1-((5-chlorothiazol-2-yl)amino)-1-oxopropan-2-yl)phenyl)pyrazin-2-yl)but-2-enamide;
95) (S,E)-4-(4-methylpiperazin-1-yl)-N-(5-(3-(1-oxo-1-((5-(trifluoromethyl)thiazol-2-yl)amino)propan-2-yl)phenyl)pyrazin-2-yl)but-2-enamide;
96) (E)-4-(2-oxa-5-azabicyclo[2.2.1]heptan-5-yl)-N-(5-(3-((S)-1-oxo-1-((5-(trifluoromethyl)thiazol-2-yl)amino)propan-2-yl)phenyl)pyrazin-2-yl)but-2-enamide;
97) (S,E)-N-(5-(3-(1-((5-chlorothiazol-2-yl)amino)-1-oxopropan-2-yl)phenyl)pyrazin-2-yl)-4-(4-methylpiperazin-1-yl)but-2-enamide;
98) (S,E)-N-(5-(3-(1-((5-chlorothiazol-2-yl)amino)-1-oxopropan-2-yl)phenyl)pyrazin-2-yl)-4-morpholinobut-2-enamide;
99) (S,E)-4-(dimethylamino)-N-(3-fluoro-5-(3-(1-oxo-1-((5-(trifluoromethyl)thiazol-2-yl)amino)propan-2-yl)phenyl)pyridin-2-yl)but-2-enamide;
100) (S,E)-4-(dimethylamino)-N-(3-methoxy-5-(3-(1-oxo-1-((5-(trifluoromethyl)thiazol-2-yl)amino)propan-2-yl)phenyl)pyridin-2-yl)but-2-enamide;
101) (S,E)-N-(3-cyano-5-(3-(1-oxo-1-((5-(trifluoromethyl)thiazol-2-yl)amino)propan-2-yl)phenyl)pyridin-2-yl)-4-(dimethylamino)but-2-enamide;
102) (S,E)-N-(5-(3-(1-oxo-1-((5-(trifluoromethyl)thiazol-2-yl)amino)propan-2-yl)phenyl)pyrazin-2-yl)-4-(pyrrolidin-1-yl)but-2-enamide;
103) (S,E)-4-(azetidin-1-yl)-N-(5-(3-(1-oxo-1-((5-(trifluoromethyl)thiazol-2-yl)amino)propan-2-yl)phenyl)pyrazin-2-yl)but-2-enamide;
104) (S,E)-N-(5-(3-(1-((5-cyclobutylthiazol-2-yl)amino)-1-oxopropan-2-yl)phenyl)pyrazin-2-yl)-4-(dimethylamino)but-2-enamide;
105) (S,E)-4-(dimethylamino)-N-(5-(3-(1-((5-(2-hydroxypropan-2-yl)thiazol-2-yl)amino)-1-oxopropan-2-yl)phenyl)pyrazin-2-yl)but-2-enamide;
106) (S,E)-4-(dimethylamino)-N-(5-(3-(1-((5-(dimethylamino)thiazol-2-yl)amino)-1-oxopropan-2-yl)phenyl)pyrazin-2-yl)but-2-enamide;
107) (E)-4-(dimethylamino)-N-(5'-(1-oxo-1-((5-(trifluoromethyl)thiazol-2-yl)amino)propan-2-yl)-[3,3'-bipyridin]-6-yl)but-2-enamide;
108) (E)-N-(5-cyano-5'-(1-oxo-1-((5-(trifluoromethyl)thiazol-2-yl)amino)propan-2-yl)-[3,3'-bipyridin]-6-yl)-4-(dimethylamino)but-2-enamide;
109) (S,E)-4-(dimethylamino)-N-(3-methoxy-5-(3-(1-oxo-1-((5-(trifluoromethyl)thiazol-2-yl)amino)propan-2-yl)phenyl)pyrazin-2-yl)but-2-enamide;
110) (S,E)-2-(3-(1-(4-(dimethylamino)but-2-enoyl)-2,3-dihydro-1H-pyrrolo[2,3-b]pyridin-5-yl)phenyl)-N-(5-(trifluoromethyl)thiazol-2-yl)propanamide;
111) (S,E)-4-(dimethylamino)-N-(5-(3-(1-oxo-1-((5-(trifluoromethyl)thiazol-2-yl)amino)propan-2-yl)phenyl)-3-(trifluoromethyl)pyridin-2-yl)but-2-enamide;
112) (S,E)-4-(dimethylamino)-N-(3-methyl-5-(3-(1-oxo-1-((5-(trifluoromethyl)thiazol-2-yl)amino)propan-2-yl)phenyl)pyridin-2-yl)but-2-enamide;
113) (S,E)-N-(3-chloro-5-(3-(1-oxo-1-((5-(trifluoromethyl)thiazol-2-yl)amino)propan-2-yl)phenyl)pyridin-2-yl)-4-(dimethylamino)but-2-enamide;
114) (S,E)-4-(diethylamino)-N-(5-(3-(1-oxo-1-((5-(trifluoromethyl)thiazol-2-yl)amino)propan-2-yl)phenyl)pyrazin-2-yl)but-2-enamide;
115) (E)-4-((R)-3-fluoropyrrolidin-1-yl)-N-(5-(3-((S)-1-oxo-1-((5-(trifluoromethyl)thiazol-2-yl)amino)propan-2-yl)phenyl)pyrazin-2-yl)but-2- enamide;
116) (S,E)-4-(dimethylamino)-N-(5-(3-(1-oxo-1-((5-(trifluoromethyl)thiazol-2-yl)amino)propan-2-yl)phenyl)pyridin-2-yl)but-2-enamide;
117) (E)-4-((S)-3-fluoropyrrolidin-1-yl)-N-(5-(3-((S)-1-oxo-1-((5-(trifluoromethyl)thiazol-2-yl)amino)propan-2-yl)phenyl)pyrazin-2-yl)but-2- enamide;
118) (E)-4-((S)-2-(methoxymethyl)pyrrolidin-1-yl)-N-(5-(3-((S)-1-oxo-1-((5-(trifluoromethyl)thiazol-2-yl)amino)propan-2-yl)pyrazin-2-yl)but-2-enamide;
119) (E)-4-(3-hydroxypyrrolidin-1-yl)-N-(5-(3-((S)-1-oxo-1-((5-(trifluoromethyl)thiazol-2-yl)amino)propan-2-yl)phenyl)pyrazin-2-yl)but-2-enamide;
120) (S,E)-N-(5-(3-(1-oxo-1-((5-(trifluoromethyl)thiazol-2-yl)amino)propan-2-yl)phenyl)pyrazin-2-yl)-4-(piperidin-1-yl)but-2-enamide;
121) (S,E)-N-(3-cyano-5-(3-(1-((5-ethylthiazol-2-yl)amino)-1-oxopropan-2-yl)phenyl)pyridin-2-yl)-4-(dimethylamino)but-2-enamide;

122) (S,E)-2-(3-(1-(4-(dimethylamino)but-2-enoyl)-2,3-dihydro-1H-pyrrolo[2,3-b]pyridin-5-yl)phenyl)-N-(5-ethylthiazol-2-yl)propanamide;
123) (E)-4-(2-oxa-5-azabicyclo[2.2.1]heptan-5-yl)-N-(3-cyano-5-(3-((S)-1-((5-ethylthiazol-2-yl)amino)-1-oxopropan-2-yl)phenyl)pyridin-2-yl)but-2-enamide;
124) (S)-N-(3-cyano-5-(3-(1-oxo-1-((5-(trifluoromethyl)thiazol-2-yl)amino)propan-2-yl)phenyl)pyridin-2-yl)acrylamide;
125) (S,E)-4-(dimethylamino)-N-(5-(3-(1-((5-ethylthiazol-2-yl)amino)-1-oxopropan-2-yl)phenyl)-3-methyl)pyridin-2-yl)but-2-enamide;
126) (S,E)-2-(3-(1-(4-(dimethylamino)but-2-enoyl)-2-methyl-1H-pyrrolo[2,3-b]pyridin-5-yl)phenyl)-N-(5-ethylthiazol-2-yl)propanamide;
127) (S,E)-2-(3-(1-(4-(dimethylamino)but-2-enoyl)-1H-pyrrolo[2,3-b]pyridin-5-yl)phenyl)-N-(5-ethylthiazol-2-yl)propanamide;
128) (E)-1-(3-(5-cyano-6-(4-(dimethylamino)but-2-enamido)pyridin-3-yl)phenyl)-N-(5-ethylthiazol-2-yl)cyclopropane-1-carboxamide;
129) (S,E)-4-(dimethylamino)-N-(5-(3-(1-((5-ethylthiazol-2-yl)amino)-1-oxopropan-2-yl)phenyl)pyridin-2-yl)-N-methylbut-2-enamide;
130) (S,E)-4-(dimethylamino)-N-(5-(3-(1-((5-ethylthiazol-2-yl)amino)-1-oxopropan-2-yl)phenyl)-3-fluoropyridin-2-yl)but-2-enamide;
131) (E)-4-(dimethylamino)-N-(6-(3-(1-((5-ethylthiazol-2-yl)amino)-1-oxobutan-2-yl)phenyl)pyridin-3-yl)but-2-enamide;
132) (S,E)-N-(3-cyano-5-(3-(1-((5-ethylthiazol-2-yl)amino)-1-oxopropan-2-yl)phenyl)pyridin-2-yl)-4-(dimethylamino)-N-methylbut-2-enamide;
133) (E)-1-(3-(1-(4-(dimethylamino)but-2-enoyl)-2,3-dihydro-1H-pyrrolo[2,3-b]pyridin-5-yl)phenyl)-N-(5-ethylthiazol-2-yl)cyclopropane-1- carboxamide;
134) (E)-1-(3-(6-(4-(dimethylamino)but-2-enamido)-5-fluoropyridin-3-yl)phenyl)-N-(5-ethylthiazol-2-yl)cyclopropane-1-carboxamide;
135) (S,E)-N-(3-cyano-5-(3-(1-((5-ethylthiazol-2-yl)amino)-1-oxopropan-2-yl)phenyl)pyridin-2-yl)-4-morpholinobut-2-enamide;
136) (S,E)-N-(3-cyano-5-(3-(1-((5-ethylthiazol-2-yl)amino)-1-oxopropan-2-yl)phenyl)pyridin-2-yl)-4-(4-methylpiperazin-1-yl)but-2-enamide;
137) (E)-N-(5-cyano-5'-(1-((5-ethylthiazol-2-yl)amino)-1-oxopropan-2-yl)-[3,3'-bipyridin]-6-yl)-4-(dimethylamino)but-2-enamide;
138) (E)-N-(3-cyano-5-(3-(1-((5-ethylthiazol-2-yl)amino)-1-oxobutan-2-yl)phenyl)pyridin-2-yl)-4-(dimethylamino)but-2-enamide;
139) (S)-2-(3-(5-cyano-6-(2-cyanoacetamido)pyridin-3-yl)phenyl)-N-(5-ethylthiazol-2-yl)propanamide;
140) N-(5-(6-(1-((5-methylthiazol-2-yl)amino)-1-oxopropan-2-yl)pyrazin-2-yl)pyridin-2-yl)acrylamide;
141) N-(2'-(1-((5-methylthiazol-2-yl)amino)-1-oxopropan-2-yl)-[3,4'-bipyridin]-6-yl)acrylamide;
142) N-(4-(3-(1-((5-methylthiazol-2-yl)amino)-1-oxopropan-2-yl)piperidin-1-yl)phenyl)acrylamide;
143) N-(5-(2-(1-((5-methylthiazol-2-yl)amino)-1-oxopropan-2-yl)thiazol-4-yl)pyridin-2-yl)acrylamide;
144) (S)-N-(3-cyclopropyl-5-(3-(1-((5-ethylthiazol-2-yl)amino)-1-oxopropan-2-yl)phenyl)pyridin-2-yl)acrylamide;
145) (S)-N-(3-((2-(dimethylamino)ethyl)(methyl)amino)-3'-(1-((5-ethylthiazol-2-yl)amino)-1-oxopropan-2-yl)-[1,1'-biphenyl]-4-yl)acrylamide;
146) (S)-N-(5-ethylthiazol-2-yl)-2-(3-(6-(vinylsulfonamido)pyridin-3-yl)phenyl)propanamide;
147) (S)-N-(3-(3-(1-((5-ethylthiazol-2-yl)amino)-1-oxopropan-2-yl)phenyl)-1-methyl-1H-pyrazol-5-yl)acrylamide;
148) (S)-N-(4-(3-(1-((5-ethylthiazol-2-yl)amino)-1-oxopropan-2-yl)phenyl)-1H-imidazol-2-yl)acrylamide; and
149) (S)-N-(4-(3-(1-((5-ethylthiazol-2-yl)amino)-1-oxopropan-2-yl)phenyl)thiazol-2-yl)acrylamide.

\* \* \* \* \*

UNITED STATES PATENT AND TRADEMARK OFFICE
CERTIFICATE OF CORRECTION

PATENT NO. : 12,110,299 B2
APPLICATION NO. : 17/277033
DATED : October 8, 2024
INVENTOR(S) : Kwang Ok Lee et al.

Page 1 of 1

It is certified that error appears in the above-identified patent and that said Letters Patent is hereby corrected as shown below:

In the Claims

In Column 150, Claim 17, Line 21, after "consisting of", please insert -- the following compounds, or a pharmaceutically acceptable salt thereof: --;

In Column 152, Claim 17, Line 12, after "54)" please delete "N-(5-(5-(1-(5-cyclopropylthiazol-2-yl)amino-1-oxopropan-2-yl)pyridin-3-yl) pyrazin-2-yl) acrylamide" and insert instead -- N-(5-(3-(1-(5-cyclopropylthiazol-2-yl)amino)-1-oxopropan-2-yl)-5-fluorophenyl)pyridin-2-yl)acrylamide; --;

In Column 153, Claim 17, Line 23, please delete "2-yl)[3", please insert instead -- 2-yl)-[3 --;

In Column 153, Claim 17, Line 32, please delete "2-yl)[3", please insert instead -- 2-yl)-[3 --;

In Column 155, Claim 17, Lines 11 and 12, please delete "methyl)pyridin" and insert instead -- methylpyridin --.

Signed and Sealed this
Thirty-first Day of December, 2024

Derrick Brent
*Acting Director of the United States Patent and Trademark Office*